(12) United States Patent
Huch Ortega et al.

(10) Patent No.: US 12,331,314 B2
(45) Date of Patent: Jun. 17, 2025

(54) CULTURE METHOD FOR ORGANOIDS

(71) Applicant: Koninklijke Nederlandse Akademie Van Wetenschappen, Utrecht (NL)

(72) Inventors: Meritxell Huch Ortega, Utrecht (NL); Johannes Carolus Clevers, Utrecht (NL); Sylvia Fernandez Boj, Utrecht (NL)

(73) Assignee: Koninklijke Nederlandse Akademie Van Wetenschappen, Utrecht (NL)

( * ) Notice: Subject to any disclaimer, the term of this patent is extended or adjusted under 35 U.S.C. 154(b) by 531 days.

(21) Appl. No.: 16/906,515

(22) Filed: Jun. 19, 2020

(65) Prior Publication Data

US 2020/0318063 A1 Oct. 8, 2020

Related U.S. Application Data

(62) Division of application No. 16/743,191, filed on Jan. 15, 2020, which is a division of application No. 15/310,905, filed as application No. PCT/EP2015/060815 on May 15, 2015, now Pat. No. 10,597,633.

(30) Foreign Application Priority Data

May 16, 2014 (GB) ...................................... 1408764
Dec. 12, 2014 (GB) ...................................... 1422184

(51) Int. Cl.
*C12N 5/071* (2010.01)
*A61K 35/39* (2015.01)
*A61K 35/407* (2015.01)

(52) U.S. Cl.
CPC ............ *C12N 5/0602* (2013.01); *A61K 35/39* (2013.01); *A61K 35/407* (2013.01); *C12N 5/067* (2013.01); *C12N 5/0671* (2013.01); *C12N 5/0676* (2013.01); *C12N 5/0677* (2013.01); *C12N 2501/01* (2013.01); *C12N 2501/11* (2013.01); *C12N 2501/115* (2013.01); *C12N 2501/119* (2013.01); *C12N 2501/12* (2013.01); *C12N 2501/15* (2013.01); *C12N 2501/155* (2013.01); *C12N 2501/19* (2013.01); *C12N 2501/30* (2013.01); *C12N 2501/345* (2013.01); *C12N 2501/415* (2013.01); *C12N 2501/42* (2013.01); *C12N 2501/999* (2013.01); *C12N 2503/02* (2013.01); *Y02A 50/30* (2018.01)

(58) Field of Classification Search
CPC .......... C12N 2501/42; C12N 2501/999; C12N 2503/02; C12N 5/0602; C12N 5/067; C12N 5/0671; C12N 5/0676; C12N 5/0677; Y02A 50/30

See application file for complete search history.

(56) References Cited

U.S. PATENT DOCUMENTS

| | | |
|---|---|---|
| 5,981,483 A | 11/1999 | Dennis et al. |
| 6,743,626 B2 | 6/2004 | Baum et al. |
| 8,642,339 B2 | 2/2014 | Sato et al. |
| 8,685,726 B2 | 4/2014 | Schulz et al. |
| 10,597,633 B2 * | 3/2020 | Huch Ortega ....... C12N 5/0676 |
| 11,591,572 B2 | 2/2023 | Clevers et al. |
| 2003/0003088 A1 | 1/2003 | Tsao et al. |
| 2003/0129751 A1 | 7/2003 | Grikscheit et al. |
| 2003/0138948 A1 | 7/2003 | Fisk et al. |
| 2003/0138951 A1 | 7/2003 | Yin |
| 2004/0175367 A1 | 9/2004 | Herlyn et al. |
| 2004/0191902 A1 | 9/2004 | Tambor et al. |
| 2004/0229355 A1 | 11/2004 | Chen et al. |
| 2007/0010008 A1 | 1/2007 | Tseng et al. |
| 2007/0036769 A9 | 2/2007 | Li et al. |
| 2007/0122903 A1 | 5/2007 | Rezania et al. |
| 2007/0128719 A1 | 6/2007 | Tseng et al. |
| 2008/0112890 A1 | 5/2008 | Lelkes et al. |
| 2008/0113433 A1 | 5/2008 | Robins et al. |
| 2008/0166327 A1 | 7/2008 | Asahara et al. |
| 2008/0182328 A1 | 7/2008 | Snyder et al. |
| 2008/0233088 A1 | 9/2008 | Guha et al. |
| 2008/0242594 A1 | 10/2008 | McKay et al. |
| 2009/0275067 A1 | 11/2009 | Taniguchi et al. |
| 2010/0047853 A1 | 2/2010 | Kuo et al. |
| 2010/0100396 A1 | 4/2010 | Daven et al. |
| 2010/0275280 A1 | 10/2010 | Clevers et al. |
| 2011/0008893 A1 | 1/2011 | Sugimura et al. |
| 2011/0191868 A1 | 8/2011 | Gupta et al. |
| 2012/0021513 A1 | 1/2012 | Schulz et al. |
| 2012/0028355 A1 | 2/2012 | Sato et al. |
| 2012/0196312 A1 | 8/2012 | Sato et al. |
| 2012/0207744 A1 | 8/2012 | Mendlein et al. |

(Continued)

FOREIGN PATENT DOCUMENTS

| | | |
|---|---|---|
| CN | 101420964 A | 4/2009 |
| CN | 103180436 A | 6/2013 |

(Continued)

OTHER PUBLICATIONS

Anonymous, Wikipedia Article "Secreted frizzled-related protein 1 also known as SFRP1 is a protein which in humans," Wayback Machine, 7 pages (Oct. 14, 2013).

Pasic et al., "Sustained activation of the HER1-ERK1/2-RSK signaling pathway controls myoepithelial cell fate in human mammary tissue," Supplementary Material, 18 pages, Genes & Development 25 (2011).

Snykers et al., "Differentiation of neonatal rat epithelial cells from biliary origin into immature hepatic cells by sequential exposure to hepatogenic cytokines and growth factors reflecting liver development", Toxicology in Vitro (21), Apr. 4, 2007, pp. 1325-1331.

(Continued)

*Primary Examiner* — Blaine Lankford
(74) *Attorney, Agent, or Firm* — McNeill PLLC

(57) ABSTRACT

The invention relates to improved culture methods for expanding epithelial stem cells and obtaining organoids, to culture media involved in said methods, and to uses of said organoids.

15 Claims, 41 Drawing Sheets

Specification includes a Sequence Listing.

(56) References Cited

U.S. PATENT DOCUMENTS

| | | | |
|---|---|---|---|
| 2013/0005737 A1 | 1/2013 | Prabhu et al. | |
| 2013/0008956 A1 | 1/2013 | Ashfield | |
| 2013/0052729 A1 | 2/2013 | Pourquie et al. | |
| 2013/0089562 A1 | 4/2013 | French et al. | |
| 2013/0189327 A1* | 7/2013 | Ortega | A61K 35/407 |
| | | | 435/405 |
| 2013/0280809 A1 | 10/2013 | Efe et al. | |
| 2014/0044713 A1 | 2/2014 | Lau et al. | |
| 2014/0243227 A1 | 8/2014 | Clevers et al. | |
| 2014/0256037 A1 | 9/2014 | Sato et al. | |
| 2014/0302491 A1 | 10/2014 | Nadauld et al. | |
| 2015/0140013 A1 | 5/2015 | Ramaswamy | |
| 2015/0231201 A1 | 8/2015 | Clevers et al. | |
| 2015/0276719 A2 | 10/2015 | Beekman et al. | |
| 2016/0002595 A1 | 1/2016 | Keller et al. | |
| 2017/0002755 A1 | 5/2017 | Sachs | |
| 2017/0003423 A1 | 5/2017 | Sachs | |
| 2017/0191030 A1 | 7/2017 | Ortega et al. | |
| 2017/0275592 A1 | 9/2017 | Sachs et al. | |
| 2017/0342385 A1 | 11/2017 | Sachs et al. | |
| 2018/0066233 A1 | 3/2018 | Ortega et al. | |
| 2018/0072995 A1 | 3/2018 | Sato et al. | |
| 2018/0187191 A1 | 7/2018 | Zeng | |
| 2018/0221441 A1 | 8/2018 | Clevers et al. | |
| 2018/0258400 A1 | 9/2018 | Ng et al. | |
| 2019/0031992 A1 | 1/2019 | Kerns et al. | |
| 2019/0100728 A1 | 4/2019 | Sato et al. | |
| 2019/0383799 A1 | 12/2019 | Beekman et al. | |
| 2020/0172861 A1 | 6/2020 | Ortega et al. | |
| 2020/0377860 A1 | 12/2020 | Freedman et al. | |
| 2021/0040454 A1 | 2/2021 | Clevers et al. | |
| 2021/0047618 A1 | 2/2021 | Clevers et al. | |
| 2024/0076624 A1 | 3/2024 | Beumer et al. | |

FOREIGN PATENT DOCUMENTS

| | | |
|---|---|---|
| CN | 103237888 A | 8/2013 |
| CN | 104508121 A | 4/2015 |
| EP | 0953633 A1 | 11/1999 |
| EP | 2012000097 A | 1/2012 |
| EP | 2412800 A1 | 2/2012 |
| EP | 2420566 A1 | 2/2012 |
| EP | 2772534 A1 | 9/2014 |
| EP | 2138571 B1 | 4/2017 |
| EP | 3318627 A1 | 5/2018 |
| EP | 3441458 A1 | 2/2019 |
| EP | 3505620 B1 | 7/2023 |
| WO | 2004050827 A2 | 6/2004 |
| WO | 2004087896 A3 | 11/2004 |
| WO | 2005040391 A1 | 5/2005 |
| WO | 2005120547 A1 | 12/2005 |
| WO | 2007141657 A2 | 12/2007 |
| WO | 2007127454 A3 | 4/2008 |
| WO | 2008046649 A1 | 4/2008 |
| WO | 2008101215 A1 | 8/2008 |
| WO | 2009022907 A2 | 2/2009 |
| WO | 2009024595 A2 | 2/2009 |
| WO | 2010011352 A2 | 1/2010 |
| WO | 2010015938 A2 | 2/2010 |
| WO | 2010016766 A2 | 2/2010 |
| WO | 2010090513 A1 | 8/2010 |
| WO | 2010090513 A2 | 8/2010 |
| WO | 2010119819 A1 | 10/2010 |
| WO | 2010129294 A3 | 4/2011 |
| WO | 2011098402 A1 | 8/2011 |
| WO | 2011043591 A3 | 9/2011 |
| WO | 2012014076 A2 | 2/2012 |
| WO | 2012025725 A1 | 3/2012 |
| WO | 2012044992 A2 | 4/2012 |
| WO | 2012068251 A2 | 5/2012 |
| WO | 2012087965 A3 | 10/2012 |
| WO | 2012140274 A2 | 10/2012 |
| WO | 2012168930 A2 | 12/2012 |
| WO | 2012140274 A9 | 3/2013 |
| WO | 2013054112 A1 | 4/2013 |
| WO | 2013061608 A1 | 5/2013 |
| WO | 2013093812 A2 | 6/2013 |
| WO | 2013074681 A9 | 11/2013 |
| WO | 2014015777 A1 | 1/2014 |
| WO | 2014066649 A1 | 5/2014 |
| WO | 2014124527 A1 | 8/2014 |
| WO | 2014127170 A1 | 8/2014 |
| WO | 2014127219 A1 | 8/2014 |
| WO | 2014145389 | 9/2014 |
| WO | 2014159356 A1 | 10/2014 |
| WO | 2014170411 A1 | 10/2014 |
| WO | 2015040142 A1 | 3/2015 |
| WO | 2015173425 A1 | 11/2015 |
| WO | 2015179393 A1 | 11/2015 |
| WO | 2015200901 A1 | 12/2015 |
| WO | 2016016894 A1 | 2/2016 |
| WO | 2016056999 A1 | 4/2016 |
| WO | 2016083612 A1 | 6/2016 |
| WO | 2016083613 A2 | 6/2016 |
| WO | 2016094457 A1 | 6/2016 |
| WO | 2017048193 A1 | 3/2017 |
| WO | 2017149025 A1 | 9/2017 |
| WO | 2017205511 A1 | 11/2017 |
| WO | 2017220586 A1 | 12/2017 |
| WO | 2018036119 A1 | 3/2018 |
| WO | 2018052953 A1 | 3/2018 |
| WO | 2018102202 A1 | 6/2018 |
| WO | 2019122388 A1 | 6/2019 |
| WO | 2019228516 A1 | 12/2019 |
| WO | 2020205755 A1 | 10/2020 |
| WO | 2020234250 A1 | 11/2020 |

OTHER PUBLICATIONS

Snykers et al., "In Vitro Differentiation of Embryonic and Adult Stem Cells into Hepatocytes: State of the Art," Stem Cells vol. 27, pp. 577-605 (2009).

Spence et al., "Directed differentiation of human pluripotent stem cells into intestinal tissue in vitro," Nature, vol. 470, No. 7332, pp. 105-109 (Feb. 3, 2011).

Stepniak et al.,"c-Jun/AP-1 controls liver regeneration by repressing p53/p21 and p38 MAPK activity," (2006) Genes Dev. 20(16):2306-14.

Supek et al., "REVIGO Summarizes and Visualizes Long Lists of Gene Ontology Terms," PLoS One 6(7): e21800, 9 pages.

Takeda et al., "Inter-conversion between intestinal stem cell populations in distinct niches," Science. Dec. 9, 2011; 334(6061): 1420-1424.

Tanimizu et al., "Notch signaling controls hepatoblast differentiation by altering the expression of liver-enriched transcription factors," Journal of Cell Science (117)(15), 2004, pp. 3165-3174.

Terry et al., "Impaired enteroendocrine development in intestinal-specific Islet1 mouse mutants causes impaired glucose homeostasis," Am J Physiol Gastrointest Liver Physiol 307: G979-G991, Sep. 11, 2014.

Tetteh et al., "Replacement of Lost Lgr5-Positive Stem Cells through Plasticity of Their Enterocyte-Lineage Daughters," Cell Stem Cell 18, 203-213, Feb. 4, 2016.

The Wnt Family of Secreted Proteins, R&D Systems' 2004 Catalog, 7 pages (Jan. 1, 2004).

Tisato et al., "Upregulation of SOCS-1 by Nutlin-3 in acute myeloid leukemia cells but not in primary normal cells," Clinics (2014) pp. 68-74.

Tojo et al., "The ALK-5 inhibitor A-83-01 inhibits Smad signaling and epithelial-to-mesenchymal transition bytransforming growth factor-? ," Cancer Sci (96)(11), 2005, pp. 791-800.

Trierweiler et al., "The transcription factor c-JUN/AP-1 promotesHBV-related liver tumorigenesis in mice," Cell Death and Differentiation 23, 576-582 (2016).

Tsai et al., "LGR4 and LGR5 Function Redundantly During Human Endoderm Differentiation", Cellular and Molecular Gastroenterology and Hepatology (2), 2016, pp. 648-662.

(56) References Cited

OTHER PUBLICATIONS

Van Es et al., "DII1 marks early secretory progenitors in gut crypts that can revert to stem cells upon tissue damage," Nat Cell Biol. Oct. 2012; 14(10): 1099-1104.

Van Es et al., "Notch/γ-Secretase inhibition turns proliferative cells in intestinal crypts and adenomas into goblet cells," vol. 435; 5 pages, Jun. 2005.

Vaughan et al., "Lineage-negative Progenitors Mobilize to Regenerate Lung Epithelium after Major Injury," HHS Public Access Nature (Jan. 29, 2015); 25 pages.

Verbeke et al., "Humanization of the mouse mammary gland by replacement of the luminal layer with genetically engineered preneoplastic human cells,"Breast Cancer Research (2014) 20 pages.

Vincan et al., "Frizzled-7 dictates three-dimensional organization of colorectal cancer cell carcinoids", Oncogene (26) 2007, pp. 2340-2352.

Voronkov et al., "Wnt/beta-Catenin Signaling and Small Molecule Inhibitors," Current Pharmaceutical Design, 19, pp. 634-664, (2013).

Williams et al., The Role of the Wnt Family of Secreted Proteins in Rat Oval "Stem" Cell-Based Liver Regeneration Wnt1 Drives Differentiation, American Journal of Pathology (176)(6), Jun. 2010, pp. 2732-2742.

Wouters et al., "Evolution of distinct EGF domains with specific functions," Protein Science (2005) 14, pp. 1091-1103.

Yan et al., "The intestinal stem cell markers Bmi1 and Lgr5 identify two functionally distinct populations," PNAS 109:2, pp. 466-471 (Jan. 10, 2012).

Yang et al., "In vitro trans-differentiation of adult hepatic stem cells into pancreatic endocrine hormoneproducing cells," PNAS (99)(12), Jun. 11, 2002, pp. 8078-8083.

Yang et al., Beta-catenin signaling in murine liver zonation and regeneration: A Wnt-Wnt situation! (2014) Hepatology 60(3):964-976.

Yin et al., "Niche-independent high-purity cultures of Lgr5+ intestinal stem cells and their progeny," Nat Methods. Jan. 2014; 11(1): 106-112.

Yoshimura et al., "Vascular endothelial cells and smooth muscle cells mediate carbachol-induced hepatocyte proliferation via muscarinic receptors and IP3/PKC signaling cascades," Cell Biol Int. Apr. 2009;33(4):516-23.

Yu et al., "Ex vivo culture of circulating breast tumor cells for individualized testing of drug susceptibility," HHS Public Access Science (Jul. 11, 2014); 345(6193) pp. 216-220.

Zaret et al., "Genetic programming of liver and pancreas progenitors: lessons for stem-cell differentiation," Nature Reviews (9), May 2009, pp. 329-340.

Zauli et al., "MDM2 Antagonist Nutlin-3 Suppresses the Proliferation and Differentiation of Human Pre-Osteoclasts Through a p53-Dependent Pathway," Journal of Bone and Mineral Research vol. 22, No. 10; (2007) 10 pages.

Zhu et al., "Chemical Strategies for Stem Cell Biology and Regenerative Medicine", The Annual Review of Biomedical Engineering (13)(1), Apr. 20, 2011, pp. 73-90.

Zilberberg et al., "A Rapid and Sensitive Bioassay to Measure Bone Morphogenetic Protein Activity," BMC Cell Biology BioMed Central (Sep. 19, 2007), 10 pages.

Zimmerman, "Lung organoid culture," Differentiation; Research in Biological Diversity, vol. 36, No. 1, pp. 86-109 (1987).

Zong et al., "Notch signaling controls liver development by regulating biliary differentiation," Development 136, pp. 1727-1739 (2009).

Zuo et al., "P63 + Krt5 + distal airway stem cells are essential for lung regeneration," Nature (2014) 17 pages.

Dou et al., "Expanding SCA-1+ mammary stem cell in the presence of oestrogen and growth hormone," Clin Transl Oncol (2012) 14:444-451 (8 pages).

Ahmed et al., "Extracellular Matrix Regulation of Stem Cell Behavior," Curr Stem Cell Rep (2016) 2:197-206 (10 pages).

Al-Lazikani et al., "Standard Conformations for the Canonical Structures of Immunoglobulins," J. Mol. Biol. (1997) 273: 927-948 (22 pages).

Andersson et al., "Pharmacokinetics of Cisplatin and Its Monohydated Coplex in Humans," J Pharm Sci. Aug. 1996; 85(8): 824 827 (4 pages).

Argiris et al., "Head and neck cancer," Lancet. May 17, 2008; 371(9625): 1695-1709 (32 pages).

Atsushi et al., "A comparison of in vitro platinum-DNA adduct formation between carboplatin and cisplatin," Int J Biochem. 1994; 26(8): 1009-1016 (8 pages).

Barretina et al., "The CancerCell Line Encyclopedia enables predictive modelling of anticancer drug sensitivity," Nature, 2012; 483(7391): 603-607 (8 pages).

Bhosale et al., "Chromosomal Alterations and Gene Expression Changes Associated with the Progression of eukoplakia to Advanced Gingivobuccal Cancer," Transl Oncol. 2017; 10(3):396-409 (14 pages).

Bigorgne et al., "TTC7A mutations disrupt intestinal epithelial apicobasal polarity," J Clin Invest. 2014; 124(1):328-337 (11 pages).

Boj et al., "Organoid Models of Human and Mouse Ductal Pancreatic Cancer," Cell. Jan. 1, 20155; 160(0): 324-338 (28 pages).

Bossi et al., "Prognostic and predictive value of EGFR in head and neck squamous cell carcinoma," Oncotarget. 2016; 7(45): 74362-74379 (18 pages).

Braakhuis et al., "The Potential of the Nude Mouse Xenograft Model for the Study of Head and Neck Cancer,"Arch Otorhinolaryngol. 1984, 239(1):69-79 (11 pages).

Byron et al."Anti-integrin monoclonal antibodies," J Cell Sci. Nov. 15, 2009; 122(Pt 22): 4009 4011 (6 pages).

Cai Y et al., "Dysregulations in the PI3K pathway and targeted therapies for head and neck squamous cell carcinoma," Oncotarget. 2017; 8(13): 2203-22217 (15 pages).

Calderwood et al., "Integrin activation," Journal of Cell Science 117(5): 657-666, 2004 (10 pages).

Castillo-González et al., "Dysregulated cholinergic network as a novel biomarker of poor prognostic in patients with head and neck squamous cell carcinoma," BMC Cancer. 2015; 15:385 (13 pages).

Cavalieri et al., "Efficacy and safety of single-agent pan-human epidermal growth factor receptor (HER) inhibitor dacomitinib in locally advanced unresectable or metastatic skin squamous cell cancer," Eur J Cancer; (2018) 97: 7-15 (9 pages).

Clarkson et al., "Oral Viral Infections—Diagnosis and Managementg," Dent. Clin. North Am. 2017, 61(2):351-363 (13 pages).

Co et al., "Controlling Epithelial Polarity: A Human Enteroid Model for Host-Pathogen Interactions," Cell Reports 26: 2509-2520, Feb. 26, 2019 (17 pages).

Cruz-Acuña et al., "Synthetic hydrogels for human intestinal organoid generation and colonic wound repair," Nature Cell Biology, Nov. 2017, 19(11): 1326-1348 (23 pages).

D'Souza et al., "Case-Control Study of Human Papillomavirus and Oropharyngeal Cancer," N Engl J Med. 2007; 356:1944-56 (13 pages).

Dijkstra et al., "Generation of Tumor-Reactive T Cells by Co-culture of Peripheral Blood Lymphocytes and Tumor Organoids," 2018, Cell 174:1586-1598 (26 pages).

Driehuis & Clevers, "WNT signalling events near the cell membrane and their pharmacological targeting for the treatment of cancer," British Journal of Pharmacology, (2017) pp. 174 4547-4563 (17 pages).

Driehuis et al., "Oral Mucosal Organoids as a Potential Platform for Personalized Cancer Therapy," Cancer Discov., 2019, 9(7):852-871 (21 pages).

Drost and Clevers, "Organoids in cancer research," Nat Rev Cancer. Jul. 2018; 18: 407-18 (12 pages).

Dutta et al., "A Key Tyrosine (Y1494) in the B4 Integrin Regulates Multiple Signaling Pathways Important for Tumor Development and Progression," Cancer Res., Nov. 1, 2008, 68(21): 8779-8787 (10 pages).

Economopoulou et al., "The emerging role of immunotherapy in head and neck squamous cell carcinoma (HNSCC): anti-tumor immunity and clinical applications," Ann Transl Med. 2016; 4(9): 173 (13 pages).

(56) References Cited

OTHER PUBLICATIONS

Egles et al., "Integrin-Blocking Antibodies Delay Keratinocyte Re-Epithelialization in a Human Three-Dimensional Wound Healing Model," PlosOne, 5(5): e10528, May 2010, 8 pages.
Etienne et al., "Visualization of herpes simplex virus type 1 virions using fluorescent colors," J Virol Methods. Mar. 2017 ; 241: 46-51 (14 pages).
Faas et al., "Virtual nanoscopy: Generation of ultra-large high resolution electron microscopy maps," J Cell Biol. 198 (3): 457-469 (13 pages).
Fitzmaurice et al., "Global, Regional, and National Cancer Incidence, Mortality, Years of Life Lost, Years Lived With Disability, and Disability-Adjusted Life-years for 32 Cancer Groups, 1990 to 2015:A Systematic Analysis for the Global Burden of Disease Study," JAMA Oncol. United States; Apr. 1, 2017; 3(4): 524-548 (56 pages).
Freed-Pastor et al., "Mutant p53: one name, many proteins," Genes Dev. 2012, 26(12):1268-1286 (20 pages).
Fritsch et al., "Characterization of the Novel and Specific PI3Ka Inhibitor NVP-BYL719 and Development of the Patient Stratification Strategy for Clinical Trials," Mol Cancer Ther. 2014; 13(5):1117-29 (14 pages).
Fujii M et al., "A Colorectal Tumor Organoid Library Demonstrates Progressive Loss of Niche Factor Requirements during Tumorigenesis," Cell Stem Cell. Jun. 2, 2016; 18:827-838 (13 pages).
Ghasemi et al., "High-throughput testing in head and neck squamous cell carcinoma identifies agents with preferential activity in human papillomavirus-positive or negative cell lines," Ocotarget, 2018, 9(40): 26064-26071 (8 pages).
Gillison et al., "A causual role for human papillomavirus in head and neck cancer," Lancet. 2004, 363(9420):1488-9 (2 pages).
Gjorevski et al., "Designer matrices for intestinal stem cell and organoid culture," Nature, Nov. 2016, 539: 660-564 (17 pages).
Gonzalez et al., "Identification of 9 Genes differentially Expressed in Head and Neck Squamous Cell Carcinoma," Arch Otolaryngol Head Neck Surg. United States; 2003; 129:754-759 (6 pages).
Griffin et al., "Human Keratinocyte Cultures in the Investigation of Early Steps of Human Papillomavirus Infection," Methods Mol Biol. 2014; pp. 219-238 (19 pages).
Guan et al., "A meta-analysis comparing cisplatin-based to carboplatinbased chemotherapy in moderate to advanced squamous cell carcinoma of head and neck (SCCHN)," Oncotarget. 2016; 7(6): 7110-7119 (10 pages).
Hall et al., "The $\alpha 1/\beta 6$ and $\alpha 6/\beta 1$ Integrin Heterodimers Mediate Cell Attachment to Distinct Sites on Laminin," The Journal of Cell Biology, Jun. 1990, 110: 2175-2184 (10 pages).
Ho et al.,"Preliminary Results From a Phase 2 Trial of Tipifarnib in HRAS-Mutant Head and Neck Squamous Cell Carcinomas," Int J Radiat Oncol Biol Phys. 2018; 100(5): 1367 (1 page).
Hoogstraat et al., "Simultaneous Detection of Clinically Relevant Mutations and Amplifications for Routine Cancer Pathology," J Mol Diagnostics. 2015; 17(1): 10-18 (9 pages).
Hughes et al., "Matrigel: A complex protein mixture required for optimal growth of cell culture," (2010) Proteomics, 10 (9):1886-90 (6 pages).
Humphries et al., "Integrin Ligands," J Cell Sci., Oct. 1, 2006; 119(Pt 19): 3901-3903 (5 pages).
Humphries, "Integrin Structure," (2000) Biochemical Society Transactions vol. 28, part 4 (31 pages).
International Search Report and Written Opinion of International Application No. PCT/EP2020/057147, dated May 14, 2020 (19 pages).
Janda et al., "Surrogate Wnt agonists that phenocopy canonical Wnt and β-catenin signalling," (2017) Nature, 545 (7653):234-237 (19 pages).
Johnson et al., "Relationships between drug activity in NCI preclinical in vitro and in vivo models and early clinical trials, " Br J Cancer. 2001; 84(10):1424-31 (8 pages).

Juric et al., "Phosphatidylinositol 3-Kinase a—Selective Inhibition With Alpelisib (BYL719) in PIK3CA-Altered Solid Tumors: Results From the First-in-Human Study," J Clin Oncol.May 1, 2018; 36(13): 1291-1299 (12 pages).
Kijima et al., "Three-Dimensional Organoids Reveal Therapy Resistance of Esphagal and Oropharyngeal Squamous Cell Carinoma Cells," Cellular and Molecular Gastroenterlogy and Hepatology, 7(1): 73-91 (19 pages).
Cassiman et al., "The Vagal Nerve Stimulates Activation of the Hepatic Progenitor Cell Compartment via Muscarinic Acetylcholine Receptor Type 3," American Journal of Pathology, Aug. 2002, 161(2): 521-530 (10 pages).
Chatterjee et al., "Induced Pluripotent Stem (iPS) Cell Culture Methods and Induction of Differentiation into Endothelial Cells," Methods Mol Biol. 2016; 1357: 311-327 (16 pages).
Hornback-Klonisch et al., "Adult stem cells and their trans-differentiation potential-perspectives and therapeutic applications," J Mol Med (Berl). 2008; 86(12): 1301-1314 (26 pages).
Murry et al. "Differentiation of embryonic stem cells to clinically relevant populations: lessons from embryonic development," Cell, 22;132(4): 661-80, Feb. 2008 (20 pages).
Oda et al., "A comprehensive pathway map of epidermal growth factor receptor signaling," Mol Syst Biol. 2005.0010: pp. 1-17, 2005 (17 pages).
Shi et al., "Directed differentiation of human pluripotent stem cells to cerebral cortex neurons and neural networks," Nat Protoc 7: 1836-1846, 2012 (11 pages).
Vickaryous et al., "Human cell type diversity, evolution, development, and classification with special reference to cells derived from the neural crest," Biol Rev Camb Philos Soc., 81(3): 425-55, Aug. 2006 (31 pages).
Wu et al., "FGF19 Regulates Cell Proliferation, Glucose and Bile Acid Metabolism vai FGFR4-Dependent and Independent Pathways," PLOS One, Mar. 2011, 6(3): e17868, pp. 1-11 (11 pages).
Yang et al., "Differentiation of Human Induced-Pluripotent Stem Cells into Smooth-Muscle Cells: Two Novel Protocols," PLoS One, 2016; 11(1): e0147155 (11 pages).
Gui et al., "Heregulin protects mesenchymal stem cells from serum deprivation and hypoxia-induced apoptosis," Mol Cell Biochem, 305:171-178 (2007).
Thenappan et al., New Therapeutics Targeting Colon Cancer Stem Cells, Curr Colorectal Cancer Rep, vol. 5, No. 4, 2009 (12 pages).
Bedke et al., "A microplate co-culture assay allows individualised compound efficacy testing in patients derived 3D tumour spheroids and autologous immune cells," European Urology Supplements, vol. 16, No. 3, Mar. 2017, e1474 (2 pages).
Chakrabarti et al., "Hedgehog Signaling Regulates PDL-1 Expression in Gastric Cancer Cells to Induce Tumor Proliferation", Gastron, Apr. 22, 2017 (2 pages).
Chakrabarti et al., "Hedgehog Signaling Regulates PDL-1 Expression in Gastric Cancer Cells to Induce Tumor Proliferation," Gastroenterology, vol. 152, No. 5, Digestive Disease Week May 2017, Suppl. 1, (2 pages).
Choo, "The HLA System: Genetics, Immunology, Clinical Testing, and Clinical Implications," Yonsei Med J. Feb. 28, 2007;48(1):11-23 (13 pages).
Clevers et al., "Modeling Development and Disease with Organoids," Cell. Jun. 16, 2016; 165(7):1586-1597 (12 pages).
Daszkiewicz et al., "A 3D image-based quantification of immune cell-tumor spheroid interactions in the presence of checkpoint inhibition," Journal of Clinical Oncology, vol. 35, No. 7_Suppl, Mar. 1, 2017, (6 pages).
Daszkiewicz et al., Abstract 4611: "A 3D in vitro culture-based method to visualize and quantify effects of immuno-modulatory drugs", Proceedings of the American Association for Cancer Research Annual Meeting 2017; Apr. 1-5, 2017; Washington, DC, Apr. 1, 2017 (4 pages).
Drost et al., "Organoid culture systems for prostate epithelial and cancer tissue", Nat. Protoc, vol. 11, No. 2, Jan. 2016 (Jan. 21, 2016), pp. 347-358 (25 pages).
Drost et al., "Sequential cancer mutations in cultured human intestinal stem cells," Nature, vol. 521, May 7, 2015 (23 pages).

(56) References Cited

OTHER PUBLICATIONS

Finnberg et al., "Application of 3D tumoroid systems to define immune and cytotoxic therapeutic responses based on tumoroid and tissue slice culture molecular signatures", ONCOTARGET, vol. 8, No. 40, Sep. 15, 2017, pp. 66747-66757 (11 pages).
Finnberg et al., Abstract 3990: "Use of 3D tumoroid systems to define immune and cytotoxic therapeutic responses based on tumoroid and tissue slice culture molecular signatures : Cancer Research", Proceedings of the American Association for Cancer Research Annual Meeting 2017; Apr. 1-5, 2017; Washington, DC., Apr. 1, 2017 (4 pages).
Gao et al., "3D Spheroid/Organoid Models of Lung Cancer to Study Lung Cancer Pathogenesis and Testing of New Therapeutics", Journal of Thoracic Oncology, vol. 12, S1544, 1 page, (Jun. 21, 2017).
Hirshhaeuser et al., "Efficacy of catumaxomab in tumor spheroid killing is mediated by its trifunctional mode of action," Cancer Immunol Immunother, vol. 59, Jul. 2010, pp. 1675-1684 (10 pages).
Kuball et al., "Facilitating matched pairing and expression of TCR chains doi: 10.1182/blood introduced into human T cells," Blood, vol. 109, No. 6, 2331-2338, 8 pages, (2007).
Nozaki et al. "Co-culture with intestinal epithelial organoids allows efficient expansion and motility analysis of intraepithelial lymphocytes", J Gastroenterol, vol. 51 pp. 206-216, 8 pages, (2016).
Purwada et al., "Modular Immune Organoids with Integrin Ligand Specificity Differentially Regulate Ex Vivo B Cell Activation" ACS Biomater. Sci. Eng., vol. 3, Jan. 2017 pp. 214-225 (12 pages).
Rabinowitz et al., Transforming Growth Factor β Signaling Controls Activities of Human Intestinal CD8+T Suppressor Cells Gastroenterology, Mar. 2013; 144(3):601-612 (13 pages).
Rennert, et al., "A microfluidically perfused three dimensional human liver model", Biomaterials, vol. 71, Aug. 25, 2015 (Aug. 25, 2015), pp. 119-131 (14 pages).
Rogoz et al., "A 3-D enteroid-based model to study T-cell and epithelial cell interaction," J Immunol Methods, Jun. 2015;421:89-95 (13 pages).
Sachs et al., "Intestinal epithelial organoids fuse to form self-organizing tubes in floating collagen gels", Development, vol. 144, Mar. 2017 pp. 1107-1112 (6 pages).
Sadelain et al., "Therapeutic T cell engineering," Nature. 2017 vol. 545, pp. 423-431, 9 pages, (May 25, 2017).
Schumacher et al., "The use of murine-derived fundic organoids in studies of gastric physiology," J Physiol, vol. 593, No. 8, Feb. 2015, pp. 1809-1827 (19 pages).
Sebestyen et al., "RhoB Mediates Phosphoantigen Recognition by Vg9Vd2 T Cell Receptor," Cell Rep. May 31, 2016;15(9):1973-85 (14 pages).
Shiina et al., MHC Genotyping in Human and Nonhuman Species by PCR-based Next-Generation Sequencing, Intech, Next Generation Sequencing—Advances, Applications and Challenges, Chapter 3, 31 pages (2016).
Tian et al., "Integrin-specific hydrogels as adaptable tumor organoids for malignant B and T cells", Biomaterials, vol. 73, Sep. 11, 2015, pp. 110-119 (21 pages).
Upton et al., "De novo synthesis of T cells from mPB CD34+ cells cultured in a 3-dimensional thymic organoid," Blood 102(11): 279a, Nov. 16, 16 Nov. 2003 (2 pages).
Van de Wetering et al., "Prospective Derivation of a Living Organoid Biobank of Colorectal Cancer Patients," Cell, 161, May 7, 2015, pp. 933-945 (14 pages).
Schuler et al., "Efficient Temporally Controlled Targeted Somatic Mutagenesis in Hepatocytes of the Mouse," 2004 Genesis 39: 167-172 (6 pages).
Sekiya & Suzuki, "Direct conversion of mouse fibroblasts to hepatocyte-like cells by defined factors," Jul. 21, 2011, Nature, vol. 475: 390-395 (6 pages).
Sekiya & Suzuki, "Hepatocytes, Rather than Cholangiocytes, Can Be the Major Source of Primitive Ductules in the Chronically Injured Mouse Liver," The American Journal of Pathology, May 2014, 184(5): 1468-1478 (11 pages).
Sell et al., "Hepatocyte Proliferation and α1,-Fetoprotein in Pregnant, Neonatal, and Partially Hepatectomized Rats," Apr. 1974, Cancer Res 34: 865-871 (8 pages).
Si-Tayeb et al., "Highly Efficient Generation of Human Hepatocyte—Like Cells from Induced Pluripotent Stem Cells," 2010, Hepatology 51(1): 297-305 (9 pages).
Stanger, B., "Cellular Homeostasis and Repair in the Mammalian Liver," 2015, Annu Rev Physiol 77: 179-200 (25 pages).
Sun et al., "The Progress on the Differentiation of the Stem Cells into Hepatocytes," Medical Recapitulate, vol. 16, No. 9, May 2010 (3 pages).
Swenson, E., "Direct Conversion of Mouse Fibroblasts to Hepatocyte-Like Cells Using Forced Expression of Endodermal Transcription Factors," 2012 Hepatology 55(1): 316-318 (9 pages).
Tanimizu et al., "Sry HMG Box Protein 9-positive (Sox9+) Epithelial Cell Adhesion Molecule-negative (EpCAM-) Biphenotypic Cells Derived from Hepatocytes Are Involved in Mouse Liver Regeneration," J Biol Chem, 289(11): 7589-7598 (12 pages).
Tarlow et al., "Bipotential Adult Liver Progenitors Are Derived from Chronically Injured Mature Hepatocytes," Nov. 6, 2014, Cell Stem Cell 15: 605-618 (15 pages).
Van Amerongen et al., "Developmental Stage and Time Dictate the Fate of Wnt/B-Catenin-Responsive Stem Cells in the Mammary Gland," Sep. 7, 2012, Cell Stem Cell 11: 387-400 (14 pages).
Verma et al., "Sustained Telomere Length in Hepatocytes and Cholangiocytes with Increasing Age in Normal Liver," 2012, Hepatology 56: 1510-1520 (11 pages).
Wang et al., "Self-renewing diploid Axin21 cells fuel homeostatic renewal of the liver," Aug. 13, 2015, Nature, 524: 180-185 (18 pages).
Yanger et al., "Adult Hepatocytes Are Generated by Self-Duplication Rather than Stem Cell Differentiation," Sep. 4, 2014, Cell Stem Cell 15: 340-349 (10 pages).
Yanger et al., "Robust cellular reprogramming occurs spontaneously during liver regeneration," 2013, Genes Dev 27: 719-724 (8 pages).
Yimlamai et al., "Hippo Pathway Activity Influences Liver Cell Fate," Jun. 5, 2014, Cell, 157(6): 1324-1338 (23 pages).
Yokoyama et al., "Regeneration of Mouse Liver after Partial Hepatectomy," 1953 Cancer Res 13: 80-85 (7 pages).
Zhu et al., "Mouse liver repopulation with hepatocytes generated from human fibroblasts," Apr. 3, 2014, Nature 508 (7494): 93-97 (34 pages).
Chong et al., "The quest to overcome resistance to EGFR-targeted therapies in cancer," Nat Med. Nov. 2013 ; 19 (11): 1389-1400 (28 pages).
Combined Search and Examination Report issued in GB Application No. GB1819224.5, dated May 29, 2019 (9 pages).
Barker et al., "Lgr proteins in epithelial stem cell biology," 2013, Development 140: 2484-2494 (11 pages).
Zhu and Ding, "Study on a 3D Hydrogel-Based Culture Model for Characterizing Growth of Fibroblasts under Viral Infection and Drug Treatment," SLAS Discovery 2017, 22(5): 626-634 (9 pages).
Zolk et al., "Transporter Gene Expression in Human Head and Neck Squamous Cell Carcinoma and Associated Epigenetic Regulatory Mechanisms," Am J Pathol. Jan. 2013; 182(1):234-43 (10 pages).
Aini et al., "Accelerated telomere reduction and hepatocyte senescence in tolerated human liver allografts," Transplant Immunology (2014), 31(2): 55-59 (28 pages).
Bahar et al., "Single-cell spatial reconstruction reveals global division of labor in the mammalian liver," Nature. Feb. 16, 2017; 542(7641): 352-356. doi:10.1038/nature21065 (29 pages).
Bartfeld et al., "In Vitro Expansion of Human Gastric Epithelial Stem Cells and Their Responses to Bacterial Infection," Gastroenterology. Jan. 2015; 148(1): 126-136.e6. doi:10.1053/j.gastro.2014.09.042 (22 pages).
Billerbeck et al., Humanized mice efficiently engrafted with fetal hepatoblasts and syngeneic immune cells develop human monocytes and NK cells, J Hepatol. Aug. 2016; 65(2): 334-343. doi:10.1016/j.jhep.2016.04.022 (20 pages).
Broutier et al., "Culture and establishment of self-renewing human and mouse adult liver and pancreas 3D organoids and their genetic manipulation," Nat Protoc 2016, 11(9): 1724-1743 (20 pages).

(56) References Cited

OTHER PUBLICATIONS

Broutier et al., "Human Primary Liver Cancer-derived Organoid Cultures for disease modelling and drug screening," Nat Med. Dec. 23, 2017(12): 1424-1435 (35 pages).
Burke et al., "Liver Zonation Occurs Through a—Catenin-Dependent, c-Myc—Independent Mechanism," Gastroenterology, 2009; 136: 2316-2324 (12 pages).
De La Coste et al., "Somatic mutations of the β-catenin gene are frequent in mouse and human hepatocellular carcinomas," Proc. Natl. Acad. Sci. USA, 95: 8847-8851, Jul. 1998 (5 pages).
Dollé et al., EpCAM and the biology of hepatic stem/progenitor cells, 2015 Am J Physiol Gastrointest Liver Physiol 308: G233-250 (18 pages).
Duncan et al., "The ploidy-conveyor of mature hepatocytes as a source of genetic variation," Nature. Oct. 7, 2010; 467(7316): 707-710 (14 pages).
Engelhardt et al., "Detection of α-foetoprotein in mouse liver differentiated hepatocytes before their progression through S phase," 1976 Nature 263: 146-148.
Evarts et al., "A precursor—product relationship exists between oval cells and hepatocytes in rat liver," Carcinogenesis 8(11): 1737-1740, 1987 (4 pages).
Fan et al. "Cholangiocarcinomas can originate from hepatocytes in mice," J Clin Invest, Aug. 2012, 122(8): 2911-2915 (5 pages).
Font-Burgada et al., "Hybrid Periportal Hepatocytes Regenerate the Injured Liver without Giving Rise to Cancer," 2015 Cell 162: 766-779 (15 pages).
Furuyama et al., Continuous cell supply from a Sox9-expressing progenitor zone in adult liver, exocrine pancreas and intestine 2011 Nat Genet 43: 34-41 (11 pages).
Greene et al., "Partial Hepatectomy in the Mouse: Technique and Perioperative Management," 2003 J Invest Surg 16: 99-102 (4 pages).
Grompe, M., "Liver Stem Cells, Where Art Thou?," Cell Stem Cell 15: 257-258, 2014 (2 pages).
Grompe, M. "Fah Knockout Animals as Models for Therapeutic Liver Repopulation," Hereditary Tyrosinemia, Advances in Experimental Medicine and Biology, 2017, 959: 215-230 (16 pages).
Hashimshony et al., "CEL-Seq2: sensitive highly-multiplexed single-cell RNA-Seq," Genome Biol 17: 77, 2016 (7 pages).
Hu et al., "Direct Conversion of Normal and Alzheimer's Disease Human Fibroblasts into Neuronal Cells by Small Molecules," Cell Stem Cell 17: 204-212, Aug. 6, 2015 (36 pages).
Huang et al., "Direct Reprogramming of Human Fibroblasts to Functional and Expandable Hepatocytes," Cell Stem Cell 14: 370-384, Mar. 6, 2014 (15 pages).
Huang et al., "Induction of functional hepatocyte-like cells from mouse fibroblasts by defined factors," Nature, Jul. 21, 2011, 475: 386-389 (7 pages).
Huch & Clevers, "Sox9 marks adult organ progenitors," Nature Genetics, Jan. 11, 2011, 43(1): 9-10 (3 pages).
Huch et al., In vitro expansion of single Lgr51 liver stem cells induced by Wnt-driven regeneration 2013 Nature 494: 247-250 (7 pages).
Tuch et al., Long-Term Culture of Genome-Stable Bipotent Stem Cells from Adult Human Liver, (2015) Cell 160: 299-312 (24 pages).
International Preliminary Report on Patentability of International Application No. PCT/EP2019/082618, dated Jun. 10, 2021 (13 pages).
International Search Report and Written Opinion of International Application No. PCT/EP2019/082618, dated Feb. 11, 2020 (15 pages).
Kamiya et a., "Oncostatin M and hepatocyte growth factor induce hepatic maturation via distinct signaling pathways," FEBS Letters 2001, 492: 90-94 (5 pages).
Katsuda et al., Conversion of Terminally Committed Hepatocytes to Culturable Bipotent Progenitor Cells with Regenerative Capacity, Cell Stem Cell 20: 41-55, Jan. 5, 2017 (16 pages).
Ke et al. "Down-regulation of Wnt signaling could promote bone marrow derived mesenchymal stem cells to differentiate into hepatocytes," BBRC, Jan. 2, 2008, 36: 342-348 (7 pages).
Khetani et al., "Microscale culture of human liver cells for drug development," Nat Biotechnol 26(1): 120-126 (20 pages).
Levy et al., "Long-term culture and expansion of primary human hepatocytes," 2015 Nat Biotechnol 33: 1264-1271 (10 pages).
Li et al., "Adult Mouse Liver Contains Two Distinct Populations of Cholangiocytes," Stem Cell Reports, 9: 478-489, Aug. 8, 2017 (12 pages).
Li et al., "Hepatoblast-Like Progenitor Cells Derived From Embryonic Stem Cells Can Repopulate Livers of Mice," Gastroenterology 139: 2158-2169 e2158 2010 (20 pages).
Li et al., "Isolation and Culture of Adult Mouse Hepatocytes," Methods Mol Biol, 633: 185-196 2010 (12 pages).
Liang et al., "Genetic and Epigenetic Variations in iPSCs: Potential Causes and Implications for Application," Cell Stem Cell 13: 149-159, Aug. 1, 2013 (11 pages).
Lin et al., "Distributed hepatocytes expressing telomerase repopulate the liver in homeostasis and injury," Nature 556: 244-248, Apr. 12, 2018 (7 pages).
Liu et al., "Osteopontin Promotes Hepatic Progenitor Cell Expansion and Tumorigenicity via Activation of β-Catenin in Mice," 2015 Stem Cells 33: 3569-3580 (12 pages).
Love et al., "Moderated estimation of fold change and dispersion for RNA-seq data with DESeq2," Genome Biology, 15: 550, 2014 (21 pages).
Lund et al., "Genetic and epigenetic stability of human pluripotent stem cells," 2012, Nat Rev Genet 13: 732-744 (14 pages).
Malato et al., "Fate tracing of mature hepatocytes in mouse liver homeostasis and regeneration," Dec. 2011, J Clin Invest, 121(12): 4850-4860 (11 pages).
Marquardt et al., "Functional and genetic deconstruction of the cellular origin in liver cancer," Nov. 2015, J Nat Rev Cancer 15: 653-667 (15 pages).
Michalopoulos, G., "Liver Regeneration after Partial Hepatectomy," Jan. 2010, Am J Pathol 176(1): 2-13 (13 pages).
Miyajima et al., "Stem/Progenitor Cells in Liver Development, Homeostasis, Regeneration, and Reprogramming," May 1, 2014, Cell Stem Cell 14: 561-574 (14 pages).
Nakamura et al., "Molecular cloning and expression of human hepatocyte growth factor," Nov. 23, 1989, Nature 342: 440-443 (4 pages).
Nault et al., "High frequency of telomerase reverse-transcriptase promoter somatic mutations in hepatocellular carcinoma and preneoplastic lesions," Jul. 26, 2013, Nature Communications, 4: 221 (7 pages).
Planas-Paz et al., "The RSPO—LGR4/5-ZNRF3/RNF43 module controls liver zonation and size," 2016, Nat Cell Biol 18: 467-479 (22 pages).
Raven et al., "Cholangiocytes act as Facultative Liver Stem Cells during Impaired Hepatocyte Regeneration," Nature. Jul. 20, 2017; 547(7663): 350-354 (35 pages).
Sachs et al., "A Living Biobank of Breast Cancer Organoids Captures Disease Heterogenity," Cell 172: 373-386 (Jan. 11, 2018).
Schaub et al., "Evidence against a Stem Cell Origin of New Hepatocytes in a Common Mouse Model of Chronic Liver Injury," Aug. 21, 2014, Cell Rep 8: 933-939 (8 pages).
International Search Report and Written Opinion for International Application No. PCT/EP2015/060815, dated Jul. 28, 2015 (15 pages).
International Search Report and Written Opinion for International Application No. PCT/EP2015/077988, dated Apr. 20, 2016 (13 pages).
International Search Report and Written Opinion for International Application No. PCT/EP2015/077990, datd Jul. 6, 2016 (17 pages).
International Search Report and Written Opinion of International Application No. PCT/EP2017/054797, dated May 31, 2017 (9 pages).
International Search Report and Written Opinion of International Application No. PCT/EP2017/065101, dated Oct. 6, 2017 (13 pages).

(56) References Cited

OTHER PUBLICATIONS

Janssen, and Depoortere, "Nutrient sensing in the gut: new roads to therapeutics? Trends in endocrinology and metabolism," 24, p. 92-100 (2013).
Jeong et al., "Neuregulin-1 induces cancer stem cell characteristics in breast cancer cell lines," Oncology Reports 32 (2014), pp. 1218-1224.
Kan et al., "MPp53-mediated growth suppression in response to Nutlin-3 in cyclin D1 transformed," Cancer Research (Nov. 2007) 9 pages.
Kemp et al., "The Roles of Wnt Signaling in Early Mouse Development and Embryonic Stem Cells", Functional Development and Embryology, 2007, pp. 1-13.
Kim et al., "Mitogenic Influence of Human R-Spondin1 on the Intestinal Epithelium" Science (309), Aug. 19, 2005, pp. 1256-1259.
Kirikoshi et al., "WNT10A and WNT6, Clustered in Human Chromosome 2q35 Region with Head-to-Tail Manner, Are Strongly Coexpressed in SW480 Cells," Biochemical and Biophysical Research Communications 283, (2001), pp. 798-805.
Kogata et al., Neuregulin 3 and Erbb Signalling Networks in Embryonic Mammary Gland Development, J Mammary Gland Biology Neoplasia (2013) 18: pp. 149-154.
Koo et al., "Stem Cells Marked by the R-Spondin Receptor LGR5," Gastroenterology 2014; 147:289-302.
Korinek et al., "Activation of ??-Catenin-Tcf Signalling in Colon Cancer by Mutation in ??-Catenin or APC," Science (Apr. 1997), 5 pages.
Korinek et al.,"Constitutive Transcriptional Activation by a β-Catenin-Tcf Complex in APC_/_Colon Carcinoma," (1997) Science 275:1784-1787.
Latorre et al., "Enteroendocrine Cells: A Review of Their Role In Brain-Gut Communication," Neurogastroenterol Motil. May 2016 ; 28(5): 620-630.
Lee et al., "Lung stem cell differentiation in mice directed by endothelial cells via a BMP4-NFATc1-Thrombospondin-1 axis," Cell. Jan. 30, 2014; 156(3): 440-455.
Lee et al., "Neuregulin Autocrine Signaling Promotes Self-Renewal of Breast Tumor-Initiating Cells by Triggering HER2/HER3 Activation," Tumor and Stem Cell Biology Cancer Research 74(1):341-52 (2014).
Lemaigre et al., "Mechanisms of Liver Development: Concepts for Understanding Liver Disorders and Design of Novel Therapies", Gastroenterology (137)(1), Jul. 1, 2009, pp. 62-79.
Little et al., "Engineering Biomaterials for Synthetic Neural Stem Cell Microenvironments," (2008) Chem. Rev 108, 1787-1796.
Macchiarini et al., "Clinical Transplantation of a Tissue-Engineered Airway," The Lancet (Nov. 19, 2008) 8 pages.
Malorni et al., "The antioxidant N-acetyl-cysteine protects cultured epithelial cells from menadione-induced cytopathology", Chemico-Biological Interactions (96), 1995, pp. 113-123.
Manandhar et al., "Glucagon-like Peptide-1 (GLP-1) Analogs: Recent Advances, New Possibilities, and Therapeutic Implications," J. Med. Chem. 2015, 58, 1020-1037.
Martin-Belmonte et al., "Cell-Polarity Dynamics Controls the Mechanism of Lumen Formation in Epithelial Morphogenesis", Current Biology (18), 2008, pp. 507-513.
McEwen et al., "Regulation of the Fibroblast Growth Factor Receptor 3 Promoter and Introm I Enhancer by Sp1 Family Transcription Factors," The Journal of Biological Chemistry, vol. 273, No. 9, pp. 5349-5357 (Feb. 27, 1998).
MediLexicon Dictionary, http://www.medilexicon.com/medicaldictionary.php?t=63274 , "Organoid", 2006, p. 1.
Mitaka, Toshihiro, "Reconstruction of hepatic organoid by hepatic stem cells", J. Hepatobiliary Pancreat Sug (9)(6), Jan. 1, 2002, pp. 697-703.
Morin et al., "Activation of β-Catenin-Tcf-Signaling in Colon Cancer by Mutations in β-Catenin or APC," Science, vol. 275, pp. 1787-1790, Mar. 21, 1997.
Munoz et al., "The Lgr5 intestinal stem cell signature: robust expression of proposed quiescent '+4' cell markers," The EMBO Journal (2012) 31, 3079-3091.
Naftalin et al., "Progesterone stimulation of fluid absorption by the rat uterine gland", Reproduction (123) 2002, pp. 633-638.
Nakamura et al., "Anti-patched-1 Antibodies Suppress Hedgehog Signaling Pathway and Pancreatic Cancer Proliferation," Anticancer Research 27: 3743-3748 (2007).
Nakamura et al.,"Crosstalk between Wnt and Notch signaling in intestinal epithelial cell fate decision," Journal of Gastroenterology, 2007, vol. 42, No. 9, p. 705.
Nakanishi et al., "Dclk1 distinguishes between tumor and normal stem cells in the intestine," 45:1 p. 98-105 (Jan. 2013).
Namkung et al., "Small-molecule activators of TMEM16A, a calcium-activated chloride channel, stimulate epithelial chloride secretion and instestinal constraction," The FASEB Journal (Nov. 25, 2011) 18 pages.
Oeztuerk-Winder et al., "Regulation of Human Lung Alveolar Multipotent Cells by a Novel p38a MAPK/miR-17-92 axis," The EMBO Journal 31, (2012) pp. 3431-3441.
Ornitz et al., "Regulation of the Fibroblast Growth Factor Receptor 3 Promoter and Intron I Enhancer by Sp1 Family Transcription Factors," The Journal of Biological Chemistry, vol. 273, No. 9 (Feb. 27, 1998), pp. 5349-5357.
Pasic et al., "Sustained activation of the HER1-ERK1/2-RSK signaling pathway controls myoepithelial cell fate in human mammary tissue," Genes & Development 25 (2011) pp. 1641-1653.
Peterson et al., "Interaction with basement membrane serves to rapidly distinguish growth and differentiation pattern of normal and malignant human breast epithelial cells," Proc. Natl. Acad. Sci. (89), Oct. 1992, pp. 9064-9068.
Pin et al., "Modelling the Spatio-Temporal Cell Dynamics Reveals Novel Insights on Cell Differentiation and Proliferation in the Small Intestinal Crypt," PLoS One, PLoS One 7(5): e37115, 14 pages (May 2012).
Robinton et al., "The promise of induced pluripotent stem cells in research and therapy," NIH Public Access Nature 481, (May 13, 2013); 24 pages.
Saha et al., "Designing synthetic materials to control stem cell phenotype," (2007) Curr Opin Chem Biol. 11(4): 381-387.
Saha et al., "Substrate Modulus Directs Neural Stem Cell Behavior," (2008) Biophysical Journal 95: 4426-4438.
Sangiorgi and Capechhi, "Bmi1 is expressed in vivo in intestinal stem cells," Nat Genet. Jul. 2008 ; 40(7): 915-920.
Sarkozi et al., "Oncostatin M is a novel inhibitor of TGF-B1-induced matricellular protein expression," Am J Physiol Renal Physiol (301), 2011, pp. F1014-F1025.
Sato et al. "Single Lgr5 stem cells build crypt villus structures in vitro without a mesenchymal niche," Nature, vol. 459, May 14, 2009, pp. 262-265.
Sato et al., "Long-term Expansion of Epithelial Organoids From Human Colon, Adenoma, Adenocarcinoma, and Barrett's Epithelium," Gastroenterology, vol. 14, pp. 1762-1772 (2011).
Sato et al., "Paneth cells constitute the niche for Lgr5 stem cells in intestinal crypts," Nature. Jan. 20, 2011; 469 (7330): 415-418.
Semler et al., "Mechanochemical Manipulation of hepatocyte Aggregation Can Selectively Induce or Repress Liver-Specific Function", Biotechnology and Bioengineering (69)(4), Sep. 1999, pp. 359-369.
Shibue et al., "Fatty acid-binding protein 5 regulates diet-induced obesity via GIP secretion from enteroendocrine K cells in response to fat ingestion," Am J Physiol Endocrinol Metab 308: E583-E591, 2015.
Smith et al., "Comparison of Biosequences," Advances in Applied Mathematics 2, (1981), pp. 482-489.
Kohno et al., "Effects of hyaluronidase on doxorubicin penetration into squamous carcinoma multicellular tumor spheroids and its cell lethality," J Cancer Res Clin Oncol. 1994; 120(5):293-7 (6 pages).
Koo et al., "Controlled gene expression in primary Lgr5 organoid cultures," Nat Methods. 2012, 9(1): 81-84 (4 pages).
Kramer et al., "Small-Molecule Inhibitors of GSK-3: Structural Insights and Their Application to Alzheimer's Disease Models," International Journal of Alzheimer's Disease, vol. 2012, Article ID 381029, 32 pages.

(56) References Cited

OTHER PUBLICATIONS

Kross et al., "Co-culture of Head and Neck Squamous Cell Carcinoma Spheroids with Autologous Monocytes Predicts Prognosis," Scand J Immunol. 2008; 67(4):392-9 (8 pages).
Laban et al., "Sorafenib sensitizes head and neck squamous cell carcinoma cells to ionizing radiation," Radiotherpy and Oncology, 2013, 109(2);286-292 (7 pages).
Lau et al., "The R-spondin protein family," Genome Biol. 2012; 13(3):242, 2012 (10 pages).
Leemans et al., "The molecular landscape of head and neck cancer," May 2018, Nat. Rev. Cancer, 18(5): 269-282 (14 pages).
Lengauer et al., "Genetic instability in colorectal cancers," Nature. Apr. 10, 1997; 386: 623-627 (5 pages).
Li and Durbin, "Fast and accurate long-read alignment with Burrows—Wheeler transform," Bioinformatics. 2010, 26(5): 589-595 (7 pages).
Li et al., "Conformational equilibria and intrinsic affinities define integrin activation," (2017) EMBO 36:629-645 (17 pages).
Luque et al., "Activated Conformations of Very Late Activation Integrins Detected by a Group of Antibodies (HUTS) Specific for a Novel RegulatoryRegion (355-425) of the Common $\beta 1$ Chain," (1996) J. Bio Chem. 271(19): 11067-11075 (9 pages).
Machiels et al., "Activity and safety of afatinib in a window preoperative EORTC study in patients with squamous cell carcinoma of the head and neck (SCCHN)," Annals of Oncology 2018; 29: 985-991 (7 pages).
Machiels et al., "Afatinib versus methotrexate as second-line treatment in patients with recurrent or metastatic squamous-cell carcinoma of the head and neck progressing on or after platinum-based therapy (LUX-Head & Neck 1): an open-label, randomised phase 3 trial, " Lancet Oncol. 2015; 16:583-594 (13 pages).
Martin et al., "Modeling antibody hypervariable loops: A combined algorithm," Proc. Natl. Acad. Sci. USA, 86: 9268-9272, Dec. 1989 (5 pages).
Maushagen et al.,"Effects of paclitaxel on permanent head and neck squamous cell carcinoma cell lines and identification of anti-apoptotic caspase 9b," J Cancer Res Clin Oncol. 2016; 142(6):1261-71.
Mayer et al., "A Phase Ib Study of Alpelisib (BYL719),a PI3K$\alpha$-Specific Inhibitor, with Letrozole in ER+/HER2-Metastatic Breast Cancer," Metastatic Breast Cancer, Clin Cancer Res. Jan. 1, 2017, 23(1): 26-34 (10 pages).
Meng et al., "Characterization of integrin engagement during defined human embryonic stem cell culture," (2010) The FASEB Journal, 24(4): 1056-1065 (17 pages).
Méry et al., "Preclinical models in HNSCC: A comprehensive review," Oral Oncol. 2017, 65: 51-56 (6 pages).
Monnet et al., "Selection of IgG variants with increased FcRn binding using random and directed mutagenesis: impact on effector functions," Frontiers in Immunology, vol. 6, Article 39, Feb. 2015 (15 pages).
Munster et al., "Abstract A46: Inhibition of PIK3CA with BYL719 canovercome resistance to cetuximab in squamous cellcarcinoma of the head and neck (SCCHN)," Mol Cancer Ther. Jul. 2015; vol. 14, Issue 7 Supplement (4 pages).
Perez et al., "Comparative cytotoxicity of Cl-973, cisplatin, carboplatin and tetraplatin in human ovarian carcinoma cell lines," Int J Cancer. 1991; 48:265-269 (5 pages).
Pokharel et al., "Integrin activation by the lipid molecule 25-hydroxycholesterol induces a proinflammatory response," Nature Communications, (2019) 10:1482 (17 pages).
Polychronopoulos et al., Structural Basis for the Synthesis of Indirubins as Potent and Selective Inhibitors of Glycogen Synthase Kinase-3 and Cyclin-Dependent Kinases, (2004) J Med Chem 47: 935-946 (12 pages).
Pyeon et al., "Production of infectious human papillomavirus independently of viral replication and epithelial cell differentiation," Proc Natl Acad Sci. 2005; 102(26):9311-9316 (6 pages).
Reed, "Plantinum-DNA adduct, nucleotide excision repair and platinum based anti-cancer chemotherapy," Cancer Treat. Rev. 1998. pp. 331-344 (14 pages).

Sachs et al., "Long-term expanding human airway organoids for disease modeling," The EMBO Journal (2019) 38: e100300 (20 pages).
Sayers and Elliott, Herpes Simplex Virus 1 Enters Human Keratinocytes by a Nectin-1-Dependent, Rapid Plasma Membrane Fusion Pathway That Functions at Low Temperature J Virol. 2016; 90(22):10379-10389 (11 pages).
Schrader et al., "Kallikrein-related peptidase 6 regulates epithelial-to-mesenchymal transition and serves as prognostic biomarker for head and neck squamous cell carcinoma patients," Mol Cancer. 2015; 14:107 (14 pages).
Shah et al., "Metabolic Imaging of Head and Neck Cancer Organoids," PLoS One, 2017, 12(1):e0170415 (17 pages).
Shaner et al., "A bright monomeric green fluorescent protein derived from Branchiostoma lanceolatum," Nat Methods. 2013; 10(5): 407-414 (8 pages).
Shattil et al., "The final steps of integrin activation: the end game," (Apr. 2010) Nature reviews, 11: 288-300 (13 pages).
Shimizu et al., "Identification of a novel therapeutic target for head and neck squamous cell carcinomas: A role for the heurotensin-neurotensin receptor 1 oncogenic signaling pathway," Int J Cancer. 2008; 123(8):1816-1823 (8 pages).
Simmini S et al., "Transformation of intestinal stem cells into gastric stem cells on loss of transcription factor Cdx2," Nat Commun. 2014; 5:5728 (10 pages).
Smith et al., "Animal models for the study of squamous cell carcinoma of the upperaerodigestive tract: A historical perspective with review of their utility and limitations. Part A. Chemically-induced de novo cancer, syngeneic animal models of HNSCC, animal models of transplanted xenogeneic human tumors, " Int. J. Cancer. 2006, 118(9):2111-22 (12 pages).
Smits et al., "Immortalized N/TERT keratinocytes as an alternative cell source in 3D human epidermal models," Sci Rep. 2017; 7(1):11838 (14 pages).
Soulières D et al., "Buparlisib and paclitaxel in patients with platinum-pretreated recurrent or metastatic squamous cell carcinoma of the head and neck (BERIL-1): a randomised, double-blind, placebo-controlled phase 2 trial," Lancet Oncol. Mar. 2017, 18: 323-35 (14 pages).
Squier et al., "Biology of Oral Mucosa and Esophagus," J Natl Cancer Inst Monogr. 2001; 29:7-15 (9 pages).
Su et al., "Relating conformation to function in integrin $\alpha 5\beta 1$," PNAS (2016) 113(27): E3872-E3881 (10 pages).
Sun et al., "Integrin activation by talin, kindlin and mechanical forces," Nature Cell Biology, Jan. 2019, 21:25-31 (7 pages).
Tanaka et al., "Head and neck cancer organoids established by modification of the CTOS method can be used to predict in vivo drug sensitivity," Oral Oncology. 2018, 87: 49-57 (9 pages).
The Cancer Genome Atlas Network, "Comprehensive genomic characterization of head and neck squamous cell carcinomas," Nature. Jan. 29, 2015; 517: 576-582 (7 pages).
Tsuchida et al., "Classification of 'activation' antibodies against integrin $\beta 1$ chain," (1997) FEBS Letters 416: 212-21 (5 pages).
Valyi-Nagy T et al., "Herpes Simplex Virus 1 Infection Promotes the Growth of a Subpopulation of Tumor Cells in Three-Dimensional Uveal Melanoma Cultures," J Virol. Oct. 2018; 92(19): e00700-18 (12 pages).
Van Jaarsveld RH et al., "Difference Makers: Chromosomal Instability versus Aneuploidy in Cancer," Trends in cancer. 2(10): 561-571 (11 pages).
Vassilev et al., "In Vivo Activation of the p53 Pathway by Small-Molecule Antagonist of MDM2," Science. 2004; 303 (5659):844-848 (7 pages).
Vlachogiannis et al., "Patient-derived organoids model treatment response of metastatic gastrointestinal cancers," Science. Feb. 23, 2018; 359(6378): 920-926 (17 pages).
Voskoglou-Nomikos et al., "Clinical Predictive Value of the in Vitro Cell Line, Human Xenograft, and Mouse Allograft Preclinical," Cancer Models1Clin Cancer Res. 2003, 9(11):4227-39 (14 pages).
Yan et al., "Expression profile analysis of head and neck squamous cell carcinomas using data from The Cancer Genome Atlas," Mol Med Rep. 2016; 13(5):4259-4265 (7 pages).

(56) References Cited

OTHER PUBLICATIONS

Yang et al., A Small Molecule Agonist of an Integrin, αLβ2*,S, Yang et al. (2006) Journal of biological chemistry, 281 (49): 37904-37912 (18 pages).
Yu et al., β1-Integrin Orients Epithelial Polarity via Rac1 and Laminin, (Feb. 2005) Molecular Biology of the cell, 16: 433-445 (13 pages).
U.S. Appl. No. 16/310,933, filed Dec. 18, 2018, Johannes Carolus Clevers.
Abud et al., "Growth of intestinal epithelium in organ culture is dependent on EGF signalling" Experimental Cell Research, Academic Press (303), 2005, pp. 252-262.
Afroze et al., "The physiological roles of secretin and its receptor," Ann Transl Med 2013;1(3):29.
Anders and Huber, "Differential expression analysis for sequence count data," Genome Biology 2010, 11:R106.
Barker et al., "Identification of stem cells in small intestine and colon by marker gene Lgr5," Nature, vol. 449,pp. 1003-1008 (Oct. 25, 2007).
Barker et al., "Lgr5+ve Stem Cells Drive Self-Renewal in the Stomach and Build Long-Lived Gastric Units In Vitro," Cell Stem Cell, vol. 6, pp. 25-36 (Jan. 8, 2010).
Bjerknes et al: "Intestinal epithelial stem cells and progenitors" Methods in Enzymology, Academic Press Inc. (419), Jan. 1, 2006, pp. 337-383.
Booth et al.: "Maintenance of functional stem cells in isolated and cultured adult intestinal epithelium" Experimental Cell Research, Academic Press (249), Jun. 15, 1999, pp. 359-366.
Bottenstein et al., "Growth of a rat neuroblastoma cell line in serum-free supplemented medium," Proc. Natl. Acad. Sci. USA, vol. 76, No. 1, pp. 514-517, (Jan. 1979).
Brewer et al., "Optimized Survival of Hippocampal Neurons in B27-Supplemented Neurobasal, a New Serum-Free Medium Combination", Journal of Neuroscience Research 35:567-576 (1993); 11 pages.
Brockbank et al., "Cryopreservation Guide", https://www.thermofisher.co.nz/Uploads/file/Scientific/Applications/Equipment-Furniture/Cryopreservation-Guide. PDF, 2007, pp. 1-30.
Buczacki et al., "Intestinal label-retaining cells are secretory precursors expressing Lgr5," Nature, vol. 495, No. 7493, pp. 65-69, Feb. 27, 2013.
Cambridge Dictionary, definition for "sealed", http://dictionary.cambridge.org/US/dictionary/english/sealed , Sep. 24, 2016, p. 1.
Capaccio et al., "Modern management of obstructive salivary diseases", Acta Otorhinolaryngologica Italica (27), 2007, pp. 161-172.
Carraway et al., "Neuregulin-2, a new ligand of ErbB3/ErbB4-receptor tyrosine kinases," Nature vol. 387; (May 29, 1997); 5 pages.
Cheng et al., "Central and Peripheral Administration of Secretin Inhibits Food Intake in Mice through the Activation of the Melanocortin System," Neuropsychopharmacology (2011) 36, 459-471.
Clotman et al., Control of liver cell fate decision by a gradient of TGFβ signaling modulated by Onecut transcription factors (2005) Genes Dev. 19(16): 1849-54.
Cole et al., "Measuring GSK3 Expression and Activity in Cells," (2008) Methods Mol Biol. 468:45-65.
Crawford et al., "The Notch Response Inhibitor DAPT Enhances Neuronal Differentiation in Embryonic Stem Cell-Derived Embryoid Bodies Independently of Sonic Hedgehog Signaling," Developmental Dynamics (236), 2007, pp. 886-892.
Crosnier et al., "Organizing cell renewal in the intestine: stem cells, signals and combinatorial control", Nature reviews—Genetics (7), May 2006, pp. 349-359.
Cuny et al., "Structure-activity relationship study of bone morphogenetic protein (BMP) signaling inhibitors," Bioorg Med Chem Lett. Aug. 1, 2008; 18(15): 4388-4392.
De Gouville et al., "Inhibition of TGF-B signaling by an ALK5 inhibitor protects rats from dimethylnitrosamine—induced liver fibrosis," British Journal of Pharmacology (2005); 12 pages.

De Lau et al., "Lgr5 homologues associate with Wnt receptors and mediate R-spondin signalling," Nature vol. 476 (Aug. 18, 2011); 6 pages.
De Lau et al., "The R-spondin/Lgr5/Rnf43 module: regulator of Wnt signal strength," Genes and Development, 28:305-316 (2014).
Dekkers et al., "A functional CFTR assay using primary cystic fibrosis intestinal organoids," Nature Medicine vol. 19, No. 7 (Jul. 2013); 10 pages.
Dong et al., "The Epithelial—Mesenchymal Transition Promotes Transdifferentiation of Subcutaneously Implanted Hepatic Oval Cells Into Mesenchymal Tumor Tissue," Stem Cells and Development (18)(9), 2009, pp. 1293-1298.
Dontu et al., "Role of Notch signaling in cell-fate determination of human mammary stem/progenitor cells," Breast Cancer Research, vol. 6, No. 6 (2004); 11 pages.
Dorrell et al., "Surface Markers for the Murine Oval Cell Response" NIH Public Access Hepatology (Oct. 2008) 17 pages.
Eccles, "The epidermal growth factor receptor/Erb-B/HER family in normal and malignant breast biology," International Journal of Developmental Biology, University of the Basque Country Pres., vol. 55, No. 7-9, pp. 685-696 (Jan. 1, 2011).
Eden et al., "GOrilla: a tool for discovery and visualization of enriched GO terms in ranked gene lists," BMC Bioinformatics 2009, 10:48.
Egerod et al., A Major Lineage of Enteroendocrine Cells Coexpress CCK, Secretin, GIP, GLP-1, PYY, and Neurotensin but Not Somatostatin Endocrinology, Dec. 2012, 153(12):5782-5795.
Farin et al., "Basic and Translational-Alimentary Tract," (2012) Gastroenterology 143:1518-1529.
Farin et al., "Visualization of a short-range Wnt gradient in the intestinal stem-cell niche," Nature:340 Feb. 18, 2016 (15 pages).
Fuchs, Ota, "Inhibition of TGF-B Signaling for the Treatment of Tumor Metastatis and Fibrotic Diseases", Bentham Science Publishers Ltd.; (2011); 15 pages.
Gerbal-Chaloin et al., "The WNT/b-Catenin Pathway Is a Transcriptional Regulator of CYP2E1, CYP1A2, and Aryl Hydrocarbon Receptor GeneExpression in Primary Human Hepatocytes," (2014) Molecular Pharmacology 86:624-634.
Ghosh et al., "Activity Assay of Epidermal Growth Factor Receptor Tyrosine Kinase Inhibitors in Triple-Negative Breast Cancer Cells Using Peptide-Conjugated Magnetic Beads," ASSAY and Drug Development Technologies, 11(1):44-51; Jan./Feb. 2011.
Grun et al., "Single-cell messenger RNA sequencing reveals rare intestinal cell types," Nature vol. 525, pp. 251-255 (Sep. 10, 2015).
Gunawardene et al., "Classification and functions of enteroendocrine cells of the lower gastrointestinal tract," Int. J. Exp. Path. (2011), 92, 219-231.
Harada et al., "Rapid formation of hepatic organoid in collagen sponge by rat small hepatocytes and hepatic nonparenchymal cells," Journal of Hepatology (39), (2003) pp. 716-723.
Haramis et al., "De novo crypt formation and juvenile polyposis on BMP inhibition in mouse intestine." Science (303) (5664), Mar. 12, 2004, pp. 1684-1686.
Hashimshony et al., "CEL-Seq: Single-Cell RNA-Seq by Multiplexed Linear Amplification," Cell Reports 2, 666-673, Sep. 27, 2012.
Hayashi et al., "Establishment and characterization of a parietal endoderm-like cell line derived from Engelbreth-Holm-Swarm tumor (EHSPEL), a possible resource for an engineered basement membrane matrix," Science Direct Matrix Biology (2004); 16 pages.
Heuberger et al., "Shp2/MAPK signaling controls goblet/paneth cell fate decisions in the intestine," 111:(9);3472-3477 (2014).
Hofer and Drenchkhahn, "Cytoskeletal markers allowing discrimination between brush cells and other epithelial cells of the gut including enteroendocrine cells," Cell Biol (1996) 105:405-412.
Hou et al., "Pluripotent Stem Cells Induced from Mouse Somatic Cells by Small-Molecule Compounds," Science Express, 10.1126/science. 1239278; 8 pages (Jul. 18, 2013). http://www.sciencemag.org/content/early/recent.
Howitt et al., "Tuft cells, taste-chemosensory cells, orchestrate parasite type 2 immunity in the gut," Science. Mar. 18, 2016; 351(6279): 1329-1333.

(56) References Cited

OTHER PUBLICATIONS

Hsieh et al., "Truncated Mammalian Notch1 Activates CBF1/RBPJk-Repressed Genes by a Mechanism Resembling That of Esptein-Barr Virus EBNA2," Molecular and Cellular Biology, (Mar. 1996). pp. 952-959.
Huch et al., "Urokinase-Type Plasminogen Activator Receptor Transcriptionally Controlled Adenoviruses Eradicate Pancreatic Tumors and Liver Metastasis in Mouse Models," NeoPlasia, vol. 11, No. 6, pp. 518-528 (Jun. 2009).
Huschtscha et al., "Normal human mammary epithelial cells proliferate rapidly in the pressure of elevated levels of the tumor suppressors p53 and p21WAF1/CIP1," Journal of Cell Science, 122, 2989-2995 (2009).
Hynds et al., "The Relevance of Human Stem Cell-Derived Organoid Models for Epithelial Translational Medicine," Europe PMC Funders Group Stem Cells (Mar. 2013); 11 pages.
Garashi et al., "Characterization of Recombinant Human Fibroblast Growth Factor (FGF)-10 Reveals Functional Similarities with Keratinocyte Growth Factor (FGF-7)," The Journal of Biological Chemistry, vol. 273, No. 21 (May 1998), pp. 13230-13235.
Blanpain et al., "Epithelial Stem Cells: Turning over New Leaves," Cell, Feb. 9, 2007, 128(3): 445-458 (24 pages).
Chai et al., "Wnt signaling induces proliferation of sensory precursors in the postnatal mouse cochlea," PNAS, May 22, 2012, 109(21):8167-8172 (6 pages).
Gonzalez et al., "Notch Inhibition Prevents Differentiation of Human Limbal Stem/Progenitor Cells in vitro," Scientific Reports (2019) 9:10373 pp. 1-11 (11 pages).
Haegebarth et al., "Wnt Signaling, Lgr5, and Stem Cells in the Intestine and Skin," The American Journal of Pathology, Mar. 2009, 174(3): 715-721 (7 pages).
Wei et al., Abstract: "Wnt Proteins in Intestinal Epithelial Progenitor Cells," R&D Systems, 2015 (1 page).
Kim et al., "Engraftment Potential of Spheroid-Forming Hepatic Endoderm Derived from Human Embryonic Stem Cells," Stem Cells and Development, vol. 22, No. 12, 2013, pp. 1818-1829 (12 pages).
Tostöes et al., "Human Liver Cell Spheroids in Extended Perfusion Bioreactor Culture for Repeated-Dose Drug Testing," Hepatology, vol. 55, No. 4, 2012, pp. 1227-1236 (10 pages).
Santhanam et al., "Upregulated Pathways and Products of Tryptophan Metabolism is Associated with the Neoplastic Transition in the Colon Epithelium," Gastroenterology 2016, 150, 4, suppl 1, p. S-492, Abstract Su1195 (1 page).
Bonner-Weir et al., "The pancreatic ductal epithelium serves as a potential pool of progenitor cells," Pediatric Diabetes, 2004; 5: 16-22 (7 pages).
Rulifson et al., "Wnt signaling regulates pancreatic β cell proliferation," PNAS, Apr. 10, 2007, 104(15): 6247-6252 (6 pages).
Besser et al., "Modifying interleukin—2 concentrations during culture improves function of T cells for adoptive immunotherapy," Cytotherapy (2009) 11(2): 206-217 (12 pages).
Dwyer et al., "A three-dimensional co-culture system to investigate macrophage-dependent tumor cell invasion," Journal of Biological Methods, vol. 3(3), e49, 10 pages (2016).
Neal et al., "Organoid Modeling of the Tumor Immune Microenvironment," Cell. Dec. 13, 2018; 175(7):1972-1988.e16.doi: 10.1016/j.cell.2018.11.021 (34 pages).
U.S. Appl. No. 16/078,354, dated Aug. 21, 2018, Johannes Carolus Clevers.
U.S. Appl. No. 16/310,933, dated Dec. 18, 2018, Johnannes Carolus Clevers.
U.S. Appl. No. 17/915,771, dated Sep. 29, 2022, Joep Beumer.
Beumer et al., "High-Resolution mRNA and Secretome Atlas of Human Enteroendocrine Cells", Cell, May 13, 2020, 181(6): 1291-1306 (40 pages).
Chang-Graham et al., "Human Intestinal Enteroids With Inducible Neurogenin-3 Expression as a Novel Model of Gut Hormone Secretion", Cellular and Molecular Gastroenterology, Sep. 10, 2019, 8(2):209-229 (21 pages).
Sinagoga et al., "Deriving functional human enteroendocrine cells from pluripotent stem cells," Development (2018) 145, dev165795, doi: 10.1242/dev.165795 (11 pages).
International Search Report and Written Opinion of International Application No. PCT/EP2021/058527, dated Aug. 25, 2021 (23 pages).
Gehart et al., "Identification of Enteroendocrine Regulators by Real-Time Single-Cell Differentiation Mapping," Cell 176, 1158-1173, Feb. 21, 2019 (33 pages).
Caporale et al., "Locoregional IL-2 Therapy in the Treatment of Colon Cancer. Cell-induced Lesions of a Murine Model," Anticancer Research 27: 985-990 (2007).
Huch et al., "In vitro expansion of single Lgr5+ liver stem cells induced by Wnt-driven regeneration," 2013 Nature 494: 247-250 and Methods (6 pages).
Seikagaku et al., "Intestinal Epithelial Stem Cells," The Journal of Japanese Biochemical Society, 2013, 85(9):743-748, partial English translation (3 pages).
Vanuytsel et al., "Major Signaling Pathways in Intestinal Stem Cells," Biochim Biophys Acta. Feb. 2013; 1830(2): 2410-2426 (42 pages).
Drakos et al., "Inhibition of p53-Murine Double Minute 2 Interaction by Nutlin-3A Stabilizes p53 and Induces Cell Cycle Arrest and Apoptosis in Hodgkin Lymphoma," Clin Cancer Res, Jun. 1, 2007, 13(11): 3380-3387 (8 pages).
Kucab et al., "Selection of TP53-mutated human TP53 knock-in (Hupki) mouse embryo fibroblasts using the MDM2 inhibitor Nutlin-3a," Mutagenesis, 29(1): 79-96, Abstracts of the 36th Annual Meeting of the United Kingdom Environmental Mutagen Society, Jul. 15-17, 2013 at The University of the West of England, Bristol, UK (18 pages).
Leonard et al., "Screening of Budesonide Nanoformulations for Treatment of Inflammatory Bowel Disease in an Inflamed 3D Cell-Culture Model," Altex, 29(3):275-285, 2012 (11 pages).
Miyachi et al., "Restoration of p53 Pathway by Nutlin-3 Induces Cell Cycle Arrest and Apoptosis in Human Rhabdomyosarcoma Cells," Clin Cancer Res, Jun. 15, 2009, 15(12): 4077-4084 (8 pages).
Noben et al., "Human intestinal epithelium in a dish: Current models for research into gastrointestinal pathophysiology," United European Gastroenterology Journal 2017, 5(8): 1073-1081 (9 pages).
Schmohl et al., "Characterization of immunologically active drugs in a novel organotypic co-culture model of the human gut and whole blood," International Immunopharmacology (2012) 14:722-728 (7 pages).
Vadstrup et al., "Ex Vivo Assay of Intestinal Mucosal Biopsies in Crohn's Disease: Reflects Inflammation and Drug Effects," PLoS One, 11(5):e0155335, May 2016 (18 pages).
Villalonga-Planells et al., "Activation of p53 by Nutlin-3a Induces Apoptosis and Cellular Senescence in Human Glioblastoma Multiforme," PLoS One, Apr. 2011, 6(4):e18588 (12 pages).
Zhao Y, et al., Cancer Research, 101st Annual Meeting of the American Association for Cancer Research, AACR 2010, Washington, DC, United States, Apr. 17, 2010-21, (Apr. 15, 2010) vol. 70, No. 8, Suppl. 1. Abstract No. 4529 (3 pages).
Basak et al., "Induced quiescence of Lgr5+ stem cells in intestinal organoids enables differentiation of hormone-producing enteroendocrine cells," Cell Stem Cell.; 20 (2), 177-190.e4 (2017).
Beumer et al., "Enteroendocrine cells switch hormone expression along the crypt-to-villus BMP signalling gradient," Nature Cell Biology. 20 (8), pp. 909-916 (2018).
Blume et al., "Temperature corrected transepithelial electrical resistance (TEER) measurement to quantify rapid changes in paracellular permeability," Die Pharmazie; 65 (1), pp. 19-24 (2010).
Boj et al., "Forskolin-induced swelling in intestinal organoids: An in vitro assay for assessing drug response in cystic fibrosis patients," Journal of Visualized Experiments, 2017 (120), pp. 1-12 (2017).
De Lau et al., "The R-spondin protein family," Genome Biology. 13:242, 2012 (10 pages).
Dinter et al., "Pharmacologic strategies for assaying BMP signaling function," (2019) Methods Mol Biol; 1891:221-233 (13 pages).

(56) References Cited

OTHER PUBLICATIONS

Grimaldi et al., A Cell Model Suitable for a High-Throughput Screening of Inhibitors of the Wnt/β-catenin pathway, Frontiers in Pharmacology, vol. 9, Article 1160, Oct. 2018 (3 pages).
Gupta et al., "Scaffolding kidney organoids on silk," Tissue Eng Regen Med. May 2019 ; 13(5): 812-822 (20 pages).
Hosic et al., "Cholinergic Activation of Primary Human Derived Intestinal Epithelium Does Not Ameliorate TNF-a Induced Injury," Cellular and Molecular Bioengineering, vol. 13, No. 5, Oct. 2020 ( 2020) pp. 487-505 (19 pages).
International Search Report and Written Opinion of International Application No. PCT/EP2022/069354, dated Nov. 1, 2022, (14 pages).
Martínez-Maqueda, et al., "HT29 Cell Line. in The Impact of Food Bio-Actives on Gut Health: In Vitro and Ex Vivo Models," Verhoeckx, K et al. (eds), Cham 20 (CH): Springer, 113-124 (2015).
Miao, Y. et al. (Next-generation surrogate Wnts support organoid growth and deconvolute Frizzled pleiotropy in vivo. Cell Stem Cell. 27 (5), 840-851 (2020).
Nusse et al., Wnt/β-Catenin Signaling, Disease, and Emerging Therapeutic Modalities, Jun. 1, 2017, Cell 169 (6):985-999.
Romier et al., "New cell-based HTRF® assays for the exploration of Wnt signalling pathway" Cisbio Bioassays, 2015 (1 page).
Sanchez-Duffhues, "Bone morphogenetic protein receptors: Structure, function and targeting by selective small molecule kinase inhibitors," (2020) Bone 138:115472 (13 pages).
Schutgens et al., "Tubuloids derived from human adult kidney and urine for personalized disease modeling," Nature Biotechnology 37: 303-313, (2019).
Singh et al., "Review on EGFR Inhibitors: Critical Updates," (2016) Mini-Reviews in Medicinal Chemistry 16:1134-1166.
Snyder et al., "Materials and Microenvironments for Engineering the Intestinal Epithelium," Ann Biomed Eng., vol. 48, No. 7, Feb. 4, 2020, pp. 1916-1940.
Srinivasan et al., TEER measurement techniques for in vitro barrier model systems. Journal of Laboratory 5 Automation. 20 (2), 107-126 (2015).
Strazzabosco et al., "Functional Anatomy of Normal Bile Ducts," The Anatomical Record, 291:653-660 (2008).
Tran and Zheng, "Modulating the wnt signaling pathway with small molecules," (2017) Protein Science 26:650-661 (12 pages).
Trenker and Jura, "Receptor tyrosine kinase activation: From the ligand perspective," Current Opinion in Cell Biology, 2020, 63:174-185 (12 pages).
Van der Vaart et al., "Modelling of primary ciliary dyskinesia using patient-derived airway organoids," EMBO reports; 2021; 22: e52058 (16 pages).
Van Es et al., "Wnt signalling induces maturation of Paneth cells in intestinal crypts," Nature Cell Biology. 7(4), 381-386 (2005).
Zhao et al., "Organoids," Nature Reviews Methods Primers, (2022) 2:94 (21 pages).
Park et al., "Differential activities and mechanisms of the four R-spondins in potentiating WNT/β-catenin signaling," J. Biol. Chem. (2018) 293(25) 9759-9769 (11 pages).
Lian et al., "Directed cardiomyocyte differentiation from human pluripotent stem cells by modulating Wnt/b-catenin signaling under fully defined conditions," Nature Protocols, vol. 8, No. 1, 2013, pp. 162-175 (14 pages).
Nantasanti et al., "Disease Modeling and Gene Therapy of Copper Storage Disease in Canine Hepatic Organoids," Stem Cell Reports, vol. 5, pp. 895-907, Nov. 10, 2015 (13 pages).
Anonymous, "CP-A31398, which restitutes mutant p53 functions, suppresses the increase of dominant negative p53 gene mutation-dependent cancer cell proliferation and metastasis," Acta Obstetrica et Gynaecologica Japonica, Published by Nihon Sanka Fujinka Gakkai Zasshi, 2006, 58(2):1-88, p. 400 (S-252) (1 page).
Sato et al., "EGFR inhibitors prevent induction of cancer stem like cells in esophageal squamous cell carcinoma by suppressing epithelial-mesenchymal transition," May 28, 2015, Cancer Biology & Therapy, 16(6): 933-940 (9 pages).
Tian et al., "Opposing activities of Notch and Wnt signaling regulate intestinal stem cells and gut homeostasis," Cell Rep. Apr. 7, 2015; 11(1): 33-42 (18 pages).
You et al., "The type III TGF-b receptor signals through both Smad3 and the p38 MAP kinase pathways to contribute to inhibition of cell proliferation," 2007, Carcinogenesis 28(12):2491-2500 (10 pages).

\* cited by examiner

Figure 3
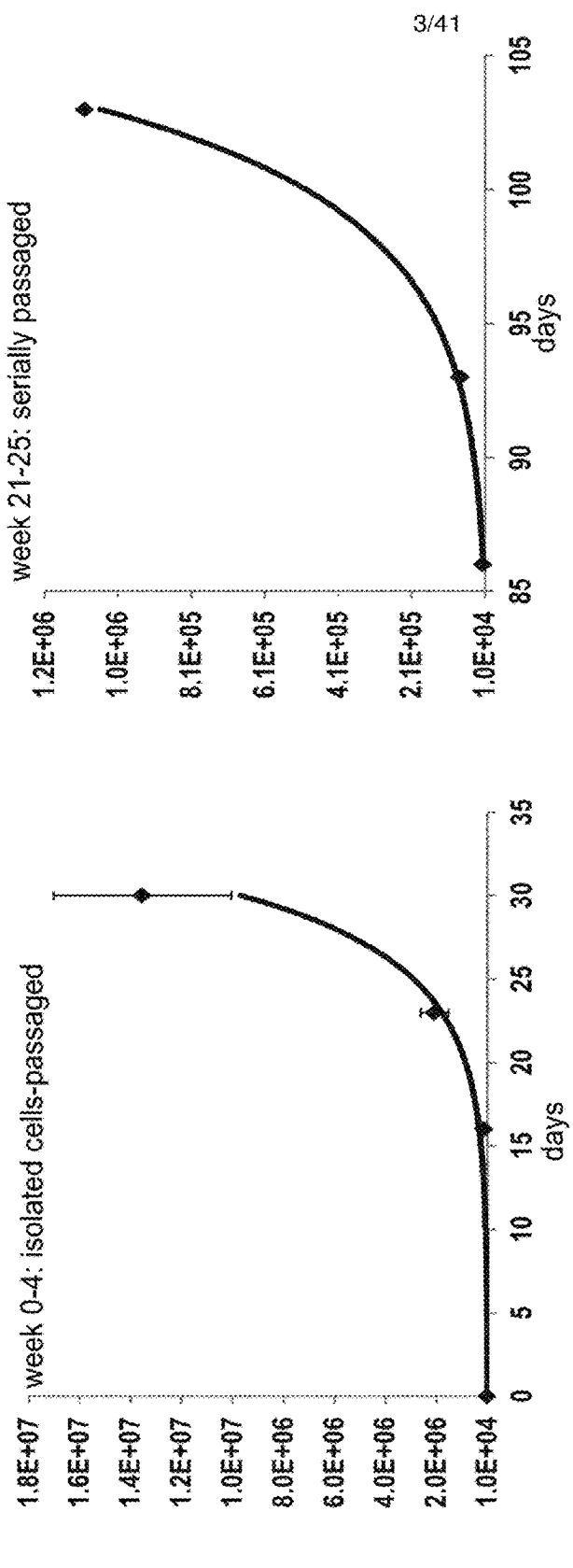
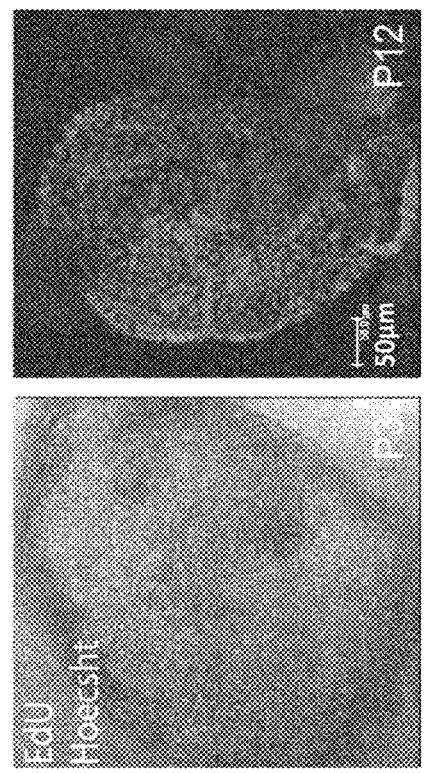
| DOUBLING TIME (H) | MEAN | SEM |
|---|---|---|
| DAY 0-DAY 16 | 100.61 | 2.79 |
| DAY 16 (P1) - DAY 30 (P3) | 52.47 | 3.01 |
| DAY 86 (P10)- DAY 103 (P12) | 57.18 | 0.00 |

Figure 5
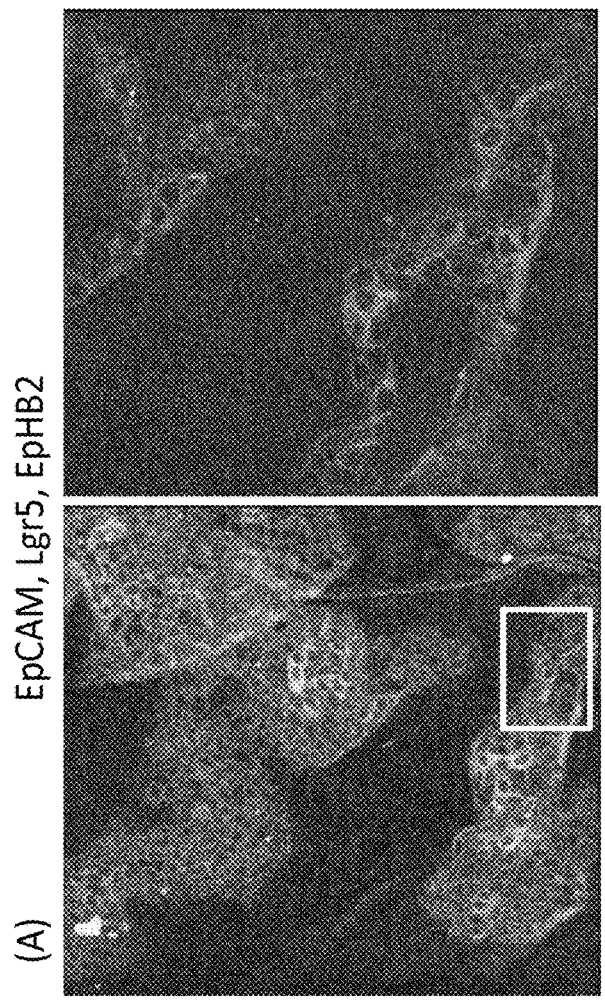
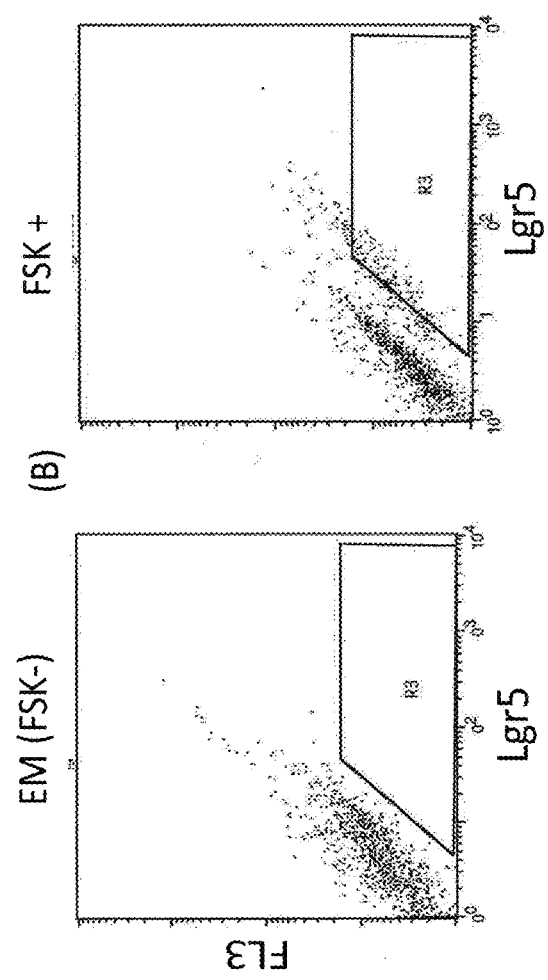

Figure 7
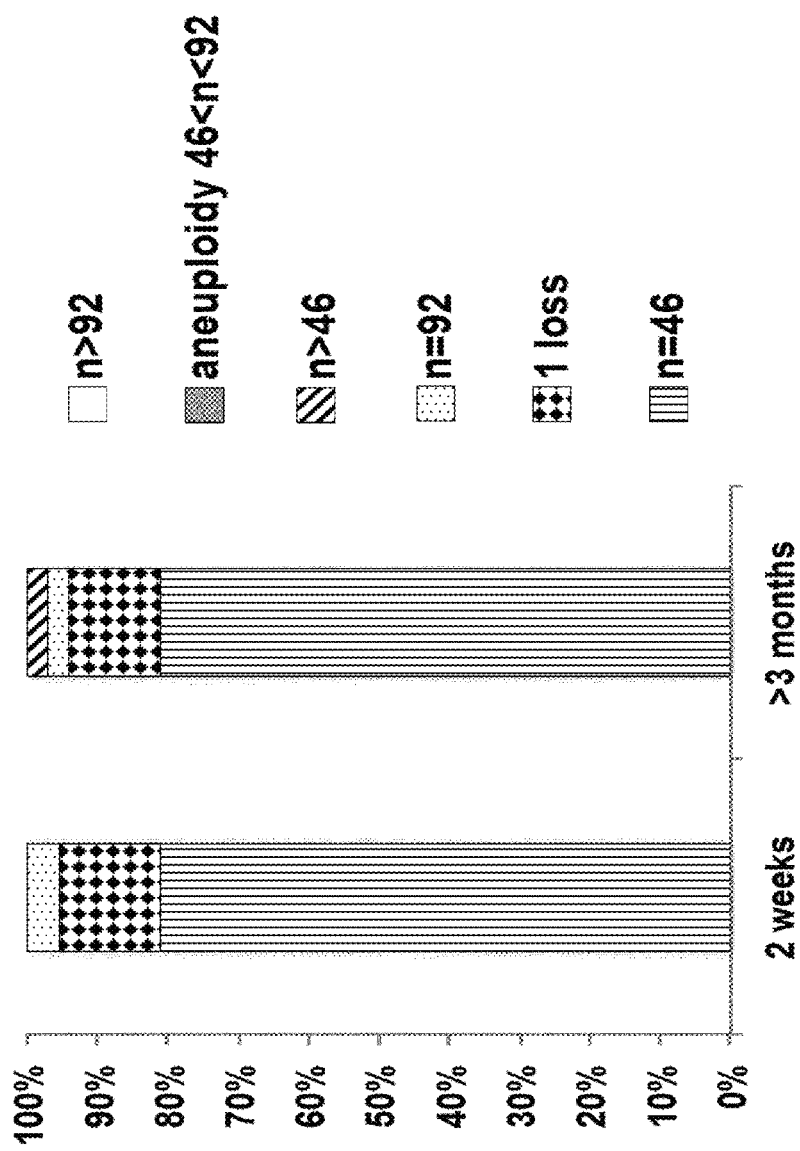
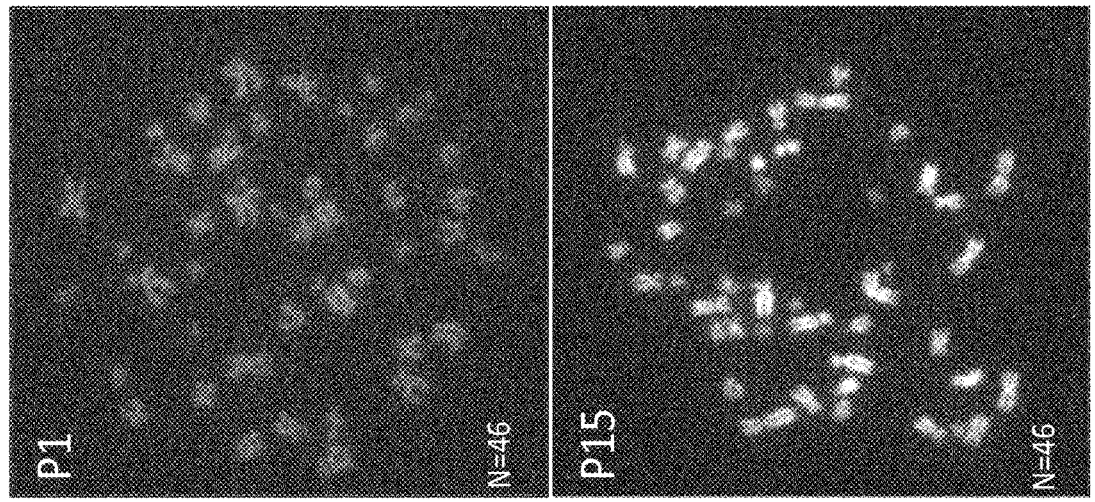

Figure 10
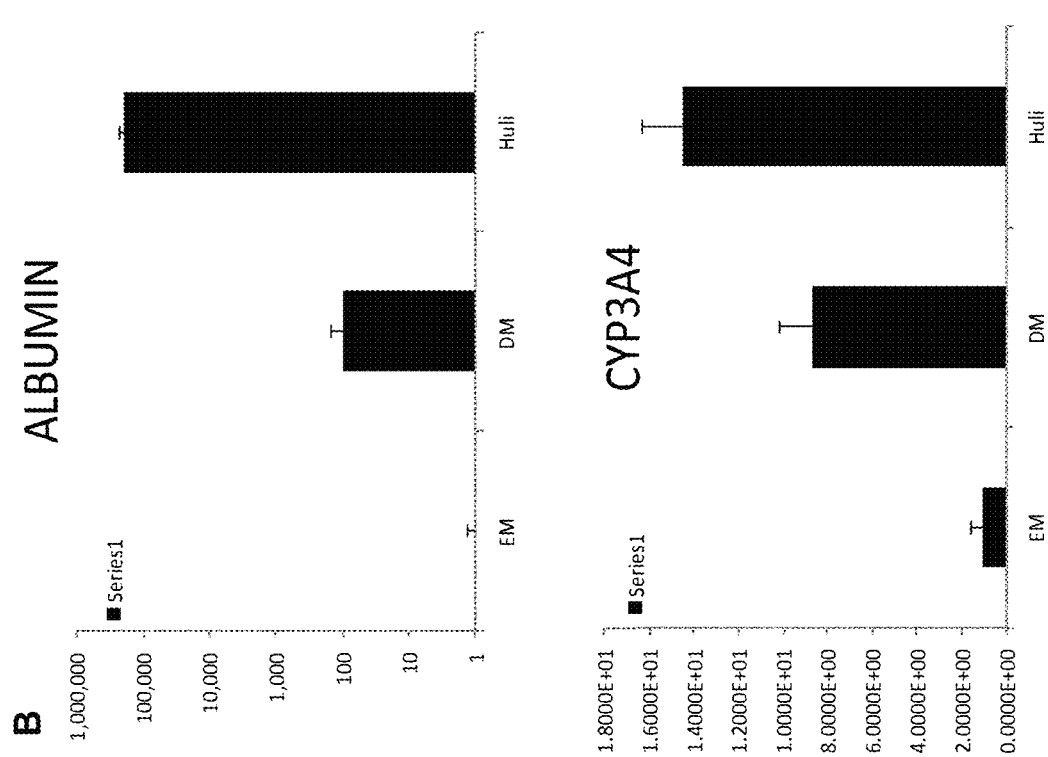
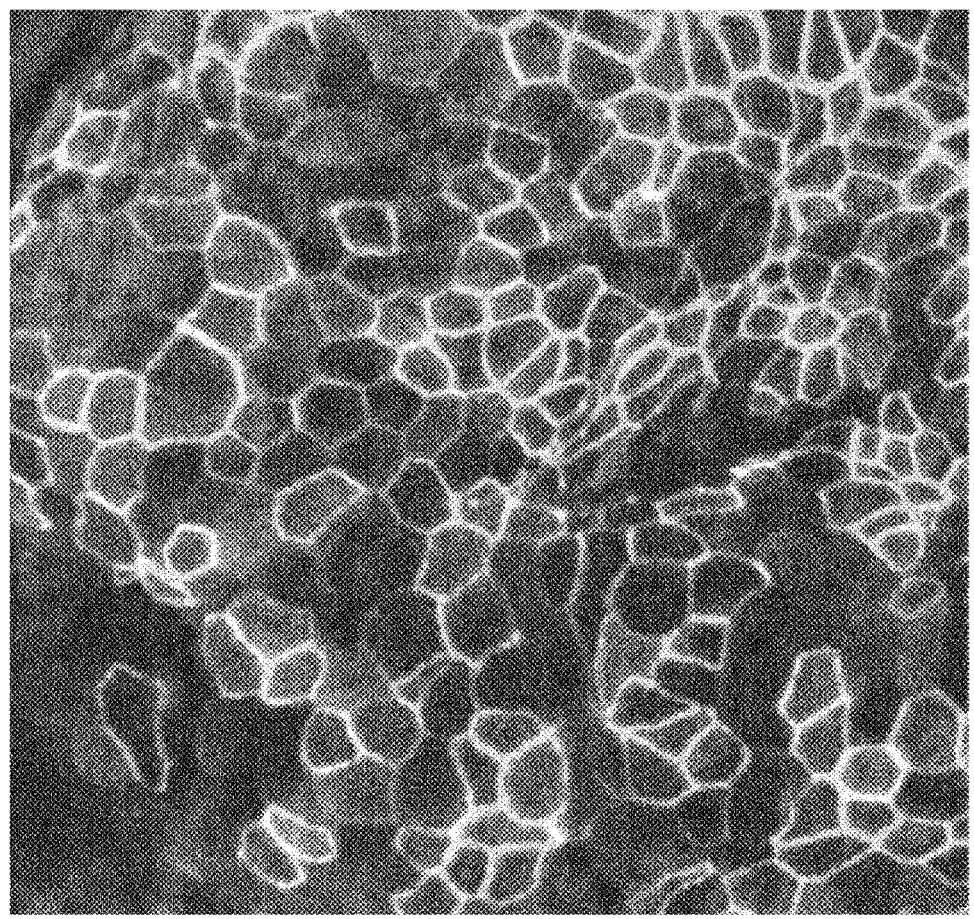

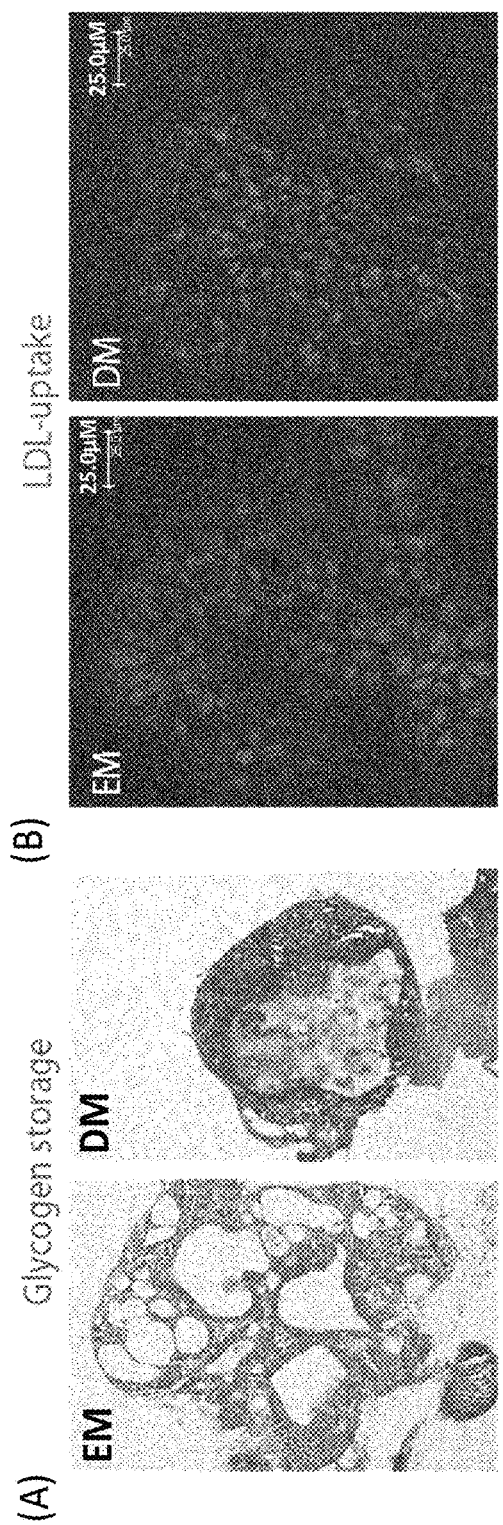
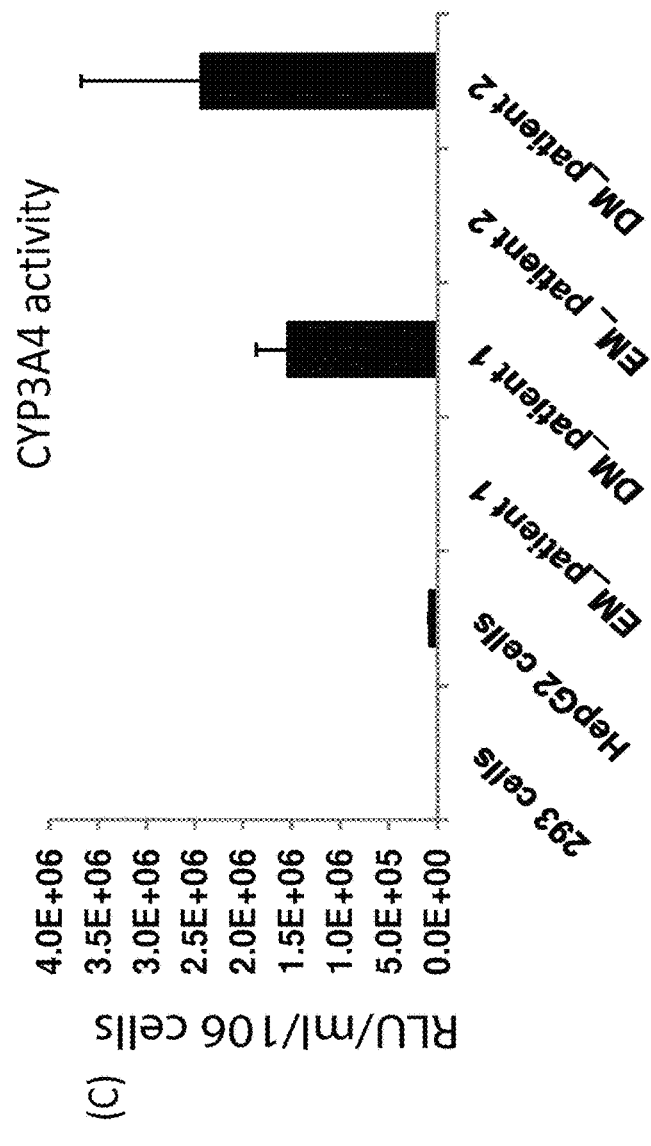
Figure 11

Figure 12: Table 2

| summary of compounds tested | effect observed | cat n + comercial |
|---|---|---|
| Egf | + | invitrogen |
| noggin | + | peprotecht |
| Rspo | + | CM |
| gastrin | + | sigma |
| FGF10 | + | peprotecht |
| HGF | + | peprotecht |
| nicotinamide | + | Sigma |
| wnt 3a | + only for initiation | CM |
| A8301 | + | Tocris 2939 |
| BMP7 | + | peprotecht |
| NKH 477 (forskolin analog) | + | Tocris 1603 |
| 8-bromo-cAMP | + | Tocris 1140 |
| cholera toxin | + | Sigma |
| forskolin | + | Tocris 1099 |
| FGF19 | + for differentiation | RD 969-FG |
| DAPT | + for differentiation | sigma |
| dexamethasone | + for differentiation | sigma |
| CHIR99021 | + | 130-095-555 |

| | | |
|---|---|---|
| jagged 1 | + mild | anaspec 61298 |
| thiazovivin | + after passage | Tocris 3845 |
| p38 inh SB202190 | + mild | Sigma SB 7076 |
| SB431542 | + mild | Tocris 1614 |
| AA (arachindonic acid) | + after initiaion | Tocris 2756 |
| PGE2 (prostaglandin E2) | + after initiaion but generates cyst-like | Tocris 2296 |
| Y- (ROCK inh) | + after initiation/passage/thawing | sigma Y-27632 |

(A)

Figure 14(contd.)
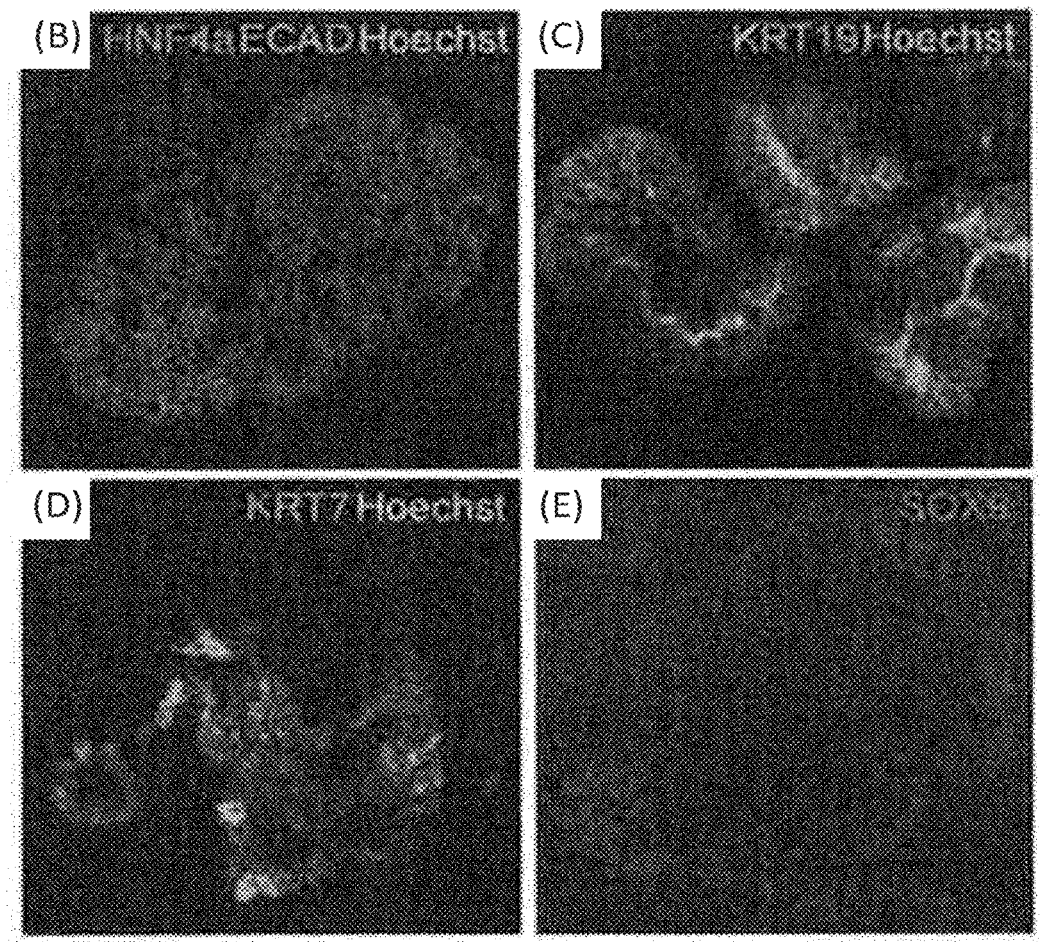
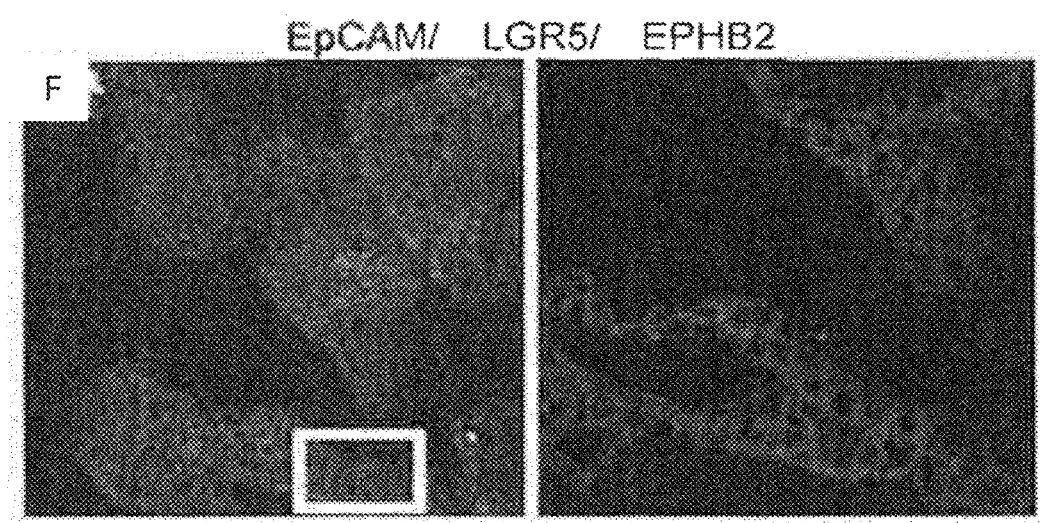

Figure 14(contd.)
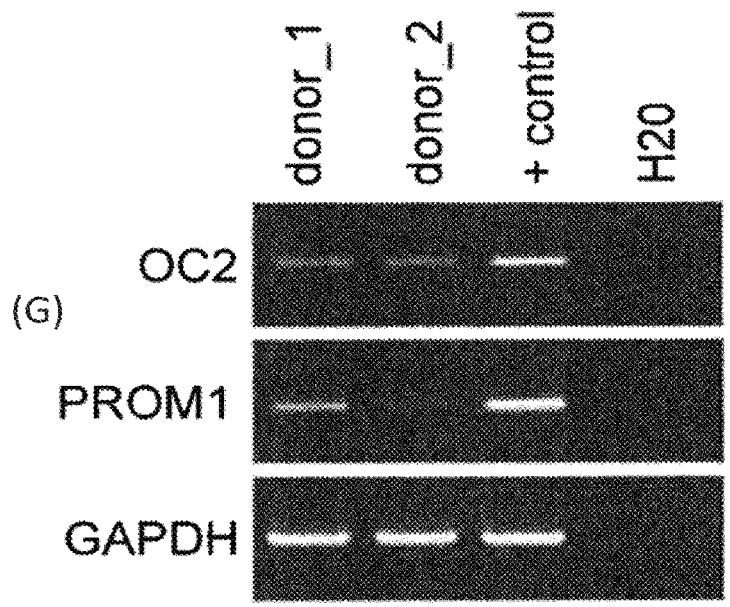
(G)
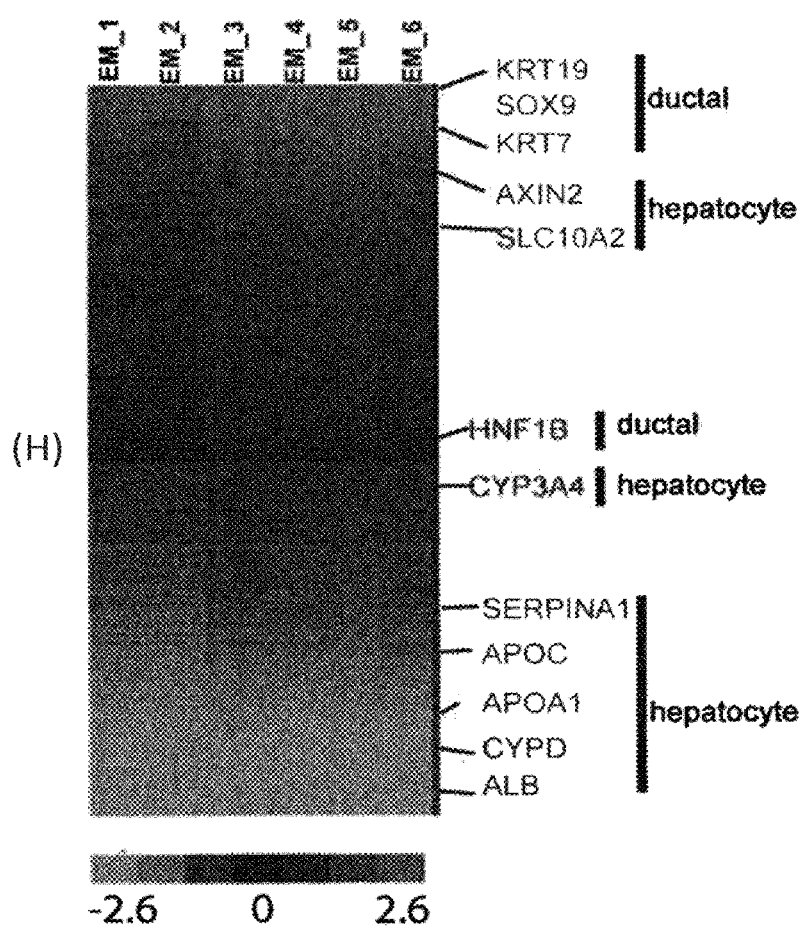
(H)

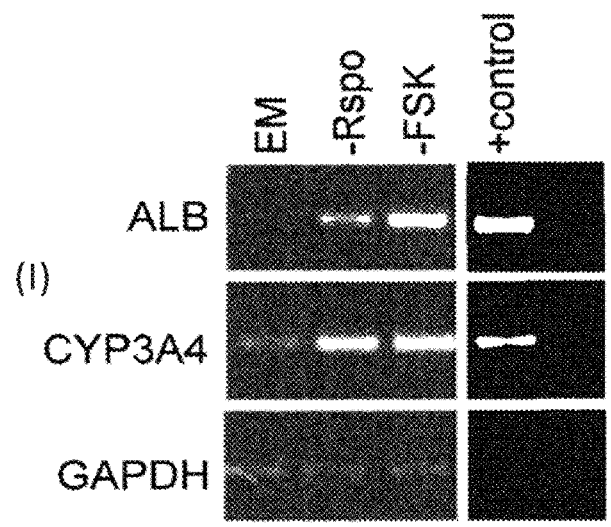
Figure 14(contd.)
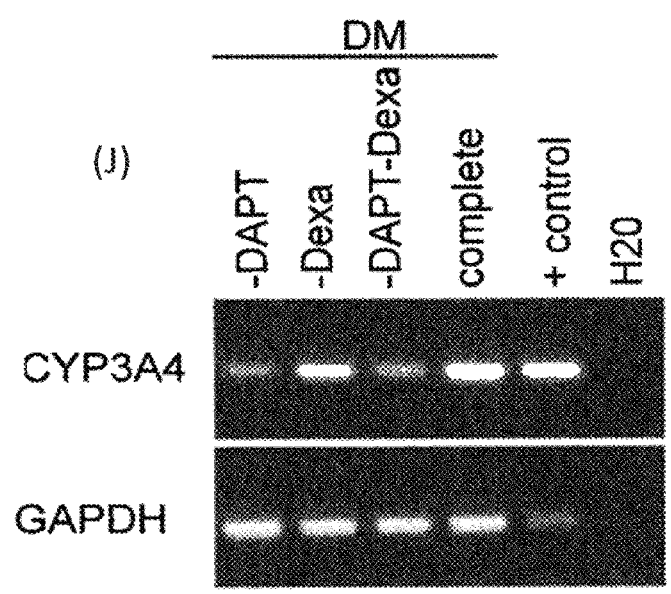

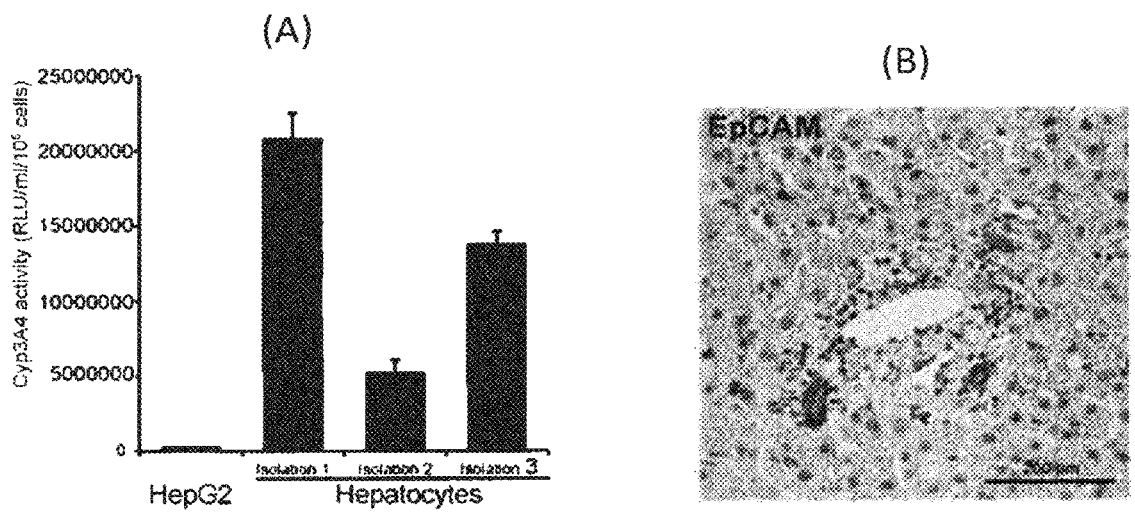
Figure 15
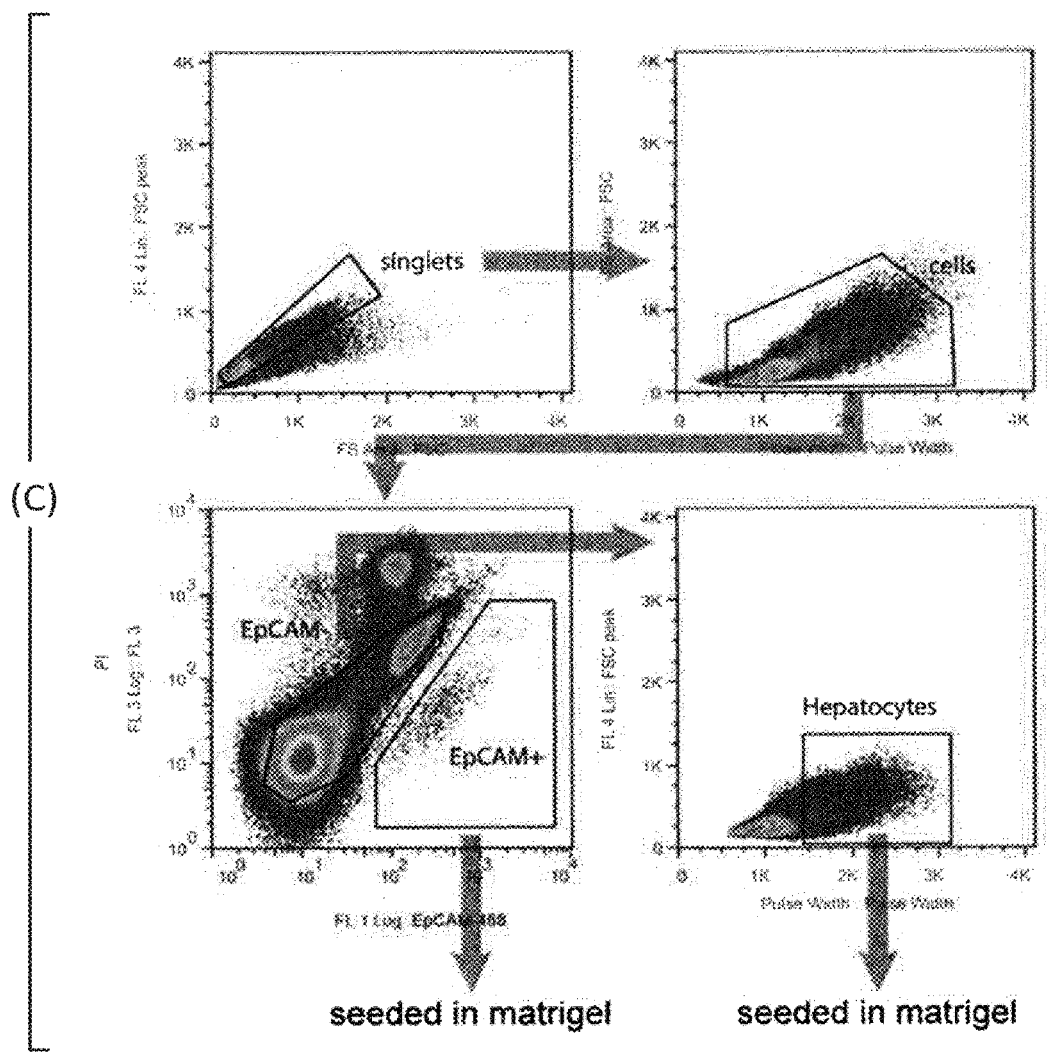

Figure 15(contd.)
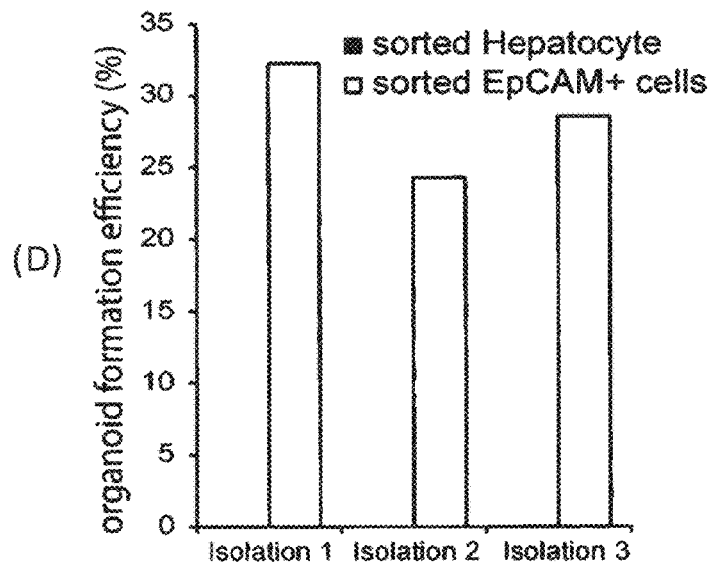
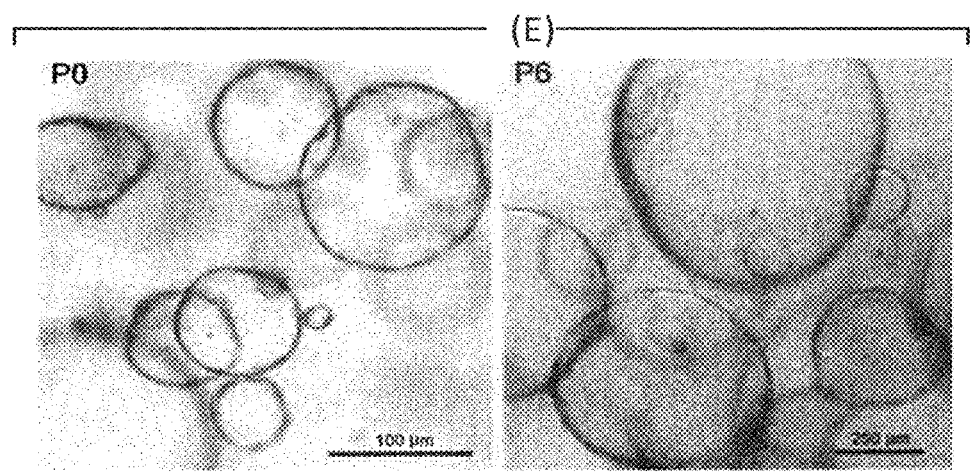
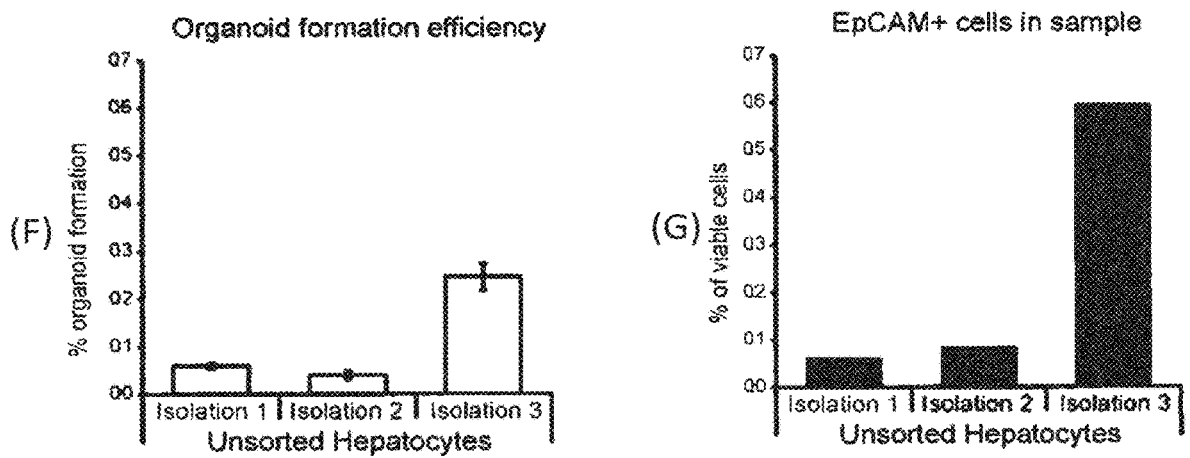

Figure 16(contd.)
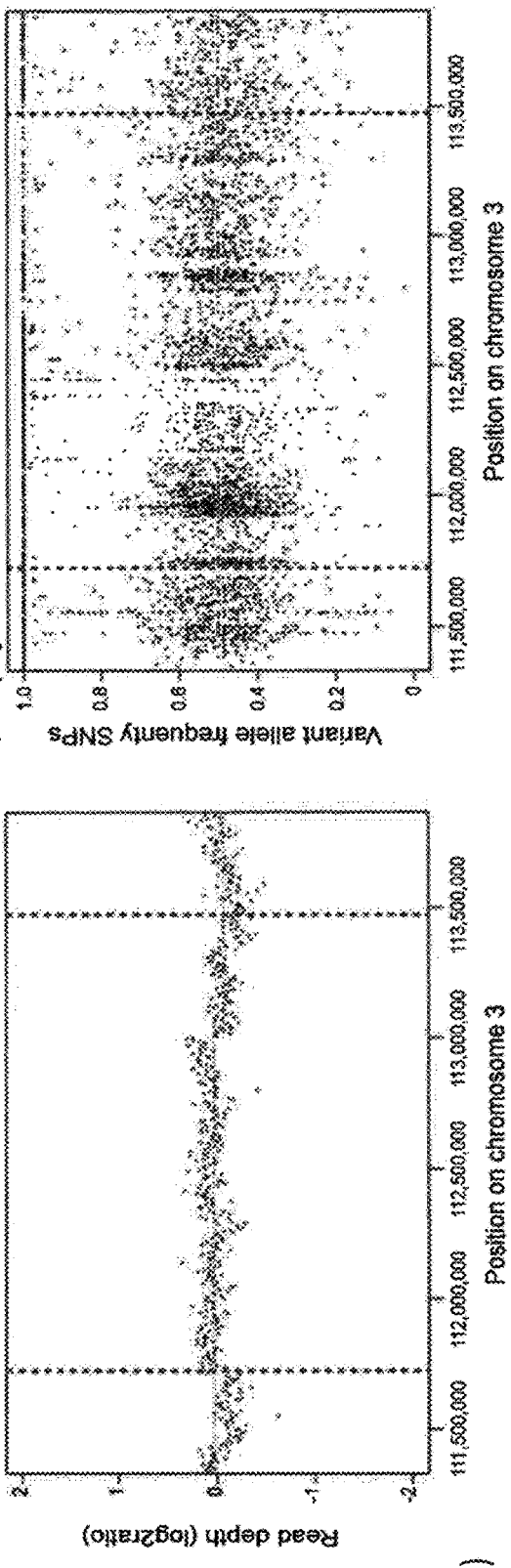
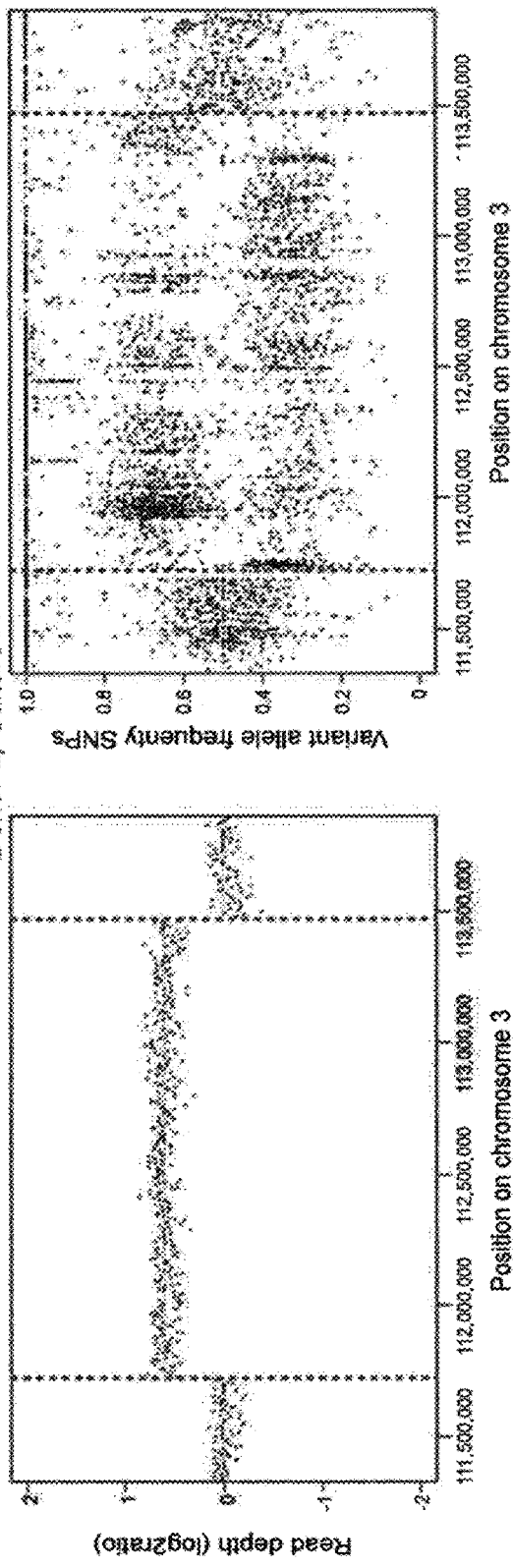
(C)

| Donor | Culture | CNV | Location | Present at early passage | Type |
|---|---|---|---|---|---|
| 1 | A | 0 | N/A | N/A | N/A |
|  | B | 0 | N/A | N/A | N/A |
| 2 | A | 2 | chr3:94,491,001-95,652,000 | Yes | Gain |
|  |  |  | chr3:111,725,000-113,472,000 | Yes | Gain |
|  | B | 0 | N/A | N/A | N/A |

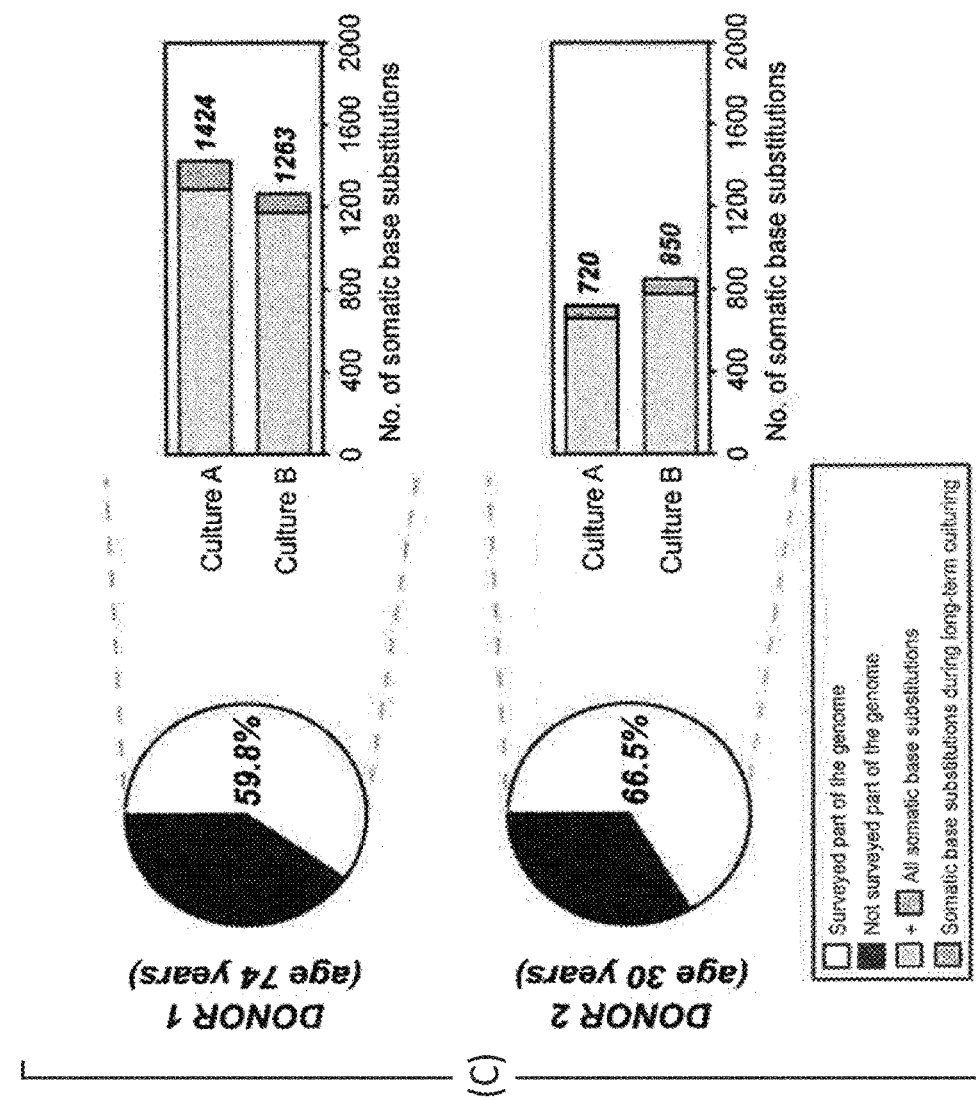
Figure 17(contd.)

Figure 18
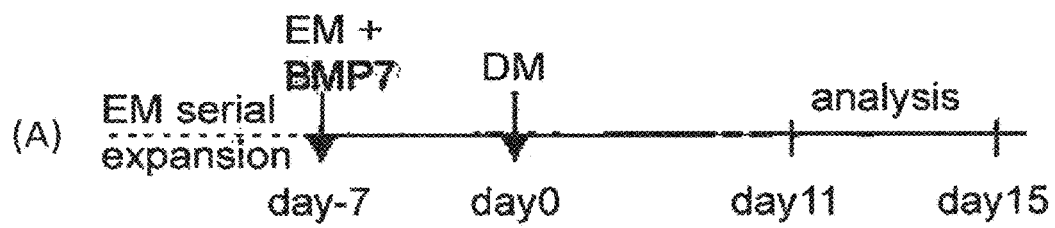
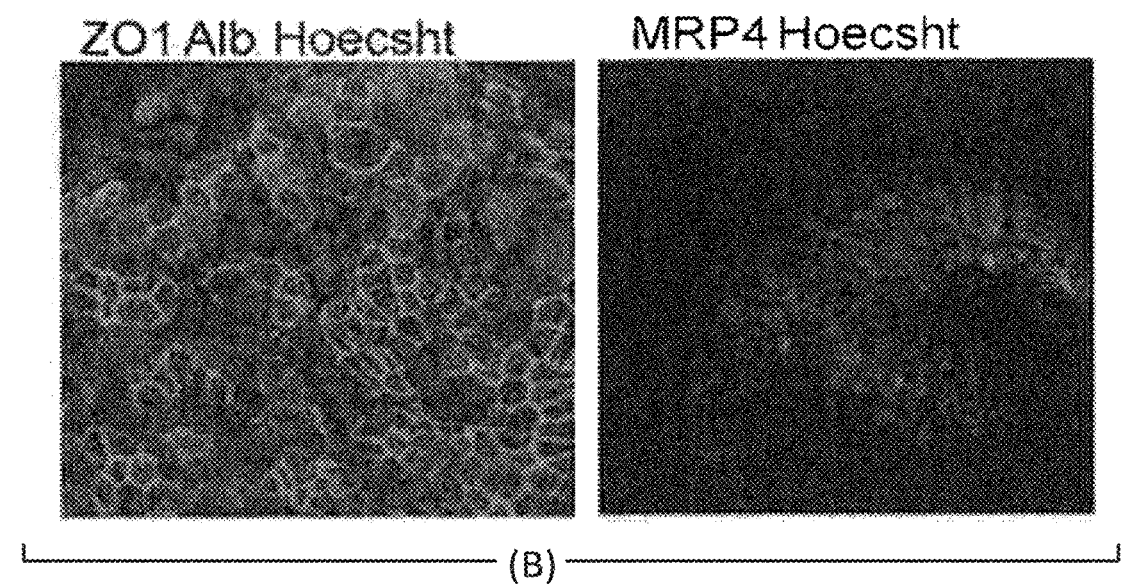
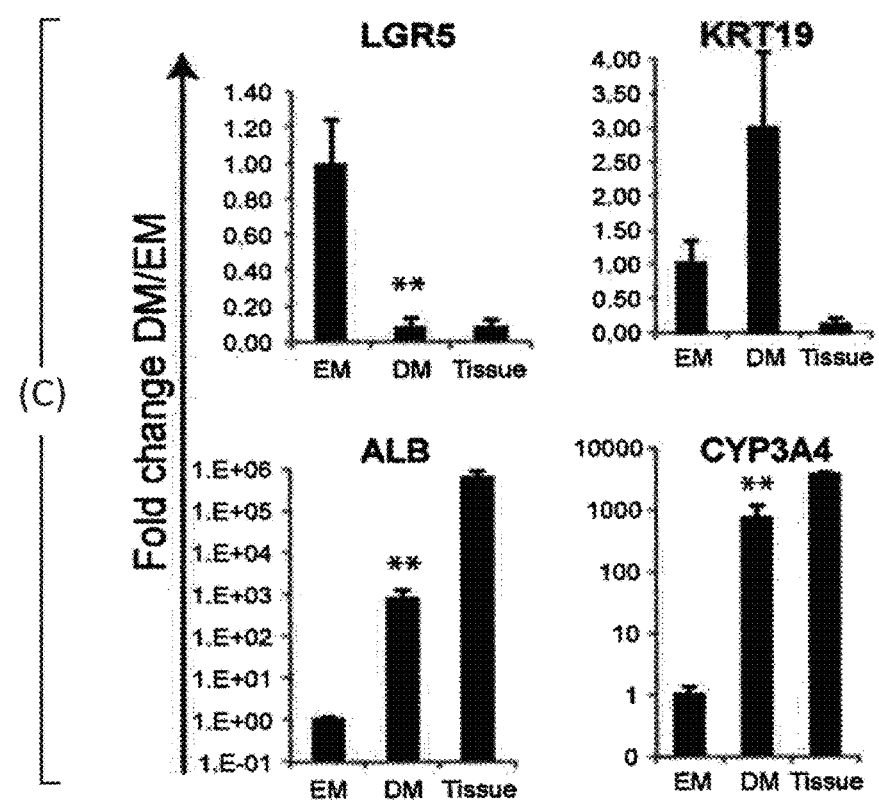

Figure 18(contd.)
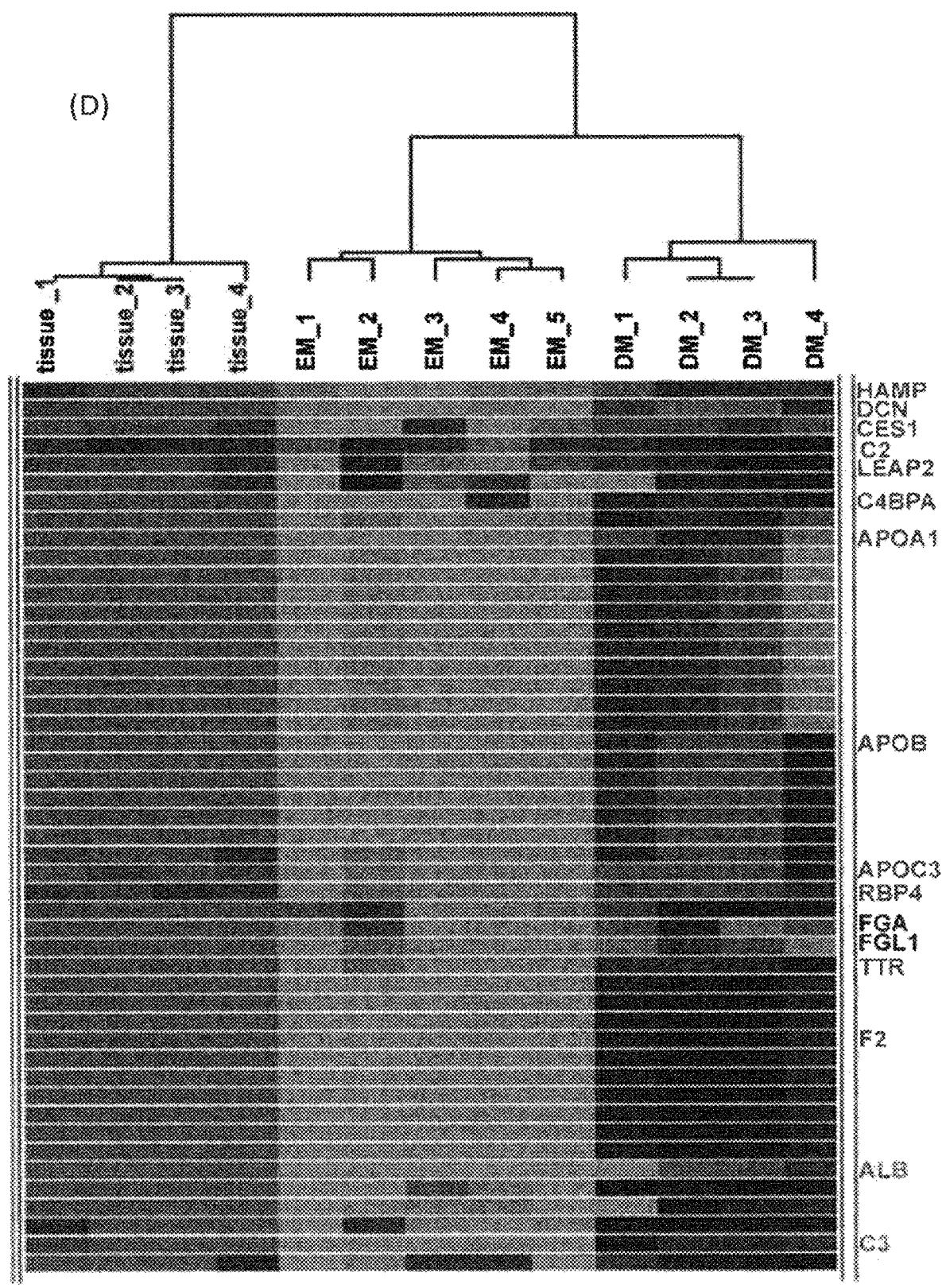

Figure 19
(A)
Glycogen storage
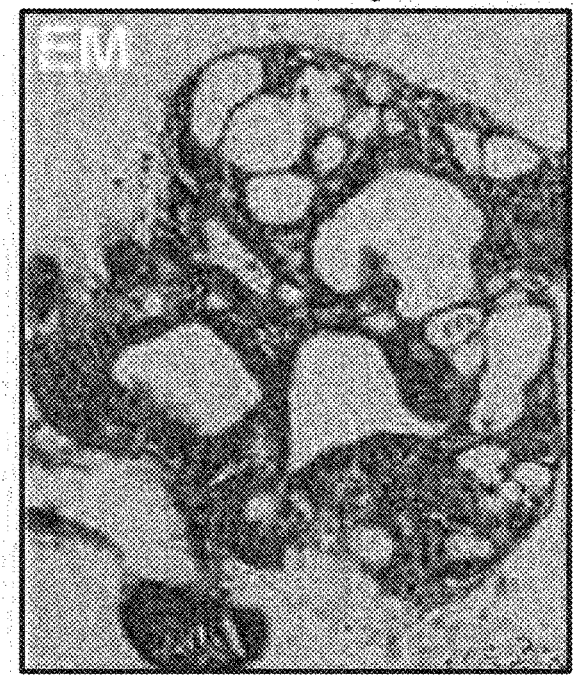 
(B)
LDL-uptake
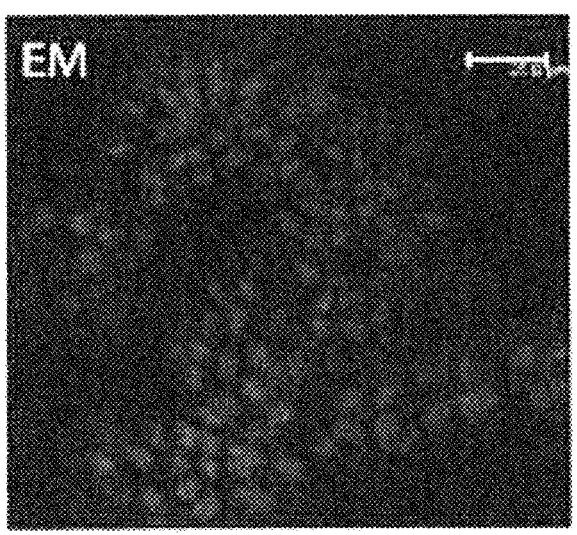 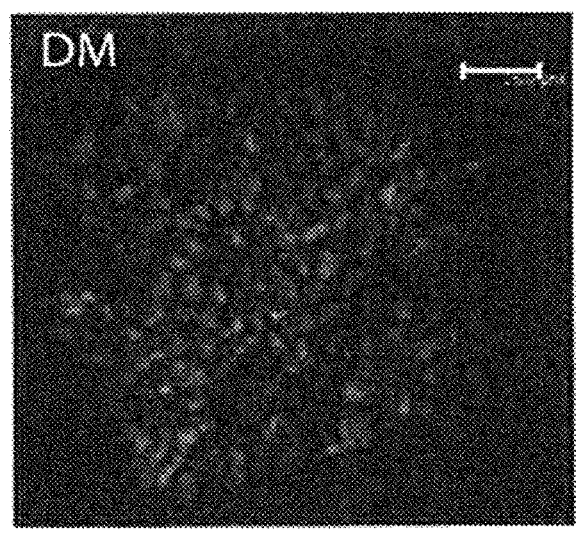

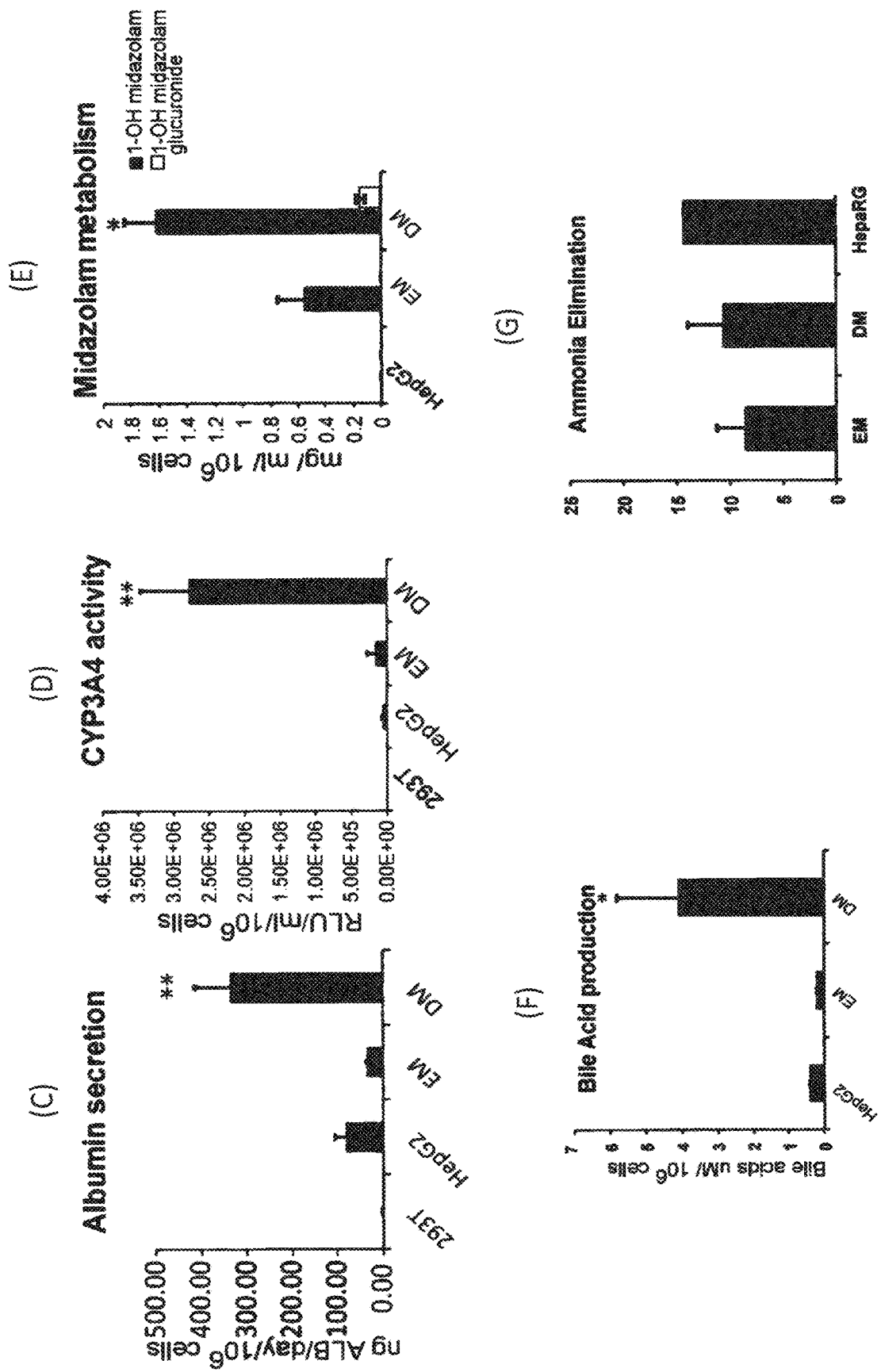
Figure 19(contd.)

Figure 19(contd.)
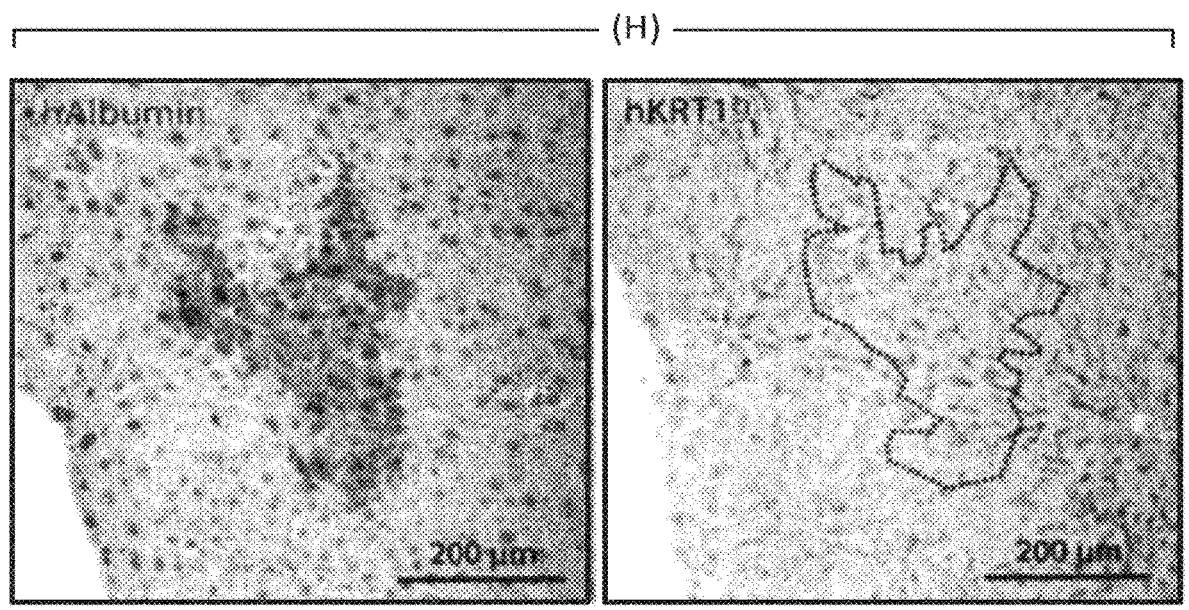
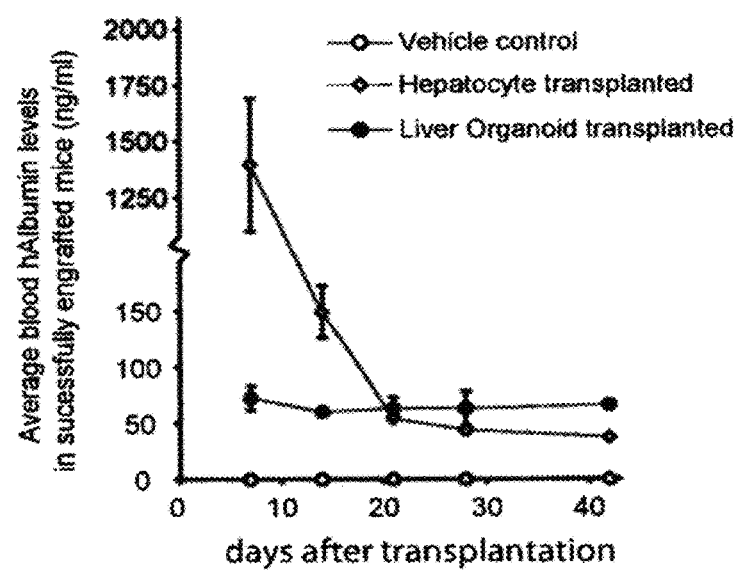

(A)

Figure 20(contd.)
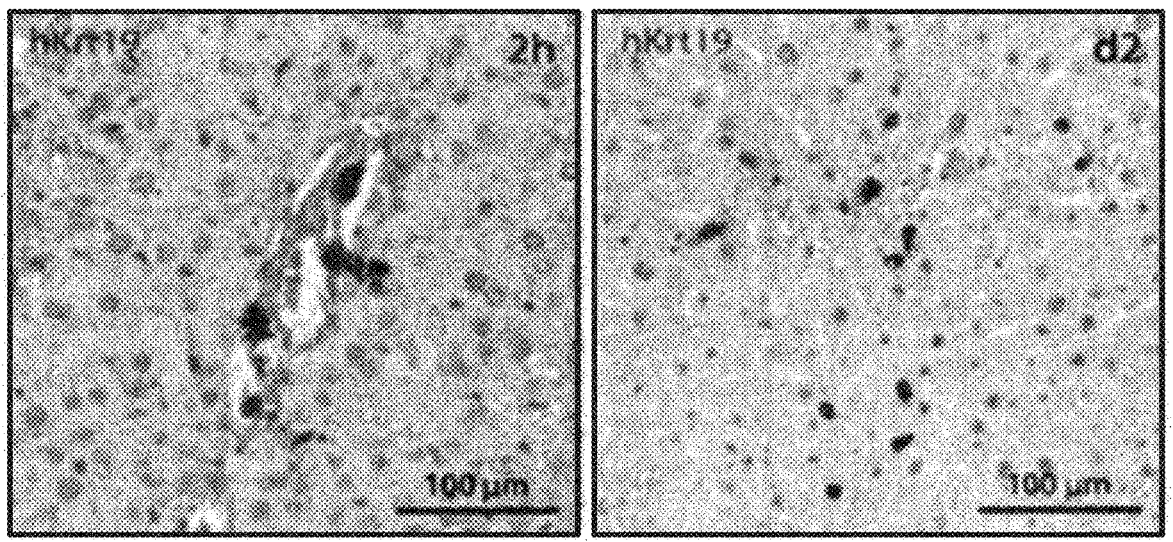
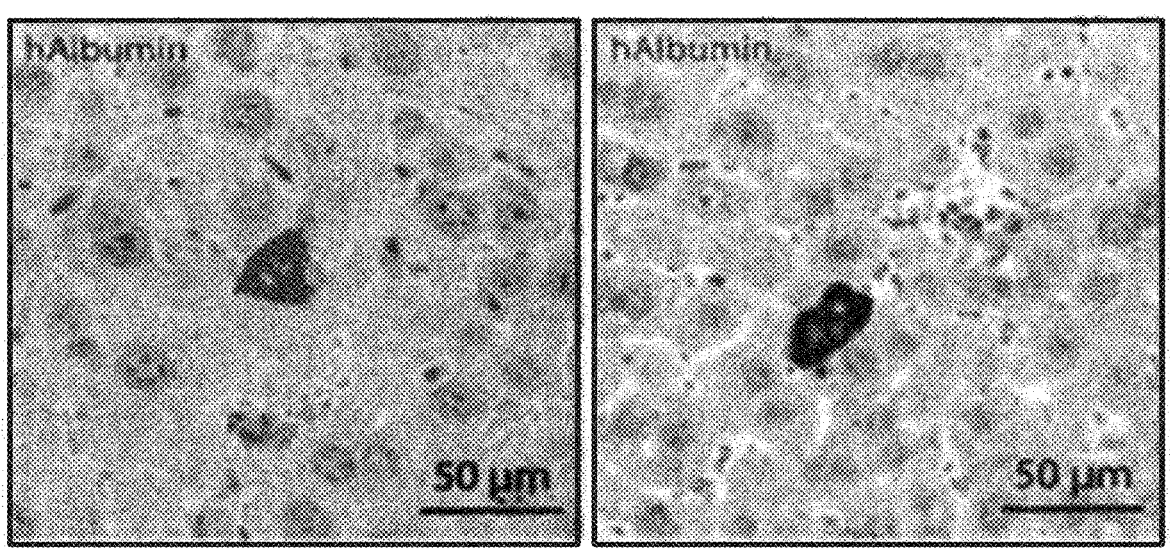

Figure 20(contd.)
(D)
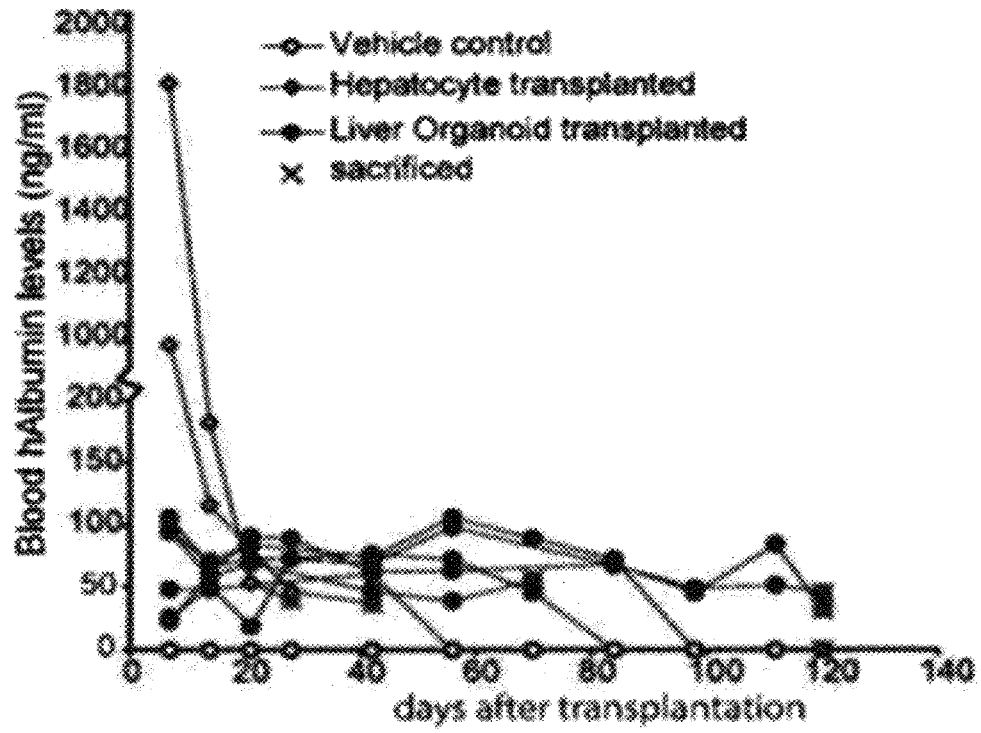
(E)
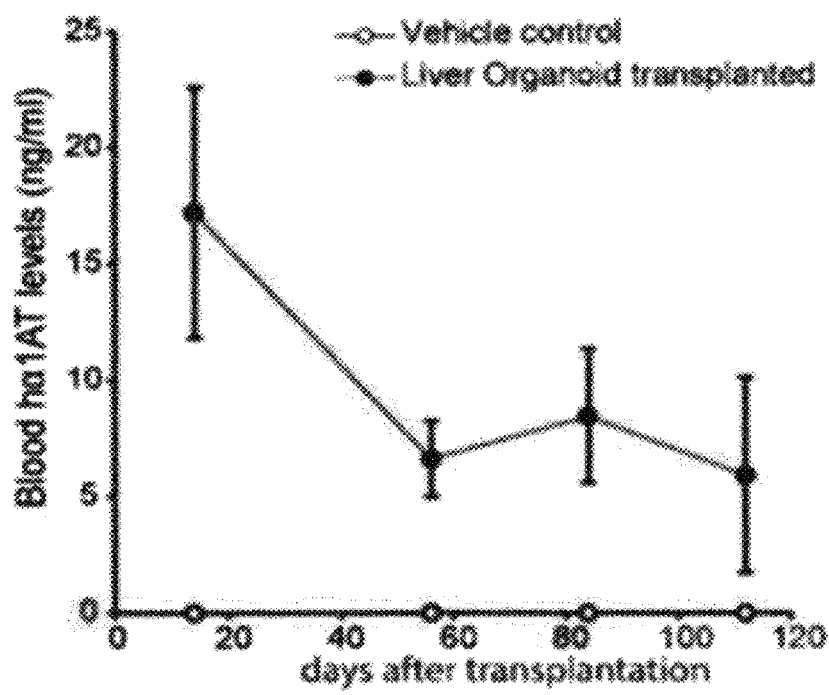

Figure 21
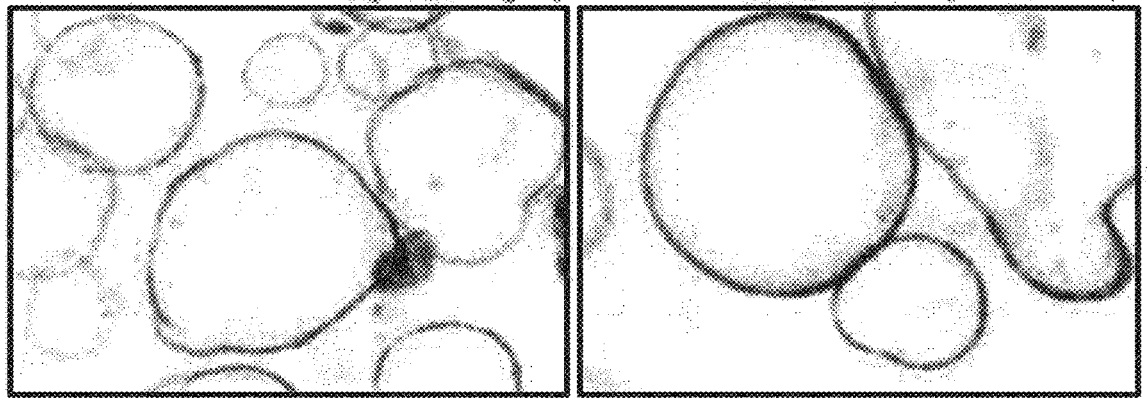
(A)
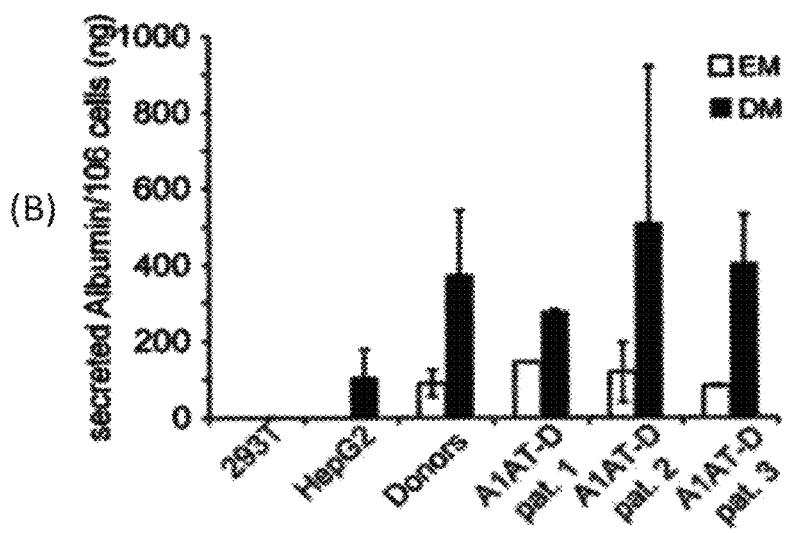
(B)
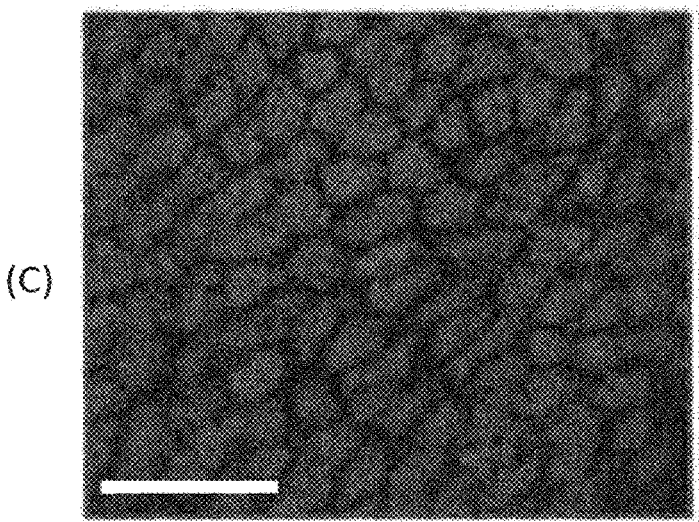
(C)

Figure 21(contd.)
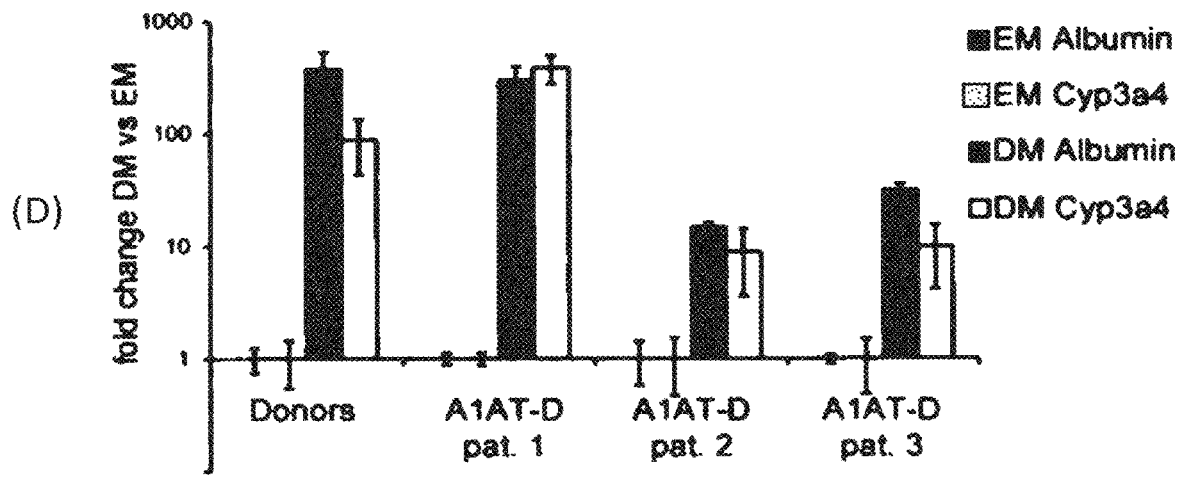
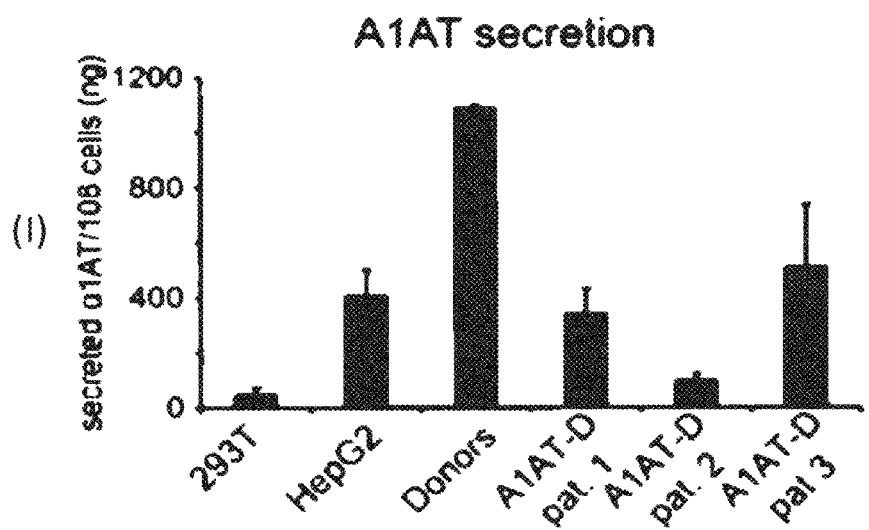
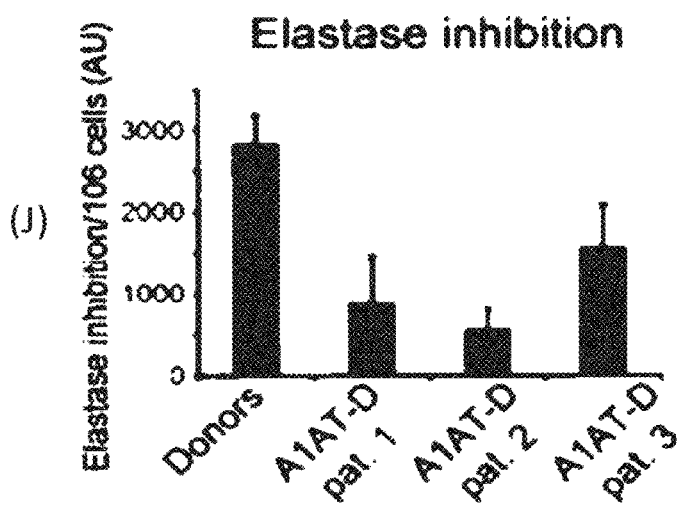

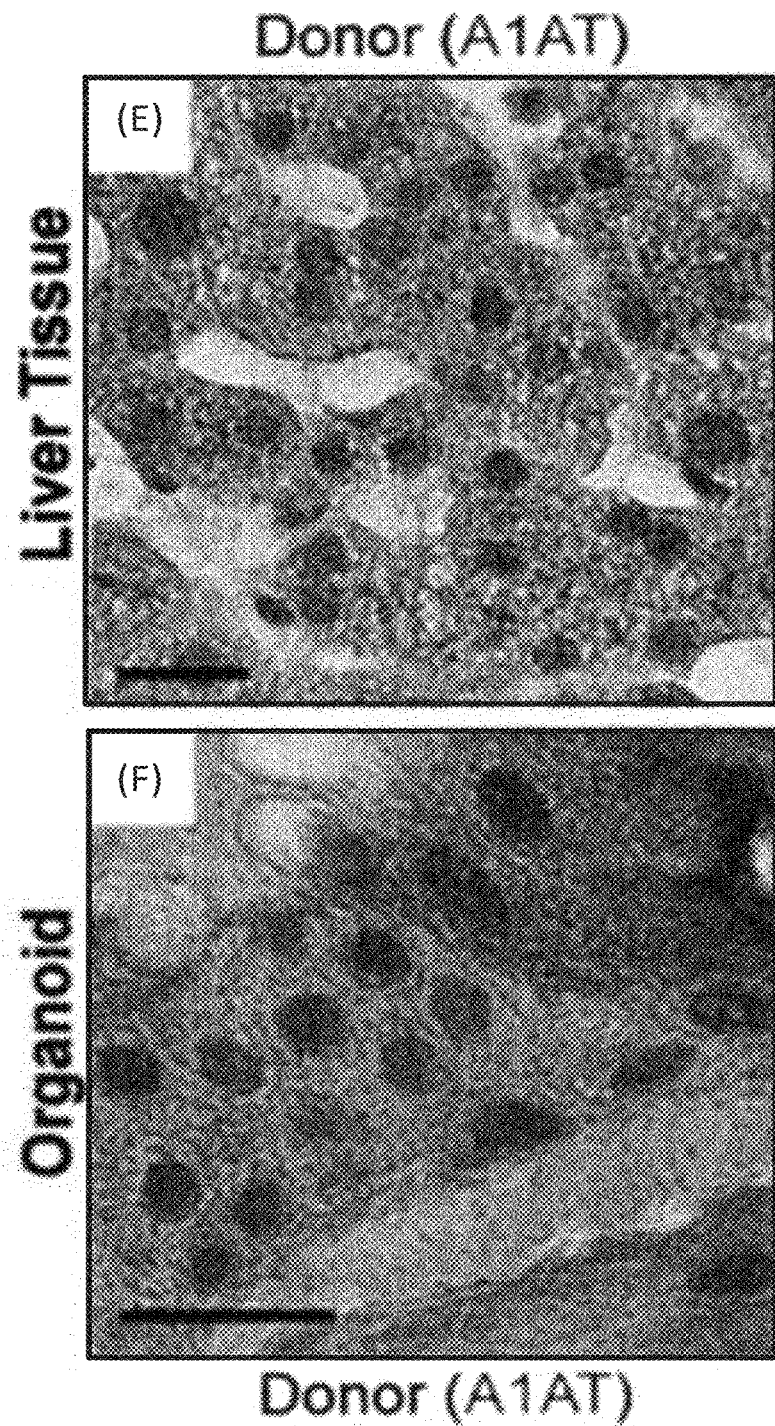
Figure 21(contd.)

Figure 21(contd.)
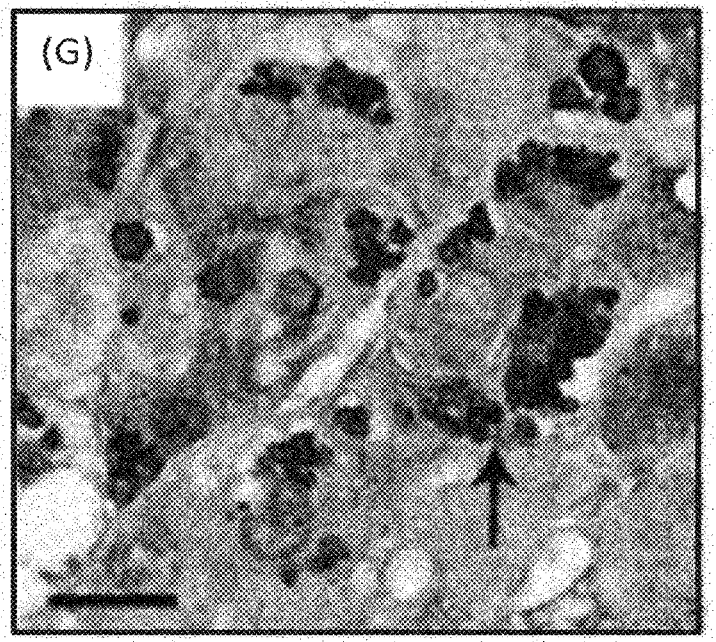
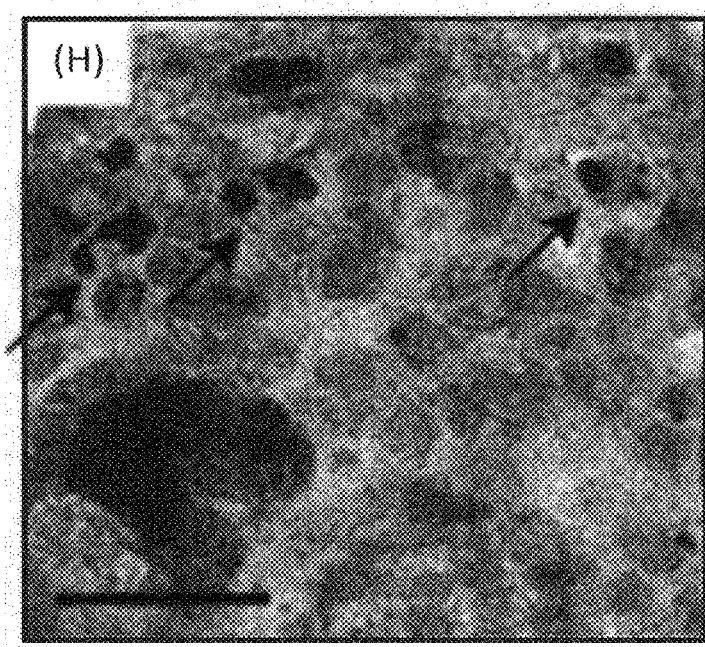
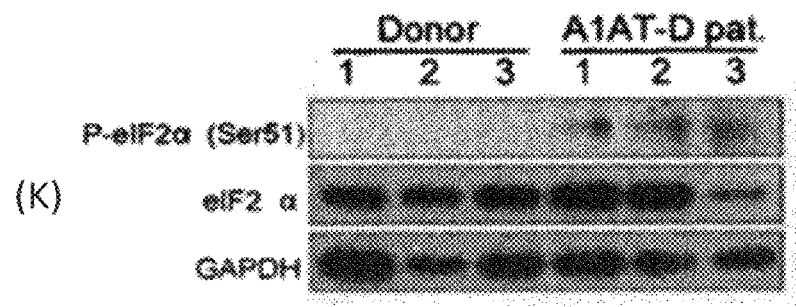

Figure 22(contd.)
(B)
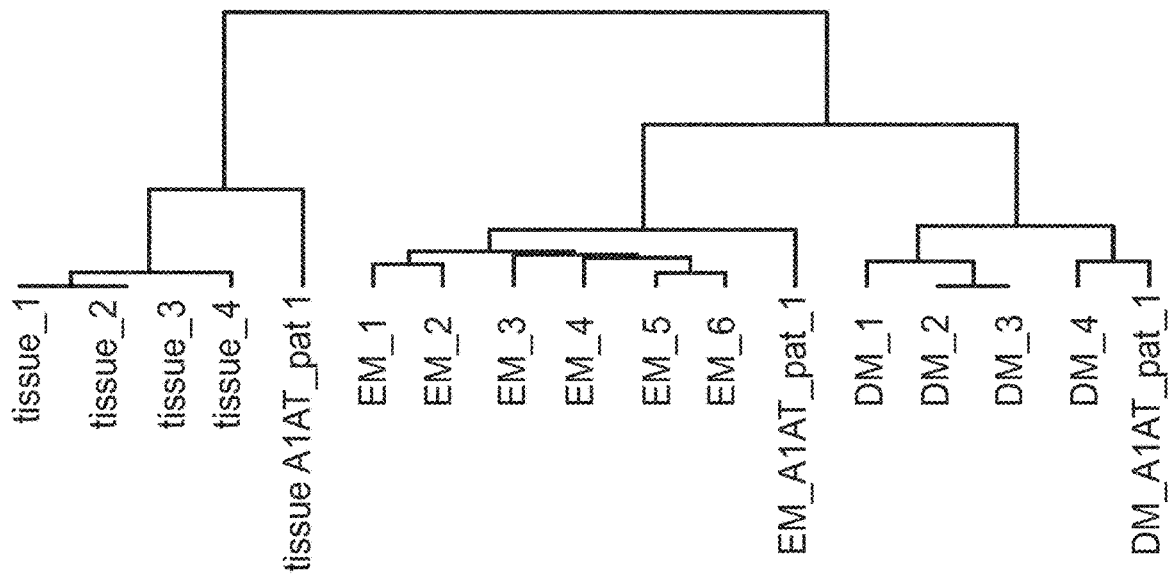
(C)
| wildtype cleaved Caspase-3 | α1AT-deficient cleaved Caspase-3 |
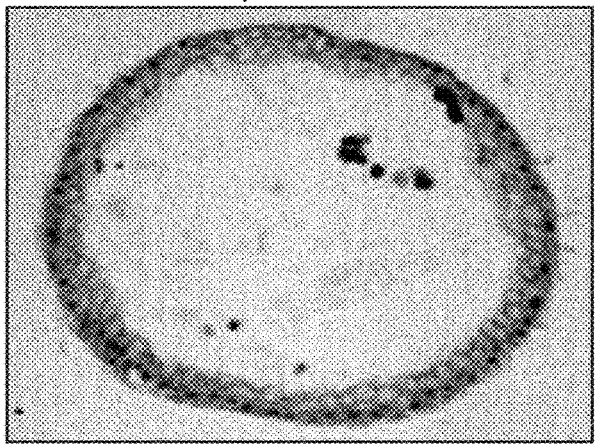
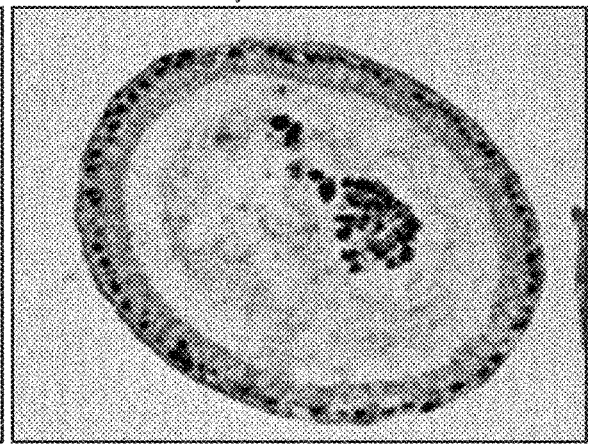

Figure 22(contd.)
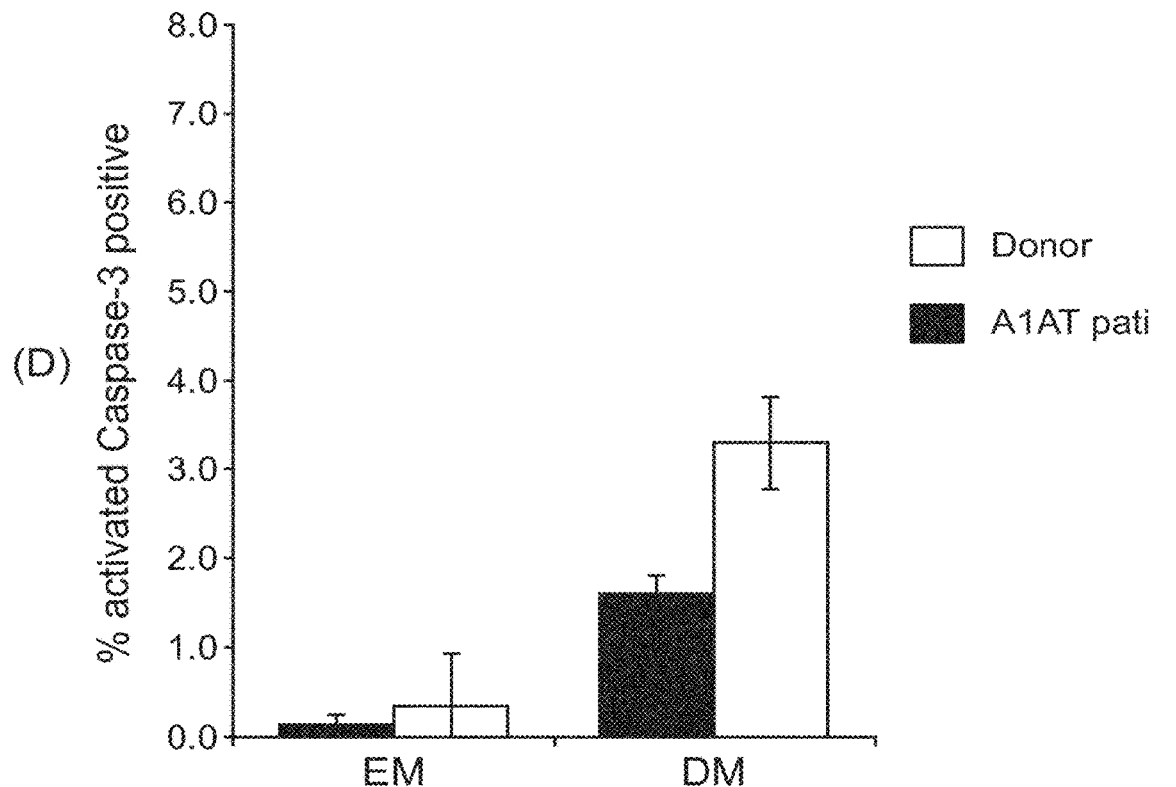
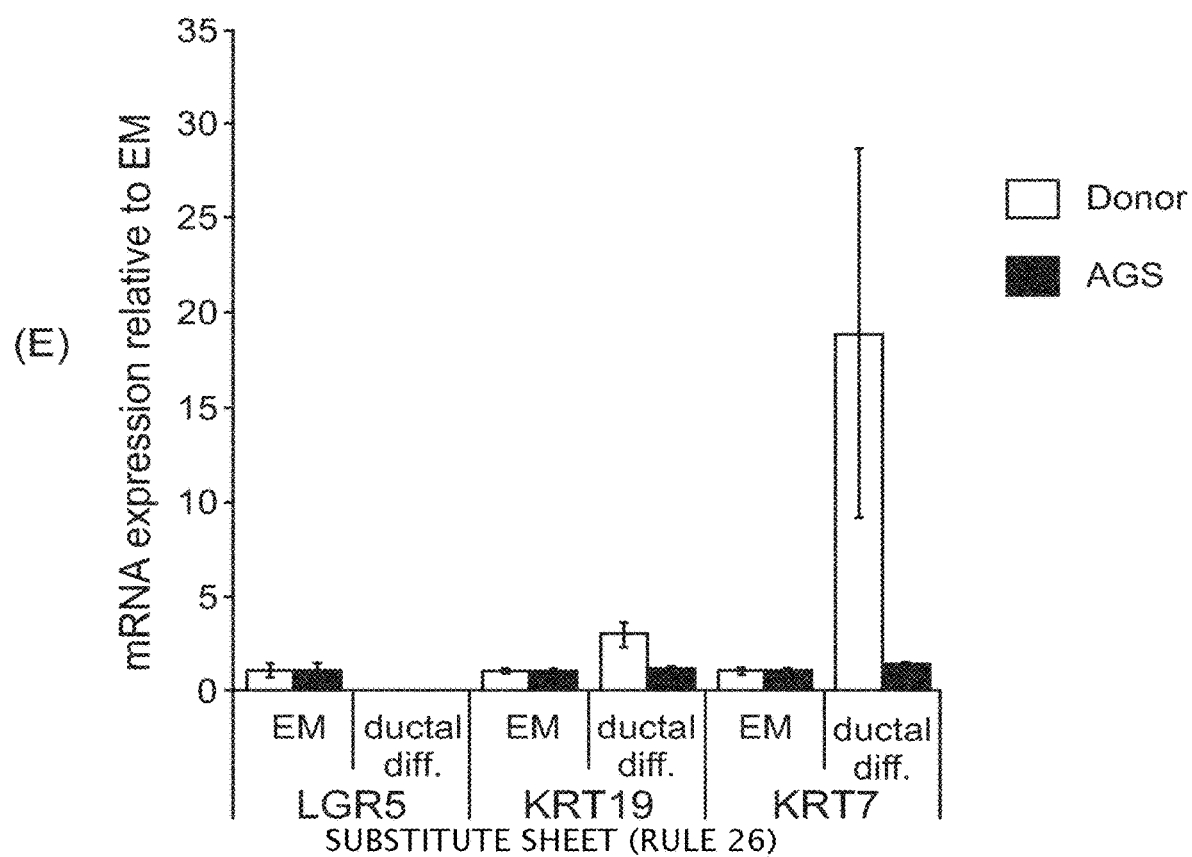

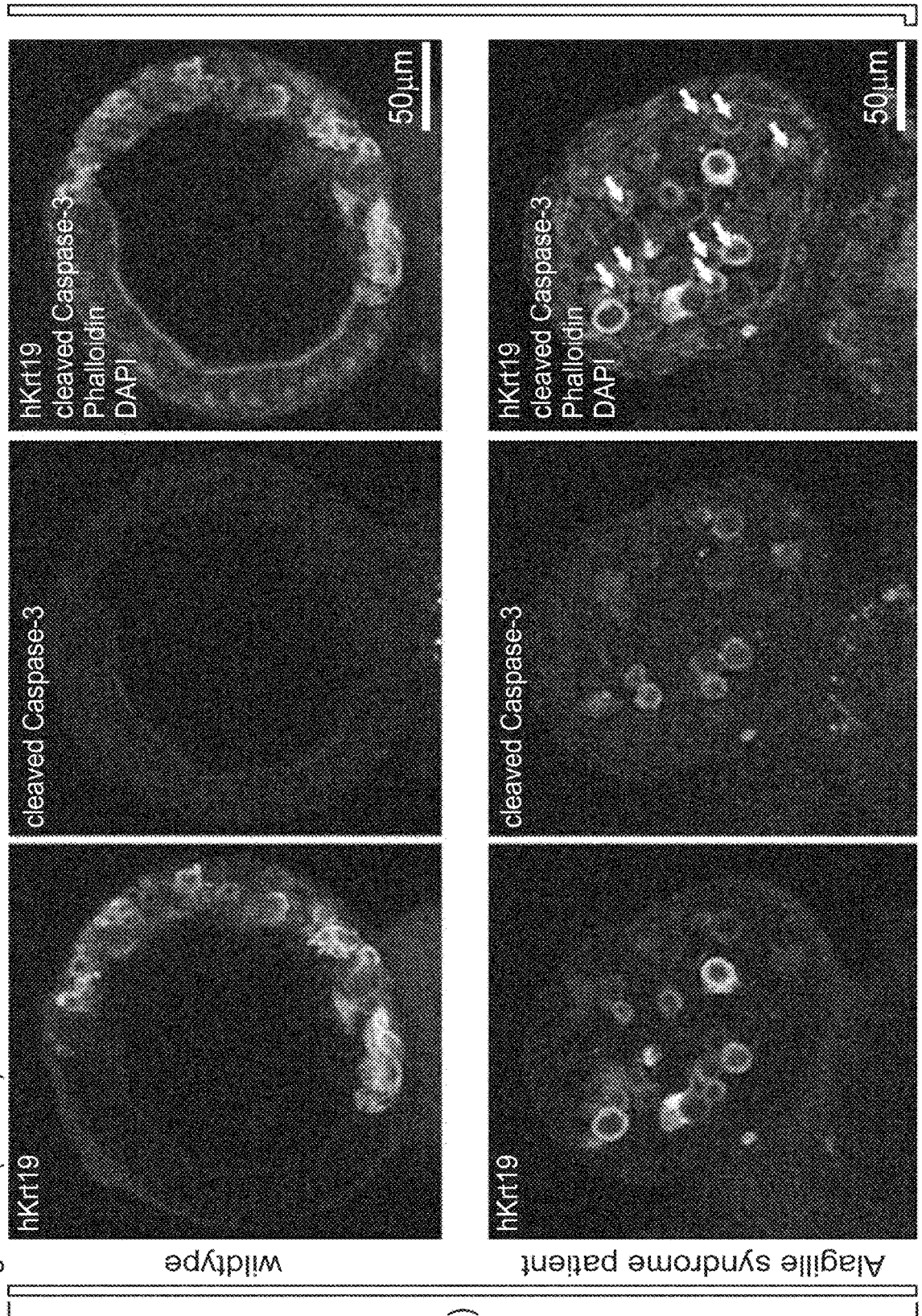
Figure 22(contd.)

CULTURE METHOD FOR ORGANOIDS

This application is a divisional of U.S. application Ser. No. 16/743,191, filed Jan. 15, 2020, which is a divisional of U.S. application Ser. No. 15/310,905, filed Nov. 14, 2016, now U.S. Pat. No. 10,597,633, which is a national phase entry pursuant to 35 U.S.C. § 371 of International Application No. PCT/EP2015/060815, filed May 15, 2015, which claims the benefit of priority of Great Britain Application No. 1408764.7, filed May 16, 2014, and Great Britain Application No. 1422184.0, filed Dec. 12, 2014, each of which is incorporated by reference herein in its entirety for any purpose.

BACKGROUND TO THE INVENTION

Recently, in the small intestine, the gene Lgr5 was identified which is specifically expressed in cycling Crypt Base Columnar (CBC) cells, which are small cells that are interspersed between the Paneth cells (Barker et al., 2007. Nature 449: 1003-1007).

Using a mouse in which a GFP/tamoxifen-inducible Cre recombinase cassette was integrated into the Lgr5 locus, it was shown by lineage tracing that the Lgr5+ CBC cells constitute multipotent stem cells which generate all cell types of the epithelium even when assessed 14 months after Cre induction.

The existence of Lgr5 in other tissues was described in WO 2009/022907 and the existence of Lgr5 cells in the liver was later described in WO 2012/014076. Methods for culturing epithelial stem cells and obtaining organoids starting from epithelial stem cells were provided in WO 2010/090513, WO 2012/014076 and WO 2012/168930 (KONINKLIJKE NEDERLANDSE AKADEMIE VAN WETENSCHAPPEN). Although these methods advantageously allow the expansion of epithelial stem cells, and provide longer-term expansion than the previously known methods, it would be advantageous to increase the length of time that the stem cells can be expanded even further, particularly for human cells.

WO 2013061608 describes methods for isolating and culturing colorectal epithelial stem cells in a medium comprising serum albumin, Wnt3a and Rspondin. The methods do not involve a culture medium comprising a TGF-beta inhibitor, FGF, nicotinamide or a BMP pathway activator and expansion times are limited.

It is, therefore, an object of the present invention to provide a method for increasing the expansion time of epithelial stem cells.

The basic architectural unit of the liver is the liver lobule. Each lobule consists of plates of hepatocytes lined by sinusoidal capillaries that radiate toward a central efferent vein. Liver lobules are roughly hexagonal with each of six corners demarcated by the presence of a portal triad (portal vein, bile duct, and hepatic artery). Although hepatocytes are the major parenchymal cell type of the liver they function in concert with cholangiocytes (biliary epithelial cells), endothelial cells, sinusoidal endothelial cells, Kupffer cells, natural killer cells and hepatic stellate cells. This complex architecture is important for hepatic function.

The existence of liver stem cells remains controversial. On one hand, tissue maintenance in the liver and liver regeneration upon certain types of injury, are not driven by stem cells but rather by division of the mature cells (hepatocytes or cholangiocytes). However, liver injury models in which hepatocyte proliferation have been inhibited also demonstrated the ability of the organ to regenerate in response to damage. This suggests that the liver can be considered as an organ with facultative stem cells.

Liver cultures derived from hepatocytes, or by differentiation of embryonic stem cells (ES) or induced pluripotent stem cells, are known but these do not expand and self-renew for long periods.

Here there is provided a method to culture epithelial stem cells and to obtain organoids that shows longer-lived maintenance, and are able to differentiate to all major differentiated cell lineages present in the corresponding in vivo tissue. The method has been exemplified with epithelial cells derived from the liver, and has also been demonstrated to work with epithelial cells derived from the pancreas. Thus the method is envisaged to be relevant to the culture of all epithelial cell types.

SUMMARY OF THE INVENTION

Accordingly, the invention provides a method for culturing epithelial stem cells, wherein said method comprises culturing one or more epithelial stem cells in contact with an extracellular matrix in the presence of a culture medium as described herein.

In particular, the invention provides a method for culturing epithelial stem cells, wherein said method comprises culturing one or more epithelial stem cells in contact with an extracellular matrix in the presence of an expansion medium as described herein. The method may optionally further comprise the step of culturing one or more epithelial cells that have been cultured in an expansion medium of the invention with a differentiation medium as described herein.

Accordingly, the invention provides a method for culturing epithelial stem cells, wherein said method comprises:
culturing one or more epithelial stem cells in contact with an extracellular matrix in the presence of an expansion medium, the expansion medium comprising a basal medium for animal or human cells to which is added:
one or more receptor tyrosine kinase ligands, one or more Wnt agonist wherein the Wnt agonist is an Lgr5 agonist, a TGF-beta inhibitor and a cAMP pathway activator.

In some embodiments, the Lgr5 agonist is Rspondin.
In some embodiments, the expansion medium further comprises a BMP pathway activator.
In some embodiments, the expansion medium further comprises one or more components selected from the group consisting of: a further Wnt agonist, a BMP inhibitor, nicotinamide, gastrin, B27, N2, and N-Acetylcysteine.

In some embodiments, in the expansion medium:
the one or more receptor tyrosine kinase ligands are selected from the group consisting of: FGF, HGF and EGF, wherein the FGF is preferably an FGF able to bind to FGFR2 or FGFR4 and is preferably FGF10;
the TGF-beta inhibitor is a small molecule inhibitor of ALK4, ALK5 or ALK7, optionally selected from the group consisting of: A83-01, SB-431542, SB-505124, SB-525334, LY 364947, SD-208 and SJN 2511;
the cAMP pathway activator is an adenylyl cyclase activator, for example, forskolin, a forskolin analog or cholera toxin, or a cAMP analog, for example 8-bromo-cAMP, or NKH477;
when Rspondin is present, the Rspondin is selected from R-spondin 1, R-spondin 2, R-spondin 3 and R-spondin 4;
when a further Wnt agonist is present, the further Wnt agonist is selected from one or more of Wnt-3a, Wnt-5, Wnt-6a, Norrin, and a GSK-inhibitor; and/or when a BMP pathway activator is present, it is selected from one or more of BMP7, BMP4 and BMP2.

In some embodiments, the method further comprises a culturing step in a differentiation medium comprising a basal medium for animal or human cells to which is added one or more receptor tyrosine kinase ligands and a Notch inhibitor.

In some embodiments, the differentiation medium further comprises one or more of: a TGF-beta inhibitor, gastrin, dexamethasone and a BMP pathway activator.

In some embodiments, in the differentiation medium:
the one or more receptor tyrosine kinase ligands are selected from one or more of the group: FGF, HGF and EGF, wherein the FGF is preferably an FGF able to bind to FGFR2 or FGFR4 and is preferably FGF19;
the Notch inhibitor is a gamma-secretase inhibitor, optionally DAPT or dibenzazepine (DBZ) or benzodiazepine (BZ) or LY-411575
when a TGF-beta inhibitor is present, it is a small molecule inhibitor of ALK4, ALK5 or ALK7 optionally selected from the group consisting of: A83-01, SB-431542, SB-505124, SB-525334, LY 364947, SD-208, SJN 2511; and/or
when a BMP pathway activator is present, it is selected from one or more of BMP7, BMP4 and BMP2.

The invention also provides a method for differentiating epithelial stem cells, wherein said method comprises:
culturing the cells in a differentiation medium comprising a basal medium for animal or human cells to which is added EGF, gastrin, FGF19, DAPT, dexamethasone, HGF and A8301.

In some embodiments, the method culturing or differentiating epithelial stem cells further comprises isolating one or more adult stem cells or obtaining and isolating an organoid.

In some embodiments, the epithelial stem cells are from the liver, pancreas, intestine, stomach, prostate, lung, breast, ovarian, salivary gland, hair follicle, skin, oesophagus or thyroid.

In some embodiments, the epithelial stem cells are from the liver or pancreas.

There is also provided a method for culturing epithelial stem cells, wherein the epithelial stem cells are from the liver and wherein said method comprises:
culturing one or more epithelial stem cells in contact with an extracellular matrix in the presence of an expansion medium, the expansion medium comprising a basal medium for animal or human cells to which is added: EGF, FGF10, HGF, Rspondin, Nicotinamide, a TGF-beta inhibitor, forskolin, gastrin, N-Acetylcysteine, and N2 and/or B27, and which is supplemented with Noggin, a further Wnt agonist, and a ROCK inhibitor;
culturing the one or more epithelial stem cells in a second expansion medium comprising a basal medium for animal or human cells to which is added: EGF, FGF10, HGF, Rspondin, Nicotinamide, a TGF-beta inhibitor, forskolin, gastrin, N-Acetylcysteine, and N2 and/or B27, and optionally BMP7; and optionally,
culturing the one or more expanded epithelial stem cells in a differentiation medium comprising a basal medium for animal or human cells to which is added EGF, gastrin, FGF19, DAPT, dexamethasone, HGF, a TGF-beta inhibitor, and optionally a BMP7.

There is also provided a method for culturing epithelial stem cells, wherein the epithelial stem cells are from the pancreas and wherein said method comprises:
culturing one or more epithelial stem cells in contact with an extracellular matrix in the presence of an expansion medium, the expansion medium comprising a basal medium for animal or human cells to which is added: EGF, FGF10, Rspondin, Noggin, a further Wnt agonist, Nicotinamide, a TGF-beta inhibitor, forskolin, PGE2, a p38 inhibitor, gastrin, N2, B27, and N-Acetylcysteine and optionally BMP7; and optionally
culturing the one or more expanded epithelial stem cells in a differentiation medium comprising a basal medium for animal or human cells to which is added EGF, gastrin, FGF19, DAPT, dexamethasone, HGF, a TGF-beta inhibitor, and optionally a BMP7.

Also provided is a culture medium of the invention. In particular, the invention provides an expansion medium, comprising a basal medium for animal or human cells to which is added one or more receptor tyrosine kinase ligands, one or more Wnt agonist wherein the Wnt agonist is an Lgr5 agonist, a TGF-beta inhibitor, and a cAMP pathway activator.

In some embodiments, the Lgr5 agonist is Rspondin.

In some embodiments, the expansion medium further comprises a BMP pathway activator.

In some embodiments, the expansion medium further comprises one or more components selected from the group consisting of: a further Wnt agonist, a BMP inhibitor, nicotinamide, gastrin, N-Acetylcysteine, and B27 and/or N2.

In some embodiments, in the expansion medium:
the one or more receptor tyrosine kinase ligands are selected from the group consisting of: FGF, HGF and EGF, wherein the FGF is preferably an FGF able to bind to FGFR2 or FGFR4 and is preferably FGF10;
the TGF-beta inhibitor is a small molecule inhibitor of ALK4, ALK5 or ALK7, optionally selected from the group consisting of: A83-01, SB-431542, SB-505124, SB-525334, LY 364947, SD-208 and SJN 2511;
the cAMP pathway activator is an adenylyl cyclase activator for example forskolin, a forskolin analog or cholera toxin, or a cAMP analog, for example 8-bromo-cAMP, or NKH477;
when Rspondin is present, the Rspondin is selected from Rspondin 1, Rspondin 2, Rspondin 3 and Rspondin 4;
when a further Wnt agonist is present, the further Wnt agonist is selected from one or more of Wnt, Wnt-3a, Norrin, and a GSK-inhibitor; and/or
when a BMP pathway activator is present, it is selected from one or more of BMP7, BMP4 and BMP2.

In some embodiments, the expansion medium comprises EGF, FGF10, Rspondin, Nicotinamide, A8301, forskolin, Noggin, Wnt, gastrin, B27 and N-Acetylcysteine.

In some embodiments, the expansion medium comprises EGF, FGF10, HGF, Rspondin, Nicotinamide, A8301, forskolin, BMP7, gastrin, N-Acetylcysteine, and N2 and/or B27.

The invention also provides a differentiation medium comprising a basal medium for animal or human cells to which is added EGF, gastrin, FGF19, DAPT, dexamethasone, HGF and A8301 and optionally a BMP pathway activator.

Organoids and populations of cells as described herein are provided. For example, the invention provides an organoid obtainable or obtained by a method of the invention.

The invention also provides an organoid which has been cultured for at least 6, 8, 10, 12, 14, 16, 18 or 20 weeks.

In some embodiments, the organoid is derived from the liver, pancreas, intestine, stomach, prostate, lung, breast, ovarian, salivary gland, hair follicle, skin, oesophagus or thyroid.

The invention also provides an organoid in a culture medium according to the invention.

In some embodiments, the organoid of the invention has a doubling time of less than 65 hours, for example, 60, 58, 56, 54, 53, 50 hours or less.

The invention provides a liver organoid, wherein the liver organoid is derived from a mouse and:
- expresses at least one, preferably all, of the following stem cell markers: lgr5, lgr4, epcam, Cd44, Tnfrsf19, Sox9, Sp5, Cd24a, Prom1, Cdca7 and Elf3; and/or
- does not express the following stem cell marker: lgr6; and/or
- expresses at least one, preferably all, of the following hepatocyte or cholangiocyte markers when grown in the expansion medium as described herein: Hnf1a, Hnf1b, Hnf4a, Hhex, Onecut1, Onecut2, Prox1, Cdh1, Foxa2, Gata6, Foxm1, Cebpa, Cebpb, Cebpd, Cebpg, Glu1, Krt7, Krt19 and Met; and/or
- does not express at least one of the following genes when grown in the expansion medium described herein: afp, Ins1, Ins2, Gcg, Ptf1a, Cela1, Cela2a, Cela3b, Neurod1, Neurod2, Neurog1, Neurog2, Neurog3, Amy2a4, Igf1r, Igf2 and Cd34; and/or
- expresses at least one of the following reprogramming genes: Klf4 and Myc; and/or
- does not express one of the following reprogramming genes: Pou5f1 and Sox2.

The invention also provides a liver organoid, wherein the liver organoid is derived from a human and:
- expresses at least one, preferably all, of the following stem cell signature genes: LGR4, TACSTD1/Epcam, CD44, SOX9, SP5, CD24, PROM1, CDCA7 and ELF3; and/or expresses at least one, preferably all, of the following reprogramming genes: KLF4, MYC, POU5F1 and SOX2; and/or
- expresses at least one, preferably all, of the following hepatocyte/cholangiocyte specific genes: HNF1A, HNF1B, HNF4A, HHEX, ONECUT1, ONECUT2, PROX1, CDH1, FOXA2, GATA6, FOXM1, CEBPA, CEBPB, CEBPD, CEBPG, GLUL, KRT7, KRT19 and MET; and/or
- does not express at least one, preferably all, of the following hepatocyte/cholangiocyte specific genes: NEUROG2, IGF1R and CD34, AFP, GCG and PTF1A, for example, it does not express NEUROG2, IGF1R and CD34; and/or
- expresses at least one, preferably all, of the following hepatocyte specific genes: TTR, ALB, FAH, TAT, CYP3A7, APOA1, HMGCS1, PPARG, CYP2B6, CYP2C18, CYP2C9, CYP2J2, CYP3A4, CYP3A5, CYP3A7, CYP4F8, CYP4V2 and SCARB1.

Uses of the organoids described herein and cells derived from the organoids are likewise provided. For example, the invention also provides the use of an organoid of the invention or a cell derived from said organoid in a drug discovery screen; toxicity assay; research of tissue embryology, cell lineages, and differentiation pathways; gene expression studies including recombinant gene expression; research of mechanisms involved in tissue injury and repair; research of inflammatory and infectious diseases; studies of pathogenetic mechanisms; or studies of mechanisms of cell transformation and aetiology of cancer.

The invention also provides an organoid of the invention, or a cell derived from said organoid, for use in medicine.

The invention also provides an organoid of the invention, or a cell derived from said organoid, for use in treating a disorder, condition or disease.

The invention also provides an organoid of the invention, or a cell derived from said organoid for use in regenerative medicine, for example, wherein the use involves transplantation of the organoid or cell into a patient.

The invention also provides a pharmaceutical formulation comprising one or more receptor tyrosine kinase ligands, a Wnt agonist wherein the Wnt agonist is an Lgr5 agonist, a TGF beta inhibitor, and a cAMP pathway activator, and a pharmaceutically acceptable diluent and/or excipient.

DETAILED DESCRIPTION OF THE INVENTION

Methods for culturing epithelial stem cells from a variety of tissues have previously been described in WO2010/090513, WO2012/014076 and WO2012/168930. The present inventors have surprisingly found that adding a cAMP pathway activator to the culture medium allows human epithelial stem cells to be cultured for an increased number of passages compared to when the cAMP pathway activator is absent from the medium.

The ability to keep the cells and resulting organoids alive for longer and increase the passage number advantageously allows more cells to be obtained from a single starting cell or from a collection of starting cells than was possible using previous methods. This enables a large number of cells to be available for various applications, for example, drug screening, in which a large amount of material is required to test various different drugs. The ability to generate the cells from a single starting source is advantageous for such applications where it is necessary to compare results between experiments. Similarly, it means that many cells are available for use in transplants and that multiple patients may be transplanted with cells obtained from a useful donor.

Culturing the cells in an expansion medium allows the cells to multiply whilst retaining their stem or progenitor cell phenotype. Organoids are formed comprising these stem or progenitor cells. Use of the expansion medium is therefore advantageous for providing increased numbers of these useful stem or progenitor cells and for obtaining organoids containing these cells.

Accordingly, there is provided a method for culturing epithelial stem cells, wherein said method comprises culturing one or more epithelial stem cells in contact with an extracellular matrix in the presence of an expansion medium, the expansion medium comprising a basal medium for animal or human cells to which is added one or more receptor tyrosine kinase ligands, one or more Wnt agonist preferably wherein the Wnt agonist is an Lgr5 agonist, a TGF-beta inhibitor and a cAMP pathway activator.

There is also provided an expansion medium comprising a basal medium for animal or human cells to which is added one or more receptor tyrosine kinase ligands, one or more Wnt agonist preferably wherein the Wnt agonist is an Lgr5 agonist, a TGF-beta inhibitor and a cAMP pathway activator, for example, for use in the above method.

In some embodiments, the expansion medium comprises a basal medium and one or more of an EGF receptor activator (e.g. EGF), an FGF receptor 2 or FGF receptor 4 activator (e.g. FGF), an HGF receptor activator (e.g. HGF) as receptor tyrosine kinase ligands, a Wnt agonist preferably wherein the Wnt agonist is an Lgr5 agonist (e.g. Rspondin), a TGF beta inhibitor a cAMP pathway activator (e.g. forskolin) and Nicotinamide.

The invention therefore provides the use of a cAMP pathway activator for culturing epithelial stem cells. The invention also provides a method for culturing epithelial stem cells which uses an expansion medium as described in WO 2012/014076 or WO2012/168930 to which a cAMP pathway activator is added.

The cAMP pathway activator may be any suitable activator which increases the levels of cAMP in a cell. The cAMP pathway involves activation of many types of hormone and neurotransmitter G-protein coupled receptors. Binding of the hormone or neurotransmitter to its membrane-bound receptor induces a conformational change in the receptor that leads to activation of the α-subunit of the G-protein. The activated G subunit stimulates, while the non-activated G subunit inhibits adenylyl cyclase. Stimulation of adenylyl cyclase catalyzes the conversion of cytoplasmic ATP to cAMP thus increasing the levels of cAMP in the cell. Therefore, the cAMP pathway activator may, for example, be an adenylyl cyclase activator. Examples of suitable adenylyl cyclase activators include forskolin, a forskolin analogue and cholera toxin. In some embodiments, the cAMP pathway activator is forskolin. In some embodiments, the cAMP pathway activator is not cholera toxin. In some embodiments the cAMP pathway activator may be a cAMP analog, for example 8-bromo-cAMP. 8-bromo-cAMP is a cell-permeable cAMP analog having greater resistance to hydrolysis by phosphodiesterases than cAMP. In some embodiments, the cAMP pathway activator is NKH477 (e.g. catalogue no. Tocris 1603).

cAMP pathway activators can be identified using methods known in the art, for example, using a competitive immunoassay which measures cAMP levels. The CatchPoint® Cyclic-AMP Fluorescent Assay Kit (Molecular Devices LLC) is an example of a commercially available kit for carrying out such an immunoassay. The cAMP in the sample or standard competes with horseradish peroxidase (HRP)-labeled cAMP conjugate for binding sites on the anti-cAMP antibodies. In the absence of cAMP, most of the HRP-cAMP conjugate is bound to the antibody. Increasing concentrations of cAMP competitively decrease the amount of bound conjugate, thus decreasing measured HRP activity. A cAMP pathway activator would result in increased levels of cAMP and decreased measured HRP activity, compared to a control.

In some embodiments, the cAMP pathway activator is used at a concentration of between about 10 nM to about 500 μM, about 10 nM to about 100 μM, about 1 μM to about 50 μM, about 1 μM to about 25 μM, about 5 μM to about 1000 μM, about 5 μM to about 500 μM, about 5 μM to about 100 μM, about 5 μM to about 50 μM, about 5 μM to about 25 μM, about 10 μM to about 1000 μM, about 10 μM to about 500 μM, about 10 μM to about 100 μM, about 10 μM to about 50 μM, about 10 μM to about 25 μM, or about 20 μM. In some embodiments the cAMP pathway activator is used at a concentration of at least 10 nM, 20 nM, 50 nM, 100 nM, 200 nM, 500 nM, 1 μM, at least 2 μM, at least 5 μM, at least 10 μM, at least 20 μM, at least 30 μM, at least 50 μM, or at least 100 μM.

The concentration selected may depend upon the cAMP pathway activator used and can be determined by the person skilled in the art depending upon the potency of the cAMP pathway activator. For example, NKH477 is generally more potent than 8-BR-cAMP and forskolin. A more potent cAMP pathway activator can be used at lower concentrations to the same effect.

For example, NKH477 can in some embodiments be used at a concentration of between about 100 nM and about 10 μM, or at a concentration of about 100 nM, about 1 μM or about 10 μM. 8-BR-cAMP or forskolin can in some embodiments be used at a concentration of between about 1 μM and about 100 μM, or at a concentration of about 1 μM, about 10 μM or about 100 μM.

Cholera toxin can in some embodiments be used at a concentration of between about 1 ng/ml and about 500 ng/ml, about 10 ng/ml and about 100 ng/ml, about 50 ng/ml and about 100 ng/ml, or about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 200 ng/ml, about 300 ng/ml, about 400 ng/ml or about 500 ng/ml.

It has also surprisingly been found that the presence of a BMP pathway activator in the expansion medium increases the number of passages possible for human cells compared to the methods described in WO2012/168930 and WO2012/014076. For example, FIG. 2 shows it allows human liver cells to be passaged 8 times as opposed to only 5 times using the previous techniques. Although this increase is not as significant as the increase obtained using a cAMP pathway activator, it is still useful as it allows more cells to be obtained than using the previous methods.

Thus in some embodiments, the expansion medium of the invention further comprises a BMP pathway activator. In some embodiments, the BMP pathway activator is selected from BMP7, BMP4 and BMP2. BMP7 is preferred. BMP7 induces the phosphorylation of SMAD1 and SMAD5. Thus in some embodiments, where BMP7 is mentioned, any compound that induces the phosphorylation of SMAD1 or SMAD5 can be used instead of BMP7.

The invention therefore provides the use of a BMP activator for culturing epithelial stem cells. The invention also provides a method for culturing epithelial stem cells which uses an expansion medium as described in WO 2012/014076 or WO2012/168930 to which a BMP activator is added.

Accordingly, in some embodiments, the expansion medium comprises a cAMP pathway activator and a BMP activator. However, in some embodiments, the expansion medium comprises a cAMP pathway activator in the absence of a BMP activator. It is also envisaged that the expansion medium may comprise a BMP activator in the absence of a cAMP pathway activator.

The epithelial stem cells of the invention are epithelial cells from epithelial tissue which express Lgr5. They are also known as Lgr5 positive cells.

Receptor Tyrosine Kinase Ligands

Epidermal growth factor (EGF), fibroblast growth factor (FGF) and hepatocyte growth factor (HGF) are preferably all present in the expansion medium. In the context of a culture medium of the invention, EGF is also referred to herein as "E", FGF is also referred to herein as "F" and HGF is also referred to herein as "H". They are also referred to herein as "receptor tyrosine kinase ligands". Many receptor tyrosine kinase ligands are mitogenic growth factors. In some embodiments, the one or more receptor tyrosine kinase ligands in the expansion medium are selected from the group consisting of: FGF, HGF and EGF, wherein the FGF is preferably an FGF able to bind to FGFR2 or FGFR4 and is preferably FGF10.

In some embodiments. the one or more receptor tyrosine kinase ligands in the expansion medium are EGF and FGF. In some embodiments. the one or more receptor tyrosine kinase ligands in the expansion medium are EGF and HGF. In some embodiments. the one or more receptor tyrosine kinase ligands in the expansion medium are HGF and FGF. In some embodiments, only one receptor tyrosine kinase ligand is included in the expansion medium, which may be selected from FGF, HGF and EGF.

Any suitable EGF may be used, for example, EGF obtained from Peprotech. EGF is preferably added to the basal culture medium at a concentration of between 5 and 500 ng/ml. A preferred concentration is at least 10, 20, 25, 30, 40, 45, or 50 ng/ml and not higher than 500, 450, 400, 350, 300, 250, 200, 150, or 100 ng/ml. A more preferred concentration is at least 50 and not higher than 100 ng/ml. An even more preferred concentration is about 50 ng/ml. In some embodiments, EGF is substituted with an alternative compound that activates the EGF receptor. For example, it is envisaged that IGF may be substituted for EGF.

The FGF used in the expansion medium is preferably an FGF able to bind to FGF receptor 2 (FGFR2) or FGF receptor 4 (FGFR4), and is preferably FGF4, FGF7 or FGF10 (preferably from Peprotech), most preferably FGF10. In some embodiments, no more than one FGF is used. In other embodiments, two or more FGF are used, e.g. 2, 3 or more. In some embodiments, FGF is substituted with a compound that activates the FGFR2 or FGFR4 pathway (a "FGF-pathway activator").

FGF10 is a protein that belongs to the fibroblast growth factor (FGF) family of proteins. FGF family members possess broad mitogenic and cell survival activities, and are involved in a variety of biological processes, including embryonic development, cell growth, morphogenesis, tissue repair, tumor growth and invasion. FGFs stimulate cells by interacting with cell surface tyrosine kinase receptors (FGFR). Four closely related receptors (FGFR1-FGFR4) have been identified. FGFR1-FGFR3 genes have been shown to encode multiple isoforms, and these isoforms can be critical in determining ligand specificity. Most FGFs bind more than one receptor (Ornitz J Biol Chem. 1998 Feb. 27; 273 (9):5349-57). However, FGF10 and FGF7 are unique among FGFs in that they interact only with a specific isoform of FGFR2, designated FGFR2b which is expressed exclusively by epithelial cells (Igarashi, J Biol Chem. 1998 273(21):13230-5). FGF10 is a preferred FGF able to bind to FGFR2 or FGFR4. In some embodiments, FGF is substituted with an alternative compound that activates FGFR2 or FGFR4.

Preferred concentrations for FGF10 are about 20, 50, 100, 250, 500 ng/ml, not higher than 500 ng/ml.

Hepatocyte growth factor/scatter factor (HGF/SF) is a morphogenic factor that regulates cell growth, cell motility, and morphogenesis by activating a tyrosine kinase signaling cascade after binding to the proto-oncogenic c-Met receptor. Any suitable HGF may be used, for example, HGF obtained from Peprotech. In some embodiments, HGF is substituted with a compound that activates the HGF receptor.

Preferred concentrations for HGF are about 1, 10, 20, 25, 50 ng/ml, not higher than 50 ng/ml.

Three or more, for example, 3, 4, 5 or more receptor tyrosine kinase ligands may be used in the expansion medium.

During culturing of stem cells, said combination of receptor tyrosine kinase ligands (e.g. EGF, FGF10 and HGF) is preferably added to the culture medium when required, for example, daily or every other day. They may be added singularly or in combination. It is preferable that they are added every second day.

Wnt Agonist

The expansion medium of the invention comprises a Wnt agonist. In the context of a culture medium of the invention, the Wnt agonist is also referred to herein as "W". The Wnt signalling pathway is defined by a series of events that occur when the cell-surface Wnt receptor complex, comprising a Frizzled receptor, LRP and LGR is activated, usually be an extracellular signalling molecule, such as a member of the Wnt family. This results in the activation of Dishevelled family proteins which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist is defined as an agent that activates TCF/LEF-mediated transcription in a cell. Wnt agonists are therefore selected from true Wnt agonists that bind and activate the Wnt receptor complex including any and all of the Wnt family proteins, an inhibitor of intracellular β-catenin degradation, a GSK inhibitor (such as CHIR9901) and activators of TCF/LEF.

In some embodiments, a Wnt agonist is a secreted glycoprotein including Wnt-I/Int-1, Wnt-2/Irp (InM-related Protein), Wnt-2b/13, Wnt-3/Int-4, Wnt-3a (R&D systems), Wnt-4, Wnt-5a, Wnt-5b, Wnt-6 (Kirikoshi H et al 2001 Biochem Biophys Res Corn 283 798-805), Wnt-7a (R&D systems), Wnt-7b, Wnt-8a/8d, Wnt-8b, Wnt-9a/14, Wnt-9b/14b/15, Wnt-10a, Wnt-10b/12, WnM I, and Wnt-16. An overview of human Wnt proteins is provided in "THE WNT FAMILY OF SECRETED PROTEINS", R&D Systems Catalog, 2004. In some embodiments, the Wnt agonist is an inhibitor of RNF43 or ZNRF3. It has been shown that RNF43 and ZNRF3 reside in the cell membrane and negatively regulate levels of the Wnt receptor complex in the membrane, probably by ubiquitination of Frizzled. Therefore, the inventors hypothesise that inhibition of RNF43 or ZNRF3 with antagonistic antibodies, RNAi or small molecule inhibitors would indirectly stimulate the Wnt pathway. RNF43 and ZNRF3 have a catalytic ring domain (with ubiquitination activity), which can be targeted in small molecule inhibitor design. Several anti-RNF43 antibodies and several anti-ZNRF3 antibodies are available commercially. In some embodiments, such antibodies are suitable Wnt agonists in the context of the invention.

The Wnt agonist in the expansion medium is preferably any agonist able to stimulate the Wnt pathway via the Lgr5 cell surface receptor, i.e. in a preferred embodiment, the Wnt agonist in the expansion medium is an Lgr5 agonist. Known Lgr5 agonists include Rspondin, fragments and derivatives thereof, and anti-Lgr5 antibodies (e.g. see WO 2012/140274 and De Lau, W. et al. Nature, 2011 Jul. 4; 476(7360):293-7). A preferred Lgr5 agonist is Rspondin. Any suitable Rspondin may be used, for example, it may be selected from one or more of Rspondin 1, Rspondin 2, Rspondin 3 and Rspondin 4 or derivatives thereof. For example, any of Rspondin 1 (NU206, Nuvelo, San Carlos, CA), Rspondin 2 ((R&D systems), Rspondin 3, and Rspondin-4) may be used. Rspondin 1, 2, 3, and 4 are also referred to herein as "Rspondin 1-4". In the context of a culture medium of the invention, Rspondin is referred to herein as "R". A preferred expansion medium of the invention is referred to as "ERFHNic" supplemented with a cAMP pathway activator. An example of an agonistic anti-Lgr5 antibody is 1D9 (available commercially from BD Biosciences, BDB562733, No.:562733). Therefore, in one embodiment, the agonist is the antibody 1D9. The VL of antibody 1D9 is represented by SEQ ID NO: 1 and the VH is represented by SEQ ID NO: 2. Therefore, in one embodiment, the agonist is an antibody comprising or consisting of SEQ ID NO: 1 and/or SEQ ID NO: 2. Fragments of Rspondin may be used as the Wnt agonist. For example, in some embodiments the Wnt agonist is a fragment of Rspondin comprising or consisting of the furin domain. Examples of Rspondin fragments are represented by the sequence of amino acids recited in SEQ ID NO: 3, SEQ ID NO: 4, SEQ ID NO: 5 or SEQ ID NO: 6 or of sequences with more than 70, 80, 90 or 99% identity to any one of SEQ ID NO: 3, SEQ ID NO: 4, SEQ ID NO: 5 or SEQ ID NO: 6.

The Wnt agonist is preferably added to the media in an amount effective to stimulate a Wnt activity in a cell by at least 10%, more preferred at least 20%, more preferred at least 30%, more preferred at least 50%, more preferred at least 70%, more preferred at least 90%, more preferred at least 100%, relative to a level of said Wnt activity in the absence of said molecule, as assessed in the same cell type. As is known to a skilled person, Wnt activity can be determined by measuring the transcriptional activity of Wnt, for example by pTOPFLASH and pFOPFLASH Tcf luciferase reporter constructs (Korinek et al., 1997. Science 275: 1784-1787).

A soluble Wnt agonist, such as Wnt-3a, may be provided in the form of Wnt conditioned media. For example, about 10% to about 30%, e.g. about 10 ng/ml to about 10 µg/ml, preferably about 1 µg/ml, Wnt conditioned media may be used.

Rspondin 1-4 may be provided in the form of Rspo conditioned media. For example, about 10% to about 30%, e.g. about 10 ng/ml to about 10 µg/ml, preferably about 1 µg/ml, Rspo conditioned media may be used.

Examples of Rspondin mimics suitable for use in the invention are provided in WO 2012/140274, which is incorporated herein by reference.

One or more, for example, 2, 3, 4 or more Wnt agonists may be used in the expansion medium. In one embodiment, the expansion medium comprises an Lgr5 agonist, for example Rspondin, and additionally comprises a further Wnt agonist. In this context, the further Wnt agonist may, for example, be selected from the group consisting of Wnt-3a, a GSK-inhibitor (such as CHIR99021), Wnt-5, Wnt-6a and Norrin. In one embodiment, the expansion medium comprises Rspondin and additionally comprises a soluble Wnt ligand, such as Wnt3a. Addition of a soluble Wnt ligand has been shown to be particularly advantageous for expansion of human epithelial stem cells (as described in WO2012/168930).

Any suitable concentration of Wnt agonist, e.g. Rspondin, may be used, for example, at least 200 ng/ml, more preferred at least 300 ng/ml, more preferred at least 500 ng/ml. A still more preferred concentration of Rspondin is at least 500 ng/ml or about 1 µg/ml.

During culturing of stem cells, said Wnt agonist may be added to the culture medium when required, for example, daily or every other day. The Wnt agonist is preferably added to the culture medium every second day.

Antibodies, such as agonistic anti-Lgr5 antibodies or antagonistic TGF-beta inhibitors (see below), used in the invention may be any antibodies, fragments, etc. A conventional antibody is comprised of two identical heavy chains and two identical light chains that are joined by disulfide bonds. Each heavy and light chain contains a constant region and a variable region. Each variable region contains three CDRs which are primarily responsible for binding an epitope of an antigen. They are referred to as CDR1, CDR2, and CDR3, numbered sequentially from the N-terminus, of which the CDR3 region comprises the most variable region and normally provides a substantial part of the contact residues to a target. The more highly conserved portions of the variable regions are called the "framework regions".

The term antibody is used herein in the broadest sense and specifically covers, but is not limited to, monoclonal antibodies (including full length monoclonal antibodies) of any isotype such as IgG, IgM, IgA, IgD and IgE, polyclonal antibodies including recombinant polyclonal antibodies, Oligoclonics, multispecific antibodies, chimeric antibodies, nanobodies, diabodies, BiTE's, Tandabs, mimetobodies, bispecific antibodies, humanized antibodies, human antibodies, deimmunised antibodies and antibody fragments. In addition, scaffolds will be covered under this term, such as Anticalins, Ankarins, etc. An antibody reactive with a the specific epitopes of the Lgr proteins discussed above can be generated by recombinant methods such as selection of libraries of recombinant antibodies in phage or similar vectors, or by immunizing an animal with the Lgr epitopes of nucleic acid encoding them.

In one embodiment, an antibody according to the invention comprises a single domain antibody, a F(ab')2, Fab, Fab', Facb, or single chain Fv (scFv) fragment. An Fc fragment, which for example activates complement and may bind to Fc receptors, can be present but is not required for an antibody and variants or derivatives thereof. A scFv fragment is an epitope-binding fragment that contains at least one fragment of an antibody heavy chain variable region (VH) linked to at least one fragment of an antibody light chain variable region (VL). The linker may be a short, flexible peptide selected to assure that the proper three-dimensional folding of the VL and VH regions occurs once they are linked so as to maintain the target molecule binding-specificity of the whole antibody from which the single-chain antibody fragment is derived. The carboxyl terminus of the VL or VH sequence may be covalently linked by a linker to the amino acid terminus of a complementary VL or VH sequence.

The antibody may be a diabody, mimetibody, nanobody, and/or a bispecific antibody. A nanobody is a single domain antibody that occurs naturally in camelids. In contrast to standard antibodies, nanobodies are relatively simple proteins comprising only a heavy chain-like variable region. Bispecific antibodies are artificially engineered monoclonal antibodies that consist of two distinct binding sites and are capable of binding two different epitopes. Examples of bispecific antibodies are discussed in more detail below in the section on dual-targeting and multi-targeting agonists.

The antibody may be a chimeric antibody comprising a binding portion, for example the variable region or part thereof of the heavy and light chains, of a non-human antibody, while the remainder portion, for example the constant region of the heavy and light chains, is of a human antibody. A chimeric antibody may be produced by recombinant processes well known in the art, and has an animal variable region and a human constant region.

The antibody may be a human antibody or a humanized antibody. The term "human antibody" means an antibody in which the variable and constant domain sequences are derived from human sequences. In a humanized antibody, only the complementarity determining regions (CDRs), which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. Methods for humanizing non-human antibodies are known in the art. As is known to the skilled person, antibodies such as rat antibodies can be humanized by grafting their CDRs onto the variable light (VL) and variable heavy (VH) frameworks of human Ig molecules, while retaining those rat framework residues deemed essential for specificity and affinity. Overall, CDR grafted antibodies consist of more than 80% human amino acid sequences.

In some embodiments, the antibody is a deimmunised antibody in which the T and B cell epitopes have been eliminated. They have reduced immunogenicity when applied in vivo.

TGF-Beta Inhibitor

The expansion medium comprises a TGF-beta inhibitor. The presence of a TGF-beta inhibitor in the expansion media is advantageous because it increases human organoid formation efficiency. TGF-beta signalling is involved in many cellular functions, including cell growth, cell fate and apoptosis. Signalling typically begins with binding of a TGF-beta superfamily ligand to a type II receptor which recruits and phosphorylates a type I receptor. The type I receptor then phosphorylates SMADs, which act as transcription factors in the nucleus and regulate target gene expression.

The TGF-beta superfamily ligands comprise bone morphogenic proteins (BMPs), growth and differentiation factors (GDFs), anti-müllerian hormone (AMH), activin, nodal and TGF-betas. In general, Smad2 and Smad3 are phosphorylated by the ALK4, 5 and 7 receptors in the TGF-beta/activin pathway. By contrast, Smad1, Smad5 and Smad8 are phosphorylated as part of the bone morphogenetic protein (BMP) pathway. Although there is some cross-over between pathways, in the context of this invention, a "TGF-beta inhibitor" or an "inhibitor of TGF-beta signalling" is preferably an inhibitor of the TGF-beta pathway which acts via Smad2 and Smad3. Therefore, in some embodiments the TGF-beta inhibitor is not a BMP inhibitor, i.e. the TGF-beta inhibitor is not Noggin. In some embodiments, a BMP inhibitor is added to the culture medium in addition to the TGF-beta inhibitor (see below).

Thus the TGF-beta inhibitor may be any agent that reduces the activity of the TGF-beta signalling pathway, preferably the signalling pathway that acts via Smad2 and/or Smad3, more preferably the signalling pathway that acts via ALK4, ALK5 or ALK7. There are many ways of disrupting the TGF-beta signaling pathway that are known in the art and that can be used in conjunction with this invention. For example, the TGF-beta signaling may be disrupted by: inhibition of TGF-beta expression by a small-interfering RNA strategy; inhibition of furin (a TGF-beta activating protease); inhibition of the pathway by physiological inhibitors; neutralisation of TGF-beta with a monoclonal antibody; inhibition with small-molecule inhibitors of TGF-beta receptor kinase 1 (also known as activin receptor-like kinase, ALK5), ALK4, ALK6, ALK7 or other TGF-beta-related receptor kinases; inhibition of Smad 2 and Smad 3 signaling e.g. by overexpression of their physiological inhibitor, Smad 7, or by using thioredoxin as an Smad anchor disabling Smad from activation (Fuchs, O. Inhibition of TGF-Signaling for the Treatment of Tumor Metastasis and Fibrotic Diseases. Current Signal Transduction Therapy, Volume 6, Number 1, January 2011, pp. 29-43(15)).

Various methods for determining if a substance is a TGF-beta inhibitor are known and might be used in conjunction with the invention. For example, a cellular assay may be used in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., Br J Pharmacol. 2005 May; 145(2): 166-177).

A TGF-beta inhibitor according to the present invention may be a protein, peptide, small-molecules, small-interfering RNA, antisense oligonucleotide, aptamer or antibody. The inhibitor may be naturally occurring or synthetic. In one embodiment, the TGF-beta inhibitor is an inhibitor of ALK4, ALK5 and/or ALK7. For example, the TGF-beta inhibitor may bind to and directly inhibit ALK4, ALK5 and/or ALK7. Examples of preferred small-molecule TGF-beta inhibitors that can be used in the context of this invention include the small molecule inhibitors listed in table 1:

TABLE 1

Small-molecule TGF-beta inhibitors targeting receptor kinases

| Inhibitor | Targets | IC50 (nM) | Mol Wt | Name | Formula |
|---|---|---|---|---|---|
| A83-01 | ALK5 (TGF-βR1) | 12 | 421.52 | 3-(6-Methyl-2-pyridinyl)-N-phenyl-4-(4-quinolinyl)-1H-pyrazole-1-carbothioamide | C25H19N5S |
|  | ALK4 | 45 |  |  |  |
|  | ALK7 | 7.5 |  |  |  |
| SB-431542 | ALK5 ALK4 ALK7 | 94 | 384.39 | 4-[4-(1,3-benzodioxol-5-yl)-5-(2-pyridinyl)-1H-imidazol-2-yl]benzamide | C22H16N4O3 |
| SB-505124 | ALK5 ALK4 | 47 129 | 335.4 | 2-(5-benzo[1,3]dioxol-5-yl-2-tert-butyl-3Himidazol-4-yl)-6-methylpyridine hydrochloride hydrate | C20H21N3O2 |
| SB-525334 | ALK5 | 14.3 | 343.42 | 6-[2-(1,1-Dimethylethyl)-5-(6-methyl-2-pyridinyl)-1H-imidazol-4-yl]quinoxaline | C21H21N5 |
| SD-208 | ALK5 | 49 | 352.75 | 2-(5-Chloro-2-fluorophenyl)-4-[(4-pyridyl)amino]pteridine | C17H10ClFN6 |
| LY-36494 | TGR-βRI | 59 | 272.31 | 4-[3-(2-Pyridinyl)-1H-pyrazol-4-yl]-quinoline | C17H12N4 |
|  | TGF-βRII | 400 |  |  |  |

TABLE 1-continued

Small-molecule TGF-beta inhibitors targeting receptor kinases

| Inhibitor | Targets | IC50 (nM) | Mol Wt | Name | Formula |
|---|---|---|---|---|---|
| | MLK-7K | 1400 | | | |
| SJN-2511 | ALK5 | 23 | 287.32 | 2-(3-(6-Methylpyridine-2-yl)-1H-pyrazol-4-yl)-1,5-naphthyridine | C17H13N5 |

In some embodiments, the TGF-beta inhibitor is a small molecule inhibitor optionally selected from the group consisting of: A83-01, SB-431542, SB-505124, SB-525334, LY 364947, SD-208 and SJN 2511.

In some embodiments, no more than one TGF beta inhibitor is present in the expansion medium. In other embodiments, more than one TGF beta inhibitor is present in the expansion medium, e.g. 2, 3, 4 or more. In some embodiments, an expansion medium of the invention comprises one or more of any of the inhibitors listed in table 1. An expansion medium may comprise any combination of one inhibitor with another inhibitor listed. For example, an expansion medium may comprise SB-525334 or SD-208 or A83-01; or SD-208 and A83-01. The skilled person will appreciate that a number of other small-molecule inhibitors exist that are primarily designed to target other kinases, but at high concentrations may also inhibit TGF-beta receptor kinases. For example, SB-203580 is a p38 MAP kinase inhibitor that, at high concentrations (for example, approximate 10 μM or more) is thought to inhibit ALK5. Any such inhibitor that inhibits the TGF-beta signalling pathway can also be used in the context of this invention.

In some embodiments, the TGF beta inhibitor is present at at least 5 nM, for example, at least 50 nM, at least 100 nM, at least 300 nM, at least 450 nM, at least 475 nM, for example 5 nM-500 mM, 10 nM-100 mM, 50 nM-700 uM, 50 nM-10 uM, 100 nM-1000 nM, 350-650 nM or more preferably about 500 nM.

A83-01 may be added to the expansion medium at a concentration of between 10 nM and 10 uM, or between 1 uM and 8 uM, or between 4 uM and 6 uM. For example, A83-01 may be added to the expansion medium at about 5 uM. The skilled person would know how to determine the concentration of other TGF beta inhibitors for use in the invention.

Prostaglandin Pathway Activator

In some embodiments, the expansion medium is supplemented with an activator of the prostaglandin signalling pathway (also called a prostaglandin pathway activator). For example, the expansion medium may be supplemented with any one or more of the compounds selected from the list comprising: Phospholipids, Arachidonic acid (AA), prostaglandin E2 (PGE2), prostaglandin G2 (PGG2), prostaglandin F2 (PGF2), prostaglandin H2 (PGH2), prostaglandin D2 (PGD2). In some embodiments, the expansion medium is supplemented with PGE2 and/or AA. In some embodiments, PGE2 is added to the expansion medium to a final concentration of at least 10 nM, at least 30 nM, at least 40 nM, at least 45 nM, at least 50 nM, for example between 10 nM and 500 nM, between 10 nM and 400 nM, between 10 nM and 300 nM, between 10 nM and 200 nM, between 10 nM and 100 nM, between 20 nM and 50 nM. In a preferred embodiment in which PGE2 is present, PGE2 is added to the expansion medium to a final concentration of 50 nM. In some embodiments, AA is added to the expansion medium to a final concentration of at least 1 ug/ml, for example at least 3 ug/ml, at least 5 ug/ml, at least 8 ug/ml, at least 9 ug/ml, at least 10 ug/ml, between 1 ug/ml and 1000 ug/ml, between 1 ug/ml and 500 ug/ml, between 1 ug/ml and 100 ug/ml, between 1 ug/ml and 50 ug/ml, or between 5 ug/ml and 10 ug/ml. In a preferred embodiment in which AA is present, AA is added to the medium to a final concentration of 10 ug/ml.

In some embodiments, PGE2 and/or AA are absent from the expansion medium of the invention. In some embodiments, a prostaglandin pathway activator is absent from the expansion medium of the invention. The inventors have observed that, at least for liver cells, the presence of prostaglandin pathway activators in the expansion medium may change the phenotype of the cells being expanded and can result in cells that do not differentiate and which have lost some stem cell markers and ductal markers.

BMP Inhibitors

In some embodiments, the expansion medium may comprise any suitable BMP inhibitor. BMPs bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (SMAD), resulting in a signal transduction pathway leading to transcriptional activity.

A BMP inhibitor is defined as an agent that binds to a BMP molecule to form a complex wherein the BMP activity is neutralized, for example by preventing or inhibiting the binding of the BMP molecule to a BMP receptor. Alternatively, said inhibitor is an agent that acts as an antagonist or reverse agonist. This type of inhibitor binds with a BMP receptor and prevents binding of a BMP to said receptor. An example of a latter agent is an antibody that binds a BMP receptor and prevents binding of BMP to the antibody-bound receptor.

A BMP inhibitor may be added to the media in an amount effective to inhibit a BMP-dependent activity in a cell to at most 90%, more preferred at most 80%, more preferred at most 70%, more preferred at most 50%, more preferred at most 30%, more preferred at most 10%, more preferred 0%, relative to a level of a BMP activity in the absence of said inhibitor, as assessed in the same cell type. As is known to a skilled person, a BMP activity can be determined by measuring the transcriptional activity of BMP, for example as exemplified in Zilberberg et al., 2007. BMC Cell Biol. 8:41.

Several classes of natural BMP-binding proteins are known, including Noggin (Peprotech), Chordin and chordin-like proteins (R&D systems) comprising chordin domains, Follistatin and follistatin-related proteins (R&D systems) comprising a follistatin domain, DAN and DAN-like proteins (R&D systems) comprising a DAN cysteine-knot domain, sclerostin/SOST (R&D systems), decorin (R&D systems), and alpha-2 macroglobulin (R&D systems).

Examples of BMP inhibitors for use in a method of the invention are Noggin, DAN, and DAN-like proteins including Cerberus and Gremlin (R&D systems). These diffusible proteins are able to bind a BMP ligand with varying degrees of affinity and inhibit their access to signalling receptors. The addition of any of these BMP inhibitors to the basal culture medium prevents the loss of stem cells.

A preferred BMP inhibitor is Noggin. In the context of a culture medium of the invention, Noggin is also referred to herein as "N". Noggin is preferably added to the basal culture medium at a concentration of at least 10 ng/ml, for example, at least 20 ng/ml, more preferred at least 25 ng/ml. A still more preferred concentration is about 25 ng/ml.

During culturing of stem cells, said BMP inhibitor may be added to the culture medium when required, for example, daily or every other day. The BMP inhibitor is preferably added to the culture medium every second day. The culture medium may be refreshed when required, for example, daily or every other day.

The BMP inhibitor and BMP pathway activator are not normally included in the expansion medium at the same time. In a preferred embodiment, the BMP inhibitor is only included in the first few days (e.g. first 2 days) of culture, preferably when Wnt, e.g. in the form of Wnt-conditioned medium is present. After the first few days (e.g. first 2 days) of culture in this "first" expansion medium (EM1), the medium is changed to a "second" expansion medium (EM2) which comprises a BMP pathway activator but does not comprise a BMP inhibitor. Thus, in some embodiments the expansion medium (e.g. EM2) does not comprise a BMP inhibitor. In some embodiments, the expansion medium (e.g. EM1) does not comprise a BMP pathway activator. In some embodiments, the expansion medium (e.g. EM2) does not comprise Wnt. In some embodiments, the expansion medium comprises either a BMP inhibitor or a BMP pathway activator.

Additional Components

The expansion medium optionally comprises Nicotinamide and is preferably supplemented with one or more (e.g. 1, 2, 3 or all) of the compounds selected from the group consisting of gastrin, B27, N-acetylcystein and N2. Thus in some embodiments the expansion medium described above further comprises one or more components selected from the group consisting of: a further Wnt agonist, a BMP inhibitor, nicotinamide, gastric, B27, N2 and N-Acetylcysteine. In some embodiments, the expansion medium described above further comprises one or more components selected from the group consisting of: nicotinamide, gastric, B27, N2 and N-Acetylcysteine.

In some embodiments, the expansion medium comprises gastrin.

B27 (Invitrogen), N-Acetylcysteine (Sigma) and N2 (Invitrogen), Gastrin (Sigma) and Nicotinamide (Sigma) are believed to control proliferation of the cells and assist with DNA stability. In the context of the invention, Nicotinamide is also referred to herein as "Nic".

In some embodiments, Nicotinamide is present at 7-15 mM, for example about 10 mM.

In some embodiments, the B27 supplement is 'B27 Supplement minus Vitamin A' (available from Invitrogen, Carlsbad, CA; www.invitrogen.com; currently catalog no. 12587010; and from PAA Laboratories GmbH, Pasching, Austria; www.paa.com; catalog no. F01-002; Brewer et al., J Neurosci Res., 35(5):567-76, 1993) may be used to formulate a culture medium that comprises biotin, cholesterol, linoleic acid, linolenic acid, progesterone, putrescine, retinyl acetate, sodium selenite, tri-iodothyronine (T3), DL-alpha tocopherol (vitamin E), albumin, insulin and transferrin. The B27 supplement minus vitamin A was shown to work particularly well in the expansion medium for the liver. The B27 Supplement supplied by PAA Laboratories GmbH comes as a liquid 50× concentrate, containing amongst other ingredients biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin. Of these ingredients at least linolenic acid, retinol, retinyl acetate and tri-iodothyronine (T3) are nuclear hormone receptor agonists. B27 Supplement may be added to a culture medium as a concentrate or diluted before addition to a culture medium. It may be used at a 1× final concentration or at other final concentrations. Use of B27 Supplement is a convenient way to incorporate biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin into a culture medium of the invention. It is also envisaged that some or all of these components may be added separately to the expansion medium instead of using the B27 Supplement. Thus, the expansion medium may comprise some or all of these components.

In some embodiments, retinoic acid is absent from the B27 Supplement used in the expansion medium, and/or is absent from the expansion medium.

'N2 Supplement' is available from Invitrogen, Carlsbad, CA; www.invitrogen.com; catalog no. 17502-048; and from PAA Laboratories GmbH, Pasching, Austria; www.paa.com; catalog no. F005-004; Bottenstein & Sato, PNAS, 76(1): 514-517, 1979. The N2 Supplement supplied by PAA Laboratories GmbH comes as a 100× liquid concentrate, containing 500 µg/ml human transferrin, 500 µg/ml bovine insulin, 0.63 µg/ml progesterone, 1611 µg/ml putrescine, and 0.52 µg/ml sodium selenite. N2 Supplement may be added to a culture medium as a concentrate or diluted before addition to a culture medium. It may be used at a 1× final concentration or at other final concentrations. Use of N2 Supplement is a convenient way to incorporate transferrin, insulin, progesterone, putrescine and sodium selenite into a culture medium of the invention. It is of course also envisaged that some or all of these components may be added separately to the expansion medium instead of using the N2 Supplement. Thus, the expansion medium may comprise some or all of these components.

In some embodiments in which the medium comprises B27, it does not also comprise N2. The embodiments of the present invention can therefore be adapted to exclude N2 when B27 is present, if desired.

In some embodiments N2 is not present in the expansion medium.

In some embodiments in which the medium comprises N2, it does not also comprise B27. The embodiments of the present invention can therefore be adapted to exclude B27 when N2 is present, if desired.

In some embodiments B27 is not present in the expansion medium.

In some embodiments the expansion medium is supplemented with B27 and/or N2.

In some embodiments the basal medium is supplemented with 150 ng/ml to 250 ng/ml N-Acetylcysteine; preferably, the basal medium is supplemented with about 200 ng/ml N-Acetylcysteine.

In some embodiments, the expansion medium further comprises one or more (e.g. 1, 2, 3, 4, 5 or all 6) of the following components: jagged 1, thiazovivin, a p38 inhibitor (e.g. SB202190), SB431542, IGF and valproic acid.

In some embodiments the basal medium may be supplemented with 40 ng/ml to 60 ng/ml EGF; preferably, the basal medium is supplemented with about or exactly 50 ng/ml EGF. For example, in some embodiments the basal medium may be supplemented with 0.5 μg/ml to 1.5 μg/ml Rspondin1; preferably, the basal medium is supplemented with about 1 μg/ml Rspondin1. For example, in some embodiments the basal medium may be supplemented with 5 nM to 15 nM gastrin; preferably, the basal medium is supplemented with about 10 nM gastrin. For example, in some embodiments the basal medium may be supplemented with 25-200 ng/ml FGF10, for example 70 ng/ml to 130 ng/ml FGF10; preferably, the basal medium is supplemented with about 100 ng/ml FGF10. For example, in some embodiments the basal medium may be supplemented with 5 mM to 15 mM Nicotinamide; preferably, the basal medium is supplemented with about 10 mM Nicotinamide. For example, in some embodiments the basal medium may be supplemented with 25 ng/ml to 100 ng/ml HGF, for example 35 ng/ml to 65 ng/ml HGF; preferably, the basal medium is supplemented with about 50 ng/ml HGF. For example, in some embodiments the basal medium may be supplemented with 35% to 65% Wnt-conditioned media; preferably, the basal medium is supplemented with about 50% Wnt-conditioned media.

Expansion Medium 1 (EM1), Expansion Medium 2 (EM2) and Differentiation Medium (DM)

In some embodiments, particularly advantageously for liver cells, the cells may first be expanded in an expansion medium as described above and further comprising a BMP inhibitor, such as Noggin. This is also referred to as the expansion medium 1 (EM1). The cells can then be expanded in a second expansion medium of the invention, as described above that does not contain Wnt or a BMP inhibitor (e.g. Noggin). This second expansion medium is sometimes referred to herein as expansion medium 2 (EM2). In some embodiments, the cells are cultured in EM2 for approximately 1 day, 2 days, 3 days, 4 days, 5 days, 6 days, 7 days or a longer time period, such as 3, 4, 5, 10, 20 or more weeks. As discussed above, the presence of the cAMP pathway activator and/or the BMP activator in the expansion medium, particularly in EM2, advantageously allows human cells to be passaged for a longer time than was possible previously. Thus, the method may comprise culturing the cells in an EM2 of the invention for 6 or more passages, for example, 7 or more, 8 or more, 9 or more, 10 or more, 12 or more, 15 or more or 18 or more passages. This was not possible prior to the present invention.

If required, the expansion medium may then be changed to a differentiation medium as described herein, such as an optimised differentiation medium, e.g. that contains a TGF-beta inhibitor and a Notch inhibitor. In some embodiments the differentiation medium comprises a basal medium for animal or human cells to which is added one or more receptor tyrosine kinase ligands and a Notch inhibitor. In some embodiments, the differentiation medium further comprises one or more of: a TGF-beta inhibitor, gastrin and dexamethasone. Typically, the differentiation medium does not contain a Wnt agonist, Rspondin or Nicotinamide. In some embodiments, the differentiation medium does not contain a prostaglandin pathway activator, such as PGE2 or AA. The differentiation medium encourages the differentiation of the cells, e.g. for liver cells, towards mature hepatocytes and cholangiocytes. These differentiated cells are preferably suitable for transplantation into humans or animals. See further comments on differentiation methods and media below.

Throughout this disclosure, statements referring to "culture medium" may apply to the "expansion medium" and/or "differentiation medium".

In some embodiments, retinoic acid is absent from the expansion medium. In some embodiments, one or more (e.g. 2, 3, 4, or all 5) of retinoic acid, FGF2, DAGKi, human sRANK ligand, and Zardaverine is absent from the expansion medium. In some embodiments, a Notch inhibitor is absent from the expansion medium.

The invention further provides the use of an expansion medium of the invention for culturing cells for at least 6 passages, for example, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60 passages or for between 6-40 passages, for example about 8-35 passages, 10-30 passages, or 12-25 passages. In practice, some embodiments of the invention comprise the use of expansion medium for around 8-50, for example, 10-50, 15-50, 20-50, 20-40 passages of the cells. For example, in some embodiments the cells may be split at a 4-6 or 4-8 dilution every 7-10 days for 2, 3, 4, 5 or 6 or more months. Preferably the cells will expand at a rate of more than two or more than three population doublings a week, for example, about 4-5 fold expansion per week. Preferably the cells are human cells. As mentioned above, human cells could be cultured for only around 5 passages using the expansion medium described in WO2012/168930 and WO2012/014076 could be used for long term culture of mouse cells. In contrast, use of a culture medium comprising a cAMP pathway activator allows human cells to be passaged many more times, for example, 6 or more, e.g. 8, 10, 12 or more, more preferably 16 or more (see FIG. 2).

As explained above, long-term culture of human cells was not possible prior to the present invention. Using the previously available methods, it was not possible to expand human liver cells in culture for more than 2 months. However, using the present invention, it is possible to culture liver cells for more than 2 months, for example at least 10 weeks, at least 3 months, etc. However, it is not always necessary to culture the cells for a long time and so use of expansion medium for shorter periods of time is also envisaged. Accordingly, in some embodiments, the invention provides the use of an expansion medium of the invention for culturing cells for at least 2 weeks, at least 1 month, at least 2 months, more preferably at least 3, at least 4, at least 5, at least 6, at least 7, at least 8, at least 9, at least 10, at least 15, at least 20, at least 24, at least 25, at least 30 or more months, for example 3 or more years. Preferably, the cells are human cells.

Preferably the epithelial stem cells are human epithelial stem cells. However, culturing non-human mammalian epithelial stem cells is also envisaged.

In some embodiments, the epithelial stem cells are selected from liver, pancreas, intestine (e.g. small intestine or colon), stomach, prostate, lung, breast, ovarian, salivary gland, hair follicle, skin, oesophagus and thyroid epithelial stem cells. In a preferred embodiment, the epithelial stem cell is a liver cell. In a further preferred embodiment, the epithelial stem cell is a pancreas cell. In some embodiments, the epithelial stem cell is a liver or a pancreas stem cell. In some embodiments, the epithelial stem cell is not a colon cell or is not a small intestine cell or is not an intestine cell.

Extracellular Matrix

As described above, the method for culturing epithelial stem cells comprises culturing one or more epithelial stem cells in contact with an extracellular matrix. Any suitable extracellular matrix may be used. Isolated epithelial stem cells are preferably cultured in a microenvironment that mimics at least in part a cellular niche in which said stem cells naturally reside. This cellular niche may be mimicked by culturing said stem cells in the presence of biomaterials, such as an extracellular matrix that provides key regulatory signals controlling stem cell fate.

A cellular niche is in part determined by the stem cells and surrounding cells, and the extracellular matrix (ECM) that is produced by the cells in said niche. In a preferred method of the invention, epithelial stem cells are cultured in contact with an ECM. "In contact" means a physical or mechanical or chemical contact, which means that for separating said resulting organoid or population of epithelial stem cells from said extracellular matrix a force needs to be used. Preferably, the epithelial stem cells are embedded in the ECM.

A culture medium of the invention may be diffused into an extracellular matrix (ECM). In a preferred method of the invention, isolated tissue fragments or isolated epithelial stem cells are attached to an ECM. ECM is composed of a variety of polysaccharides, water, elastin, and glycoproteins, wherein the glycoproteins comprise collagen, entactin (nidogen), fibronectin, and laminin. ECM is secreted by connective tissue cells. Different types of ECM are known, comprising different compositions including different types of glycoproteins and/or different combination of glycoproteins. Said ECM can be provided by culturing ECM-producing cells, such as for example fibroblast cells, in a receptacle, prior to the removal of these cells and the addition of isolated tissue fragments or isolated epithelial stem cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (type I, III, and V), chondroitin sulfate proteoglycan, hyaluronic acid, fibronectin, and tenascin-C. Alternatively, said ECM is commercially provided. Examples of commercially available extracellular matrices are extracellular matrix proteins (Invitrogen) and basement membrane preparations from Engelbreth-Holm-Swarm (EHS) mouse sarcoma cells (e.g. Matrigel™ (BD Biosciences)). A further example is Reduced Growth Factor BME 2 (Basement Membrane Extract, Type 2, Pathclear). A synthetic extracellular matrix material, such as ProNectin (Sigma Z378666) may be used. Mixtures of extracellular matrix materials may be used, if desired. The use of an ECM for culturing stem cells enhanced long-term survival of the stem cells and the continued presence of undifferentiated stem cells. In the absence of an ECM, stem cell cultures could not be cultured for longer periods and no continued presence of undifferentiated stem cells was observed. In addition, the presence of an ECM allowed culturing of three-dimensional tissue organoids, which could not be cultured in the absence of an ECM. The extracellular matrix material will normally be a drop on the bottom of the dish in which cells are suspended. Typically, when the matrix solidifies at 37° C., the medium is added and diffuses into the ECM. The cells in the medium stick to the ECM by interaction with its surface structure, for example interaction with integrins. A fibronectin solution of about 1 mg/ml (stock solution) used at approximately 1 µg/cm$^2$ may be used to coat a cell culture vessel, or between about 1 µg/cm$^2$ to about 250 µg/cm$^2$, or at about 1 mg/cm$^2$ to about 150 mg/cm$^2$. In some embodiments, a cell culture vessel is coated with fibronectin at between 8 µg/cm$^2$ and 125 µg/cm$^2$.

An example of an ECM for use in a method of the invention comprises at least one glycoprotein, such as laminin.

A preferred ECM for use in a method of the invention comprises at least two distinct glycoproteins, such as two different types of collagen or a collagen and laminin. The ECM can be a synthetic hydrogel extracellular matrix or a naturally occurring ECM. A further preferred ECM comprises laminin, entactin, and collagen IV. A further preferred ECM is provided by Matrigel™ (BD Biosciences), which comprises laminin, entactin, and collagen IV. In some embodiments the extracellular matrix is a laminin-containing extracellular matrix such as Matrigel™ (BD Biosciences).

In some embodiments, the single stem cell, population of cells, or tissue fragment is embedded in matrigel, which is optionally growth factor reduced and/or phenol red-free.

In some embodiments, the culture medium is placed on top of the ECM. The culture medium can then be removed and replenished as and when required. In some embodiments, the culture medium is replenished every 1, 2, 3, 4, 5, 6 or 7 days. If components are "added" or "removed" from the media, then this can in some embodiments mean that the media itself is removed from the ECM and then a new media containing the "added" component or with the "removed" component excluded is placed on the ECM.

In some embodiments the culture medium of the invention is in contact with an extracellular matrix or a 3D matrix that mimics the extracellular matrix by its interaction with the cellular membrane proteins, such as integrins.

There is further provided an expansion medium of the invention and an extracellular matrix, e.g. supplied as a kit.

The method may advantageously comprise passaging the organoids obtained using the culture method. In some embodiments, one week to 10 day old organoids are removed from the extracellular matrix and mechanically dissociated into small fragments before being transferred to fresh extracellular matrix. The skilled person would know how to split the organoids in order to passage them so that they can multiply without exceeding the concentration limit for their container. In some embodiments, passaging is performed for at least 2 months, for example for 2, 3, 4, 5, 6, 7, 8, 9, 10, 12, 15, 18, 20, 24 or more months. In some embodiments, passaging is performed in 1:4 to 1:8 split ratios once per week for at least 2 months, for example for 2, 3, 4, 5, 6, 7, 8, 9, 10, 12, 15, 18, 20, 24 or more months. In some embodiments, the method comprises passaging the organoids more than 6 times, e.g. more than 7, 8, 9, 10, 12, 15, 18, 20, 25, 30 times. The passaging interval can be adapted as necessary. Suitable examples are twice per week, once per week, once every 10 days, once every two weeks, for example once every 7-10 days. The split of the culture medium can be adapted as necessary. Suitable examples are 1:3-1:10 dilutions, e.g. 1:3-1:9, 1:4-1:8, 1:4-1:6 dilutions. Prior to the present invention, it was not possible to passage human liver organoids this many times or to keep them in culture long-term. In particular, prior to the present invention, it was possible to passage human liver cells only 5 times, when passage at a rate of 1 passage per week, when using the medium described in WO2012/014076 which comprises a TGF-beta inhibitor.

In some embodiments, the method comprises culturing the organoid or a population of epithelial stem cells for at least 6, 8, 10, 12, 14, 16, 18, 20 or 25 weeks.

The expansion medium preferably induces or promotes the survival and/or proliferation of cells during at least 42, 50, 75, 100, 125, 150, 175, 200, 250, 300, 365 days of culture. Proliferation can be assessed using techniques known in the art such as BrdU staining, Edu staining, Ki67 staining and the use of growth curves assay can be done. For example, from 10 biliary ducts, it is possible after 6 days to dilute to 6 wells with 10 organoids per well (60 new organoids). In each passage of 6 days we can generate around 360 organoids. By performing 1 passage/week over 32 weeks we are able to generate over 11,000 (11520) new organoid structures in only 7 months. This is important for the industry, since the availability of cells and organoids for transplantation poses a significant problem. For a mouse transplant, for example, a minimum of $10^5$ cells are required. Possibly $10^6$, or $10 \times 10^6$ might be required for a human transplant, in order for a graft to be successful.

Put another way, media used according to the invention are capable of expanding a population of stem cells to form organoids for at least 6, at least 10, at least 20, at least 30, at least 40, at least 50, at least 60, at least 70, at least 80, at least 90 or at least 100, passages under appropriate conditions.

Isolation of Epithelial Stem Cells for Culture

In a preferred embodiment, the epithelial stem cells to be cultured in the expansion method and/or from which the organoids are derived are obtained from adult tissue, i.e. the epithelial stem cells are adult epithelial stem cells. In this context "adult" means mature tissue, i.e. includes newly-born baby or child but excludes embryonic or foetal. In a preferred embodiment the epithelial stem cells are not derived from embryonic stem cells or embryonic stem cell lines, e.g. which have been differentiated in vitro.

Cells taken directly from live tissue, i.e. freshly isolated cells, are also referred to as primary cells. In some embodiments the epithelial stem cells are primary epithelial stem cells. Primary cells represent the best experimental models for in vivo situations. In a preferred embodiment of the invention, the epithelial stem cells are (or are derived from) primary epithelial stem cells. Primary cell cultures in can be passaged to form secondary cell cultures. With the exception cancer cells, traditional secondary cell cultures have limited lifespan. After a certain number of population doublings (e.g. 50-100 generations) cells undergo the process of senescence and stop dividing. Cells from secondary cultures can become immortalized to become continuous cell lines. Immortalization can occur spontaneously, or may be virally- or chemically-induced. Immortalized cell lines are also known as transformed cells. By contrast, the methods of the present invention allow continuous passaging of epithelial stem cells without immortalisation or transformation. Thus in some embodiments, the epithelial stem cells are not immortalised or transformed cells or are not derived from an immortalised cell line or a transformed cell line. An advantage of the present invention is that the epithelial stem cells, undergoing multiple rounds of expansion and passaging, retain the characteristics of primary cells and have minimal or no genotypic or phenotypic changes.

The epithelial stem cells may be obtained by any suitable method. In some embodiments, cells are isolated by collagenase digestion, for example, as described in the examples and in Dorell et al., 2008 (Hepatology. 2008 October; 48(4):1282-91. Surface markers for the murine oval cell response. Dorrell C, Erker L, Lanxon-Cookson K M, Abraham S L, Victoroff T, Ro S, Canaday P S, Streeter P R, Grompe M). In some embodiments, collagenase digestion is performed on a tissue biopsy. In some embodiments, collagenase and accutase digestion are used to obtain the epithelial stem cells for use in the invention.

In some embodiments, the method comprises culturing a fragment of tissue which comprises epithelium. In some embodiments, the epithelial stem cells are isolated from a tissue fragment. For example, in the context of liver, the tissue fragment may comprise a liver biliary duct or biliary duct tissue. In the context of the intestine, the tissue fragment may comprise a crypt or part of a crypt.

Stem cells are not necessarily always present in the liver but can appear in response to injury or stimulation of Lgr, e.g. by Rspondin, for example in the context of the methods or media of the present invention. Liver epithelial stem cells can be derived from ductal cells, and so, as mentioned above, in some embodiments, the method of the invention comprises culturing a liver biliary duct or biliary duct tissue, or comprises culturing cells isolated from the liver biliary duct or from biliary duct tissue. In addition, crude hepatocyte preparations (not differentially sorted), can be cultured to form organoids. Such preparations comprise both hepatocytes and residual ductal cells. Alternatively, ductal cells can be sorted using the EpCAM+ marker, and these cells allow organoids to be obtained with high efficiency (see Example 14). Therefore, in some embodiments, the method of the invention comprises culturing ductal cells or crude hepatocyte preparations, preferably comprising ductal cells. In some embodiments, the epithelial stem cells cultured in the context of the invention are not hepatocytes and/or are not derived from hepatocytes. In some embodiments, the invention provides the use of isolated ductal cells for generating organoids.

A preferred method for obtaining the epithelial stem cells for culturing is based on the fact that epithelial stem cells according to the invention express Lgr5 and/or Lgr6 on their surface; these proteins belong to the large G protein-coupled receptor (GPCR) superfamily (see, for example, WO 2009/022907, the contents of which are incorporated herein in their entirety). The Lgr subfamily is unique in carrying a large leucine-rich ectodomain important for ligand binding. A preferred method therefore comprises preparing a cell suspension from said epithelial tissue as described above, contacting said cell suspension with an Lgr5 and/or 6 binding compound (such as an antibody, e.g. an anti-Lgr5 monoclonal antibody, e.g. as described in WO 2009/022907), isolating the Lgr5 and/or 6 binding compound, and isolating the stem cells from said binding compound.

An organoid is preferably obtained using a cell from an adult tissue, preferably an epithelial stem cell from an adult tissue, more preferably an epithelial stem cell from an adult tissue expressing Lgr5.

A liver organoid may also be obtained from any cell which upon damage or culturing expresses Lgr5 and is therefore an Lgr5-expressing stem cell. Consequently, it is not necessary for the liver epithelial cells to express Lgr5 before they are contacted with the expansion medium. Culturing the liver epithelial cells in the expansion medium of the invention leads to Lgr5 expression in the stem cells.

In some embodiments the epithelial stem cells are normal cells. In alternative embodiments, the epithelial stem cells are cancer stem cells. Thus, it is envisaged that the stem cells may be Lgr5 positive cancer stem cells. Accordingly, the cells may be obtained from a tumour, if required.

In another preferred embodiment, an organoid originates from a single cell, preferably expressing Lgr5. In some embodiments the single cell comprises a nucleic acid construct comprising a nucleic acid molecule of interest.

In some embodiments, the starting cell to be cultured is a single cell. A single cell suspension comprising the epithelial stem cells can be mechanically generated, e.g. for the liver from the isolated biliary duct. Small tissue fragments generated in this way by mechanical disruption are preferably split at a ratio of about 1:6. If necessary, such fragments can be incubated for a short time (only 2 or 3 minutes) in trypsin at a dilution of approximately 1:2. It has been found that at this stage epithelial stem cells treated with trypsin yielded rather low survival rates: if the cells are split into individual cells, then those with stem cell properties survive. This fraction is rather small (approximately 3-12% of the total cell population).

Preferred Lgr5 and/or 6 binding compounds comprise antibodies, such as monoclonal antibodies that specifically recognize and bind to the extracellular domain of either Lgr5 or Lgr6, such as monoclonal antibodies including mouse and rat monoclonal antibodies (see, for example, WO 2010/016766, the contents of which are incorporated herein in their entirety). Using such an antibody, Lgr5 and/or Lgr6-expressing stem cells can be isolated, for example with the aid of magnetic beads or through fluorescence-activated cell sorting, as is clear to a skilled person. Using a method of the invention, it is possible to isolate one single Lgr5 and/or Lgr6 expressing cell and to apply a method of the invention to it. An organoid or a population of liver epithelial stem cells may therefore be derived from one single cell.

Alternatively, it is also envisaged that a population of cells may be used as the starting point, for example, a population of cells contained in a liver fragment as described above. Thus, the methods of the invention are not restricted to using single cells as the starting point.

In a further aspect, there is provided a method for obtaining an organoid comprising culturing epithelial stem cells in an expansion medium using a method as described herein.

In some embodiments, the method comprises culturing the epithelial stem cells or obtaining the organoid/population of adult epithelial stem cells from a single cell. Advantageously, this allows a homogenous population of cells to form. In some embodiments, the method comprises culturing the stem cells in an expansion medium of the invention for a period of time, for example, at least 1 month, at least 6 weeks, at least 2 months, and then dissociating the cells to a single cell density, seeding one or more cells at a ratio of 1 cell per container (e.g. per well), and expanding the cells using an expansion medium of the invention.

Following culturing, the method may further comprise obtaining and/or isolating one or more epithelial stem cells or an organoid. For example, following culture of the stem cells, it may be useful to remove one or more stem cells and/or one or more organoids cultured in the expansion medium from the culture medium for use in subsequent applications. For example, it may be useful to isolate a single cell for culture using the differentiation medium of the invention. Alternatively, it may be useful to obtain a population of cells for culture using the differentiation medium of the invention.

Any one of a number of physical methods of separation known in the art may be used to select the cells of the invention and distinguish these from other cell types. Such physical methods may involve FACS and various immuno-affinity methods based upon makers specifically expressed by the cells of the invention. As described herein, LGR5 is a cell marker expressed at high levels in the cells of the invention. Therefore, by way of illustration only, the cells of the invention may be isolated by a number of physical methods of separation, which rely on the presence of this marker. Similarly, any of the other markers expressed by the cells may be used.

In one embodiment, the cells of the invention may be isolated by FACS utilizing an antibody, for example, against one of these markers. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, Alexa Fluor® 488, GFP, CFSE, CFDA-SE, DyLight 488, PE, PerCP, PE-Alexa Fluor® 700, PE-Cy5 (TRI-COLOR®), PE-Cy5.5, PI, PE-Alexa Fluor® 750, and PE-Cy7. This list is provided by way of example only, and is not intended to be limiting.

It will be apparent to a person skilled in the art that FACS analysis using an anti-Lgr5 antibody will provide a purified cell population. However, in some embodiments, it may be preferable to purify the cell population further by performing a further round of FACS analysis using one or more of the other identifiable markers, for example, Hnf4A and/or Sox9, but others may also be used.

In another embodiment, the cells of the invention may be isolated by immuno-affinity purification, which is a separation method well known in the art. By way of illustration only, the cells of the invention may be isolated by immuno-affinity purification directed towards c-kit. As will be apparent to one skilled in the art, this method relies upon the immobilisation of antibodies on a purification column. The cell sample is then loaded onto the column, allowing the appropriate cells to be bound by the antibodies, and therefore bound to the column. Following a washing step, the cells are eluted from the column using a competitor which binds preferentially to the immobilised anti-c-kit antibody, and permits the cells to be released from the column.

It will be apparent to a person skilled in the art that immuno-affinity purification using an immobilised antibody will provide a purified cell population. However, in some embodiments, it may be preferable to purify the cell population further by performing a further round of immuno-affinity purification using one or more of the other identifiable markers, for example Hnf4A, and use an aliquot of the isolated clones to ascertain the expression of other relevant intracellular markers.

It will be apparent to a person skilled in the art that the sequential purification steps are not necessarily required to involve the same physical method of separation. Therefore, it will be clear that, for example, the cells may be purified through a FACS step using an anti-Lgr5 antibody, followed by an immuno-affinity purification step using a SSEA-1 affinity column. In certain embodiments, the cells may be cultured after isolation for at least about 15, at least about 20 days, at least about 25 days, or at least about 30 days. In certain aspects, the cells are expanded in culture longer to improve the homogeneity of the cell phenotype in the cell population.

Other features of this method are defined in the part of the description dedicated to definitions. Single-cell suspensions or small clusters of cells (2-50 cells/cluster) will normally be seeded, rather than large clusters of cells, as in known in the art. As they divide, such cells will be seeded onto a support at a density that promotes cell proliferation. Typically, when single cells are isolated the plating density of at least 1-500 cells/well is used, the surface of the well is 0.32 cm². When clusters are seeded the plating density is preferably 250-2500 cells/cm². For replating, a density of between about 2500 cells/cm² and about 5,000 cells/cm² may be used in some embodiments. During replating, single-cell suspensions or small cluster of cells will normally be seeded, rather than large clusters of cells, as in known in the art.

Methods and Culture Media for Cancer Cells and Cancer Organoids

In some embodiments, the epithelial stem cell is a cancer cell or a non-cancerous tumour cell e.g. is derived from a tumour. Where the term "cancer" is used herein, it is to be understood that it applies equally non-cancerous (benign) tumours. Cancer cells tend to have mutations that constitutively activate or deactivate certain growth pathways and which mean that certain factors in the culture medium that may normally be required for growth, are no longer necessary. For example, many colon cancers result in constitutive activation of the Wnt pathway. In such cases, a culture medium would not require a Wnt agonist. Other mutations would allow other factors to be left out of the culture media described herein. Other epithelial cancers (carcinomas) or non-cancerous tumours (e.g. adenomas) can also be grown in culture media of the invention.

In a preferred embodiment, a cancer organoid obtained from cancer stem cells is grown in a culture medium that is suitable for growth of the corresponding normal tissue organoid obtained from normal stem cells, optionally with certain factors excluded from the medium. For example, a stomach cancer organoid obtained by culturing stomach cancer stem cells may be grown in the same culture conditions as a normal gastric organoid obtained by culturing gastric stem cells, optionally with certain factors excluded from the medium. In another example, a pancreatic cancer organoid obtained by culturing pancreatic cancer stem cells may be grown in the same culture conditions as a normal pancreatic organoid obtained by culturing pancreatic stem cells, optionally with certain factors excluded from the medium. In another example, a prostate cancer organoid obtained by culturing prostatic cancer stem cells may be grown in the same culture conditions as a normal prostate organoid obtained by culturing prostatic stem cells, optionally with certain factors excluded from the medium. In another example, a liver cancer organoid obtained by culturing liver cancer stem cells may be grown in the same culture conditions as a normal liver organoid obtained by culturing liver stem cells, optionally with certain factors excluded from the medium. In many situations it may be preferable (or at least more convenient) to grow cancer organoids in the normal tissue medium (without any factors excluded). The normal tissue medium should allow cancers with all genetic backgrounds to grow, without excluding any particular cancer mutations.

Therefore, in some embodiments, the invention provides a culture medium for culturing cancer cells, for example cancer stem cells, such as adenocarcinoma or carcinoma cells from a tissue type of interest, wherein the culture medium comprises or consists of the components of the culture medium used for culturing the cells from the corresponding non-cancerous tissue type of interest, optionally wherein one or more of the following are excluded from the medium that is used to culture the non-cancerous cells of the tissue type of interest: Forskolin, Wnt-3a, EGF, Noggin, Rspondin, TGF-beta inhibitor, p38 inhibitor, nicotinamide, gastrin, FGF10 and HGF.

Expansion Organoids and Populations of Cells

The invention provides an organoid or a population of epithelial stem cells obtainable or obtained by a method of the invention. Thus, in some embodiments, the method further comprises obtaining and/or isolating an organoid.

An organoid obtained using the expansion methods of the invention is also referred to herein as an "expansion organoid". An expansion organoid comprises at least one Lgr5+ epithelial stem cell, which can divide and produce further Lgr5+ epithelial stem cells or can generate differentiated progeny, e.g. progenitor cells. It is to be understood that in a preferred expansion organoid, the majority of cells are expanding cells (i.e. dividing cells) that retain an undifferentiated phenotype. Although some spontaneous differentiation may occur, the cell population is generally an expanding population. The length of time that the organoids can continue to be expand whilst maintaining a core presence of Lgr5+ stem cells and whilst maintaining genotypic and phenotypic integrity of the cells, is an important feature of the organoids that distinguishes them from many of the organoids in the prior art. The organoids also have a distinctive structure that arises from these cellular properties, as described in detail below.

It should be noted that, at any time, the expansion organoids, or cells from the expansion organoids can be transferred to a differentiation medium and be allowed to or induced to differentiate into all major differentiated cell lineages present in the corresponding in vivo tissue Image analysis may be used to assess characteristics of cells in culture such as cell morphology; cell structures; evidence for apoptosis or cell lysis; and organoid composition and structure. Many types of imaging analysis are well known in the art, such as electron microscopy, confocal microscopy, stereomicroscopy, fluorescence microscopy. Histological analysis can reveal basic architecture and cell types.

An expansion organoid of the invention preferably has a three dimensional structure, i.e. the organoid is preferably a three-dimensional organoid. In a preferred embodiment the expansion organoid comprises only epithelial cells, i.e. non-epithelial cells are absent from the organoid. This is because the culture medium of the invention is specifically designed to expand Lgr5+ epithelial stem cells. Therefore, even if other cell types are transiently present in the culture medium, e.g. in the tissue fragment that is the starting material of the invention, these cells are unlikely to survive and instead will be replaced by the longer term expansion of the Lgr5+ stem cells which generate a pure population of epithelial cells.

In some embodiments, the epithelial cells surround a lumen. In some embodiments, the epithelial cells surrounding the lumen are polarized, (meaning that proteins are differentially expressed on the apical or basolateral side of the epithelial cell). In some embodiments the organoids comprise stem cells which are able to actively divide and which are preferably able to differentiate to all major differentiated cell lineages present in the corresponding in vivo tissue, e.g. when the organoid or cell is transferred to a differentiation medium.

In some embodiments, the organoid is a three-dimensional organoid, comprising crypt-like domains surrounding a central lumen, and contain intestinal stem cells that are polarised, residing in the bases of the structures that can actively divide and give rise to all major differentiated cell lineages present in the intestine.

In some embodiments the organoids of the invention have a section which is formed of multiple layers. Multiple layers of cells are also referred to herein as regions of "pseudo-stratified" cells. By "pseudo-stratified" it is meant that there are multiple (more than one) layers of cells. Such cells often tend to have their nuclei more central to the cells, i.e. not polarized. The cells in the multilayer section may organise themselves to include a gap, or lumen between the cells.

In some embodiments the organoids of the invention comprise single monolayers that are folded (or invaginated) to form two or more layers. It can sometimes be difficult to distinguish between folded (or invaginated) monolayers and regions of stratified cells. In some embodiments an organoid comprises both regions of stratified cells and regions of folded monolayers. In some embodiments the organoids of the invention have a section which is formed of multiple layers and a section comprising a single monolayer of cells. In some embodiments the organoids of the invention comprise or consist of a single monolayer of cells.

During expansion liver and/or pancreas epithelial cells acquire a columnar shape typical of ductal cells, while when differentiating, the cells acquire a more polygonal shape typical of hepatocyte cells (e.g. see FIG. 10). Thus in some embodiments, the cells of the organoid are a columnar shape or a polygonal shape.

Structurally, organoids according to the invention are often elongated in shape. They may include one or more budding structure—a single cell epithelial layer with similarities to ducts or islets. Thus, organoids according to the invention may possess a layer of cells with at least one bud and a central lumen.

Under confocal microscopy, the structures may stain positive for keratin. They may include cells with polarised nuclei and small cytoplasm.

The organoids in the outside of the matrigel tend to be larger than the organoids in the center of the matrigel, perhaps because they have better access to the necessary growth factors.

In some embodiments the organoids of the invention comprise or consist of epithelial cells. In some embodiments, the organoids comprise or consist of a single layer of epithelial cells. In some embodiments non-epithelial cells are absent from the organoids. In some embodiments, the organoids of the invention comprise all the differentiated cell types that exist in their corresponding in vivo tissue counterpart.

Metaphase spreads of organoids more than 3 months old consistently revealed 46 chromosomes in each of the 20 cells taken from three different donors.

Morphologically, the cells appear like their corresponding in vivo tissue counterpart. The organoid may be derived from liver, pancreas, intestine (e.g. small intestine or colon), stomach, prostate, lung, breast, ovarian, salivary gland, hair follicle, skin, oesophagus or thyroid epithelial stem cells, i.e. the organoids may be liver, pancreas, intestine (e.g. small intestine or colon), stomach, prostate, lung, breast, ovarian, salivary gland, hair follicle, skin, oesophagus or thyroid organoids.

There is provided an organoid or a population of epithelial stem cells which has been cultured in expansion media of the invention for at least 2 months, for example at least 10 weeks, at least 12 weeks, at least 14 weeks, at least 16 weeks, at least 4 months, at least 5 months, at least 6 months, at least 9 months, at least one year. Preferably, the cells are human cells.

Advantageously, use of forskolin and other cAMP pathway activators allows the cells and organoids to be cultured long-term. It is not possible to culture human epithelial stem cells or organoids for two months or more in the culture medium described in WO2012/014076 or WO2012/168930. Therefore, such organoids or populations of epithelial stem cells that had been cultured long-term did not exist before the present invention. Accordingly, there is provided an organoid or a population of stem cells that has been cultured/passaged or that is capable of being cultured/passaged as described herein. For example, there is provided an organoid or a population of stem cells that has been passaged or which is capable of being passaged at a split ratio of 1:4-1:6 every 7-10 days for more than 6 or more weeks, for example, for 2 months, 3 months, 4 months, 5 months or 6 or more months. In one embodiment, there is provided an organoid or a population of stem cells that has been passaged or which is capable of being passaged for more than 18 passages at a split ratio of 1:4-1:6 every 10 days for more than 5 months.

In some embodiments, the organoid or population of epithelial stem cells in the expansion medium has a doubling time of less than 65 hours, for example, 60, 58, 56, 54, 53, 50 hours or less. In some embodiments, the doubling time is measured between passages 1-3 ("P1" to "P3"). In some embodiments, the doubling time is measured between passages 10-12 ("P10" to "P12"). In some embodiments, the doubling time between P1 to P3 is shorter than between P10 to P12, for example a doubling time of about 52 hours between P1 to P3 and a doubling time of about 57 hours at P10 to P12. In some embodiments, the doubling time for human epithelial stem cells in the expansion medium of the invention is shorter than the doubling time for human epithelial stem cells in the expansion medium described in WO2012/014076 or WO2012/168930. In some embodiments, the organoid or population of epithelial stem cells in the expansion medium is growing exponentially.

In some embodiments, there is provided an organoid in the expansion medium of the invention, wherein there are 12 or more organoids per container (e.g. per well), for example, 15, 20, 30, 40, 50, 60 or more organoids per container. In some embodiments, the number of organoids per container is measured at passage 6 or passage 7. Advantageously, use of the expansion medium of the invention, which contains a cAMP pathway activator, may make it possible to form more cells and organoids per well than if a cAMP pathway activator is absent because of the increased passage number possible using the expansion medium of the invention. Thus, in some embodiments, there is provided an organoid in the expansion medium of the invention which is capable of forming 12 or more organoids per container (e.g. per well), e.g. 15, 20, 30, 40, 50 or 60 more organoids per container. In some embodiments, the culture method of the invention comprises splitting the cells in each container before the maximum number of organoids has been formed in each container.

Use of a cAMP pathway activator in the expansion medium allows larger organoids to be obtained than when a cAMP pathway activator is absent. This is apparent from FIG. 2A which shows the size of organoids obtained in the absence of the cAMP pathway activator (left hand panel) with the size of organoids obtained in the presence of the cAMP pathway activator (right hand panel).

Accordingly, in some embodiments, an expansion organoid according to the present invention comprises a population of at least $1 \times 10^3$ cells, at least $1 \times 10^4$ cells, at least $1 \times 10^5$ cells, or more. In some embodiments, each organoid comprises between approximately $1 \times 10^3$ cells and $5 \times 10^3$ cells; generally, 10-20 organoids may be grown together in one well, for example of a 24 well plate. In some embodiments, a single organoid may be grown in a well.

In some embodiments, organoids are at least 50 µm, at least 60 µm, at least 70 µm, at least 80 µm, at least 90 µm, at least 100 µm, at least 125 µm, at least 150 µm, at least 175 µm, at least 200 µm, at least 250 µm or more in diameter at the widest point. In contrast to mature hepatocytes, for example, which grow to confluence for a short period of time, before dying, liver epithelial stem cells cultured using the method of the invention are self-renewing and can be cultured long-term. It has been found that the self-renewing population of cells are those which are capable of expressing Lgr5 on their surface. Lgr5 negative cells do not self-renew. The term "self-renewing" should be understood to represent the capacity of a cell to reproduce itself whilst maintaining the original proliferation and differentiation properties of cells of the invention. Such cells proliferate by dividing to form clones, which further divide into clones and therefore expand the size of the cell population without the need for external intervention, without evolving into cells with a more restricted differentiation potential.

Within the context of the invention, a tissue fragment is a part of an adult tissue, preferably a human adult tissue. Preferably an organoid as identified herein is therefore not a tissue fragment.

In some embodiments, the organoid or population of epithelial stem cells that has been cultured in an expansion medium of the invention expresses the Lgr5 stem-cell surface marker. Advantageously, use of a cAMP pathway activator such as forskolin in the expansion medium increases the amount of Lgr5 positive cells that are present compared to when the cAMP pathway activator is absent. Using previously available methods which did not comprise cAMP pathway activators, human liver stem cells lost their stemness after around two months in culture and then died. The present methods allow the cells to be cultured for longer periods of time and more cells to be obtained leading to increased percentage of stem cells. In some embodiments, the Lgr5 cells represent at least 1% of the culture population, e.g. at least 1.25%, at least 1.5%, at least 1.75%, at least 2%, at least 2.25%, at least 2.5%, at least 2.75%, at least 3%, at least 4%, at least 5% of the culture population. For example, in some embodiments, the Lgr5 cells represent 1%-5%, for example 1.25-4%, 1%-3%, 1.25%-3%, 1.5-3% of the culture population. In some embodiments, it is envisaged that the percentage of Lgr5 positive cells may be higher, for example, if the cells carry a mutation that affects Lgr5 expression, such as a mutation in the Wnt pathway or if the expansion medium comprises high amounts of Wnt. Thus it is also envisaged that Lgr5 cells may represent at least 4%, at least 8%, at least 10%, at least 20%, at least 30%, at least 40% of the culture population.

Accordingly, an organoid preferably comprises cells that express Lgr5. For example, in some embodiments, at least 1%, more preferably at least 1.25%, at least 1.5%, at least 1.75%, at least 2%, at least 2.25%, at least 2.5%, at least 2.75%, at least 3% of the cells in the organoid express Lgr5. Similarly, the invention provides a cell or a population of cells which express Lgr5, wherein said cells are obtained from an organoid of the invention. The progeny of such cells is also encompassed by the invention.

In some embodiments, the organoid or cell derived from said organoid in an expansion medium of the invention comprises cells which express Lgr5, wherein Lgr5 expression is upregulated compared to expression of Lgr5 in an organoid or a population of epithelial stem cells in an expansion medium corresponding to a expansion medium of the invention but without a cAMP pathway activator. Preferably, expression of Lgr5 is upregulated by 25%, for example, by 50%, 75%, 100%, 125%, 150%, 200%, 250%, 300% or more.

In a preferred embodiment, an organoid could be cultured during at least 2, 3, 4, 5, 6, 7, 8, 9, 10 weeks or 1, 2, 3, 4, 5, 6, 7, 8, 9, 10 months or longer. In some embodiments, the organoid is expanded or maintained in culture for at least 3 months, preferably at least 4 months, at least 5 months, at least 6 months, at least 7 months, at least 9 months, or at least 12 months or more. Advantageously, use of the culture methods provided by the present invention results in organoids and/or cell populations being formed in which the number of chromosomes remains stable when the cells or organoids are cultured long-term. Thus, in some embodiments, the organoids or population of epithelial stem cells of the invention has a stable chromosome number after 2, 4, 6, 8, 10, 12 or 14 weeks or after 4, 5, 6 or more months in culture in an expansion medium of the invention. Preferably, at least 65%, at least 70%, more preferably at least 75%, more preferably at least 80%, more preferably at least 90%, more preferably at least 95%, more preferably at least 99% of the cells have the correct number of chromosomes after 2, 4, 6, 8, 10, 12 or 14 weeks or after 4, 5, 6 or more months culture in an expansion medium of the invention. For human epithelial cells, the correct number of chromosomes is 46. Of course, it is to be understood that cancer cells in cancer organoids, e.g. derived from cancer stem cells, would not necessarily have the correct number of chromosomes as genomic instability is a feature of certain cancers.

The expansion organoid of the invention preferably comprises at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS. In some embodiments, there is provided one or more frozen organoids of the invention. Also provided is a method for preparing organoids for freezing comprising dissociating organoid cultures and mixing them with a freezing medium such as Recovery cell culture freezing medium (Gibco) and freezing following standard procedures. A method for thawing frozen organoids is also provided which comprises thawing frozen organoids, embedding the thawed organoids in an extracellular matrix (e.g. Matrigel) and culturing the organoids in an expansion medium of the invention. Advantageously, initially after thawing the culture medium may be supplemented with Y-27632, for example, about 10 uM Y-27632. In some embodiments, the culture medium is supplemented with Y-27632 for the first 1, 2, 3, 4, 5 or less days after thawing, preferably for the first 3 or 4 days. In some embodiments, Y-27632 is not present in the culture medium after the first 3, 4, 5, 6 or more days, preferably after the first 3 or 4 days. This freezing method can be used for expansion organoids of the invention.

Culturing in Differentiation Medium

Optionally, the organoids or cells expanded using the expansion medium may then be cultured in a differentiation medium to differentiate them into cells which express mature differentiation markers. Thus, in some embodiments, cells can be grown in a first "expansion" culture medium (also referred to herein as EM), followed by culturing the cells in a second "differentiation" culture medium (also referred to herein as DM). Accordingly, the methods of the invention may optionally further comprise the step of culturing epithelial stem cells in a differentiation medium using a method as described herein. The method may optionally comprise the further step of obtaining and/or isolating one or more of the resulting organoids/cells/populations of cells from the culture medium. However, in some embodiments, the step of culturing in DM media is not carried out, for example in some methods, cells are transplanted and allowed to differentiate in vivo.

In some embodiments, the epithelial stem cells are isolated from the expansion medium prior to culturing in the differentiation medium. In other embodiments, cells are not isolated prior to culturing in the differentiation medium but the culture medium components are simply changed so that the components of the differentiation medium are added rather than replenishing the components of the expansion medium.

Accordingly, in some embodiments, the method further comprises culturing the cells in a differentiation medium which comprises or consists of a basal medium for animal or human cells to which is added: one or more receptor tyrosine kinase ligands and a Notch inhibitor. In some embodiments, the differentiation medium further comprises one more more of: a TGF-beta inhibitor, gastrin and dexamethasone.

In one embodiment the method further comprises culturing the cells in a differentiation medium which comprises or consists of a basal medium for animal or human cells to which is added: EGF, a TGF-beta inhibitor, a Notch inhibitor and a prostaglandin pathway activator, such as PGE2 and/or AA. This medium is described in WO 2012/168930 and is useful for differentiating the cells. Preferably, the differentiation medium also comprises Noggin, Gastrin, FGF and/or HGF. In some embodiments the differentiation medium comprises a p38 inhibitor.

For example, in one embodiment, the differentiation medium comprises EGF, a TGF-beta inhibitor, FGF (for example, FGF10, FGF19, or any other suitable FGF family member) and a Notch inhibitor. In one embodiment, the TGF-beta inhibitor is A83-01 and/or the Notch inhibitor is a gamma-secretase inhibitor (e.g. DAPT or DBZ). FGF may optionally be replaced by HGF or alternatively both FGF and HGF may be present or absent in the differentiation medium. In some embodiments, EGF might be replaced by HGF or another receptor tyrosine kinase ligand. Dexamethasone may also be added, for example at a concentration of between 10 nM to 10 uM. The differentiation medium may optionally include a prostaglandin pathway activator, such as PGE2 or AA. However, this component may also be excluded from the differentiation medium. In some embodiments, oncostatin M may also be added, for example at a concentration range between 1 ng/ml to 1 mg/ml, e.g. in the case of liver to help differentiation to hepatocyte fate.

In one embodiment, the differentiation medium comprises or consists of a basal medium for animal or human cells to which is added:
Epidermal Growth Factor, FGF10 and HGF as receptor tyrosine kinase ligands;
a Notch inhibitor;
a TGF-beta inhibitor; and
a prostaglandin pathway activator, such as PGE2 and/or AA.

This culture medium is particularly preferred for liver cells. In some embodiments, the DM comprises or consists of a basal medium to which is added: 50 ng/ml EGF, 100 ng/ml FGF10, 50 nM A8301 and 10 µM DAPT.

In some embodiments, the differentiation medium comprises or consists of a basal medium (for example comprising Advanced DMEM/F12, B27 (50×), n-Acetylcystein (1 mM) glutamin/glutamax), Noggin (preferably 100 ng/ml), EGF (preferably 50 ng/ml), gastrin (preferably 10 nM), TGF-beta inhibitor, such as A83-01 (preferably 50 nM) and a Notch inhibitor (for example DAPT/DBZ) (preferably 10 µM).

In a particularly preferred embodiment, the differentiation medium comprises or consists of a basal medium comprising an EGF receptor activator (e.g. EGF), an FGF (preferably a FGF receptor 4 activator, e.g. FGF19), an HGF receptor activator (e.g. HGF), a Notch inhibitor, and a TGF-beta inhibitor, more preferably EGF, FGF, HGF, a Notch inhibitor, and a TGF-beta inhibitor.

Preferably, the differentiation medium further comprises a glucocorticoid, for example, dexamethasone or cortisone. In some embodiments, dexamethasone is used at a concentration of between 10 nM to 10 µM.

In some embodiments, the differentiation medium additionally comprises gastrin.

Accordingly, in a preferred embodiment, the differentiation medium comprises or consists of a basal medium comprising EGF, FGF, HGF, a Notch inhibitor, a TGF-beta inhibitor, a glucocorticoid and gastrin.

Any suitable EGF receptor activator as described herein may be used, and is preferably EGF.

The FGF used in the differentiation medium is an FGF able to bind to FGF receptor 4 (FGFR4), and is preferably FGF19 (preferably from Peprotech). In some embodiments, no more than one FGF is used. In other embodiments, two or more FGF are used, e.g. 2, 3 or more. In some embodiments, FGF is substituted with a compound that activates the FGFR4 pathway. The FGF in the differentiation medium is preferably FGF19.

Any suitable HGF receptor activator as described herein may be used, and is preferably HGF.

Any suitable Notch inhibitor may be used. In some embodiments the Notch inhibitor is a gamma-secretase inhibitor, for example DAPT, dibenzazepine (DBZ), benzodiazepine (BZ) or LY-411575. One or more Notch inhibitors may be used, for example, 2, 3, 4 or more.

Any suitable TGF-beta inhibitor, as described herein may be used. Non-limiting examples of suitable TGF-beta inhibitors are small molecule inhibitors, for example selected from the group consisting of: A83-01, SB-431542, SB-505124, SB-525334, LY 364947, SD-208, SJN 2511. Advantageously, in some embodiments, the TGF beta inhibitor is present at 10 times higher concentration than in WO2012/168930. Accordingly, in some embodiments, a TGF beta inhibitor (e.g. A83-01) is added to the DM at a concentration of between 250-750 nM, for example, 400-600 nM or about 500 nM. Use of TGF beta inhibitor at this higher concentration in the context of a differentiation medium for liver which also comprises EGF, FGF, HGF and a Notch-inhibitor leads to better expression of hepatocyte markers which is indicative of better differentiation. Using culture methods not involving forskolin (e.g. in WO 2012/014076), only about 30% of the cells in the liver organoids express hepatocyte markers. For the differentiated liver organoids of the present invention, a greater percentage of cells express hepatocyte markers. For example, in some embodiments, the differentiating organoids comprise more than about 30%, more than about 40%, more than about 50%, more than about 60% cells expressing hepatocyte markers. However, in some embodiments, a TGF beta inhibitor is absent from the differentiation medium and the specific examples of differentiation media described herein can be adapted accordingly to omit the TGF beta inhibitor.

In one embodiment, the TGF beta inhibitor is A83-01 and/or the Notch inhibitor is DAPT.

Accordingly, in a preferred embodiment, the differentiation medium comprises EGF, FGF19, HGF, DAPT and A83-01. More preferably, the differentiation medium comprises EGF, FGF19, HGF, DAPT and A83-01 and further comprises dexamethasone and/or gastrin.

In some embodiments, the differentiation medium further comprises a BMP activator, for example BMP7, BMP4 or BMP2. Preferably, the BMP activator is BMP7.

For example, in some embodiments, the differentiation medium comprises EGF, gastrin, HGF, FGF19, A8301, DAPT, BMP7 and dexamethasone. For example, it may comprise about 50 ng/ml EGF, about 10 nM gastrin, about 25 ng/ml HGF, about 100 ng/ml FGF19, about 500 nM A8301, about 10 μM DAPT, about 25 ng/ml BMP7 and about 30 uM Dexamethasone.

In some embodiments, the differentiation medium comprises one or more receptor tyrosine kinase inhibitor (preferably EGF, HGF and FGF19), a TGF-beta inhibitor (preferably A8301), a Notch inhibitor (preferably DAPT) and a BMP activator (preferably BMP7).

In another embodiment, the differentiation medium additionally comprises Oncostatin M.

In some embodiments, the differentiation medium does not comprise Rspondin and/or Wnt. In some embodiments, the differentiation medium does not comprise a Wnt agonist. In some embodiments, the differentiation medium does not comprise Wnt. In some embodiments, the differentiation medium does not comprise Nicotinamide.

In some embodiments, retinoic acid is absent from the differentiation medium. A cAMP pathway activator is preferably absent from the differentiation medium. In some embodiments, the differentiation medium does not comprise a BMP inhibitor. In some embodiments, the differentiation medium does not comprise PGE2 and/or AA. In some embodiments, the differentiation medium does not comprise a prostaglandin pathway activator.

The invention provides a differentiation medium as described herein, use of a differentiation medium as described herein, for example in the methods and uses described herein, methods of using a differentiation medium as described herein, and cells and organoids obtainable/obtained by culturing using a differentiation medium as described herein.

There is provided a method of culturing epithelial stem cells using a differentiation medium as described herein. Preferably, the method involves culturing expanded epithelial stem cells using a differentiation medium as described herein. The epithelial stem cells may have been expanded by any suitable method. Preferably, they have been expanded using one or more expansion media according to the invention. Alternatively, they may have been expanded using expansion media as described in WO2012/168930 or WO2012/014076.

In some embodiments, the method comprises culturing the epithelial stem cells in the expansion medium for 5 or more days, for example 7, 9, 10 or 14 or more days or at least one month or at least two months and then culturing the resulting cells in the differentiation medium. However, the cells may be cultured in the expansion medium for longer if desired. As explained herein, use of an expansion medium of the invention advantageously allows human epithelial stem cells to be cultured long-term and so the cells may be cultured as described herein before being cultured in differntiation medium.

In some embodiments, the cells are cultured in the differentiation medium for 5-14 days, for example, 7-12 days, more preferably 9-11 days.

The method may comprise changing the medium for fresh medium during the course of the culturing because the components of the medium are used up during culturing. It will be clear to the skilled person how often the medium needs to be changed for fresh medium. In some embodiments, the medium is changed every other day, but it is also envisaged that it may be changed every day or every two days or as required.

The methods for culturing epithelial stem cells and/or obtaining an organoid in expansion or differentiation medium are carried out in vitro.

Following culturing in expansion or differentiation medium, the method may further comprise obtaining and/or isolating one or more epithelial stem cells or an organoid. For example, following culture of the stem cells, it may be useful to remove one or more stem cells, differentiated cells and/or one or more organoids cultured in the expansion or differentiation medium from the culture medium for use in subsequent applications.

Differentiated Organoids and Populations of Cells

Organoids can be cultured in a differentiation medium, as described above, such that they differentiate into functional cell types (e.g. see Example 15). The invention further provides a differentiated organoid or a population of differentiated epithelial cells.

In one embodiment, the invention provides a differentiated organoid or a population of epithelial cells obtainable or obtained by a method of the invention, which comprises culturing epithelial stem cells in a differentiation medium of the invention.

Illustrative examples of organoids generated using the differentiation medium and methods of the invention are given in the accompanying figures.

It can be seen that differentiated organoids according to the invention may possess a cystic structure, with on the outside, a layer of cells with at least one bud and a central lumen. In some embodiments, they are elongated in shape. The organoids may have a section which is formed of multiple layers; such cells often tend to have their nuclei more central to the cells, i.e. not polarized. The cells in the multilayer section may organise themselves to include a gap, or lumen between the cells. They may include cells with polarised nuclei and small cytoplasm. In some embodiments, the differentiated organoids have a single layered stratified epithelium.

Although not limiting, the organoids in the outer part of the extracellular matrix tend to be larger than the organoids in the centre of the extracellular matrix, perhaps because they have better access to the necessary growth factors.

A differentiated organoid of the invention preferably has a three dimensional structure, very similar to that of the expansion organoid (see features described above in section about expansion organoids and populations of cells, which also apply here). In some embodiments, the epithelial cells exist in distinct dividing domains and differentiating domains. In some embodiments, all differentiated cell types of the normal in vivo tissue are present in said organoid. Differentiated cell types express differentiation markers which are known in the art. Differentiated cell types can be identified using such markers by methods known in the art (see below).

A differentiated organoid according to the present invention may comprise a population of cells of at least $1 \times 10^3$ cells, at least $1 \times 10^4$ cells, at least $1 \times 10^5$ cells, at least $1 \times 10^6$ cells, at least $1 \times 10^7$ cells or more. In some embodiments, each organoid comprises between approximately $1 \times 10^3$ cells and $5 \times 10^3$ cells; generally, 10-20 organoids may be grown together in one well, for example of a 24 well plate.

It is clear to the skilled person that an organoid of the invention is not a naturally occurring tissue fragment and/or does not comprise a blood vessel. For example, in the case of a liver organoid of the invention, does not comprise a naturally occurring liver lobule or a naturally occurring bile duct. Similarly, an intestinal organoid of the invention does not comprise a naturally occurring crypt or a naturally occurring villus.

The differentiation medium described herein preferably induces or promotes a specific differentiation of cells during at least five days of culture. Differentiation may be measured by detecting the presence of a specific marker associated with the particular tissue lineage, e.g. the liver lineage, as defined herein. Differentiation may be measured by detecting the presence of a specific marker associated with the tissue lineage, e.g. the liver lineage, as defined herein. Depending on the identity of the marker, the expression of said marker may be assessed by RTPCR or immuno-histochemistry after at least 5, 7, 8, 9, 10, 11, 12, 13, 14, 15, 16 or more days of culture in a differentiation medium as defined herein.

The term "expressed" is used to describe the presence of a marker within a cell. In order to be considered as being expressed, a marker must be present at a detectable level. By "detectable level" is meant that the marker can be detected using one of the standard laboratory methodologies such as PCR, blotting or FACS analysis. A gene is considered to be expressed by a cell of the population of the invention if expression can be reasonably detected after 30 PCR cycles, which corresponds to an expression level in the cell of at least about 100 copies per cell. The terms "express" and "expression" have corresponding meanings. At an expression level below this threshold, a marker is considered not to be expressed. The comparison between the expression level of a marker in a cell of the invention, and the expression level of the same marker in another cell, such as for example an embryonic stem cell, may preferably be conducted by comparing the two cell types that have been isolated from the same species. Preferably this species is a mammal, and more preferably this species is human. Such comparison may conveniently be conducted using a reverse transcriptase polymerase chain reaction (RT-PCR) experiment.

The differentiated organoid of the invention preferably comprises at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS. The viable cells preferably possess corresponding in vivo functions or characteristics. For example, viable liver cells preferably possess hepatic functions or characteristics or hepatocytes.

Also provided is a differentiated organoid or a differentiated population of liver epithelial cells of the invention in a differentiation medium of the invention. In one embodiment, there is provided an organoid in a differentiation medium, for example as described herein.

In an embodiment, a differentiated organoid is an organoid which is still being cultured using a method of the invention and is therefore in contact with an extracellular matrix. Preferably, a differentiated organoid is embedded in a non-mesenchymal extracellular matrix.

The organoid or population of epithelial stem cells may be from any mammalian tissue, but is preferably from a human. In some embodiments, it is from a mouse, rabbit, rat, guinea pig or other non-human mammal.

Culture Media

The invention provides a cell culture medium as described herein. A cell culture medium (for example, the expansion medium or differentiation medium) that is used in a method of the invention comprises any suitable basal medium, subject to the limitations provided herein. Basal media for cell culture typically contain a large number of ingredients, which are necessary to support maintenance of the cultured cells. Suitable combinations of ingredients can readily be formulated by the skilled person, taking into account the following disclosure. A basal medium for use in the invention will generally comprises a nutrient solution comprising standard cell culture ingredients, such as amino acids, vitamins, lipid supplements, inorganic salts, a carbon energy source, and a buffer, as described in more detail in the literature and below. In some embodiments, the culture medium is further supplemented with one or more standard cell culture ingredient, for example selected from amino acids, vitamins, lipid supplements, inorganic salts, a carbon energy source, and a buffer.

The skilled person will understand from common general knowledge the types of culture media that might be used as the basal medium in the cell culture mediums of the invention. Potentially suitable cell culture media are available commercially, and include, but are not limited to, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

For example, the basal medium may be selected from DMEM/F12 and RPMI 1640 supplemented with glutamine, insulin, Penicillin/streptomycin and transferrin. In a further preferred embodiment, Advanced DMEM/F12 or Advanced RPMI is used, which is optimized for serum free culture and already includes insulin. In this case, said Advanced DMEM/F12 or Advanced RPMI medium is preferably supplemented with glutamine and Penicillin/streptomycin. AdDMEM/12 (Invitrogen) supplemented with N2 and B27 is also preferred. Preferably, the basal medium is advancedDMEM/F12.

In some embodiments, the basal medium comprises Advanced DMEM F12, hepes, penicillin/streptomycin, Glutamin, NAcetyl Cystein, B27, N2 and Gastrin. In some embodiments, culture is initiated with a basal medium comprising N2 and Gastrin and penicillin/streptomycin but these are later withdrawn. For example, in some embodiments, N2 and Gastrin and penicillin/streptomycin are present in an EM1 medium of the invention but not in an EM2 or DM. For example, in some embodiments, N2 and Gastrin and penicillin/streptomycin are present in an EM1 and EM2 medium of the invention but not in a DM. In particularly preferred embodiments, the basal medium is Advanced DMEM/F12 or a DMEM variant supplemented with penicillin/streptomycin, N2, B27, glutamine and gastrin.

In some embodiments, the basal culture medium comprises or consists of Advanced DMEM/F12 supplemented with penicillin/streptomycin, 10 mM HEPES, Glutamax, 1×N2, 1×B27 (all from Invitrogen) and 1 mM N-acetylcysteine (Sigma)).

It is furthermore preferred that said cell culture medium is supplemented with a purified, natural, semi-synthetic and/or synthetic growth factor and does not comprise an undefined component such as fetal bovine serum or fetal calf serum. Various different serum replacement formulations are commercially available and are known to the skilled person. Where a serum replacement is used, it may be used at between about 1% and about 30% by volume of the medium, according to conventional techniques.

As will be apparent to the skilled reader, the preferred culture methods of the invention are advantageous because feeder cells are not required. Feeder cell layers are often used to support the culture of stem cells, and to inhibit their differentiation. A feeder cell layer is generally a monolayer of cells that is co-cultured with, and which provides a surface suitable for growth of, the cells of interest. The feeder cell layer provides an environment in which the cells of interest can grow. Feeder cells are often mitotically inactivated (e.g. by irradiation or treatment with mitomycin C) to prevent their proliferation. The use of feeder cells is undesirable, because it complicates passaging of the cells (the cells must be separated from the feeder cells at each passage, and new feeder cells are required at each passage). The use of feeder cells can also lead to contamination of the desired cells with the feeder cells. This is clearly problematic for any medical applications, and even in a research context, complicates analysis of the results of any experiments performed on the cells. As noted elsewhere herein, the culture media of the invention are particularly advantageous because they can be used to culture cells without feeder cell contact, i.e. the methods of the invention do not require a layer of feeder cells to support the cells whose growth is being sponsored.

Accordingly, the compositions of the invention may be feeder cell-free compositions. A composition is conventionally considered to be feeder cell-free if the cells in the composition have been cultured for at least one passage in the absence of a feeder cell layer. A feeder cell-free composition of the invention will normally contain less than about 5%, less than about 4%, less than about 3%, less than about 2%, less than about 1% feeder cells (expressed as a % of the total number of cells in the composition) or preferably no feeder cells at all.

The culture media used in the invention may comprise serum, or may be serum-free and/or serum-replacement free, as described elsewhere herein. Culture media and cell preparations are preferably GMP processes in line with standards required by the FDA for biologics products and to ensure product consistency.

A culture medium of the invention will normally be formulated in deionized, distilled water. A culture medium of the invention will typically be sterilized prior to use to prevent contamination, e.g. by ultraviolet light, heating, irradiation or filtration. The culture medium may be frozen (e.g. at −20° C. or −80° C.) for storage or transport. The medium may contain one or more antibiotics to prevent contamination. The medium may have an endotoxin content of less that 0.1 endotoxin units per ml, or may have an endotoxin content less than 0.05 endotoxin units per ml. Methods for determining the endotoxin content of culture media are known in the art.

A preferred cell culture medium is a defined synthetic medium that is buffered at a pH of 7.4 (preferably with a pH 7.2-7.6 or at least 7.2 and not higher than 7.6) with a carbonate-based buffer, while the cells are cultured in an atmosphere comprising between 5% and 10% $CO_2$, or at least 5% and not more than 10% $CO_2$, preferably 5% $CO_2$.

The invention also provides a composition or cell culture vessel comprising cells and/or organoids according to any one of the aspects of the invention described above, and a culture medium according to any one of the aspects of the invention described above. For example, such a composition or cell culture vessel may comprise any number of cells or organoids cultured according to a method of the invention, in a culture medium as described above.

According to a still further aspect of the invention, there is provided a hermetically-sealed vessel containing a culture medium of the invention. In some embodiments, the culture medium is an expansion medium. In some embodiments, the culture medium is a differentiation medium. Hermetically-sealed vessels may be preferred for transport or storage of the culture media, to prevent contamination. The vessel may be any suitable vessel, such as a flask, a plate, a bottle, a jar, a vial or a bag.

Compositions and Other Forms of the Invention

The invention provides a composition comprising a culture medium according to the invention and stem cells. The invention also provides a composition comprising a culture medium according to the invention and organoids. Furthermore, the invention provides a composition comprising a culture medium according to the invention and an extracellular matrix.

The invention also provides a composition comprising a culture medium of the invention, an extracellular matrix and epithelial stem cells of the invention. The invention also provides a composition comprising a culture medium of the invention, an extracellular matrix and one or more organoids of the invention. The invention also provides a culture medium supplement that can be used to produce a culture medium as disclosed herein. A 'culture medium supplement' is a mixture of ingredients that cannot itself support stem cells, but which enables or improves stem cell culture when combined with other cell culture ingredients. The supplement can therefore be used to produce a functional cell culture medium of the invention by combining it with other cell culture ingredients to produce an appropriate medium formulation. The use of culture medium supplements is well known in the art.

The invention provides a culture medium supplement that comprises an inhibitor according to the invention. The supplement may contain any inhibitor (or combination of inhibitors) disclosed herein. The supplement may also contain one or more additional cell culture ingredients as disclosed herein, e.g. one or more cell culture ingredients selected from the group consisting of amino acids, vitamins, inorganic salts, carbon energy sources and buffers.

A culture medium or culture medium supplement may be a concentrated liquid culture medium or supplement (e.g. a 2× to 250× concentrated liquid culture medium or supplement) or may be a dry culture medium or supplement. Both liquid and dry culture media or supplements are well known in the art. A culture medium or supplement may be lyophilised.

A culture medium or supplement of the invention will typically be sterilized prior to use to prevent contamination, e.g. by ultraviolet light, heating, irradiation or filtration. A culture medium or culture medium supplement may be frozen (e.g. at −20° C. or −80° C.) for storage or transport. In some embodiments, the culture medium may be stored as a liquid (e.g. at approximately 4° C.). In some embodiments, the culture medium may be split and stored as two components: a frozen component (e.g. at between approximately −20° C. and approximately −80° C.) and a liquid component (e.g. at approximately 4° C.). In particular, temperature-sensitive or time-sensitive degradable material is preferably included in the frozen component, whereas less sensitive material (for example DMEM or FCS) can be stored in the liquid form and thus included in the liquid component for storage and shipping.

The invention also provides a hermetically-sealed vessel containing a culture medium or culture medium supplement of the invention. Hermetically-sealed vessels may be preferred for transport or storage of the culture media or culture media supplements disclosed herein, to prevent contamination. The vessel may be any suitable vessel, such as a flask, a plate, a bottle, a jar, a vial or a bag.

The invention also provides a kit comprising a culture medium, culture medium supplement and/or a composition of the invention. In some embodiments, the kit further comprises at least one other additional component, for example selected from the list comprising: an ECM (for example, Matrigel™), a population of cells and an organoid.

Uses of Organoids and Populations of Cells

The invention provides the use of an organoid of the invention or cells derived from said organoid in drug screening, (drug) target validation, (drug) target discovery, toxicology and toxicology screens, personalized medicine, regenerative medicine and/or as ex vivo cell/organ models, such as disease models.

Cells and organoids cultured according to the media and methods of the invention are thought to faithfully represent the in vivo situation. This is true both for expanded populations of cells and organoids grown from normal tissue and for expanded populations of cells and organoids grown from diseased tissue. Therefore, as well as providing normal ex vivo cell/organ models, the organoids of the invention can be used as ex vivo disease models.

Organoids of the invention can also be used for culturing of a pathogen and thus can be used as ex vivo infection models. Examples of pathogens that may be cultured using an organoid of the invention include viruses, bacteria, prions or fungi that cause disease in its animal host. Thus an organoid of the invention can be used as a disease model that represents an infected state. In some embodiments of the invention, the organoids can be used in vaccine development and/or production.

Diseases that can be studied by the organoids of the invention thus include genetic diseases, metabolic diseases, pathogenic diseases, inflammatory diseases etc, for example including, but not limited to: cystic fibrosis, inflammatory bowel disease (such as Crohn's disease), carcinoma, adenoma, adenocarcinoma, colon cancer, diabetes (such as type I or type II), Barrett's esophagus, Gaucher's disease, alpha-1-antitrypsin deficiency, Lesch-Nyhan syndrome, anaemia, Schwachman-Bodian-Diamond syndrome, polycythaemia vera, primary myelofibrosis, glycogen storage disease, familial hypercholestrolaemia, Crigler-Najjar syndrome, hereditary tyrosinanaemia, Pompe disease, progressive familial cholestasis, Hreler syndrome, SCID or leaky SCID, Omenn syndrome, Cartilage-hair hypoplasia, Herpes simplex encephalitis, Scleroderma, Osteogenesis imperfecta, Becker muscular dystrophy, Duchenne muscular dystrophy, Dyskeratosis congenitor etc.

For instance, Example 17, shows that liver organoids are suitable disease models for alpha-1 antitrypsin (A1AT) deficiency and Alagille Syndrome (see further comments below).

Traditionally, cell lines and more recently iPS cells have been used as ex vivo cell/organ and/or disease models (for example, see Robinton et al. Nature 481, 295, 2012). However, these methods suffer a number of challenges and disadvantages. For example, cell lines cannot be obtained from all patients (only certain biopsies result in successful cell lines) and therefore, cell lines cannot be used in personalised diagnostics and medicine. iPS cells usually require some level of genetic manipulation to reprogramme the cells into specific cell fates. Alternatively, they are subject to culture conditions that affect karotypic integrity and so the time in culture must be kept to a minimum (this is also the case for human embryonic stem cells). This means that iPS cells cannot accurately represent the in vivo situation but instead are an attempt to mimic the behaviour of in vivo cells. Cell lines and iPS cells also suffer from genetic instability.

By contrast, the organoids of the invention provide a genetically stable platform which faithfully represents the in vivo situation (e.g. see Examples 7 and 15). The organoids of the invention can also be expanded continuously, providing a good source of genetically stable cells. In particular, an expanding population can be "split", meaning that the organoid is split apart and all cells of the organoid are divided into new culture dishes or flasks. The divided cells are removed from the organoid and can then themselves be cultured and expanded to produce new organoids containing further expanded populations that can then be split again. Splits are also referred to herein as "passages". An organoid of the invention may be cultured for 1 or more passages, for example, 1, 2, 3, 4, 5, 6, 7, 8, 9, 10, 15, 20, 25, 30 or more passages, for example, 20-30 passages, 30-35 passages, 32-40 passages or more. In some embodiments, an expanding cell population or organoid is split once a month, once every two weeks, once a week, twice a week, three times a week, four times a week, five times a week, six times a week or daily. Thus the organoids of the invention can provide an ongoing source of genetically stable cellular material. In some embodiments, the expanding organoids of the invention comprise all differentiated cell types that are present in the corresponding in vivo situation. In other embodiments, the organoids of the invention may be differentiated to provide all differentiated cell types that are present in vivo. Thus the organoids of the invention can be used to gain mechanistic insight into a variety of diseases and therapeutics, to carry out in vitro drug screening, to evaluate potential therapeutics, to identify possible targets (e.g. proteins) for future novel (drug) therapy development and/or to explore gene repair coupled with cell-replacement therapy.

In some embodiments, the organoids have less than 5000, less than 4000, less than 3000, less than 2000, less than 1500, less than 1250, less than 1000, or less than 800 base substitutions per culture after 13 weekly passages, as determined by whole genome sequencing analysis (e.g. in Example 15). In some embodiments, the organoids are free from chromosomal aberrations. In some embodiments, the organoids contain less than 50, less than 20, less than 10, less than 5, less than 2, less than 1, or zero copy number variations (CNVs). In some embodiments, the organoids have a mutational frequency that is less than 10-fold, less than 5-fold or less than 2-fold higher than the mutational frequency of germ line cells. In some embodiments, the organoids have a mutational frequency that is less than 10-fold, less than 5-fold or less than 2-fold lower than the mutational frequency of germ line cells. In some embodiments, the organoids have the same mutational frequency as germ line cells have. In some embodiments, the organoids have a mutational frequency that is between 10-fold higher and 10-fold lower, or between 5-fold higher and 5-fold lower, or between 2-fold higher and 2-fold lower than the mutational frequency of germ line cells. In some embodiments, mutational frequency is determined by whole genome sequencing analysis of base substitutions or of copy number variations. The comparator germ line cell is preferably from the same organism as the organoid, e.g. in the context of these embodiments, a human organoid is preferably compared to a human germ line cell.

The organoids of the invention can be frozen and thawed and put into culture without losing their genetic integrity or phenotypic characteristics and without loss of proliferative capacity. Thus the organoids can be easily stored and transported. Thus in some embodiments, the invention provides a frozen organoid.

For these reason the organoids or expanded populations of cells of the invention can be a tool for drug screening, target validation, target discovery, toxicology and toxicology screens and personalized medicine.

Accordingly, in a further aspect, the invention provides the use of an organoid or cell derived from said organoid according to the invention in a drug discovery screen, toxicity assay or in medicine, such as regenerative medicine. For example, any one of the small intestinal, colon, pancreatic, gastric, liver or prostate organoids may be used in a drug discovery screen, toxicity assay or in medicine, such as regenerative medicine.

Mucosal Vaccines

An additional important use of the organoids is in the development of mucosal vaccinations. Mucosal vaccines are vaccines that are administered via the mucosa. This can be any mucosal surface such as via the nose, mouth, or rectum. They can be administered via an inhaler, a spray or other external aids. This has several clear benefits over injections such as that no medical staff are needed for administering the vaccine, which may be important, for example in developing countries.

In the intestine, M cells (or "microfold cells") are cells found in the follicle-associated epithelium of the aggregated lymphoid nodules of the ileum. They transport organisms and particles from the gut lumen to immune cells across the epithelial barrier, and thus are important in stimulating mucosal immunity. They have the unique ability to take up antigen from the lumen of the small intestine via endocytosis or phagocytosis, and then deliver it via transcytosis to dendritic cells (an antigen presenting cell) and lymphocytes (namely T cells) located in a unique pocket-like structure on their basolateral side.

Organoids can in some cases develop into M cells when stimulated with RANK ligand (e.g. see FIG. 49 of WO2012/169830). Therefore, in some embodiments of the invention, the expanded cell population comprises M cells. In some embodiments of the invention, an organoid comprises M cells. In some embodiments, there is provided a method for obtaining M cells or an organoid comprising M cells, wherein the method comprises stimulating an organoid with RANK ligand.

The efficiency of mucosal vaccines can be substantially increased when they are targeted to M cells. Therefore, the expanded stem cell population or organoid of the invention can be used for testing the ability of M cells to take up pathogens or antigens and to present them to the immune system. Therefore, in some embodiments the invention provides the use of an organoid of the invention in drug screening, for example in vaccine development and/or vaccine production. For example, in some embodiments the organoid may be used for the development or production of vaccines against viral, bacterial, fungal or other parasitic infections, for example (but not limited to) cholera, Respiratory syncytial virus (RSV), Rotavirus and HIV. In a particular embodiment, the invention provides organoids that have been differentiated in a culture medium of the invention comprising RANKL, for use in mucosal vaccine development.

Drug Screening

For preferably high-throughput purposes, said organoid of the invention is cultured in multiwell plates such as, for example, 96 well plates or 384 well plates. Libraries of molecules are used to identify a molecule that affects said organoids. Preferred libraries comprise antibody fragment libraries, peptide phage display libraries, peptide libraries (e.g. LOPAP™, Sigma Aldrich), lipid libraries (BioMol), synthetic compound libraries (e.g. LOP AC™, Sigma Aldrich) or natural compound libraries (Specs, TimTec). Furthermore, genetic libraries can be used that induce or repress the expression of one of more genes in the progeny of the stem cells. These genetic libraries comprise cDNA libraries, antisense libraries, and siRNA or other non-coding RNA libraries. The cells are preferably exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death. Said organoid of the invention can also be used to identify drugs that specifically target epithelial carcinoma cells, but not said organoid of the invention.

The ability to obtain a useful organoid of the invention in short time periods (days) shows that the organoids would be highly useful for testing individual patient responses to specific drugs and tailoring treatment according to the responsiveness. In some embodiments, wherein the organoid is obtained from a biopsy from a patient, the organoid is cultured for less than 21 days, for example less than 14 days, less than 13 days, less than 12 days, less than 11 days, less than 10 days, less than 9 days, less than 8 days, less than 7 days (etc).

The organoids are also useful for wider drug discovery purposes (e.g. see WO2013/093812 which describes screening for drugs for cystic fibrosis or cholera. This publication describes disease models for cystic fibrosis and cholera). Therefore, in some embodiments, the organoids of the invention could be used for screening for cystic fibrosis drugs. Equally, the drug screening methods of the invention may use any organoid disease model. Other examples of these are provided in the present application such as A1AT and AGS disease models. However, drug screening methods are not limited to use with organoid disease models but can be used with any of the organoids described herein. It will be understood by the skilled person that the organoids of the invention would be widely applicable as drug screening tools for infectious, inflammatory and neoplastic pathologies of the human gastrointestinal tract and other diseases of the gastrointestinal tract and infectious, inflammatory and neoplastic pathologies and other diseases of other tissues described herein including pancreas, liver and prostate. In some embodiments the organoids of the invention could be used for screening for cancer drugs.

In some embodiments, the organoids of the invention can be used to test libraries of chemicals, antibodies, natural product (plant extracts), etc for suitability for use as drugs, cosmetics and/or preventative medicines. For instance, in some embodiments, a cell biopsy from a patient of interest, such as tumour cells from a cancer patient, can be cultured using culture media and methods of the invention and then treated with a a chemical compound or a chemical library. It is then possible to determine which compounds effectively modify, kill and/or treat the patient's cells. This allows specific patient responsiveness to a particular drug to be tested thus allowing treatment to be tailored to a specific patient. Thus, this allows a personalized medicine approach.

The added advantage of using the organoids for identifying drugs in this way is that it is also possible to screen normal organoids (organoids derived from healthy tissue) to check which drugs and compounds have minimal effect on healthy tissue. This allows screening for drugs with minimal off-target activity or unwanted side-effects.

Drugs for any number of diseases can be screened in this way. For example the organoids of the invention can be used for screening for drugs for cystic fibrosis, Barrett's esophagus, carcinomas, adenocarcinomas, adenomas, inflammatory bowel disease (such as Crohn's disease), liver disease etc. The testing parameters depend on the disease of interest. For example, when screening for cancer drugs, cancer cell death is usually the ultimate aim. For cystic fibrosis, measuring the expansion of the organoids in response to the drugs and stimuli of CFTR is of interest. In other embodiments, metabolics or gene expression may be evaluated to study the effects of compounds and drugs of the screen on the cells or organoids of interest.

Therefore, the invention provides a method for screening for a therapeutic or prophylactic drug or cosmetic, wherein the method comprises:

culturing an expanded cell population (for example, an organoid) of the invention, for example with a culture medium of the invention, optionally for less than 21 days;

exposing said expanded cell population (for example, an organoid) of the invention to one or a library of candidate molecules;

evaluating said expanded cell populations (for example, organoids) for any effects, for example any change in the cell, such as a reduction in or loss of proliferation, a morphological change and/or cell death;

identifying the candidate molecule that causes said effects as a potential drug or cosmetic; and optionally providing said candidate molecule, e.g. as a drug or cosmetic.

In some embodiments, computer- or robot-assisted culturing and data collection methods are employed to increase the throughput of the screen. In some embodiments, the organoid is derived from a patient biopsy. In some embodiments, the candidate molecule that causes a desired effect on the cultured expanded cell population (for example, an organoid) is administered to said patient.

Accordingly, in one aspect, there is provided a method of treating a patient comprising:

(a) obtaining a biopsy from the diseased tissue of interest in the patient;
(b) culturing the biopsy to obtain an organoid;
(c) screening for a suitable drug using a screening method of the invention; and
(d) treating said patient with the drug obtained in step (c).

In some embodiments, the drug or cosmetic is used for treating, preventing or ameliorating symptoms of genetic diseases, metabolic diseases, pathogenic diseases, inflammatory diseases etc, for example including, but not limited to: cystic fibrosis, inflammatory bowel disease (such as Crohn's disease), carcinoma, adenoma, adenocarcinoma, colon cancer, diabetes (such as type I or type II), Barrett's esophagus, Gaucher's disases, alpha-1-antitrypsin deficiency, Lesch-Nyhan syndrome, anaemia, Schwachman-Bodian-Diamond syndrome, polycythaemia vera, primary myelofibrosis, glycogen storage disease, familial hypercholestrolaemia, Crigler-Najjar syndrome, hereditary tyrosinanaemia, Pompe disease, progressive familial cholestasis, Hreler syndrome, SCID or leaky SCID, Omenn syndrome, Cartilage-hair hypoplasia, Herpes simplex encephalitis, Scleroderma, Osteogenesis imperfecta, Becker muscular dystrophy, Duchenne muscular dystrophy, Dyskeratosis congenitor etc.

In some embodiments, the invention provides methods for screening for drugs for regenerative medicine, e.g. drugs for regenerating the liver.

Target Discovery

In some embodiments, the organoids of the invention can be used for target discovery. Cells of the organoids originating from healthy or diseased tissue may be used for target identification. The organoids of the invention may be used for discovery of drug targets for cystic fibrosis, inflammatory bowel disease (such as Crohn's disease), carcinoma, adenoma, adenocarcinoma, colon cancer, diabetes (such as type I or type II), Barrett's esophagus Gaucher's disease, alpha-1-antitrypsin deficiency, Lesch-Nyhan syndrome, anaemia, Schwachman-Bodian-Diamond syndrome, polycythaemia vera, primary myelofibrosis, glycogen storage disease, familial hypercholestrolaemia, Crigler-Najjar syndrome, hereditary tyrosinanaemia, Pompe disease, progressive familial cholestasis, Hreler syndrome, SCID or leaky SCID, Omenn syndrome, Cartilage-hair hypoplasia, Herpes simplex encephalitis, Scleroderma, Osteogenesis imperfecta, Becker muscular dystrophy, Duchenne muscular dystrophy, Dyskeratosis congenitor etc. Organoids cultured according to the media and methods of the invention are thought to faithfully represent the in vivo situation. For this reason they can be a tool to find novel (molecular) targets in specific diseases.

To search for a new drug target, a library of compounds (such as siRNA) may be used to transduce the cells and inactivate specific genes. In some embodiments, cells are transduced with siRNA to inhibit the function of a (large) group of genes. Any functional read out of the group of genes or specific cellular function can be used to determine if a target is relevant for the study. A disease-specific read out can be determined using assays well known in the art. For example, cellular proliferation is assayed to test for genes involved in cancer. For example, a Topflash assay as described herein, may be used to detect changes in Wnt activity caused by siRNA inhibition. Where growth reduction or cell death occurs, the corresponding siRNA related genes can be identified by methods known in the art. These genes are possible targets for inhibiting growth of these cells. Upon identification, the specificity of the identified target for the cellular process that was studied will need to be determined by methods well known in the art. Using these methods, new molecules can be identified as possible drug targets for therapy.

Target and Drug Validation Screens

Patient-specific organoids obtained from diseased and/or normal tissue can be used for target validation of molecules identified in high throughput screens. The same goes for the validation of compounds that were identified as possible therapeutic drugs in high throughput screens. The use of primary patient material expanded in the organoid culture system can be useful to test for false positives, etc from high throughput drug discovery cell line studies.

In some embodiments, the organoid of the invention can be used for validation of compounds that have been identified as possible drugs or cosmetics in a high-throughput screen.

Toxicity Assay

Said expanded stem cell population (for example, organoid of the invention), such as liver, intestinal organoids or pancreatic organoids, can further replace the use of cell lines such as Caco-2 cells in toxicity assays of potential novel drugs or of known or novel food supplements.

Toxicology screens work in a similar way to drug screens (as described above) but they test for the toxic effects of drugs and not therapeutic effects. Therefore, in some embodiments, the effects of the candidate compounds are toxic.

Culturing Pathogens

Furthermore, an organoid of the invention can be used for culturing of a pathogen, such as a norovirus which presently lacks a suitable tissue culture or animal model.

Regenerative Medicine and Transplantation

The invention provides the use of organoids in regenerative medicine and/or transplantation. The invention also provides methods of treatment wherein the method comprises transplanting an organoid into an animal or human.

The organoids can be transplanted into an animal or human and fully differentiate into functional cells in vivo (for example, see Example 16). Alternatively, the organoids can be differentiated in vitro, e.g. using the differentiation media and methods of the invention, prior to transplantation into a human or animal (for example, see Example 16).

Organoids of the invention, such as liver, intestinal organoids or pancreatic organoids are useful in regenerative medicine, for example in treatment of cirrhosis of the liver, post-radiation and/or post-surgery repair of the intestinal epithelium, in the repair of the intestinal epithelium in patients suffering from inflammatory bowel disease such as Crohn's disease and ulcerative colitis, and in the repair of the intestinal epithelium in patients suffering from short bowel syndrome. Further use is present in the repair of the intestinal epithelium in patients with hereditary diseases of the small intestine/colon. Cultures comprising pancreatic organoids are also useful in regenerative medicine, for example as implants after resection of the pancreas or part thereof and for treatment of diabetes such as diabetes I and diabetes II.

In an alternative embodiment, the organoids or cells isolated from the organoids are are reprogrammed into related tissue fates such as, for example, pancreatic cells including pancreatic beta-cells or hepatocytes or ductal cells for the liver. The culturing methods of the present invention will enable to analyse for factors that trans-differentiate the closely related epithelial stem cell to a pancreatic cell, including a pancreatic beta-cell or a hepatocyte.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the epithelial stem cells of an organoid or derived from an organoid are ex vivo treated by a gene therapy approach and are subsequently transferred to the mammal, preferably a human being in need of treatment.

Since small biopsies taken from adult donors can be expanded without any apparent limit or genetic harm, the technology may serve to generate transplantable epithelium for regenerative purposes. The fact that organoids can be frozen and thawed and put into culture without losing their 3D structure and integrity and without significant cell death further adds to the applicability of organoids for transplantation purposes. Furthermore, in some embodiments, organoids embedded in, or in contact with, an ECM can be transplanted into a mammal, preferably into a human. In another embodiment, organoids and ECM can be transplanted simultaneously into a mammal, preferably into a human.

The skilled person will understand that an ECM can be used as a 3D scaffold for obtaining tissue-like structures comprising expanded populations of cells or organoids according to the invention. Such structures can then be transplanted into a patient by methods well known in the art. An ECM scaffold can be made synthetically using ECM proteins, such as collagen and/or laminin, or alternatively an ECM scaffold can be obtained by "decellularising" an isolated organ or tissue fragment to leave behind a scaffold consisting of the ECM (for example see Macchiarini et al. The Lancet, Volume 372, Issue 9655, Pages 2023-2030, 2008). In some embodiments, an ECM scaffold can be obtained by decellularising an organ or tissue fragment, wherein optionally said organ or tissue fragment is from the pancreas, liver, intestine, stomach or prostate.

The invention provides an organoid of the invention or cells derived from said organoid for use in transplantation into a mammal, preferably into a human. Also provided is a method of treating a patient in need of a transplant comprising transplanting an organoid of the invention or cells derived from said organoid into said patient, wherein said patient is a mammal, preferably a human.

Advantageously, the invention enables a small biopsy to be taken from an adult donor and expanded without any apparent limit or genetic harm and so the technology provided herein may serve to generate transplantable epithelium for regenerative purposes.

The invention provides a method of treating an insulin-deficiency disorder such as diabetes in a patient, or a patient having a dysfunctional pancreas, comprising transplanting a pancreatic organoid of the invention or cells from a pancreatic organoid of the invention into the patient. The invention also provides a method for treating a liver disease or condition in a patient, wherein said method comprises transplanting a liver organoid, or cells from a liver organoid of the invention, into a patient.

In some embodiments, the cells or organoid do not express or secrete insulin upon transplantation into the patient but differentiate within the patient such that they secrete insulin. For example, the ability to secrete insulin may not be detectable immediately upon transplantation, but may be present by about one month after transplantation, for example, by 6 weeks, 2 months or 3 months after transplantation.

The patient is preferably a human, but may alternatively be a non-human mammal, such as a cat, dog, horse, cow, pig, sheep, rabbit or mouse.

Thus, included within the scope of the invention are methods of treatment of a human or non-human animal patient through cellular therapy. Such cellular therapy encompasses the application of the stem cells or organoids of the invention to the patient through any appropriate means. Specifically, such methods of treatment involve the regeneration of damaged tissue. In accordance with the invention, a patient can be treated with allogeneic or autologous stem cells or organoids. "Autologous" cells are cells which originated from the same organism into which they are being re-introduced for cellular therapy, for example in order to permit tissue regeneration. However, the cells have not necessarily been isolated from the same tissue as the tissue they are being introduced into. An autologous cell does not require matching to the patient in order to overcome the problems of rejection. "Allogeneic" cells are cells which originated from an individual which is different from the individual into which the cells are being introduced for cellular therapy, for example in order to permit tissue regeneration, although of the same species. Some degree of patient matching may still be required to prevent the problems of rejection. Thus in some embodiments the transplantation involves autologous cells. In some embodiments, the transplantation involves allogeneic cells.

Generally the cells or organoids of the invention are introduced into the body of the patient by injection or implantation. Generally the cells will be directly injected into the tissue in which they are intended to act. Alternatively, the cells will be injected through the portal vein. In some embodiments, the cells are injected into an artery. In some embodiments, the cells are injected intrasplenically. For humans, injection through the portal vein or into an artery is preferred. A syringe containing cells of the invention and a pharmaceutically acceptable carrier is included within the scope of the invention. A catheter attached to a syringe containing cells of the invention and a pharmaceutically acceptable carrier is included within the scope of the invention.

The skilled person will be able to select an appropriate method and route of administration depending on the material that is being transplanted (i.e. population of cells, single cells in cell suspension, organoids or fragments of organoids) as well as the organ that is being treated.

As discussed above, organoids or cells of the invention can be used in the regeneration of tissue. In order to achieve this function, cells may be injected or implanted directly into the damaged tissue, where they may multiply and eventually differentiate into the required cell type, in accordance with their location in the body. Alternatively, the organoid can be injected or implanted directly into the damaged tissue. Tissues that are susceptible to treatment include all damaged tissues, particularly including those which may have been damaged by disease, injury, trauma, an autoimmune reaction, or by a viral or bacterial infection. In some embodiments of the invention, the cells or organoids of the invention are used to regenerate the colon, small intestine, pancreas, oesophagus or gastric system.

For example, in one embodiment, the cells or organoids of the invention are injected into a patient using a Hamilton syringe.

The skilled person will be aware what the appropriate dosage of cells or organoids of the invention will be for a particular condition to be treated.

In one embodiment the organoids or cells of the invention, either in solution, in microspheres or in microparticles of a variety of compositions, will be administered into the artery irrigating the tissue or the part of the damaged organ in need of regeneration. Generally such administration will be performed using a catheter. The catheter may be one of the large variety of balloon catheters used for angioplasty and/or cell delivery or a catheter designed for the specific purpose of delivering the cells to a particular local of the body. For certain uses, the cells or organoids may be encapsulated into microspheres made of a number of different biodegradable compounds, and with a diameter of about 15 µm. This method may allow intravascularly administered cells or organoids to remain at the site of damage, and not to go through the capillary network and into the systemic circulation in the first passage. The retention at the arterial side of the capillary network may also facilitate their translocation into the extravascular space.

In another embodiment, the organoids or cells may be retrograde injected into the vascular tree, either through a vein to deliver them to the whole body or locally into the particular vein that drains into the tissue or body part to which the cells or organoids are directed. For this embodiment many of the preparations described above may be used.

In another embodiment, the cells or organoids of the invention may be implanted into the damaged tissue adhered to a biocompatible implant. Within this embodiment, the cells may be adhered to the biocompatible implant in vitro, prior to implantation into the patient. As will be clear to a person skilled in the art, any one of a number of adherents may be used to adhere the cells to the implant, prior to implantation. By way of example only, such adherents may include fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment, the organoids or cells of the invention may be embedded in a matrix, prior to implantation of the matrix into the patient. Generally, the matrix will be implanted into the damaged tissue of the patient. Examples of matrices include collagen based matrices, fibrin based matrices, laminin based matrices, fibronectin based matrices and artificial matrices. This list is provided by way of illustration only, and is not intended to be limiting.

In a further embodiment, the organoids or cells of the invention may be implanted or injected into the patient together with a matrix forming component. This may allow the cells to form a matrix following injection or implantation, ensuring that the cells or organoids remain at the appropriate location within the patient. Examples of matrix forming components include fibrin glue liquid alkyl, cyanoacrylate monomers, plasticizers, polysaccharides such as dextran, ethylene oxide-containing oligomers, block co-polymers such as poloxamer and Pluronics, non-ionic surfactants such as Tween and Triton'8', and artificial matrix forming components. This list is provided by way of illustration only, and is not intended to be limiting. It will be clear to a person skilled in the art, that any combination of one or more matrix forming components may be used.

In a further embodiment, the organoids or cells of the invention may be contained within a microsphere. Within this embodiment, the cells may be encapsulated within the centre of the microsphere. Also within this embodiment, the cells may be embedded into the matrix material of the microsphere. The matrix material may include any suitable biodegradable polymer, including but not limited to alginates, Poly ethylene glycol (PLGA), and polyurethanes. This list is provided by way of example only, and is not intended to be limiting.

In a further embodiment, the cells or organoids of the invention may be adhered to a medical device intended for implantation. Examples of such medical devices include stents, pins, stitches, splits, pacemakers, prosthetic joints, artificial skin, and rods. This list is provided by way of illustration only, and is not intended to be limiting. It will be clear to a person skilled in the art, that the cells may be adhered to the medical device by a variety of methods. For example, the cells or organoids may be adhered to the medical device using fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

The organoid or population of epithelial stem cells or population of differentiated cells obtained using a method of the invention have a variety of uses. For example, the invention provides the use of the organoid or population of epithelial stem cells/differentiated cells as described herein in a drug discovery screen; toxicity assay; research of embryology, cell lineages, and differentiation pathways; gene expression studies including recombinant gene expression; research of mechanisms involved in injury and repair; research of inflammatory and infectious diseases; studies of pathogenetic mechanisms; or studies of mechanisms of cell transformation and aetiology of cancer.

In one aspect, the invention provides the use of an organoid or population of epithelial stem cells/differentiated cells as described herein in a drug discovery screen, toxicity assay or in regenerative medicine. Similarly, the invention provides the use of the progeny of organoids of the invention for these uses.

Toxicity assays may be in vitro assays using an organoid or part thereof or a cell derived from an organoid. Such progeny and organoids are easy to culture and more closely resemble primary epithelial cells than, for example, epithelial cell lines such as Caco-2 (ATCC HTB-37), 1-407 (ATCC CCL6), and XBF (ATCC CRL 8808) which are currently used in toxicity assays. It is anticipated that toxicity results obtained with organoids more closely resemble results obtained in patients. A cell-based toxicity test is used for determining organ specific cytotoxicity. Compounds that are tested in said test comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analysed to determine the concentration that inhibited end point by 50 percent (TC50).

For example, according to this aspect of the invention, a candidate compound may be contacted with cell or organoid as described herein, and any change to the cells or in activity of the cells may be monitored.

For high-throughput purposes, said organoids are cultured in multiwell plates such as, for example, 96 well plates or 384 well plates. Libraries of molecules are used to identify a molecule that affects said organoids. Preferred libraries comprise antibody fragment libraries, peptide phage display libraries, peptide libraries (e.g. LOPAP™, Sigma Aldrich), lipid libraries (BioMol), synthetic compound libraries (e.g. LOP ACT™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. The cells are preferably exposed to multiple concentrations of a test agent for certain period of time. At the end of the exposure period, the cultures are evaluated. The term "affecting" is used to cover any change in a cell, including, but not limited to, a reduction in, or loss of, proliferation, a morphological change, and cell death. Said organoids can also be used to identify drugs that specifically target epithelial carcinoma cells, but not said organoids.

Organoids according to the invention can further replace the use of cell lines such as Caco-2 cells in drug discovery screens and in toxicity assays of potential novel drugs or known drugs or known or novel food supplements.

Furthermore, such organoids can be used for culturing of a pathogen.

The invention further provides an organoid of the invention or a cell derived from said organoid of the invention for use in therapy. In one embodiment, there is provided an expansion organoid of the invention or cell derived from said organoid of the invention for use in therapy. In another embodiment, there is provided a differentiated organoid of the invention or a population of differentiated cells of the invention for use in therapy. Also provided is an organoid of the invention or a cell derived from said organoid for use in treating a disease or condition as described herein.

Similarly, there is provided a method of treating a disease or condition as described herein comprising administering one or more organoids of the invention, or cell derived from said organoid.

The inventors have also demonstrated successful transplantation of organoids into immunodeficient mice (see example 7 of WO 2012/014076), with transplanted liver organoid-derived cells generating both cholangyocytes and hepatocytes in vivo. Therefore, in one embodiment the invention provides organoids or organoid-derived cells of the invention for transplanting into human or animals.

In some embodiments, the expanded organoids, or cells therefrom, are transplanted into a human or animal. These organoids or cells may differentiate in vivo (e.g. see example 16). In this embodiment, it may be advantageous to administer factors that promote differentiation to the human or animal, either locally or systemically. For example, in some embodiments, the human or animal may be administered forskolin in before, during and/or after transplantation. In an alternative embodiment, the organoids are differentiated in vitro prior to transplantation into the human or animal, preferably using a culture medium and method described herein.

The use of human organoids for transplantation purposes is advantageous over the use of fetal or adult cells (e.g. hepatocytes for the liver or beta cells for the pancreas) for a number of reasons. Firstly, the culture methods of the invention provide unlimited expansion of cells and hence, an unlimited supply. In particular, the inventors have shown that under the correct culture conditions (e.g. using the expansion culture medium of the invention), that Lgr5+ cells can undergo more than 1000 divisions in vitro. Therefore, Lgr5+ cells can be extracted from the organoids and repassaged providing a continual self-renewing source of transplantable cells with differentiation potential. For example, Lgr5+ cells can be extracted from liver organoids and repassaged providing a continual self-renewing source of transplantable hepatocyte- and cholangiocyte-generating cells with differentiation potential. By contrast, fetal or adult cells (such as hepatocytes or beta cells) which are derived from donor organs only provide a single round of transplantation. Furthermore, donor cells can only be kept alive for a few days but lose their phenotypic properties. This means the transplants must be made as soon as the donor becomes available. Organoid-derived cells, on the other hand, retain their phenotype over multiple divisions and over prolonged periods of time meaning that they are ready and available for transplantation at any stage. This could also allow the organoid-derived cells to be used as a temporary treatment to extend the lifespan of patients for patients on the waiting list for transplants. A further advantage of the organoids of the invention is that they can be frozen and later be defrosted without loss of function. This enables cell banking, easy storage and rapid availability for acute use. This could be useful for example, in the preparation of an "off-the-shelf" product, for example, in the case of liver, that might be used for the treatment of acute liver toxicity. Organoids can also be grown from cells or tissue fragments taken as small biopsies from live donors minimising any ethical objections to the treatment. The donor may even be from the patient that is to be treated, which could reduce any negative side-effects associated with transplantation of foreign cells and organs and reduce the need for immunosuppressive drugs.

In some embodiments, the invention also provides a pharmaceutical formulation comprising the components of the culture medium described herein and a pharmaceutically acceptable diluent and/or excipient. For example, there is provided a pharmaceutical formulation comprising a Wnt agonist (e.g. Rspondin), a TGF beta inhibitor, and a cAMP pathway activator (e.g. forskolin) and a pharmaceutically acceptable diluent and/or excipient. There is also provided a pharmaceutical formulation comprising one or more of an EGF receptor activator (e.g. EGF), a Wnt agonist (e.g. Rspondin), an FGF receptor 2 or FGF receptor 4 activator (e.g. FGF), an HGF receptor activator (e.g. HGF), a TGF beta inhibitor and Nicotinamide, and a cAMP pathway activator (e.g. forskolin) and a pharmaceutically acceptable diluent and/or excipient. In a preferred embodiment, the pharmaceutical formulation does not comprise a basal medium. In some embodiments, the pharmaceutical formulation does not comprise an extracellular matrix. It is envisaged that such formulations may be suitable for promoting expansion of stem cells in vivo, e.g. for regenerative therapy. Such formulations may be administered in situ (e.g. at the site of tissue damage) or systemically. Alternatively, the formulations may be formulated so that it is suitable for administration by any administration routes known in the art, for example intravenous, subcutaneous, intramuscular administration, mucosal, intradermal, intracutaneous, oral, and ocular. A pharmaceutical formulation may be thus be in any form suitable for such administration, e.g. a tablet, infusion fluid, capsule, syrup, etc.

Accordingly, included within the scope of the invention are methods of treatment of a human or non-human animal patient through cellular therapy. The term "animal" here denotes all mammalian animals. The patient may be at any stage of development, including embryonic and foetal stages. For example, the patient may be an adult, or the therapy may be for pediatric use (e.g. newborn, child or adolescent). Such cellular therapy encompasses the administration of cells or organoids generated according to the invention to a patient through any appropriate means. Specifically, such methods of treatment involve the regeneration of damaged tissue. The term "administration" as used herein refers to well recognized forms of administration, such as intravenous or injection, as well as to administration by transplantation, for example transplantation by surgery, grafting or transplantation of tissue engineered cell populations derived from cells or organoids according to the present invention. In the case of cells, systemic administration to an individual may be possible, for example, by infusion into the superior mesenteric artery, the celiac artery, the subclavian vein via the thoracic duct, infusion into the heart via the superior vena cava, or infusion into the peritoneal cavity with subsequent migration of cells via subdiaphragmatic lymphatics, or directly into liver sites via infusion into the hepatic arterial blood supply or into the portal vein.

In some embodiments, between $10^4$ and $10^{13}$ cells per 100 kg person are administered per infusion. Preferably, between about $1\text{-}5\times10^4$ and $1\text{-}5\times10^7$ cells may be infused intravenously per 100 kg person. More preferably, between about $1\times10^4$ and $10\times10^6$ cells may be infused intravenously per 100 kg person. In some embodiments, a single administration of cells or organoids is provided. In other embodiments, multiple administrations are used. Multiple administrations can be provided over an initial treatment regime, for example, of 3-7 consecutive days, and then repeated at other times.

It is also possible to reconstitute an organoid from one single cell expressing Lgr5 as defined herein. This single cell may have been modified by introduction of a nucleic acid construct as defined herein, for example, to correct a genetic deficiency or mutation. It would also be possible to specifically ablate expression, as desired, for example, using siRNA. Potential polypeptides to be expressed could be any of those that are deficient in metabolic diseases, including, for example, a polypeptide deficiency in metabolic liver disease, such as AAT (alpha antitrypsin). For elucidating physiology, we might also express or inactivate genes implicated in the Wnt, EGF, FGF, BMP or notch pathway. Also, for screening of drug toxicity, the expression or inactivation of genes responsible for liver drug metabolism (for example, genes in the CYP family) would be of high interest. This is particularly relevant when the cells of the invention are liver cells.

In one embodiment, the expanded epithelial stem cells may be reprogrammed into related tissue fates such as, for example, liver cells including a hepatocyte and a cholangiocyte cell. The culturing methods of the present invention will enable to analyse for factors that trans-differentiate the closely related epithelial stem cell to a liver cell, including a hepatocyte and a cholangiocyte cell.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a non-functional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment. For example, organoid-derived cells may be genetically modified in culture before transplantation into patients.

Thus, in some embodiments, the organoid or population of epithelial stem cells is for use in medicine, e.g. for treating a disorder, condition or disease and/or for use in regenerative medicine.

In one preferred embodiment, for example, if an organoid is to be used for regenerative medicine, the method may start from epithelial cells or from a tissue fragment in which the cells or tissue fragment are autologous or allogeneic. "Autologous" cells are cells which originated from the same organism into which they are being re-introduced for cellular therapy, for example in order to permit tissue regeneration. An autologous cell does not, in principle, require matching to the patient in order to overcome the problems of immune rejection, and/or reduces the need for immune suppression interventions upon transplant. "Allogeneic" cells are cells which originated from an individual which is different from the individual into which the cells are being introduced for cellular therapy, for example in order to permit tissue regeneration, although of the same species. Some degree of patient matching may still be required to prevent the problems of rejection. Techniques for minimising tissue rejection will be known to those of skill in the art.

In embodiments in which the organoids and/or cells are transplanted into a patient, it can be advantageous to administer the cells in a scaffold. Accordingly, there is provided a scaffold comprising one or more organoids of the invention or cells derived from said organoids. A scaffold provides a two-dimensional or three dimensional network. Suitable synthetic materials for such a scaffold comprise polymers selected from porous solids, nanofibers, and hydrogels such as, for example, peptides including self-assembling peptides, hydrogels composed of polyethylene glycol phosphate, polyethylene glycol fumarate, polyacrylamide, polyhydroxyethyl methacrylate, polycellulose acetate, and/or co-polymers thereof (see, for example, Saha et al., 2007. Curr Opin Chem Biol. 11(4): 381-387; Saha et al., 2008. Biophysical Journal 95: 4426-4438; Little et al., 2008. Chem. Rev 108, 1787-1796). As is known to a skilled person, the mechanical properties such as, for example, the elasticity of the scaffold influences proliferation, differentiation and migration of stem cells. A preferred scaffold comprises biodegradable (co)polymers that are replaced by natural occurring components after transplantation in a subject, for example to promote tissue regeneration and/or wound healing. It is furthermore preferred that said scaffold does not substantially induce an immunogenic response after transplantation in a subject.

Said scaffold is supplemented with natural, semi-synthetic or synthetic ligands, which provide the signals that are required for proliferation and/or differentiation, and/or migration of stem cells. In a preferred embodiment, said ligands comprise defined amino acid fragments. Examples of said synthetic polymers comprise Pluronic® F127 block copolymer surfactant (BASF), and Ethisorb® (Johnson and Johnson). In some embodiments the cells are cultured in the scaffold. In other embodiments, they are cultured and then added to the scaffold.

The uses of the present invention may use a single organoid or they may use more than one organoid, for example, 2, 3, 4, 5, 10, 15, 20, 30, 50, 100, 200 or more organoids. Advantageously, the methods of the present invention allow a great number of organoids and epithelial stem cells to be generated in a short period of time, because they result in exponential growth, thereby ensuring that sufficient cells are available for use in the application of interest. Wherever there is reference herein to a "method of treatment" or "method for treatment", for example involving the organoids or cells obtained from the organoids of the invention, this also refers equally to organoids or cells "for use in treatment" and to organoids or cells "for use in the manufacture of a medicament".

The invention is exemplified below in relation to the liver and pancreas.

Expansion Medium (EM) for Liver

The inventors previously described a culture medium suitable for culturing liver epithelial stem cells which contained EGF, a Wnt agonist, FGF and Nicotinamide in WO2012/014076 and WO2012/168930. It has surprisingly been found that adding a cAMP pathway activator to the culture medium allows human liver epithelial stem cells to be cultured long-term. Although the culture medium described in WO2012/168930 and WO2012/014076 could be used for long term culture of mouse cells, it could only be used for short term culture of human cells for around 5 passages. In contrast, use of a culture medium comprising a cAMP pathway activator allows the cells to be passaged many more times, for example, 16 or more (see FIG. 2).

Culturing the cells in an expansion medium allows the cells to multiply whilst retaining their progenitor cell phenotype. Organoids are formed comprising these progenitor cells. Use of the expansion medium is therefore advantageous for providing increased numbers of these useful progenitor cells and for obtaining organoids containing these cells.

Accordingly, the invention provides a liver expansion medium comprising an EGF receptor activator (e.g. EGF), a Wnt agonist, an FGF receptor 2 or FGF receptor 4 activator (e.g. FGF), an HGF receptor activator (e.g. HGF), a TGF beta inhibitor and Nicotinamide, characterised in that the expansion medium further comprises a cAMP pathway activator and/or a BMP activator.

Expansion Medium (EM1) for Liver

In some embodiments, additional components are added at the beginning of the culture process to establish the culture. The inventors have found that a liver expansion medium as described herein additionally comprising Wnt and a BMP inhibitor (e.g. Noggin) is ideal for stimulating initial expansion of cells. The inventors have found that this medium is optimal for stimulating initial expansion of cells for the first few days. Therefore, this first expansion medium is sometimes referred to herein as EM1.

In alternative embodiments, EM1 is an EM1 as described in WO2012/168930 or WO2012/014076. Thus, in some embodiments, EM1 does not comprise a cAMP pathway activator and/or a BMP activator. In some embodiments, EM1 does not comprise a BMP activator. In some embodiments, EM1 comprises a cAMP pathway activator but does not comprise a BMP activator.

In some embodiments, the EM1 is used for just 1 passage or 1 week. In embodiments in which EM1 comprises a serum component, it is advantageous to culture the cells in EM1 for no longer than about a week because the serum component can negatively affect the cells. Thus, in some embodiments, an EM1 medium is used for culturing cells from day 0 to day 10, for example from days 0-7, days 0-6, days 0-5, days 0-4, days 0-3, days 0-2, days 0-1, wherein day 0 is the day that the cells are isolated from their tissue of origin and day 1 is the subsequent day. In some embodiments, the EM1 medium is used only for the first day, first two days or first three to four days of culture. In some embodiments, EM1 medium is used for only 1 passage, or for no more than 2 or 3 passages. However, the cells can be cultured in EM1 for longer periods if required.

Thus, in some embodiments, the Wnt and the BMP inhibitor (e.g. Noggin) are removed or not replenished after approximately 1 day, 2 days, 3 days, 4 days, 5 days, 6 days, 7 days or less, for example 3-4 days.

In some embodiments, the EM1 medium is used subsequent to a freezing step or any other transportation step involving a medium or temperature change that does not combine with optimal growth. This "EM1" medium is preferred for expanding liver cells during the first few days of culture.

Accordingly, the invention provides a liver EM1 as described herein, methods of using EM1 as described herein, as well as uses of EM1 as described herein.

More specifically, the invention provides an expansion medium as described herein, which additionally comprises Wnt and a BMP inhibitor.

In some embodiments, the EM1 of the invention comprises or consists of a basal medium for animal or human cells to which is added EGF, a Wnt agonist (e.g. Rspondin), FGF (e.g. FGF10), HGF, a TGF beta inhibitor, Nicotinamide, a BMP inhibitor and Wnt. This EM1 may further comprise a cAMP pathway activator. In some embodiments, this EM1 further comprises gastrin. An example of this EM1 medium is termed "ENRFHWNicTi (EGF, Noggin, Rspondin, FGF, HGF, Wnt (e.g. Wnt 3a), Nicotinamide, TGF beta inhibitor) supplemented with a cAMP pathway activator".

Any suitable Wnt may be used in EM1. Wnt3a is a preferred example. Other examples include Wnt CM (Barker and Huch, Cell Stem Cell, 2010, 8, 6(1):25-36), CHIR9901 (e.g. Stemgent), Wnt3a recombinant protein, or any other GSK3b inhibitor.

Wnt conditioned media (Wnt CM) preferably comprises Advanced DMEM, P/S, B27, N2 and also FCS. 293T cells transfected with Wnt3A expression plasmid produce Wnt. The whole medium is taken after a few days (i.e. with secreted Wnt) and used as the Wnt source.

In some embodiments, EM1 comprises EGF, a Wnt agonist (e.g. any one of Rspondin 1-4), FGF (e.g. FGF10), HGF, Nicotinamide, gastrin, a TGF-beta inhibitor, a cAMP pathway activator (e.g. forskolin), Noggin and Wnt.

In some embodiments, EM1 is supplemented with a ROCK inhibitor. This is particularly advantageous in the case of starting the cultures from a frozen stock or from a single cell. Y27632 is the preferred ROCK inhibitor for use in the invention.

Thus, in some embodiments, immediately after initiation of the culture the expansion medium is supplemented with one or more (e.g. 2, 3 or all) of a BMP inhibitor (e.g. Noggin), Wnt (e.g. Wnt CM, Wnt3a recombinant protein, CHIR9901 or any other GSK3b inhibitor), and a ROCK inhibitor (e.g. Y27632).

In some embodiments, the expansion medium is additionally supplemented with thiazovivin (for example at about 2 uM, conveniently available through use of hES cell cloning recovery solution (Stemgent)). Use of thiazovivin is advantageous as it helps increase the efficiency of organoid establishment. For example, in some embodiments, the expansion medium is initially supplemented with one or more (e.g. 2, 3, 4 or all) of about 25 ng/ml Noggin, about 1 µg/ml Wnt CM (Barker and Huch, 2010, supra), about 10 µM Y27632 and hES cell cloning recovery solution (Stegent).

Other supplementary compounds that may be added to EM1, i.e. immediately after initiation, are one or more prostaglandin pathway activators, for example, arachidonic acid and/or prostaglandin E2.

Any combination of two or more of the supplementary compounds described herein as being suitable for use immediately after initiation may be added to the expansion medium.

In some embodiments, EM1 comprises EGF, a Wnt agonist (e.g. Rspondin, e.g. Rspondin 1), FGF (e.g. FGF10), HGF, Nicotinamide, a TGF beta inhibitor (e.g. A83.01), and a cAMP pathway activator (e.g. FSK). EM1 is optionally supplemented with one or more (e.g. 1, 2 or 3 of): i) N2 and B27 without retinoic acid, ii) N-Acetylcysteine, and iii) gastrin, and further comprises one or more of (e.g. 1, 2, 3 or 4 of): i) a BMP inhibitor (e.g. Noggin), ii) Wnt (e.g. Wnt CM), iii) a ROCK inhibitor (e.g. Y27632), and iv) thiazovivin (e.g. hES Cell cloning recovery solution).

For example, EM1 may comprise about 50 ng/ml EGF, about 1 µg/ml Wnt agonist (e.g. Rspondin, e.g. Rspondin 1), about 100 ng/ml FGF (e.g. FGF10), about 25 ng/ml HGF, about 10 mM Nicotinamide, about 5 µM TGF beta inhibitor (e.g. A83.01), about 10 µM cAMP pathway activator (e.g. FSK), and further comprises one or more of (e.g. 1, 2, 3 or 4 of): i) about 25 ng/ml BMP inhibitor (e.g. Noggin), ii) about 1 µg/ml Wnt (e.g. Wnt CM), iii) about 10 uM ROCK inhibitor (e.g. Y27632), and iv) thiazovivin (e.g. hES Cell cloning recovery solution). This EM1 is optionally supplemented with one or more of i) N2 and B27 without retinoic acid, ii) about 1.25 mM N-Acetylcysteine, and about 10 nM gastrin.

In a preferred embodiment, EM1 comprises EGF, Rspondin, FGF10, HGF, Nicotinamide, A83.01, forskolin, and further comprises one or more of (e.g. 1, 2, 3 or 4 of): i) Noggin, ii) Wnt, iii) a ROCK inhibitor (e.g. Y27632), and iv) thiazovivin (e.g. hES Cell cloning recovery solution). In this preferred embodiment, EM1 is optionally supplemented with one or more of i) N2 and B27 without retinoic acid, ii) N-Acetylcysteine, and gastrin.

In an exemplified embodiment, EM1 comprises about 50 ng/ml EGF, about 1 µg/ml Rspondin, about 100 ng/ml FGF10, about 25 ng/ml HGF, about 10 mM Nicotinamide, about 5 uM A83.01, about 10 uM forskolin, N2 and B27 without retinoic acid, about 1.25 mM N-Acetylcysteine, about 10 nM gastrin, about 25 ng/ml Noggin, about 1 µg/ml Wnt CM, about 10 µM Y27632, and thiazovivin (e.g. hES Cell cloning recovery solution).

In some embodiments, the invention provides a culture medium for expanding liver cells, comprising or consisting of a basal medium, EGF, FGF10, HGF, any one of Rspondin 1-4, Noggin, nicotinamide, gastrin, a TGF-beta inhibitor, Wnt-3a, and a cAMP pathway activator.

When expanding mouse liver cells, the TGF-beta inhibitor (e.g. A83-01) may be excluded from the EM1 described above. When expanding human liver cells, the TGF-beta inhibitor is preferably present in EM1.

In some embodiments, the cAMP pathway activator is not present in an EM1 of the invention. Accordingly, the statements provided above may be adapted to remove reference to the cAMP pathway activator as necessary.

The expansion medium which additionally comprises the additional components for initiating the culture is referred to herein as expansion medium 1 ("EM1").

As discussed above, the methods may comprise culturing the stem cells in an expansion medium of the invention comprising supplementary components (i.e. in EM1) for the first 1, 2, 3, 4, 5, 6, 7 or less days, preferably for the first 3 or 4 days. After this, the method may then comprise culturing the stem cells in an expansion medium which does not comprise one or both of a BMP inhibitor (such as Noggin) and Wnt. Accordingly, the expansion medium preferably does not comprise these supplementary components after the first 3, 4, 5, 6, 7 or more days, preferably after the first 3 or 4 days.

Expansion Medium 2 "EM2" for Liver

The expansion medium in which the additional components for initiating the culture are not present is referred to herein as expansion medium 2 ("EM2").

Accordingly, the invention provides an expansion medium of the invention, as described herein, which preferably does not comprise one or both of Noggin and Wnt. This expansion medium may be referred to as "EM2". In some embodiments, EM2 does not comprise Noggin. In some embodiments, EM2 does not comprise a BMP inhibitor. In some embodiments, EM2 does not comprise Wnt. In some embodiments, EM2 does not comprise Noggin (and preferably does not comprise a BMP inhibitor) or Wnt.

Accordingly, in some embodiments, the EM2 of the invention comprises or consists of a basal medium for animal or human cells to which is added EGF, a Wnt agonist, FGF, HGF, a TGF beta inhibitor, and Nicotinamide, and wherein EM2 is characterised in that it further comprises a cAMP pathway activator and/or a BMP activator. Preferably, EM2 comprises a cAMP pathway activator and optionally additionally comprises a BMP activator.

More preferably, in some embodiments, the EM2 of the invention comprises or consists of a basal medium for animal or human cells to which is added EGF, a Wnt agonist, FGF, HGF, a TGF beta inhibitor, and Nicotinamide, wherein the EM2 does not comprise Noggin (more preferably does not comprise a BMP inhibitor) and/or Wnt3a (more preferably does not comprise Wnt), and wherein EM2 is characterised in that it further comprises a cAMP pathway activator and/or a BMP activator. Preferably, EM2 comprises a cAMP pathway activator and optionally additionally comprises a BMP activator.

As explained above, the inventors have found that this medium may be used for long-term expansion of human cells. Use of this EM2 is therefore advantageous compared to the EM2 described in WO2012/168930 and WO2012/014076 which could be used for long term culture of mouse cells, but which could not be used for long term culture of human cells.

In some embodiments, EM2 does not comprise Y27632. In some embodiments, EM2 does not comprise a ROCK inhibitor. Thus, in some embodiments, EM2 is an expansion medium of the invention which does not comprise Noggin, Wnt or a Rock inhibitor.

In some embodiments, EM2 does not comprise any of Noggin, Wnt CM (Barker and Huch, 2010, supra), a ROCK inhibitor (e.g. Y27632) and hES cell cloning recovery solution (Stegent).

In some embodiments, EM2 does not comprise a Notch inhibitor.

In some embodiments, EM2 comprises or consists of a basal medium to which is added: EGF, a Wnt agonist, FGF, HGF, Nicotinamide, a TGF beta inhibitor and a cAMP pathway activator. The Wnt agonist is optionally Rspondin (e.g. Rspondin 1, 2, 3 or 4) and the cAMP pathway activator is optionally forskolin (this medium is elsewhere referred to as ERFHNic+TGFbi+FSK).

Advantageously, EM2 may comprise a BMP activator, for example, selected from BMP7, BMP4 and BMP2. BMP7 is preferred. It has surprisingly been found that adding a BMP activator such as BMP7 to the culture medium allows the liver cells to be cultured for a longer term. The invention therefore provides the use of BMP7 for culturing epithelial stem cells, such as liver stem cells. Similarly, the invention therefore provides the use of a BMP activator for culturing stem cells, such as liver stem cells. The invention also provides a method for culturing epithelial stem cells (particularly liver stem cells) which uses an expansion medium as described in WO2012/014076 or WO2012/168930 to which a BMP activator such as BMP7 is added.

Advantageously, in some embodiments, BMP7 is present in EM2 but not in EM1. In some embodiments, about 25 ng/ml BMP7 is added. In some embodiments, BMP7 is not present in the EM2 of the invention and the specific examples described herein can be adapted accordingly.

In some embodiments, the EM2 comprises EGF, a Wnt agonist (e.g. Rspondin), FGF (e.g. FGF10), HGF, nicotinamide, a TGF beta inhibitor (e.g. A83.01), and a cAMP inhibitor (e.g. forskolin). Preferably, EM2 further comprises a BMP activator (e.g. BMP7).

For example, EM2 may comprise about 50 ng/ml EGF, about 1 µg/ml Wnt agonist (e.g. Rspondin), about 100 ng/ml FGF (e.g. FGF10), about 25 ng/ml HGF, about 10 mM Nicotinamide, about 5 uM TGF beta inhibitor (e.g. A83.01), and about 10 µM cAMP pathway activator (e.g. FSK) and preferably further comprises about 25 ng/ml BMP activator (e.g. BMP7).

In an exemplary embodiment, EM2 comprises EGF, FGF (preferably FGF10), HGF, Rspondin, Nicotinamide, TGF-beta inhibitor (e.g. A83.01) and forskolin and preferably further comprises BMP7.

In a further exemplary embodiment, EM2 comprises about 50 ng/ml EGF, about 100 ng/ml FGF10, about 25 ng/ml HGF, about 1 µg/ml Rspondin conditioned media, about 10 mM Nicotinamide, about 5 µM A83.01 and about 10 µM forskolin and preferably further comprises about 25 ng/ml BMP7.

EM2 may further be supplemented with one or more of (e.g. 1, 2 or 3 of): i) N2 and B27 without retinoic acid, ii) N-Acetylcysteine, and iii) gastrin.

Thus, in one embodiment, EM2 comprises EGF, Rspondin, FGF (e.g. FGF10), HGF, Nicotinamide, TGF beta inhibitor (e.g. A83.01), cAMP pathway activator (e.g. FSK), BMP7, N2 and B27 without retinoic acid, N-Acetylcysteine, and gastrin.

For example, in a preferred embodiment EM2 comprises EGF, Rspondin, FGF10, HGF, Nicotinamide, A83.01, forskolin, BMP7, N2 and B27 without retinoic acid, N-Acetylcysteine, and gastrin. In an exemplified embodiment, EM2 comprises about 50 ng/ml EGF, about 1 µg/ml Rspondin, about 100 ng/ml FGF10, about 25 ng/ml HGF, about 10 mM Nicotinamide, about 5 µM A83.01, about 10 µM forskolin, about 25 ng/ml BMP7, N2 and B27 without retinoic acid, about 1.25 mM N-Acetylcysteine, and about 10 nM gastrin.

The basal medium used in EM2 is preferably supplemented with B27, N2 and N-Acetylcysteine. In some embodiments, the basal medium is Advanced-DMEM/F12. However, any other suitable basal medium may be used.

In some embodiments, the medium used as an EM1 cell culture medium comprises all the components of an EM2 culture medium of the invention and additionally comprises Wnt and a BMP inhibitor, for example, Wnt-3a and Noggin. In some embodiments, EM1 does not comprise a BMP pathway activator.

Isolation of Liver Epithelial Stem Cells for Culture

The liver epithelial stem cells to be cultured in the expansion method may be obtained by any suitable method.

Preferably they are obtained from a human liver and so are human liver epithelial stem cells. However, liver epithelial stem cells from non-human animals are also envisaged for use in the invention, for example, non-human mammals such as mouse, rabbit, rat, pig, cow, sheep, horse, dog, cat.

In some embodiments, the liver cells for use in the methods of invention are isolated from a liver biopsy. In some embodiments, liver cells are isolated by collagenase digestion, for example, as described in the examples and in Dorell et al., 2008 (Hepatology. 2008 October; 48(4):1282-91. Surface markers for the murine oval cell response. Dorrell C, Erker L, Lanxon-Cookson K M, Abraham S L, Victoroff T, Ro S, Canaday P S, Streeter P R, Grompe M).

In some embodiments, collagenase digestion is performed on a liver biopsy. In some embodiments, collagenase and accutase digestion are used to obtain the liver cells for use in the invention.

In some embodiments, the method comprises culturing a fragment of liver which comprises liver epithelium. In some embodiments, the epithelial stem cells are isolated from a liver fragment or a liver biliary duct, more preferably from biliary duct tissue. In some embodiments, the epithelial stem cells are obtained from adult liver tissue.

Methods for the isolation of bile duct tissue are known to those of skill in the art. For example, biliary duct may be isolated from a liver using collagenase digestion. Briefly, an adult liver tissue may be washed in a cold (4-10° C.) culture medium, preferably Advanced-DMEM/F12 (Invitrogen) and then, the tissue can be chopped into pieces of around 5 mm and further washed with cold dissociation buffer (collagenase, dispase, FBS in DMEM media). The tissue fragments are preferably incubated with the dissociation buffer for about 2 h at about 37° C. Then, the tissue fragments can be vigorously suspended in 10 ml of cold (4-10° C.) isolation buffer with a 10 ml pipette. The first supernatant containing dead cells is preferably discarded and the sediment preferably suspended with dissociation buffer (e.g. 10-15 ml). After further vigorous suspension of the tissue fragments the supernatant is enriched in biliary ducts. A suspension containing biliary ducts can in this way be obtained and biliary ducts are collected under the microscope and retained in cold media (DMEM+5-10% FBS). This procedure may be repeated until at least 10-20 biliary ducts/well are collected. Then, the isolated biliary ducts may be precipitated. Isolated bile ducts are preferably seeded in 50 ul of matrigel at an approximate ratio of 20 biliary ducts/well.

Liver Expansion Organoids and Populations of Cells

The invention provides a liver organoid or a population of liver epithelial stem cells obtainable or obtained by a method of the invention.

Illustrative examples of liver organoids generated using the expansion medium and methods of the invention are given in the accompanying figures. In one embodiment, an expansion organoid of the invention has a structure essentially as presented in FIG. 8. In one embodiment, an expansion organoid of the invention exhibits cell staining essentially as presented in FIG. 8.

In some embodiments, a liver organoid is a three-dimensional organoid, with a cystic structure. Under expansion conditions the organoid may consist of stem cells and progenitor cells where two domains are defined: (1) A duct-like domain, formed by a single-layer cubical epithelia (positive for the ductal marker Krt19) with cells lining a central lumen; and (2) a pseudo-stratified epithelial domain where krt19 positive cells are detected. This architecture (areas with single layer epithelia together with areas of pseudostratified epithelia) resembles the embryonic liver bud. Under expansion conditions fully differentiated cells are not present, although expression of hepatocyte/hepatoblast-specific markers can in some embodiments be detected.

In a further embodiment, a liver organoid is a three-dimensional organoid comprising two domains: (1) a single-layered epithelium preferably formed by polarized cells with basal nuclei, preferably expressing cytokeratin epithelial markers (for example, KRT19 and KRT7), and (2) a pseudo-stratified epithelium, preferably comprising non-polarized E-Cadherin+, HNF4a+ and/or some KRT7+ cells. In some embodiments, SOX9 and EPHB2 are detectable in almost all the cells within an organoid. In some embodiments, LGR5 is expressed in the organoid, preferably within the EPHB2+ cell population. In some embodiments the organoid has a duct-like phenotype. In a most preferred embodiment, a liver organoid has a combination or all of the features recited in this paragraph and/or the paragraphs above.

Preferably, a liver organoid cultured using expansion media of the invention comprising a TGF beta inhibitor may be cultured for at least 4 weeks, more preferably at least 5 weeks at 5 fold expansion a week or two or more population doublings per week (e.g. for at least 10 doublings, at least 20 doublings, more preferably at least 25 doublings, for example, at least 30 doublings). Preferably, a liver organoid cultured using expansion media of the invention comprising a prostaglandin pathway activator in addition to a TGF beta inhibitor may be cultured for at least 7 weeks, more preferably at least 8 weeks at 2 or more doublings (e.g. 2-3 doublings) per week (i.e. at least 15 doublings, at least 25 doublings, at least 30 doublings, at least 32 doublings, at least 35 doublings, e.g. 32-40 doublings or at least 40 doublings, for example, at least 50 doublings). Thus, preferably, a liver organoid of the invention, for example a human liver organoid, is obtained using expansion media of the invention.

Liver Expansion Organoids—Other Cellular Markers

In some embodiments, an expansion liver organoid or population of liver epithelial stem cells that has been cultured in an expansion medium of the invention comprises one or more cells that express one or more of (e.g. one, two or all three of): progenitor cell markers, ductal markers and hepatocyte markers. In some embodiments, the markers are cell surface markers. In other embodiments, the markers are not found on the cell surface. Examples of progenitor cell markers are Lgr5 and CD133. Preferably an expansion liver organoid comprises cells that express Lgr5, more preferably which express Lgr5 and CD133. Examples of ductal markers are Sox9, Krt19, Krt7 and OC2. Preferably an expansion liver organoid comprises cells that express all of Sox9, Krt19, Krt7 and OC2 but in some embodiments, the cells may comprise only one, two or three of these markers. Examples of hepatocyte markers are Hnf4a and Gapdh. Preferably an expansion liver organoid comprises cells that express both of Hnf4a and Gapdh, but in some embodiments, the cells may comprise only one of these markers. In some embodiments, the liver organoid or population of liver epithelial stem cells that has been cultured in an expansion medium of the invention expresses one or more (e.g. 2, 3, 4, or all 5) of Lgr5, CD133, Krt19, Krt7 and Hnf4a In some embodiments, the liver organoid or population of liver epithelial stem cells that has been cultured in an expansion medium of the invention expresses one or more (e.g. 2, 3, 4, 5, 6 or all 7) of Lgr5, CD133, Sox9, Krt19, OC02, Hnf4a and Gapdh.

In some embodiments, an expansion liver organoid of the present invention exhibits a marker profile as shown in FIG. 8 as shown by cell staining.

Advantageously, using an expansion medium of the invention produces a human expansion liver organoid having an increased ductal phenotype and a decreased hepatocyte phenotype compared to using an expansion medium described in WO2012/014076. Ductal cells are less mature than hepatocytes. Thus, advantageously, by including a cAMP pathway activator in the expansion medium, the resulting cells have more of a progenitor cell phenotype than when a cAMP pathway activator is absent. The ability to generate large numbers of cells having a ductal phenotype opens up new possibilities for research and therapies that require use of these ductal cells.

Accordingly, in some embodiments, a liver organoid of the invention has a ductal phenotype when cultured in expansion medium of the invention (e.g. EM1 or EM2).

Using an expansion method of the present invention, ductal markers are upregulated compared to when liver epithelial stem cells are cultured in an expansion medium described in WO 2012/014076. Therefore, in some embodiments, the invention provides a liver expansion organoid or a population of liver epithelial stem cells in which ductal marker expression is higher than in a liver expansion organoid or a population of liver epithelial stem cells obtained using the same expansion medium but in the absence of a cAMP pathway activator.

Using an expansion method of the present invention, hepatocyte markers are downregulated compared to when liver epithelial stem cells are cultured in an expansion medium described in WO 2012/014076. Therefore, the invention provides a liver expansion organoid or a population of liver epithelial stem cells in which hepatocyte marker expression is lower than in a liver expansion organoid or a population of liver epithelial stem cells obtained using the same expansion medium but in the absence of a cAMP pathway activator.

In some embodiments, the expansion organoid has less than 50% cells which express hepatocyte markers, for example, less than 40%, less than 30%, less than 20%, less than 10%, less than 5% of the cells. In some embodiments, at least 3% of the cells in a liver expansion organoid express hepatocyte markers, for example, at least 5%, at least 15%, at least 25%, at least 35%, at least 45%. For example, 5-50% of the cells may express hepatocyte markers. For example, the expansion liver organoid obtained by the methods and media of the present invention may comprise approximately 30% hepatocyte lineage cells (cells expressing markers characteristic of the hepatocyte lineage).

In some embodiments, the well-known liver transcription factors as HNF1a, HNF1b and HNF4a are expressed in expansion organoids.

In some embodiments, a liver expansion organoid or population of liver epithelial stem cells cultured in an expansion medium of the invention does not express the mature hepatocyte marker albumin.

In one embodiment, a human expanded liver cell population or expansion organoid of the invention:
  a) expresses at least one (e.g. 1, 2, 3, 4, 5, 6, 7, 8, 9), preferably all of the following stem cell signature genes: LGR4, LGR5, TACSTD1/Epcam, CD44, SOX9, SP5, CD24, PROM1, CDCA7 and ELF3; and/or
  b) expresses at least one (e.g. 1, 2, 3, 4), preferably all of the following reprogramming genes: KLF4, MYC, POU5F1 and SOX2; and/or
  c) expresses at least one (e.g. 1, 2, 3, 4, 5, 6, 7, 8, 9, 10, 11, 12, 13, 14, 15, 16, 17, 18, 19), preferably all of the following hepatocyte/cholangiocyte specific genes: HNF1A, HNF1B, HNF4A, HHEX, ONECUT1, ONECUT2, PROX1, CDH1, FOXA2, GATA6, FOXM1, CEBPA, CEBPB, CEBPD, CEBPG, GLUL, KRT7, KRT19 and MET; and/or
  d) does not express at least one (e.g. 1, 2, 3, 4, 5, 6), preferably all of the following hepatocyte/cholangiocyte specific genes: NEUROG2, IGF1R and CD34, AFP, GCG and PTF1A, for example, it does not express NEUROG2, IGF1R and CD34;
wherein the expression of the genes is preferably detected by measuring expression at the mRNA level, for example, using a microarray.

More preferably a human liver cell population or organoid of the invention has all of features a) to d) above.

The human liver cell population or organoids of the invention also preferably express Lgr5 and/or Tnfrsf19, preferably both. In some embodiments, the human liver cell population or organoids, when cultured in expansion medium of the invention express Lgr5 and/or Tnfrsf19, preferably both. Preferably, expression of Lgr5 and/or Tnfrsf19 is detected by RT PCR. In some embodiments, Lgr5 and/or Tnfrsf19 are present at much lower levels of expression in organoids or cells when cultured in the differentiation medium compared to their level of expression organoids or cells when cultured in the expansion medium (for example at least 2-fold, at least 3-fold, at least 4-fold, at least 5-fold, at least 10-fold, at least 15-fold lower). Previously it was not possible to grow human liver organoids for a sufficient length of time to perform expression analysis of the markers.

In one embodiment, a mouse expanded liver cell population or expansion organoid of the invention:
  a) expresses at least one (e.g. 1, 2, 3, 4, 5, 6, 7, 8, 9, 10, 11), preferably all of the following stem cell markers: lgr5, lgr4, epcam, Cd44, Tnfrsf19, Sox9, Sp5, Cd24a, Prom1, Cdca7 and Elf3; and/or
  b) does not express the following stem cell marker: lgr6; and/or
  c) expresses at least one (e.g. 1, 2, 3, 4, 5, 6, 7, 8, 9, 10, 11, 12, 13, 14, 15, 16, 17, 18, 19), preferably all of the following hepatocyte or cholangiocyte markers when grown in expansion medium of the invention: Hnf1a, Hnf1b, Hnf4a, Hhex, Onecut1, Onecut2, Prox1, Cdh1, Foxa2, Gata6, Foxm1, Cebpa, Cebpb, Cebpd, Cebpg, Glul, Krt7, Krt19 and Met; and/or
  d) does not express at least one (e.g. 1, 2, 3, 4, 5, 6, 7, 8, 9, 10, 11, 12, 13, 14, 15, 16, 17) of the following genes when grown in expansion medium of the invention: afp, Ins1, Ins2, Gcg, Ptf1a, Cela1, Cela2a, Cela3b, Neurod1, Neurod2, Neurog1, Neurog2, Neurog3, Amy2a4, Igf1r, Igf2 and Cd34; and/or
  e) expresses at least one (e.g. 1, 2 or 3) of the following reprogramming genes: Klf4, Myc and Pou5f1 and/or
  f) does not express the following reprogramming gene: Sox2,
wherein the expression of the genes is preferably detected by measuring expression at the mRNA level, for example, using a microarray.

More preferably a mouse liver cell population or organoid of the invention has all of features a) to f) above.

Also provided is a liver expansion organoid or an expanded population of liver epithelial stem cells of the invention in an expansion medium of the invention.

In an embodiment, a liver expansion organoid is a liver organoid which is still being cultured using a method of the invention and is therefore in contact with an extracellular matrix. Preferably, a liver expansion organoid is embedded in a non-mesenchymal extracellular matrix.

Culturing Liver Organoids in Differentiation Medium

In one embodiment, the differentiation medium comprises EGF, a TGF-beta inhibitor, and a Notch inhibitor. In one embodiment, the TGF-beta inhibitor is A83-01 and/or the Notch inhibitor is DAPT. In one embodiment, the differentiation medium further comprises Gastrin. In one embodiment, the differentiation medium further comprises FGF, HGF or alternatively both FGF and HGF may be present or absent in the differentiation medium. Dexamethasone may also be added, for example at a concentration of between 10 nM to 10 uM. The liver differentiation medium may optionally include a prostaglandin pathway activator, such as PGE2 or AA. However, this component may also be excluded from the differentiation medium. In some embodiments, oncostatin M may also be added, for example at a concentration range between 1 ng/ml to 1 mg/ml, to help differentiation to hepatocyte fate.

In some embodiments, the differentiation medium comprises one or more receptor tyrosine kinase inhibitor (preferably EGF, HGF and FGF19), a TGF-beta inhibitor (preferably A8301), a Notch inhibitor (preferably DAPT) and a BMP activator (preferably BMP7).

As discussed in WO 2012/168930, Rspondin1 and Nicotinamide both inhibit the expression of the mature hepatocyte marker CYP3A11 and yet promote the expression of the hepatoblast marker albumin. Therefore, to increase differentiation of the cells to more mature liver fates, Rspondin and Nicotinamide may be removed from the cell culture. The expression of specific biliary transcription factors is highly upregulated in expansion cultures containing Rspondin1, indicating that the culture gene expression was unbalanced towards a more biliary cell fate. Notch and TGF-beta signalling pathways have been implicated in biliary cell fate in vivo. In fact, deletion of Rbpj (essential to achieve active Notch signalling) results in abnormal tubulogenesis (Development. 2009 May; 136(10):1727-39. Notch signaling controls liver development by regulating biliary differentiation. Zong Y, Panikkar A, Xu J, Antoniou A, Raynaud P, Lemaigre F, Stanger B Z) and the addition of TGF-beta to liver explants facilitates the biliary differentiation in vitro (Genes Dev. 2005 Aug. 15; 19(16):1849-54. Control of liver cell fate decision by a gradient of TGF beta signaling modulated by Onecut transcription factors. Clotman F, Jacquemin P, Plumb-Rudewiez N, Pierreux C E, Van der Smissen P, Dietz H C, Courtoy P J, Rousseau G G, Lemaigre F P). Since both Notch and TGF-beta signalling pathways were highly upregulated in the liver cultures (see WO 2012/168930), the inventors reasoned that inhibition of biliary duct cell-fate might trigger the differentiation of the cells towards a more hepatocytic phenotype. It was found that addition of a TGF-beta inhibitor (such as A8301) and a Notch inhibitor (such as DAPT) to a differentiation medium that preferably does not contain Rspondin or Wnt, enhances the expression of mature hepatocyte markers and increases the number of hepatocyte-like cells. Conversely, withdrawal or exclusion of the TGF-beta inhibitor (such as A8301) and/or the Notch inhibitor (such as DAPT) in the differentiation medium can promote differentiation to the biliary fate. In addition, withdrawal or exclusion of the cAMP activator (such as forskolin) can promote differentiation e.g. to the biliary fate. In some embodiments, the invention provides a differentiation medium with an alteration as described in this paragraph.

Differentiated Liver Organoids and Populations of Cells

Organoids can be cultured in a differentiation medium, as described above, such that they differentiate into functional cell types (e.g. see Example 15). Thus the invention provides a method for producing cells expressing hepatocyte markers, wherein the method comprises culturing cells in a differentiation medium of the invention. The invention further provides a differentiated liver organoid or a population of differentiated liver epithelial cells.

In one embodiment, the invention provides a differentiated liver organoid or a population of liver epithelial cells obtainable or obtained by a method of the invention, which comprises culturing liver epithelial stem cells in a differentiation medium of the invention.

Illustrative examples of organoids generated using the differentiation medium and methods of the invention are given in the accompanying figures.

A preferred liver differentiated organoid comprises or consists of a cystic structure with on the outside a layer of cells with buds and a central lumen. This liver organoid may have one or more (e.g. 2, 3, or all 4) of the following characteristics: (a) having a cell density of $>5\times10^5$ cells/cm$^3$, preferably $>10\times10^5$ cells/cm$^3$; (b) having a thickness equivalent to 2-30 layers of cells, preferably a thickness equivalent to 2-15 layers of cells; (c) the cells mutually contact in three dimensions, (d) demonstrate a function inherent to healthy liver tissue, (e) have a domain which constitutes the main body of the organoid and is formed by a multilayered epithelia with non-polarized cells wherein albumin expression may be detected.

Generally, use of the differentiation medium of the present invention allows organoids and cells to be obtained which express low levels of or no ductal markers. Expression of higher levels of hepatocyte markers compared to ductal markers indicates that the cells are similar to mature liver cells rather than being similar to liver progenitor cells. Accordingly, there is provided a differentiated organoid or a population of differentiated liver cells in which hepatocyte markers are upregulated compared to ductal markers.

In some embodiments, the liver organoid or population of liver epithelial stem cells that has been cultured in a differentiation medium of the invention expresses one or more mature hepatocyte markers. In some embodiments, the liver organoid or population of liver epithelial stem cells expresses one or more (e.g. 2 or all 3) of the mature hepatocyte markers albumin, Cyp3A4 and zona occuludens (ZO1). Preferably, the level of expression of the mature hepatocyte markers is upregulated compared to the level of expression in an organoid or adult liver stem cell that has been cultured only in an expansion medium of the invention without also having been cultured in a differentiation medium of the invention. Preferably, the level of upregulation is 3× or more, more preferably 5×, 8×, 15, 30×, 50×, 75×, 90×, or 100× or more. For example, the expression of albumin is preferably increased by at least 75 times, more preferably at least 85 times, more preferably at least 95 times (e.g. see FIG. 10).

In some embodiments, a differentiated liver organoid or population of liver epithelial cells has hepatocyte morphology, for example, polygonal cell shapes. In some embodiments, a differentiated liver organoid or population of liver epithelial cells has high expression of hepatocyte markers, such as one or more or all selected from albumin, tyrosine aminotransferase (TAT), apolipoproteins, cytochrome enzymes (e.g. CYP3A4) and complement factors (e.g. C3). In some embodiments, a differentiated liver organoid or population of liver epithelial cells, can perform one or more or all of the following functions: accumulate glycogen; take up LDL, secrete bile acid salts, and detoxify ammonia (for example, see Examples 11 and 16). It is to be understood that all the hepatocyte-type features are readily combinable and that a liver organoid of the invention may exhibit any combination of the above characteristics. In some embodiments, a differentiated liver organoid or population of liver epithelial cells shows stronger hepatocyte function than an expansion organoid, as measured by any one or more of the above characteristics compared to the reference cell line HepG2. In some embodiments, the liver organoid or population of liver epithelial stem cells that has been cultured in a differentiation medium of the invention expresses at least one (e.g. 1, 2, 3, 4, 5, 6, 7, 8, 9, 10, 11, 12, 13, 14, 15, 16, 17, 18), preferably all of the following hepatocyte specific genes: TTR, ALB, FAH, TAT, CYP3A7, APOA1, HMGCS1, PPARG, CYP2B6, CYP2C18, CYP2C9, CYP2J2, CYP3A4, CYP3A5, CYP3A7, CYP4F8, CYP4V2 and SCARB1.

In some embodiments, at least 10% of the cells in a differentiated liver organoid express a hepatocyte surface marker, for example, at least 20%, at least 30%, at least 40%, at least 50%, at least 60%, at least 70%, at least 80%, at least 90% of the cells, for example, about 25%-90%, about 40-80% of the cells.

In some embodiments, the differentiated organoid has less than 10% cells which express ductal markers, for example, less than 5% or less than 2% of the cells.

In some embodiments, the differentiated organoids stain positive for keratin under confocal microscopy.

In some embodiments, the differentiated liver organoid comprises cells that express cholangiocyte markers.

Preferably, culturing the organoids or cells in a differentiation medium of the invention produces differentiated liver organoids and cells which have a liver-like functional phenotype. In some embodiments, the liver organoid or population of liver epithelial stem cells that has been cultured in a differentiation medium of the invention expresses hepatocyte markers is capable of accumulating glycogen. In some embodiments, it is capable of uptaking LDL. In some embodiments it has active cytochrome activity, for example Cytochrome P450 activity. In some embodiments, it is capable of secreting A1AT. In some embodiments, it has Cyp3a activity.

In one embodiment, there is provided a liver organoid in a differentiation medium comprising a basal medium for animal or human cells to which is added EGF, gastrin, FGF19, DAPT, dexamethasone, HGF and A8301.

Uses of Liver Organoids and Populations of Cells

The liver organoid or population of liver epithelial stem cells or population of differentiated liver cells obtained using a method of the invention have a variety of uses. For example, the invention provides the use of the liver organoid or population of liver epithelial stem cells/differentiated cells as described herein in a drug discovery screen; toxicity assay; research of liver embryology, liver cell lineages, and differentiation pathways; gene expression studies including recombinant gene expression; research of mechanisms involved in liver injury and repair; research of inflammatory and infectious diseases of the liver; studies of pathogenetic mechanisms; or studies of mechanisms of liver cell transformation and aetiology of liver cancer.

In one aspect, the invention provides the use of a liver organoid or population of liver epithelial stem cells/differentiated cells as described herein in a drug discovery screen, toxicity assay or in regenerative medicine. Similarly, the invention provides the use of the progeny of liver organoids of the invention for these uses.

Toxicity assays may be in vitro assays using a liver organoid or part thereof or a cell derived from a liver organoid. Such progeny and liver organoids are easy to culture and more closely resemble primary epithelial cells than, for example, epithelial cell lines such as Caco-2 (ATCC HTB-37), 1-407 (ATCC CCL6), and XBF (ATCC CRL 8808) which are currently used in toxicity assays. It is anticipated that toxicity results obtained with liver organoids more closely resemble results obtained in patients. A cell-based toxicity test is used for determining organ specific cytotoxicity. Compounds that are tested in said test comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analysed to determine the concentration that inhibited end point by 50 percent (TC50).

For example, induction of cytochrome P450 enzymes in liver hepatocytes is a key factor that determines the efficacy and toxicity of drugs. In particular, induction of P450s is an important mechanism of troublesome drug-drug interactions, and it is also an important factor that limits drug efficacy and governs drug toxicity. Cytochrome P450 induction assays have been difficult to develop, because they require intact normal human hepatocytes. These cells have proven intractable to production in numbers sufficient to sustain mass production of high throughput assays.

The invention provides the use of liver organoids or populations of liver cells according to the invention for use in regenerative medicine, for example in post-radiation and/or post-surgery repair of the liver epithelium, in the repair of the epithelium in patients suffering from chronic or acute liver failure or disease. Liver diseases for which the liver organoid or cells derived from said organoid may be used include, but are not limited to Hepatocellular Carcinoma, Alagille Syndrome, Alpha-1-Antitrypsin Deficiency, Autoimmune Hepatitis, Biliary Atresia, Chronic Hepatitis, Cancer of the Liver, Cirrhosis, Liver Cysts, Fatty Liver Disease, Galactosemia Gilbert's Syndrome, Primary Biliary Cirrhosis, Hepatitis A, Hepatitis B, Hepatitis C, Primary Sclerosing Cholangitis, Reye's Syndrome, Sarcoidosis, Tyrosinemia, Type I Glycogen Storage Disease, Wilson's Disease, Neonatal Hepatitis, Non-alchoholic SteatoHepatitis, Porphyria, and Hemochromatosis.

In some embodiments, the liver organoids or populations of liver cells are used for therapy of genetic conditions. Genetic conditions that lead to liver failure could benefit from cell-based therapy in the form of partial or full cell replacement using cells cultured according to the media and/or methods of the invention. A non-limiting list of genetic conditions that lead to liver failure and which are treatable by the present invention includes: Progressive familial intrahepatic cholestasis, Glycogen storage disease type III, Tyrosinemia, Deoxyguanosine kinase deficiency, Pyruvate carboxylase deficiency, Congenital dyserythropoietic anemia, Polycystic Liver Disease Polycystic Kidney Disease, Alpha-1 antitrypsine deficiency, Ureum cycle defects, Organic acidemiea, lysosomal storage diseases, and Fatty Acid Oxydation Disorders. Other conditions that may also benefit from cell-based therapy include Wilson's Disease and Hereditary Amyloidosis (FAP). Other non-hepatocyte related causes of liver failure that would require a full liver transplant to reach full therapeutic effect, may still benefit from some temporary restoration of function using cell-based therapy using cells cultured according to the media and/or methods of the invention. A non-limiting list of examples of such conditions which may be treatable by the organoids and/or populations of cells of the present invention includes: Primary Biliary Cirrhosis, Primary Sclerosing Cholangitis, Aglagille syndrome, Homozygous Familial hypercholesterolemia, Hepatitis B with cirrhosis, Hepatitis C with cirrhosis, Budd-Chiari syndrome, Primary hyperoxaluria, Autoimmune Hepatitis, and Alcoholic liver disease. This is exemplified in Example 17, which shows that liver organoids are suitable disease models for alpha-1 antitrypsin (A1AT) deficiency and Alagille Syndrome. In fact, the inventors thereby provide the first ever experimental model for human Alagille Syndrome. Thus in some embodiments, the invention provides the use of a liver organoid as a disease model, for example, for any of the diseases listed above. In some embodiments, the invention provides the use of a liver organoid as a disease model for alpha-1 antitrypsin (A1AT) deficiency or Alagille Syndrome (AGS). In some embodiments, the invention provides a disease model for alpha-1 antitrypsin (A1AT) deficiency or Alagille Syndrome (AGS).

In some embodiments, the disease model for A1AT deficiency comprises A1AT-Protein aggregates. In some embodiments, the disease model for A1AT deficiency has reduced secretion of the A1AT. This mimics reduced A1AT serum levels in patients. In some embodiments, supernatants from the disease model for A1AT deficiency have a reduced ability to block elastase activity compared to wild-type, e.g. as detected as described in the examples under "Elastase inhibition assay". In some embodiments, the disease model for A1AT deficiency shows signs of ER stress, such as phosphorylation of eIF2α and/or a slight increase in apoptosis in the differentiated state compared to wild type. In some embodiments, the disease model for A1AT deficiency is characterised by any combination or all of these features. In a preferred embodiment, the disease model is an organoid as described herein. In some embodiments, the disease model for AGS has reduced ability to differentiate to the biliary fate compared to wild type, as detectable, for example by failure to upregulate biliary markers such as KRT19 and KRT7. In some embodiments, in the disease model for AGS, biliary cells are reduced in numbers and/or unable to integrate into the epithelium, as detectable for example by KRT19 staining. For example, in this disease model, biliary cells may round up and undergo apoptosis. In some embodiments, the disease model for AGS is characterised by any combination or all of these features. In a preferred embodiment, the disease model is an organoid as described herein.

The liver organoids of the invention may be used in a method of treating a hereditary disease that involves malfunctioning hepatocytes. Such diseases may be early onset or late onset. Early onset disease include metabolite related organ failure (e.g. alpha-1-antitrypsin deficiency), glycogen storage diseases (e.g. GSD II, Pompe's disease), tyrosinemia, mild DGUOK, CDA type I, Ureum cycle defects (e.g. OTC deficiency), organic academia and fatty acid oxidation disorders. Late onset diseases include primary hyperoxaluria, familial hypercholesterolemia, Wilson's disease, Hereditary Amyloidosis and Polycystic liver disease. Partial or full replacement with healthy hepatocytes arising from liver organoids of the invention may be used to restore liver function or to postpone liver failure. Accordingly, the invention provides the use of the liver organoids and/or populations of liver cells for restoration of liver function or to postpone liver failure.

The liver organoids of the invention may be used in a method of treating chronic liver failure arising due to hereditary metabolic disease or as a result of hepatocyte infection. Treatment of a hereditary metabolic disease may involve administration of genetically modified autologous liver organoids of the invention. Treatment of hepatocyte infections may involve administration of allogeneic liver organoids of the invention. In some embodiments, the liver organoids are administered over a period of 2-3 months.

The liver organoids of the invention may be used to treat acute liver failure, for example, as a result of liver intoxication which may result from use of paracetamol, medication or alcohol. In some embodiments, the therapy to restore liver function will comprise injecting hepatocyte suspension from frozen, ready to use allogenic hepatocytes obtained from organoids of the invention. The ability to freeze suitable organoids means that the organoids can be available for immediate delivery and so it is not necessary to wait for a blood transfusion.

In the case of replacement or correction of deficient liver function, it may be possible to construct a cell-matrix structure from one or more liver organoids generated according to the present invention. Thus in some embodiments, there is provided a cell-matrix structure derived from a liver organoid and suitable for use in therapy as described herein.

It is thought that only about 10% of hepatic cell mass is necessary for adequate function. This makes implantation of organoid unit compositions into children especially preferable to whole organ transplantation, due to the relatively limited availability of donors and smaller size of juvenile organs. For example, an 8-month-old child has a normal liver that weighs approximately 250 g. That child would therefore need about 25 g of tissue. An adult liver weighs approximately 1500 g; therefore, the required implant would only be about 1.5% of the adult liver. In some embodiments, therefore, the treatment described in this section is for children. In other embodiments it is for adults.

In some embodiments, the transplantation step involves a scaffold, such as a polymer scaffold. When organoid units according to the invention are implanted, optionally attached to a polymer scaffold, proliferation in the new host will occur, and the resulting hepatic cell mass replaces the deficient host function. The inventors have shown that it is possible to generate mature hepatocytes from adult liver stem cells or liver tissue fragments comprising stem cells that are suitable for transplantation into non-human animals or humans. Using the expansion culture medium according to the invention, the inventors have demonstrated that it is possible to maintain and expand a population of liver stem cells. Using the differentiation culture medium according to the invention, the inventors have shown that hepatoblasts can be differentiated in vivo to mature hepatocytes suitable for transplantation purposes. Hence, the inventors provide a new source of hepatocytes for liver regeneration, replacement or correction of deficient liver function.

In some embodiments it is desirable to repopulate/replace 10-20% of a patient's liver with healthy hepatocytes arising from a liver organoid of the invention.

In some embodiments, the invention provides the liver organoids or populations of liver cells obtained from the expansion and/or differentiation media for use in therapy. Such organoids and populations of cells are useful for treating ductal cell disease. For example, such organoids and populations of cells may be used to treat diseases of the ductal tree, for example diseases caused by a mutations in Jagged1 (JAG1), for example Alagille syndrome, or mutations in the transporter ABCB4, for example Low Phospholipid associated Cholelithiasis. Other non-heriditary cholangiopathies such as Primary Biliary Cirrhosis, Primary sclerosis cholangitis and Caroli disease may also be treated using the liver organoids or expanded populations of liver cells of the invention. Such diseases may benefit from expanding duct-cells in culture. Other diseases that could be treated with organoids or expanded populations of liver cells of the invention include hereditary liver diseases where bilirubin metabolism is affected. Such diseases would benefit from hepatocyte transplants. Examples of known hereditary defects in bilirubin metabolism are Crigler-Najjar syndrome (mutation in UGT1A1 gene), Dubin-Johnson syndrome (mutation in cMOAT), and Rotor syndrome (mutations in SLCO1B1 and SLCO1B3).

Thus, in some embodiments, the liver organoid or population of liver epithelial stem cells is for use in treating a liver disorder, condition or disease or for use in regenerative medicine.

The inventors have found that Lgr5 is not detectable in healthy liver, although residual Lgr5 may be detected. Thus, the invention further provides a method of diagnosing liver injury comprising detecting whether Lgr5 is expressed, wherein the expression of Lgr5 protein indicates liver injury. The invention also provides a method of monitoring the repair or regeneration of the liver by monitoring the expression of Lgr5 in the liver. Lgr5 expression may be detected by any suitable method, for example, flow cytometry, immunohistochemistry or by use of PCR methods. Anti-Lgr5 antibodies suitable for use in such diagnosis are known, e.g. see WO2012/140274. Accordingly there is provided an anti-Lgr5 antibody for use in diagnosing liver injury.

Pancreas

It has similarly been shown that adding a cAMP pathway activator to culture medium for pancreas epithelial stem cells increases the number of passages that are possible for human cells (see Example 13). Methods for culturing pancreatic cells are described in WO2010/090513.

Accordingly, there are provided methods and culture media for culturing epithelial stem cells, organoids and populations of cells obtainable using the methods and media described herein and uses of said organoids and populations of cells, wherein the epithelial stem cells are derived from the pancreas.

For example, there is provided a method for culturing epithelial stem cells, for example to obtain a pancreatic organoid, wherein said method comprises:

culturing one or more epithelial stem cells from pancreas in contact with an extracellular matrix in the presence of an expansion medium, the expansion medium comprising a basal medium for animal or human cells to which is added:
one or more receptor tyrosine kinase ligands, an Rspondin, Nicotinamide, and a TGF-beta inhibitor; and a cAMP pathway activator.

In some embodiments, the culture medium further comprises one or more components selected from a BMP inhibitor (e.g. Noggin), a prostaglandin pathway activator, Wnt, Gastrin, B27 and N-acetylcholine. The paragraphs elsewhere in the application that discuss these components e.g. in relation to the liver embodiments, apply equally to the pancreatic embodiments.

In some embodiments, the culture medium further comprises a p38 inhibitor (e.g. SB202190).

In a preferred embodiment, the culture medium comprises EGF (e.g. about 50 ng/ml), FGF10 (e.g. about 100 ng/ml), Rspondin (e.g. about 1 µg/ml), Nicotinamide (e.g. about 10 mM), A8301 (e.g. about 500 nM), Forskolin (e.g. about 10 µM) Noggin (e.g. about 10% CM), Wnt (e.g. about 1 µg/ml), Gastrin (e.g. about 10 nM) and B27 1×, NAc (e.g. about 1.25 mM), and optionally PGE2 (e.g. about 1 µM) and optionally a p38 inhibitor (e.g. about 10 µM).

In some embodiments, the methods for culturing epithelial stem cells to obtain a pancreatic organoid, further comprise the step of differentiating the cells using differentiation media and methods described elsewhere in this application.

The invention further provides a pancreatic organoid or cell obtained from the pancreatic organoids for use in the treatment of diabetes (e.g. diabetes type I or type II), pancreatitis, pancreatic cancer or cystic fibrosis, whereby the treating optionally comprises transplantation of the organoid or cells obtained from the pancreatic organoid into a patient in need thereof. In some embodiments, the transplanted cells are insulin secreting cells. In other embodiments, the cells are progenitor cells that mature further after transplantation into insulin secreting cells.

Other Tissues

It is also envisaged that adding a cAMP pathway activator to culture medium for other epithelial stem cells, including intestine (e.g. small intestine or colon), stomach, prostate, lung, breast, ovarian, salivary gland, hair follicle, skin, oesophagus or thyroid will also increase the number of passages possible for human cells. Thus the methods, media, organoids and populations of cells, and uses of said organoids and populations of cells, also apply to these tissues.

Definitions

As used herein, the verb "to comprise" and its conjugations is used in its non-limiting sense to mean that items following the word are included, but items not specifically mentioned are not excluded. In addition the verb "to consist" may be replaced, if necessary, by "to consist essentially of" meaning that a product as defined herein may comprise additional component(s) than the ones specifically identified, said additional component(s) not altering the unique characteristic of the invention. In addition a method as defined herein may comprise additional step(s) than the ones specifically identified, said additional step(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

As used herein, the term "about" or "approximately" means that the value presented can be varied by +/−10%. The value can also be read as the exact value and so the term "about" can be omitted. For example, the term "about 100" encompasses 90-110 and also 100.

All patent and literature references cited in the present specification are hereby incorporated by reference in their entirety.

The following examples are offered for illustrative purposes only, and are not intended to limit the scope of the present invention in any way.

DESCRIPTION OF FIGURES

The invention will now be described further with references to the following figures in which:

FIG. 3: (A) Graph showing number of cells per well (indicating proliferation potential) at each passage in weeks 0-4. (B) Graph showing number of cells per well at each passage in weeks 21-25. (C) Table showing mean doubling time for early and late passaged cells (up to the twelfth passage at day 103). (D) Image showing EdU incorporation the third and twelfth passage.

FIG. 5: (A) Images showing Lgr5 expression in human liver culture. (B) Flow cytometry analysis of Lgr5 positive cells cultured with and without forskolin. (C) Graph showing qPCR analysis of the expression of LGR5 in 4 week old cultures treated in the presence or absence of FSK.

FIG. 7: (A) Images of stained chromosomes at passage 1 and passage 15. (B) Graph showing percentage of cells with normal/abnormal chromosome count at 2 weeks and at more than 3 months of culture.

FIG. 10: (A) Immunofluorescence staining of mature hepatocyte markers in differentiated organoids, showing albumin (ALB, red) and zona occuludens (ZO-1, green) positive cells. (B) Graph showing expression of albumin and Cytochrome p450 3A4 isoform upon differentiation by qPCR analysis. Graphs indicate mean±SEM of 3 independent experiments in 3 independent donor derived cultures. EM, expansion medium including FSK. DM, differentiation medium. HuLi, whole lysate from human liver.

FIG. 11: (A) Images showing glycogen storage determined by PAS (Periodic-Acid Schiff) staining in cultures grown in EM or DM for 11 days. Magnification, 10×. (B) Images showing LDL uptake analysed using Dil-ac-LDL fluorescent substrate (red) in cultures maintained in EM or DM (right) for 11 days. Scale bar, 25 µm. (C) Graph showing Cyp3a4 expression in cells cultured in DM for 11 days. Results are expressed as RLU per ml per million cells. HEK293T cells and HepG2 cells were used as negative and positive controls respectively. Triplicates for each condition were analysed. Results are shown as mean±SEM of 2 independent experiments in 4 independent donor-derived cultures.

FIG. 12: Table 2: List of compounds tested in the culture medium and effect on organoid expansion/differentiation.

FIG. 15: Human liver culture of ductal origin. (A) Cyp3A4 activity of Percoll purified primary human hepatocytes after 4 days in culture in comparison to HepG2 cells. (B) EpCAM marks bileducts in human liver sections. Hepatocytes are EpCAM negative. (C) sorting strategy to purify EpCAM+ ductal cells and Hepatocytes. In the first step, singlets were gated to avoid contamination by cell aggregates. Subsequently, large debris and erythrocytes were excluded. From this population, EpCAM+PI− (viable) cells were sorted as the ductal population. For hepatocyte sorting large EpCAM− cells were selected. (D) Organoid formation efficiency of sorted ductal and hepatocyte populations after 14 days. Organoids bigger than 100 µm were scored. (E) EpCAM+ sort derived organoids at passage 0 and passage 6. (F-G) Organoid formation efficiency of unsorted, Percoll purified hepatocytes (F) and the respective percentage of residual EpCAM+ cells (G).

and organoid culture (lower panel). (D) Summary of the copy number analysis of the different organoid cultures of the two donors. Somatic CNVs were exclusively observed in culture A derived from donor 2, which were already present in the parental culture.

Figure 17:
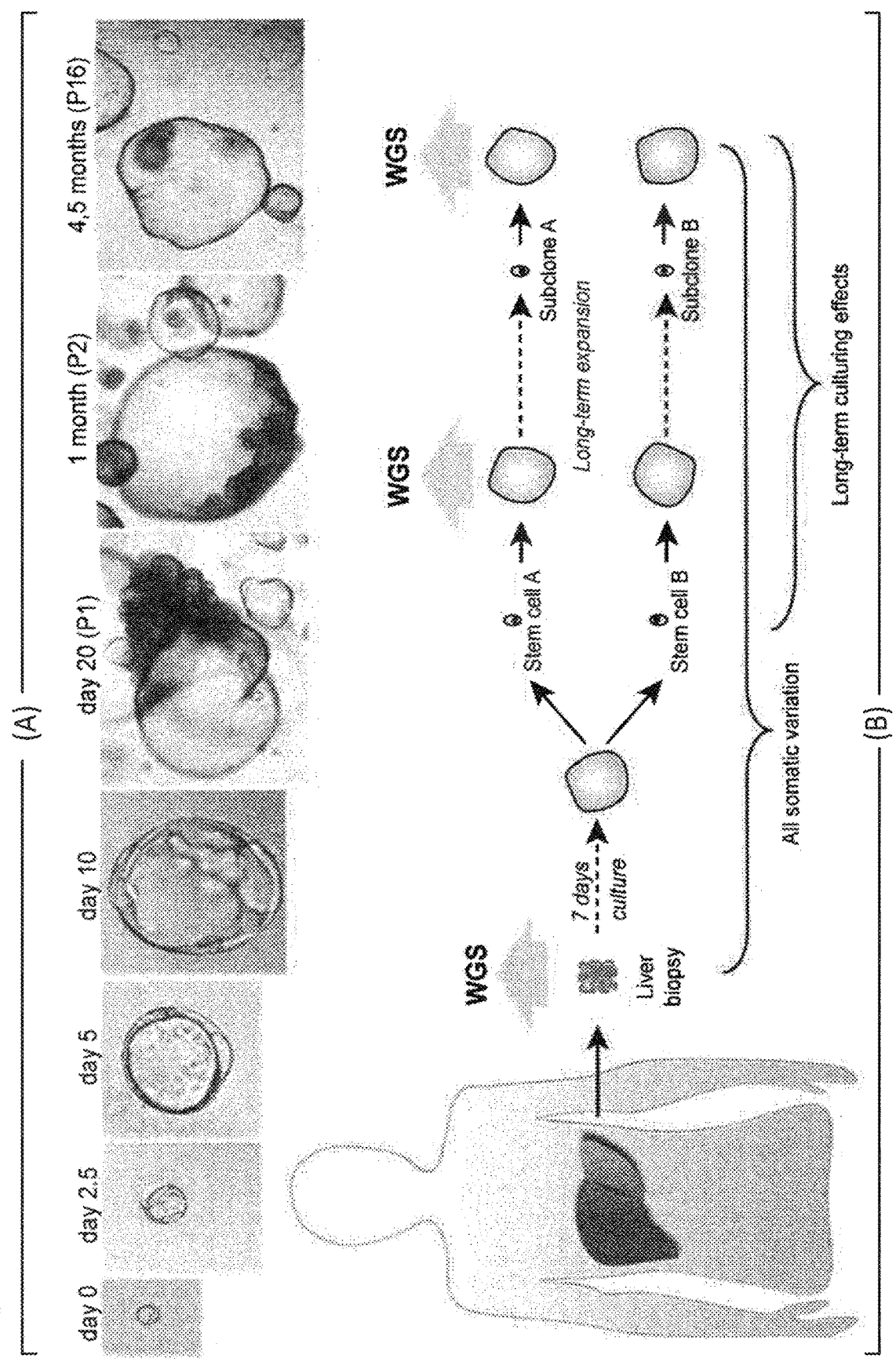

FIG. 17: Human liver organoids are genetically stable after months of expansion in culture. Genetic stability of human liver cultures was analyzed in clonally grown cultures that had been expanded for >3 months (~120 days) in our complete human liver medium. (A) Human liver biopsies were dissociated into single cells and clonal cultures were obtained by seeding sorted cells at a ratio of 1 cell per well. As illustrated, cells quickly proliferated and expanded in culture. DIC images of growing single cells from human liver cultures. Magnifications: 40× (days 0-10), 4× (day 20-onwards). (B-D) Genetic stability of the human liver organoid cultures clonally expanded long-term in vitro. (B) Schematic overview of the experimental setup. Two independent donor liver biopsies were minced and cultured for one week. Subsequently, single liver stem cells were isolated and clonally expanded to obtain two independent organoid cultures per donor (culture A and culture B). These cultures were subjected to long-term expansion after which a second clonal expansion step was performed. The resulting organoid cultures were subjected to whole genome sequencing (WGS) analysis. To obtain all somatic variation present in the cultures, variants were filtered for presence in the original biopsy. To determine the effect of long-term culturing on genomic stability, somatic variation was filtered for presence in earlier passages. (C) Number of somatic base substitution observed in the different organoid cultures. The pie-chart indicates the percentage of the genome that was surveyed per donor. The right panels indicate the absolute numbers of base substitution observed in the surveyed part of the genome. Indicated are the total number of somatic base substitutions per culture and the number induced by long-term culturing. (D) Effect of somatic base substitutions on protein-coding DNA. Left panels indicate the total number of somatic base substitutions per donor and the left panel indicates the part that affects protein-coding DNA.

FIG. 18: Upon differentiation liver organoid cultures upregulate hepatocyte genes. Human liver cultures were expanded for at least 1 month in culture and transferred to our differentiation medium as described in Experimental Procedures. (A) Scheme of the experimental plan. (B-C) Expression of hepatocyte genes was determined by immunofluorescence (B) or qPCR (C) 11 days later. (B) Immunofluorescence staining showing albumin (ALB, dark) and zona occuludens (ZO-1, light) positive cells all over the organoid, indicating that the cells start expressing hepatocyte markers. (C) qPCR analysis indicated that both, albumin and Cytochrome p450 3A4 isoform were highly expressed upon differentiation. Graphs indicate mean±SEM of 3 independent experiments in 3 independent donor derived cultures. EM, expansion medium including FSK. DM, differentiation medium, Tissue, whole lysate from human liver. **, p<0.01 when comparing EM vs DM. (D) Whole genome transcriptome analysis of human liver cultures grown in our expansion medium (EM) or after being cultured 11 days in our defined Differentiation medium (DM). Heat map indicates cluster of genes highly expressed in liver tissue and in organoid cultures upon differentiation. Of note, this cluster contains genes essential for liver function, as the indicated in dark. Light, downregulated; Dark, upregulated.

FIG. 19: Differentiated liver organoids exhibit hepatocyte functions in vitro and in vivo. To test whether the cells could have differentiated towards functional hepatocytes in vitro, we determined the ability of the cultures to retain some hepatocyte functions in vitro, upon differentiation. (A), Glycogen accumulation was determined by PAS (Periodic-Acid Schiff) staining in organoids grown in EM or DM for 11 days. PAS positive staining was exclusively observed in the organoids after Differentiation (DM), indicating that the cells exhibit capacity to accumulate glycogen. Magnification, 10×. (B) LDL uptake was analysed using Dil-ac-LDL fluorescent substrate in cultures maintained in EM (left) or DM (right) for 11 days. Only cultures maintained in DM incorporated the substrate. Nuclei were counter-stained with DRAQ5. Scale bar, 25 μm. (C) Albumin production during 24 h was measured in the supernatant of liver organoids. Results are expressed as mean±SEM of 2 independent experiments in 4 independent donor-derived cultures. (D) CYP3A4 activity was measured as described in methods in cultures kept in DM for 11 days. Results are expressed as RLU per ml per million cells. HEK293T cells and HepG2 cells were used as negative and positive controls respectively. Note that organoids upon DM exhibit similar the CYP3A4 activity as fresh isolated hepatocytes. Triplicates for each condition were analyzed. Results are shown as mean±SEM of 2 independent experiments in 4 independent donor-derived cultures. (E), Midazolam metabolism is performed exclusively by functional CYP3A3/4/5 enzymes. 3 different organoid cultures from 2 different donors and HepG2 cells were plated and cultured for 11 days as described, then midazolam was added to the medium (5 μM) and after 24 hours, concentrations of 1-OH midazolam and 1-OH midazolam glucuronide were determined as described in methods. Duplicates for each condition and donor were analyzed. Results are shown as mean±SEM of 2 independent experiments. (F) Bile acid production was measured as described in methods. Results are shown as ±SEM of 2 independent experiments in 2 independent donor-derived cultures. Duplicates for each condition and donor were analyzed. (G) Ammonia elimination was measured as described in methods. Results are shown as ±SEM of n=3 independent experiments in 2 independent donor-derived cultures and are expressed as nM/h/million cells. (H) Retrorsine/CCl4 treated Balbc/nude mice were transplanted with 1-2×106 human liver organoid cells and sacrificed after 120 days. The presence of foci of human Albumin positive, but human KRT19 negative hepatocytes proves successful engraftment and differentiation in mouse liver. (I) Average serum levels of human Albumin in mouse circulation after transplantation. Results are shown as ±SEM of 2 vehicle control animals, 2 primary hepatocyte transplanted mice and 6 human liver organoid transplanted animals. **, p<0.01 and *, p<0.05 when comparing EM vs DM.

Figure 20:
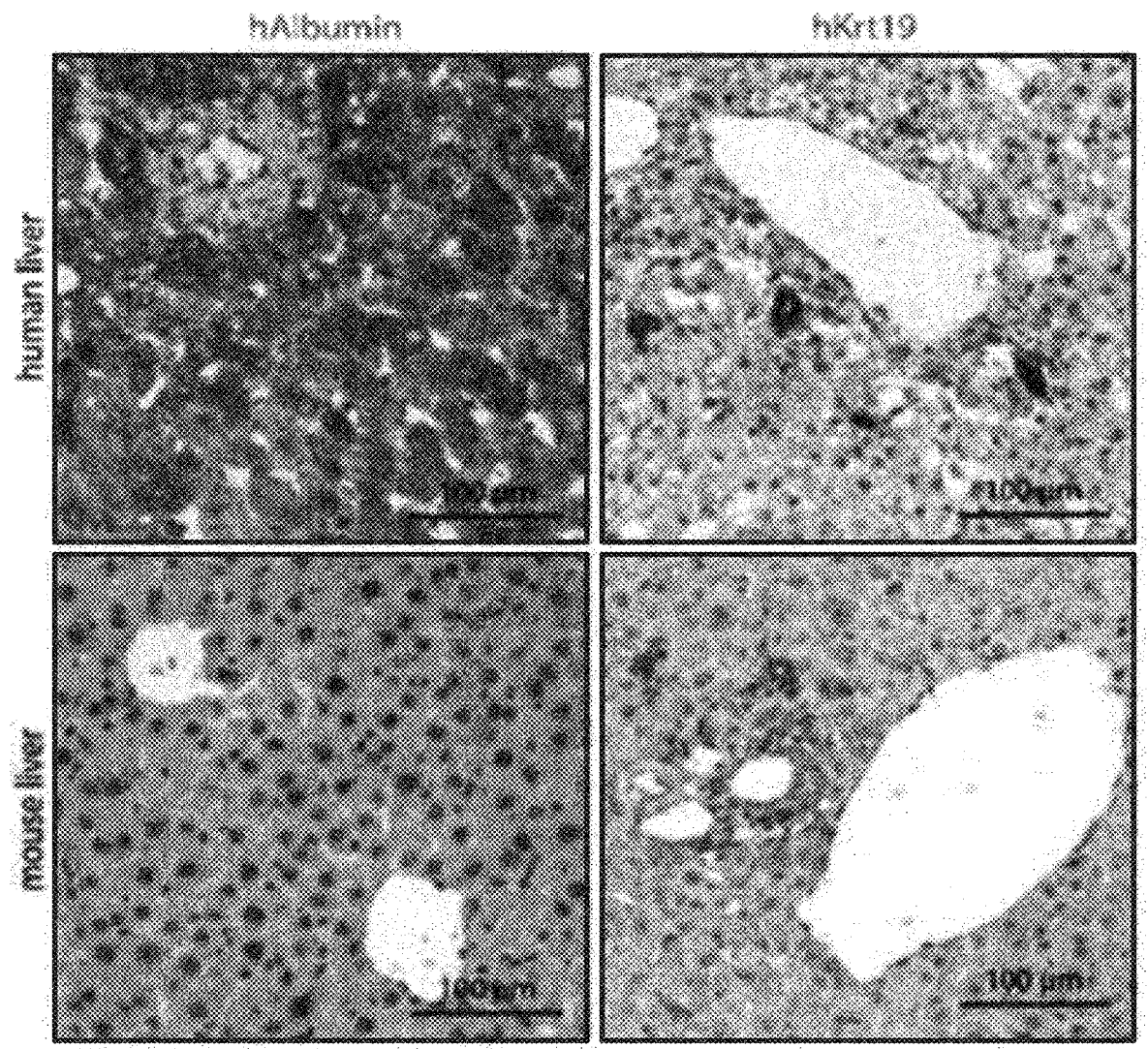

FIG. 20: Transplantation of human liver organoids into damaged mouse liver. (A) Control staining for human specific Albumin (hAlbumin) and Kertatin-19 (hKrt19) antibodies. hAlbumin recognises human but not mouse hepatocytes, whereas hKrt19 stains human but not mouse bile ducts. (B) Liver sections of mice sacrificed 2 hours or 2 days after human liver organoid cell transplantation stained for hKrt19. After 2 hours human cells are mostly seen in blood vessels in and around portal veins, whereas cells start to engraft in the tissue 2 days after the transplant. (C) Example singlet or doublet human Albumin positive hepatocytes observed in the liver of human liver organoid transplanted Balbc/nude mice. (D) Human serum Albumin levels of individual transplanted mice over 120 days. (E) Average human serum alpha-1-antitrypsin levels of transplanted mice over 120 days. Results are shown as ±SEM of 2 vehicle control animals and 3 human liver organoid transplanted animals.

FIG. 21: Human A1AT deficiency liver cultures as an in vitro disease model. (A) Representative pictures of A1AT deficient patient derived liver organoids at Passage 2 and Passage 11 (4× magnification). (B) ELISA measurement of Albumin secretion in supernatant from donor and A1AT deficient patient organoids in EM or after 11 days in DM. Patients and donors show a similar level of albumin release. Results are expressed as mean±SEM of 2 independent experiments. (C) A1AT deficient patient organoids were differentiated for 11 days and incubated with DiI-Ac-LDL as described in materials and methods. Fluorescence microscopy shows robust LDL uptake in patient organoids. Scale bar, 50 μm (D) Fold induction of Albumin and CYP3A4 mRNA levels after 11 days of differentiation of donor and A1AT deficient patient organoids. Results are expressed as mean±SEM of 2 independent experiments (E-H) Immunohistochemistry for A1AT on liver tissue (E/G) and liver derived organoids from a healthy donor (F) and a representative A1AT deficient patient (H). Arrows indicate A1AT protein aggregates in patient derived liver tissue (G) and organoids (H). Scale bar, 20 μm. (I) ELISA measurement of A1AT secretion in supernatants from Donor and patient organoids after 11 days of differentiation. Results are expressed as mean±SEM of 2 independent experiments. (J) Enzymatic measurement of Elastase inhibition by supernatants of differentiated donor and patient derived organoid cultures (as described in materials and methods). Supernatants from all 3 patients show reduced inhibition of Elastase activity. Results are expressed as mean±SEM of 2 independent experiments (K) Western blot of total lysates from donor and A1AT deficient patient organoids after 11 days of differentiation. Increased eIF2α phosphorylation at Ser51 was detected in the 3 patients. Representative image is shown. Pat., patient.

Figure 22:
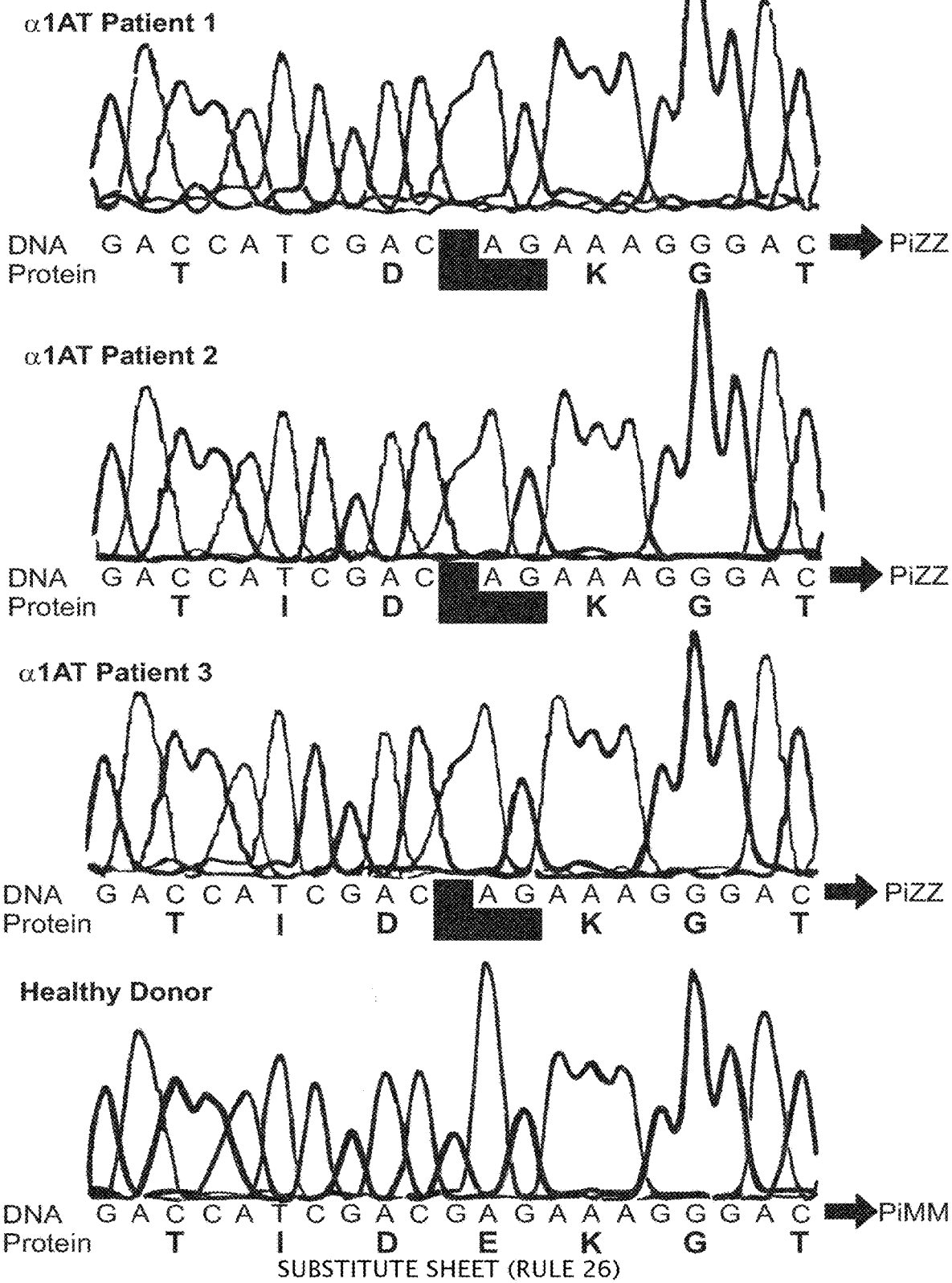

FIG. 22: Organoids from A1AT deficiency and AGS patients mimic disease phenotypes in vitro. (A) SERPIN1A Sanger Sequencing of Donor #1 and a1AT Patient #1. Chromatograms of 3 A1AT-deficient patients (PiZZ) and 1 donor with wildtype SERPINA1 (PiMM). The homozygous G to A mutation causes an amino acid change from glutamic acid to lysine at position 342. (B) Clustering analysis of the different donors (1-5) and a1AT Patient (A1AT_pat) organoids and tissues. Note that, regarding differentiation ability, the behaviour of a1AT Patient derived organoids resembles donor derived organoids. i.e. organoids in EM cluster cluster with donor EM organoids and a1AT-D organoids cultured in DM cluster with donor derived organoids cultured in DM conditions. (C) histological staining for cleaved caspase-3 in d nor and a1AT Patient derived organoids differentiated in DM for 11 days. (D) quantification of apoptotic cells in wildtype and a1AT Patient derived organoids in EM and after differentiation in DM. Results are shown as ±SEM of 6 random sections of organoids per 2 independent donors and patients. (E) qRT-PCR of Lgr5 and ductal markers (Krt19 and Krt7) in EM and after ductal differentiation. AGS patients fail to upregulate ductal markers upon differentiation. (F) Immunofluorescence of differentiated wildtype and AGS patient organoids. Krt19 positive cells in AGS patient organoids do not integrate into the epithelium and show signs of apoptosis (arrows). EM, expansion medium. DM, differentiation medium, ductal diff, ductal differentiation medium (see text). AGS, Alagille syndrome.

EXAMPLES

Figure 1:
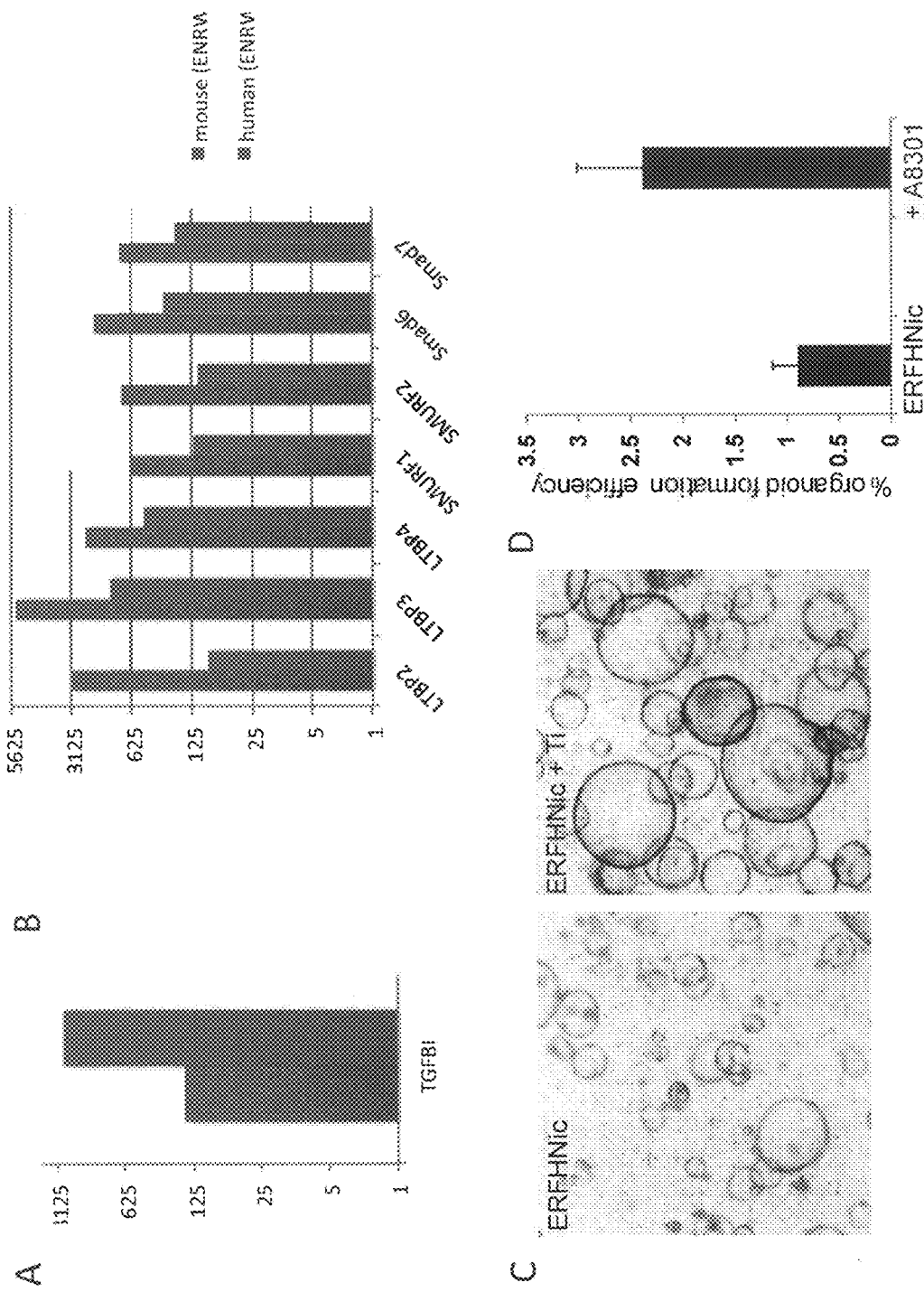
FIG. 1: (A) Expression profile for TGF-beta in human and mouse liver organoids. (B) Expression profile for TGF-beta inhibitors in human and mouse liver organoids. (C) Image showing growth of human liver organoids with and without a TGF-beta inhibitor. (D) Graph indicating the percentage of colony formation efficiency in human organoid cultures with and without a TGF-beta inhibitor.

Example 1: TGF-Beta (TGFb) Inhibition Increases Human Liver Organoid Formation Efficiency Human liver tissue was digested using collagenase dissociation and liver cells isolated as described in Material and Methods. Cells were cultured in mouse liver medium containing Egf, Rspo, Fgf10, Hgf and Nicotinamide (ERFHNic) and 2-4 weeks after, RNA was isolated and analysed for expression of TGFb signaling pathway regulators. (FIG. 1A) Expression profile showed that human liver organoids express high levels of TGFb while (FIG. 1B) TGFb inhibitors (SMAD6, SMAD7) or sequesters (LTBP2, LTBP3) were almost absent in the human liver cultures when cultured under mouse medium conditions. Graphs represent the absolute value as obtained from the microarray. Note that the data is represented in logarithmic scale. (FIG. 1C-D) Human liver cells isolated by collagenase dissociation were dissociated to single cell, counted and 3000 or 10000 cells were seeded per well in a 48 well plate. Mouse liver culture medium (ERFHNic) or the same medium supplemented with A8301 (+A) was overlaid and organoids were allowed to grow. Organoids numbers were counted 15 days after seeding. Treatment with A8301 significantly increased organoid formation efficiency. (FIG. 1C) DIC images of organoids treated with mouse liver medium supplemented (right panel) or not (left panel) with the ALK5/6 inhibitor A8301. (FIG. 1D) Graph indicating the % of colony formation efficiency in cultures seeded in the presence or absence of A8301. Experiments were performed in triplicate. Five different donor derived cultures were counted. Results are expressed as mean±SEM of 5 independent experiments. The organoid efficiency results shown in FIG. 1D illustrate that many more organoids are formed when a TGF beta inhibitor is present in the medium compared to when it is absent.

Figure 2:
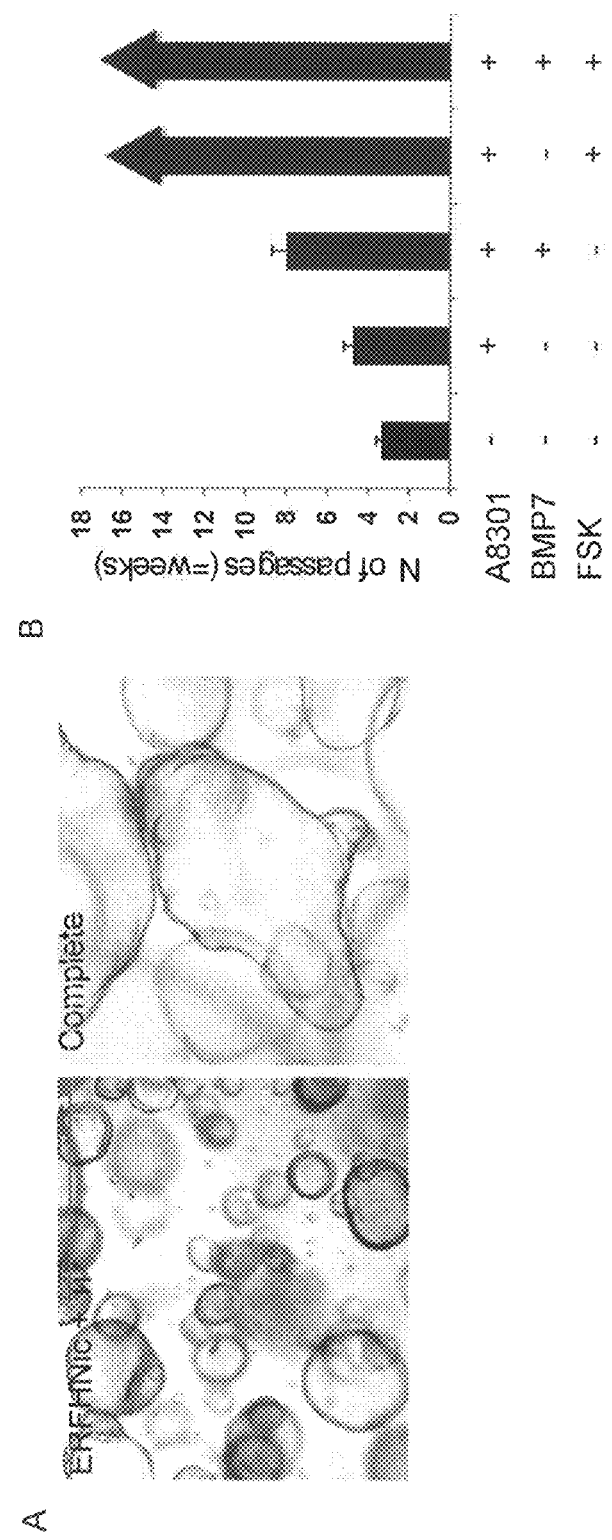
FIG. 2: (A) Image showing growth of human liver organoids in culture medium with and without FSK and BMP7. (B) Graph showing number of passages in a culture medium comprising a TGF-beta inhibitor (A8301), BMP7 and/or forskolin (FSK).

Example 2: FSK and BMP7 are Useful for the Long-Term Culture of Human Liver Organoids Human liver cells isolated by collagenase dissociation were dissociated to single cell, counted and 3000 or 10000 cells were seeded per well in a 48 well plate. Mouse liver culture medium (ERFHNic) or medium supplemented with A8301 or A8301 and BMP7 or A8301 and BMP7 and Forskolin (FSK) was overlaid as indicated and organoids were allowed to grow. The cultures were split every week 7-10 days at a ratio of 1:4-1:6 dilution. All the cultures started to grow and proliferate however, the cultures grown in mouse medium or medium supplemented with A8301 only or BMP7 and A8301 arrested proliferation after some weeks in culture and could not be expanded any further as indicated in the graph. Supplementing the culture medium with A8301 combined with FSK significantly increased the expansion efficiency of the cultures which have been able to grow for >18 passages at a split ratio of 1:4-1:6 every 7-10 days for >5 months. The results are shown in FIG. 2.

Example 3: Under FSK Supplemented Medium, Cells Maintain their Proliferation Potential Over Time To quantify the proliferation capacity of the human liver cultures, expansion ratios, in vitro growth curves and EdU incorporation, at early and late passages, were analysed in human liver cultures grown in complete medium (ENRFHNic supplemented with A8301 and FSK as described in methods). (FIG. 3A-C) Cell numbers were counted by Trypan blue exclusion at the indicated time points, in at least 3 independent human liver cultures (independent donor material). The cultures followed an exponential growth curve within each time window analysed. Graphs illustrate the number of cells counted per well at each passage from passage P1-P4 (FIG. 3A), P16-P18 (FIG. 3B). The doubling time, or amount of time the culture needs to double its original size was calculated as follows: doubling time=ln(2)/growth rate for each time window analysed. Note that the doubling time was essentially maintained once the culture had started to expand from day 16 onwards, indicating that the expansion potential is maintained within the time period analysed. (D) Similar EdU incorporation was detected in early and late passages, again indicating that the cells maintain their proliferation potential in vitro after long-term culturing.

Figure 4:
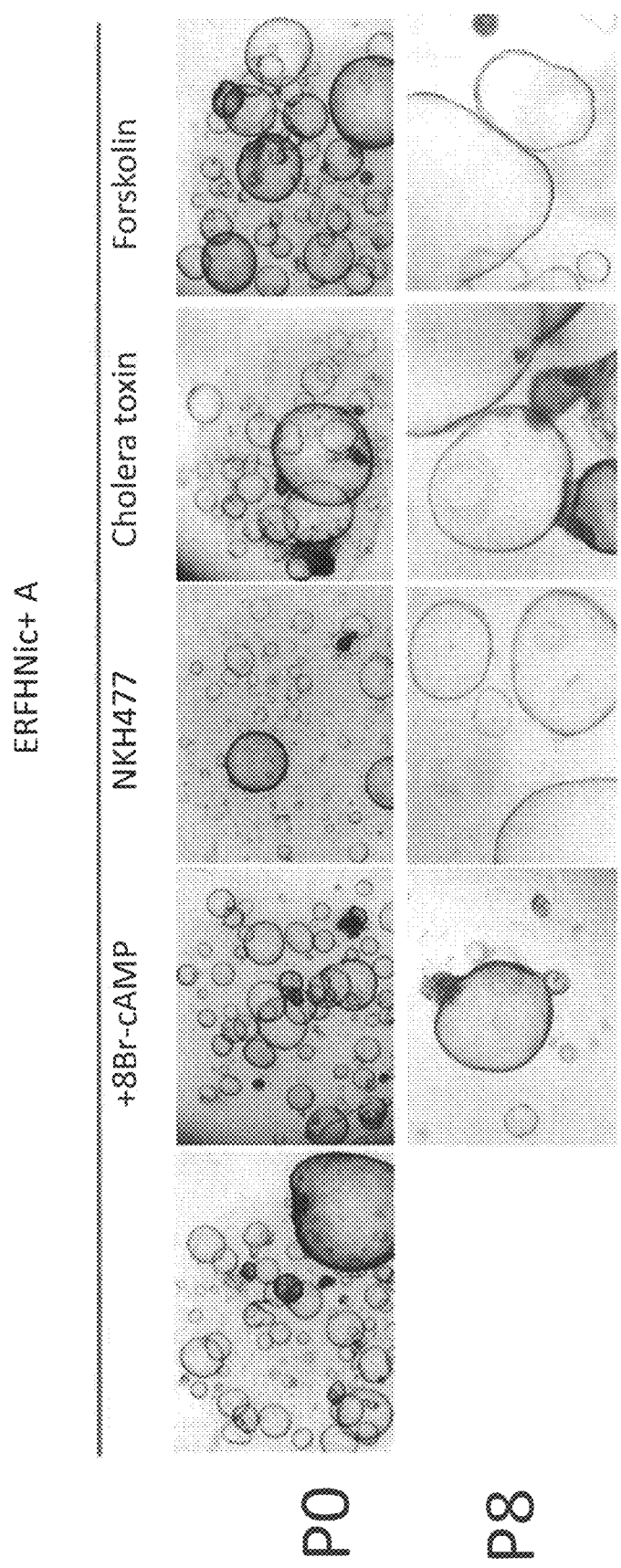
FIG. 4: Images showing human liver organoids cultured with various different cAMP agonists (8Br-cAMP, NKH477, Cholera toxin and forskolin) at passage 0 and passage 8.

Example 4: Other cAMP Activators Also Maintain the Human Liver Cultures for Long Term Human liver organoids were seeded in mouse medium supplemented with A8301 and with one of the cAMP activators as indicated in FIG. 4. Cholera toxin was used at a concentration of 100 ng/ml. Only the cultures that were treated with cAMP activators were able to be expanded>2 months (P8). The results are shown in FIG. 4.

Example 5: Human Liver Cultures Treated with FSK Express High Levels of LGR5

Lgr5 expression was analysed in cultures grown in our defined culture medium by immunofluorescence and flow cytometry analysis. (FIG. 5A) Confocal image of a human liver organoid showing that the organoids are formed by epithelial derived cells positive for EPCAM (blue). The stem cell marker Lgr5 (green) was restricted to a subset of cells within the organoid, while the Wnt target gene EPHB2 (red) was broadly expressed, but colocalized with LGR5 as expected. Flow cytometry analysis of LGR5 positive cells is shown in FIG. 5B. Staining was performed on single cells isolated from a culture that had been cultured for >4 weeks in the presence or absence of FSK. Only in the presence of FSK Lgr5 cells could be readily detected as a 1-3% of the culture population. Experiment was performed in 2 independent human liver donor cultures. (FIG. 5C) qPCR analysis of the expression of LGR5 in 4 week old cultures treated in the presence or absence of FSK. LGR5 expression levels are 2-3× upregulated upon treatment with FSK.

Example 6: Wnt Signaling and cAMP are Important for the Growth of the Cultures

Figure 6:
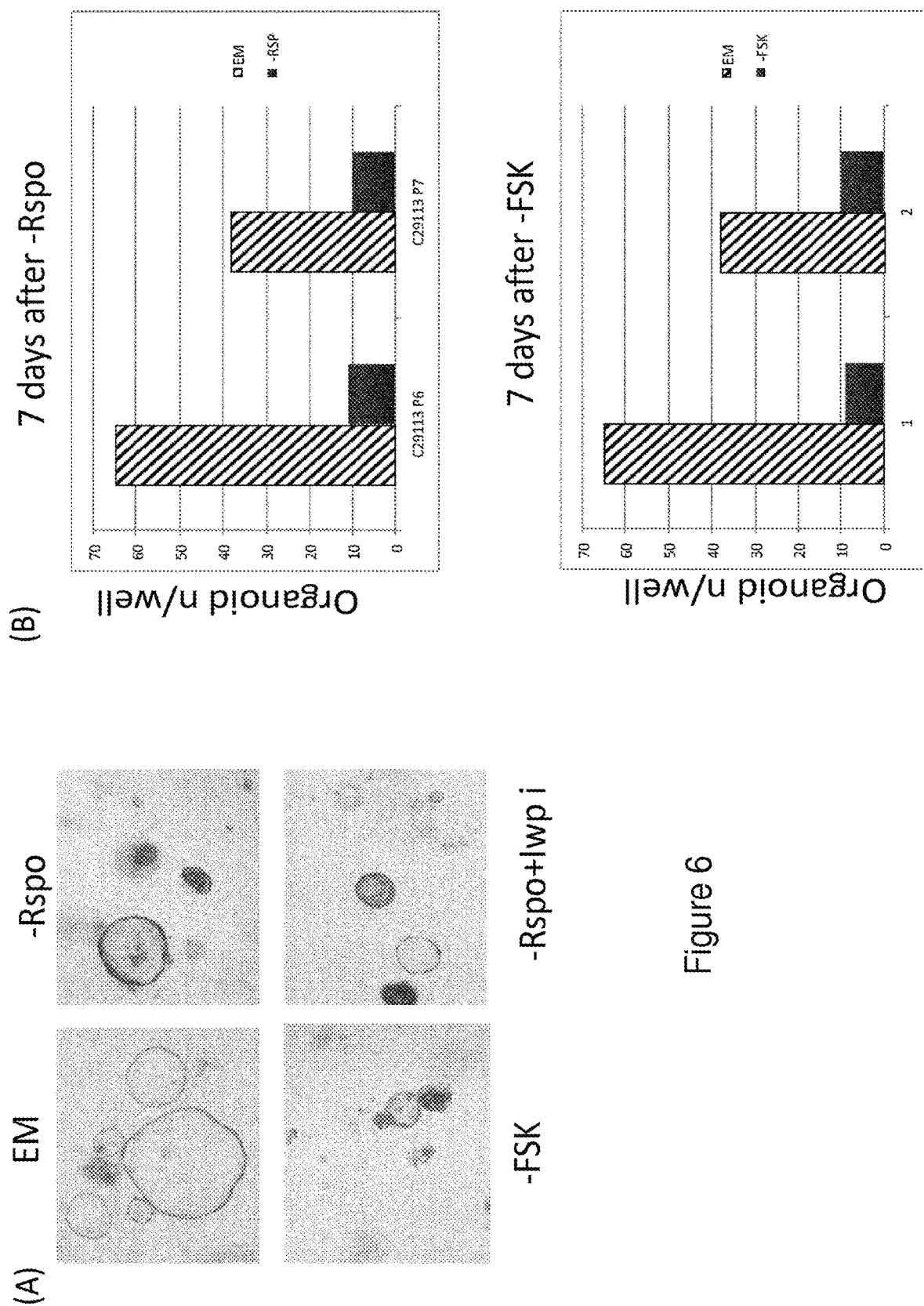
FIG. 6: (A) Images showing human liver organoids grown in the complete medium comprising FSK (EM) or transferred to a medium without Rspo (−Rspo), without FSK (−FSK) and without Rspo including the porcupine inhibitor (−Rspo+IWIP). (B) Graphs showing organoids per well 7 days after removal of Rspondin (−Rspo) or FSK (−FSK).

Expanding human liver organoids grown in complete medium as described in Methods were maintained in that medium (EM) or transferred to a medium without Rspo (−Rspo), without FSK (−FSK) and without Rspo including the porcupine inhibitor (−Rspo+IWIP). Organoid numbers were counted 1 week later. The results show that both, cAMP and Wnt are essential signaling pathways to maintain the human liver culture in vitro. (FIG. 6A) DIC images of the cultures treated with the different compounds as indicated in the figure. (FIG. 6B) Graphs indicating the number of organoids in the presence/absence of the compounds in 2 independent human liver cultures.

Example 7: Human Liver Cultures Maintain Chromosome Numbers Over Time

Genetic stability of the human liver organoids cultured for long-term. (FIG. 7A) Representative image of a chromosome spread illustrating a normal count (n=46) of a metaphase of a cell cultured for 16 days (P1) or cultured for 100 days (P15). The table illustrates the % of cells with chromosomal counts as indicated.

Figure 8:
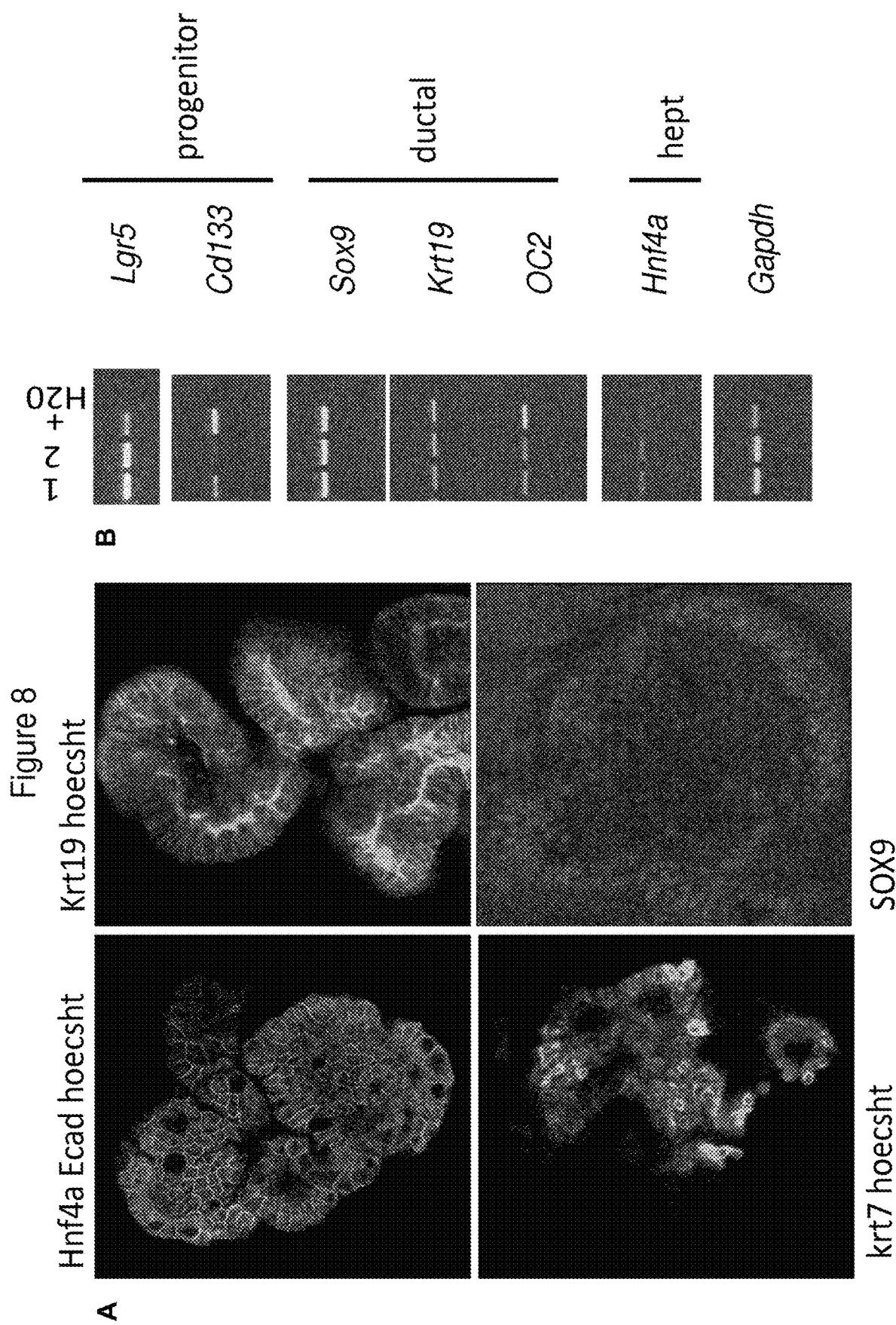
FIG. 8: (A) Images showing immunofluorescence staining of expression markers of the ductal (Sox9, Krt19 and Krt7) and hepatocyte (Hnf4a) lineages. (B) RT-PCR results on a gel showing expression of progenitor (Lgr5 and CD133), ductal (Sox9, Krt19 and OC2), and hepatic markers (Hnf4a).
Figure 9:
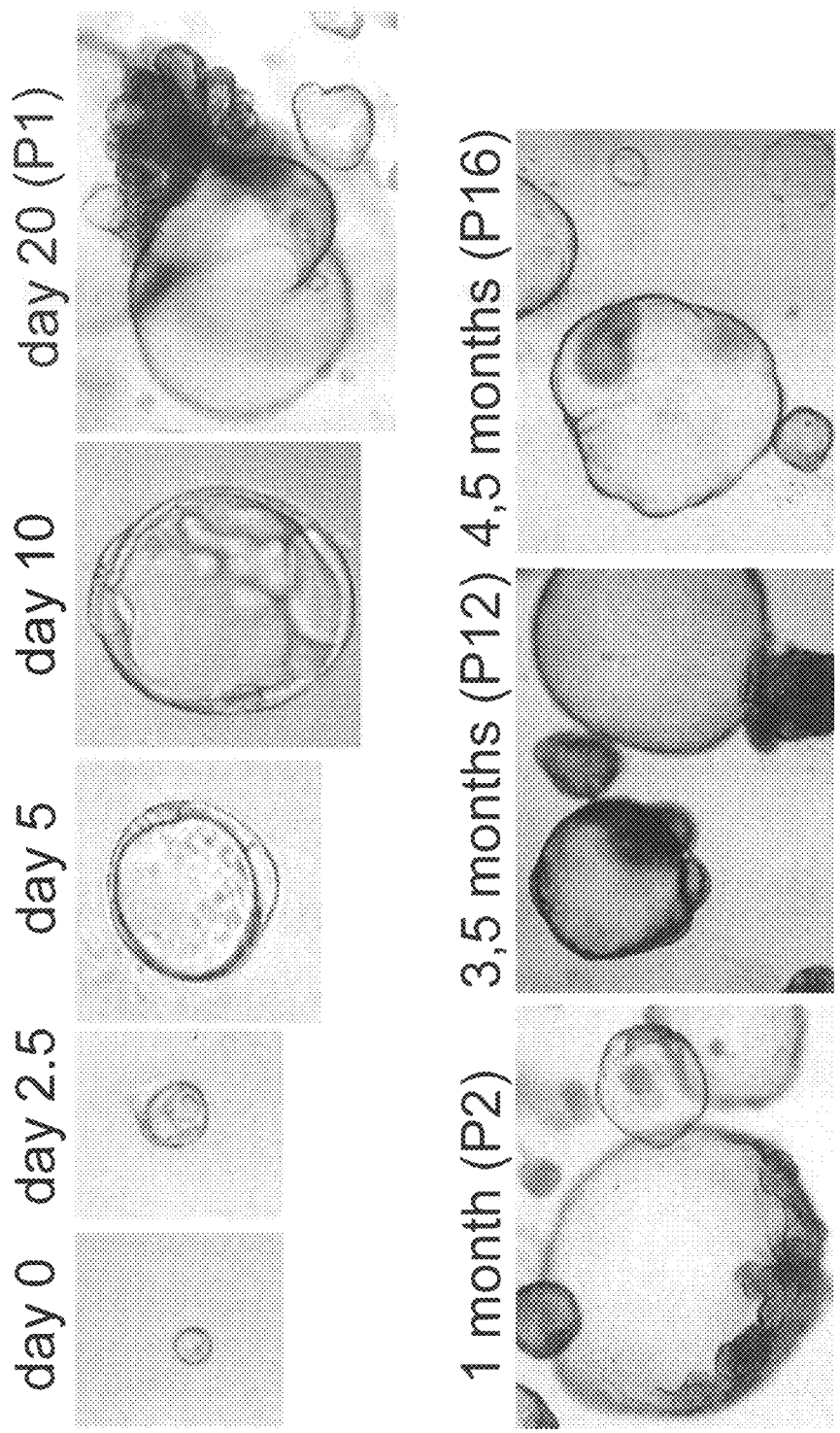
FIG. 9: Images of growing organoids from single cells from human liver cultures. Magnifications: 40× (days 0-10), 4× (day 20 onwards).
Figure 13:
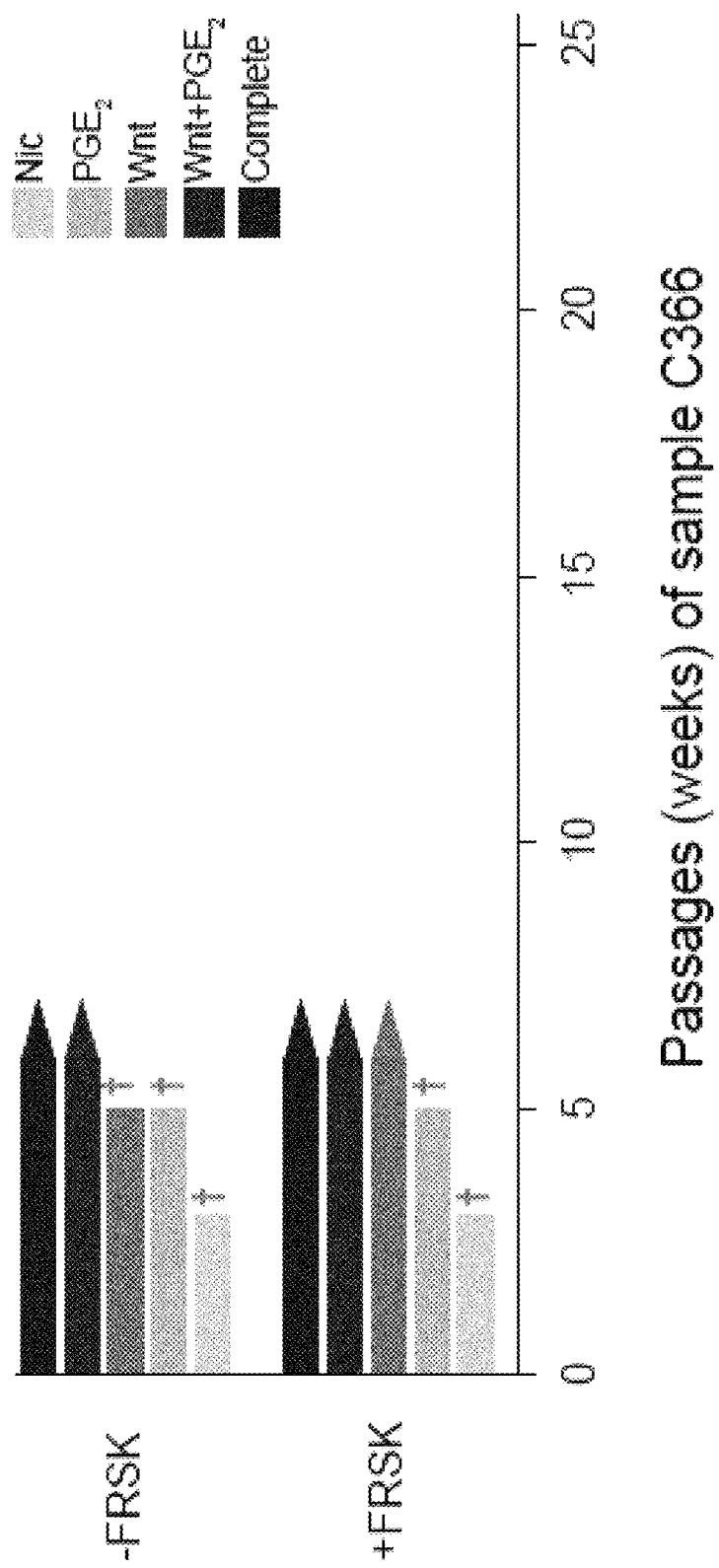
FIG. 13: Representative image of sample C366 cultured in 10 different conditions from P0 until P6.
Figure 13:
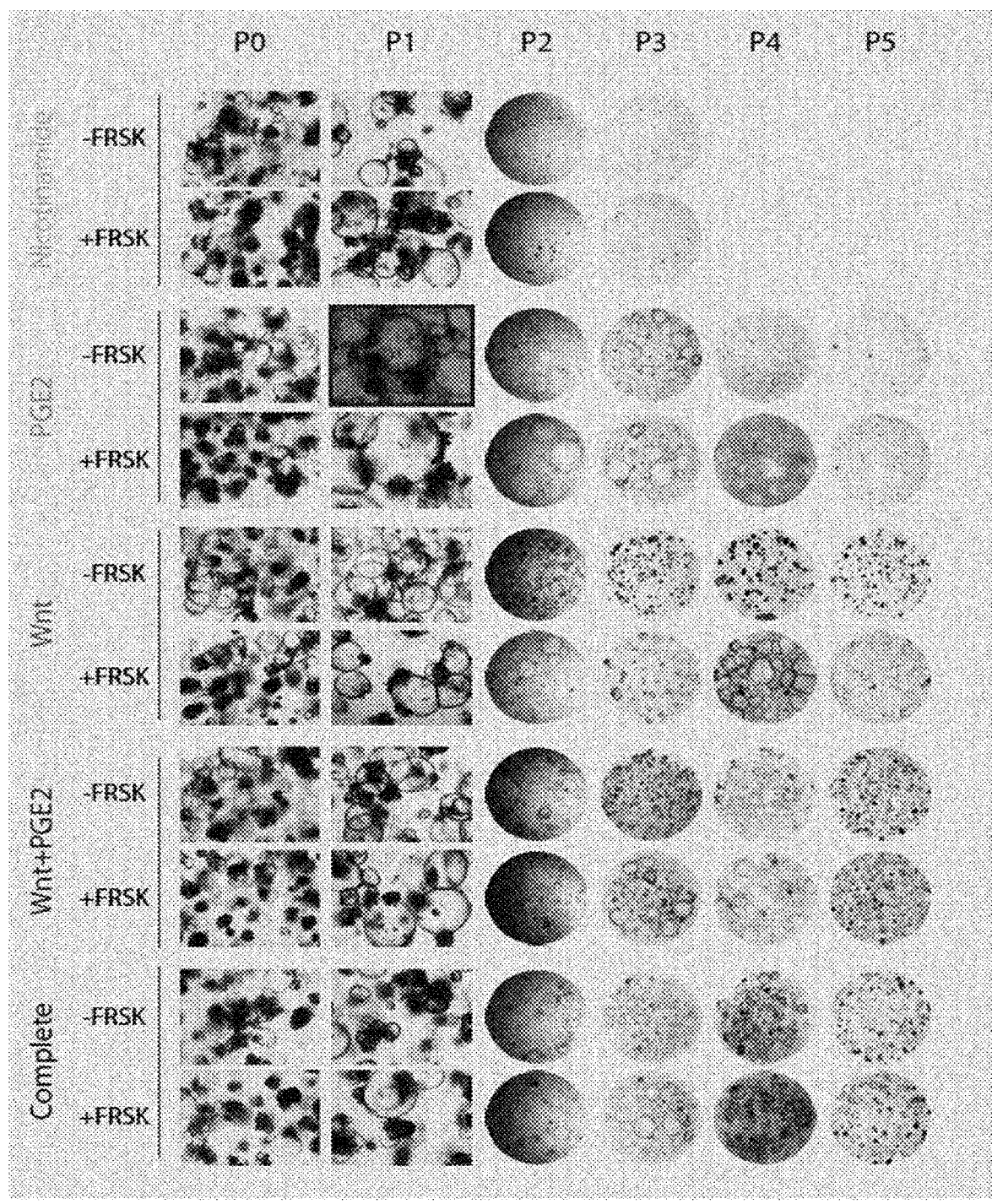

Example 8: Human Liver Organoids Express Markers of the Ductal and Hepatocyte Lineages Gene expression was analysed by immunofluorescence (A) or RT-PCR (B) analysis in human liver cultures grown in our defined complete expansion medium as described in methods. (FIG. 8A) Human liver cultures expressed progenitor (LGR5, CD133) ductal (KRT19 and KRT7) and hepatocyte (HNF4A) markers.

Figure 14:
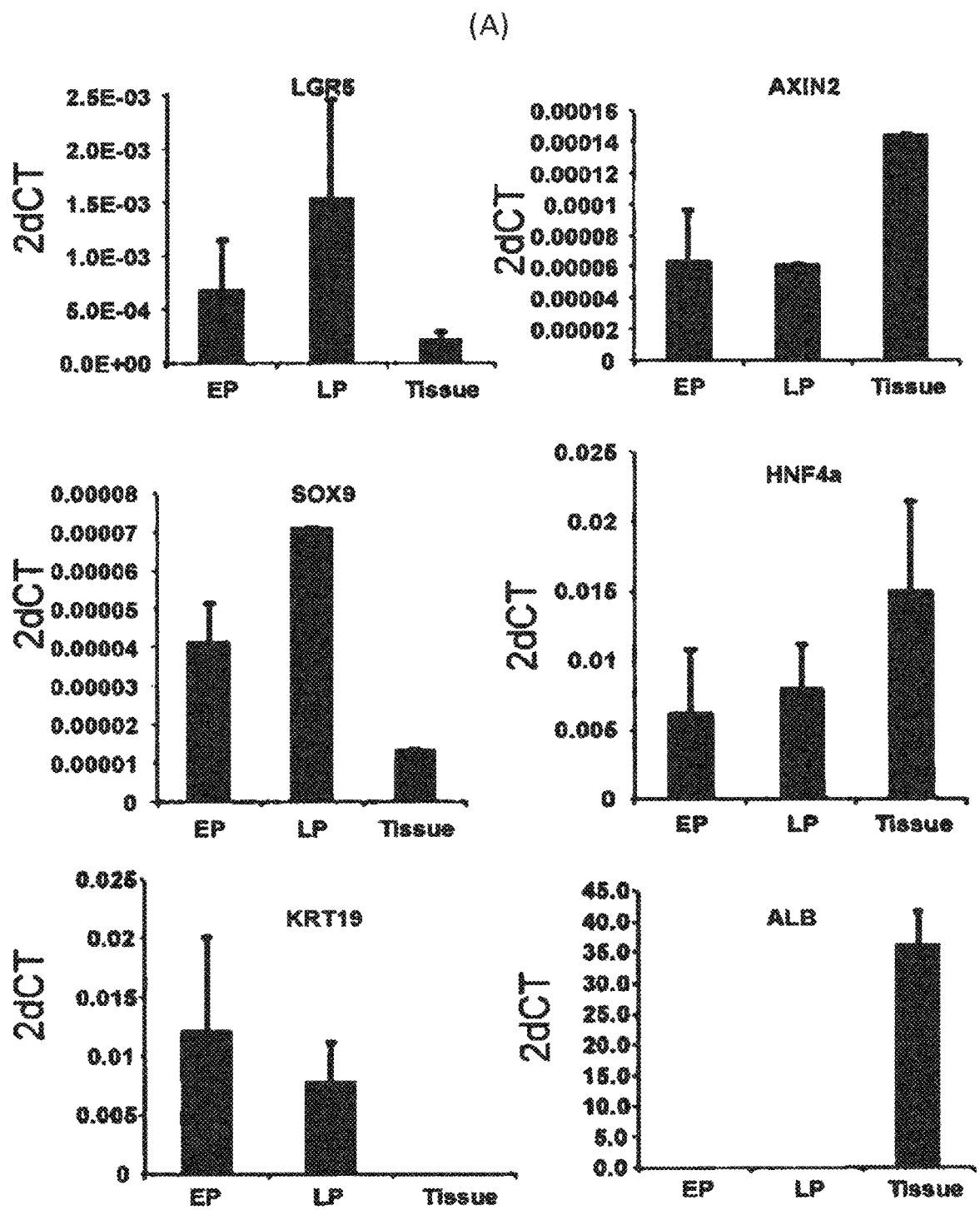
FIG. 14: Human liver organoids express Lgr5 and markers of the ductal and hepatocyte lineages. Gene expression was analyzed by RT-PCR (A) and immunofluorescence (B) in human liver cultures grown in our defined expansion medium as described in Experimental Procedures. (A) Gene expression was analyzed at early (EP) and late (LP) passages. Human liver cultures expressed progenitor (LGR5, SOX9), ductal (KRT19, SOX9) and hepatocyte (HNF4A) markers but they do not express albumin (ALB) while in expansion medium. Results are indicated as 2-dCt (2ΔΔCT). Values represent mean±SEM of 3 independent experiments in 5 independent donor derived cultures. 2ΔΔCT were calculated using the housekeeping gene GAPDH as reference gene for normalization. (B-F) Confocal images of a human liver organoid showing that the organoids are formed by epithelial derived structures positive for ECAD and the hepatocyte marker HNF4 (B), and the ductal markers (KRT19, C; KRT7, D) and SOX9 (E). Nuclei were counterstained with Hoechst. (F) Confocal images of a human liver organoid showing that the organoids are formed by epithelial derived cells positive for EPCAM. The stem cell marker Lgr5 was restricted to a subset of cells within the organoid, while the Wnt target gene EPHB2 was broadly expressed, but co-localized with LGR5, as expected. (G) Representative image of RT-PCR analysis of indicated genes in 2 independent human liver donor-derived organoid cultures maintained in Expansion medium (EM) for 2 months in culture. Note expression of progenitor marker PROM1 and ductal marker OC2 (ONECUT2). (H) Heat map of genes>2 fold differentially expressed between human liver tissue and organoid in expansion medium. Dark, upregulated. Light, downregulated, (I) Representative image of RT-PCR analysis of indicated genes in 1 donor derived culture maintained under complete expansion medium (EM) or after withdrawal of Rspondin (Rspo) or Forskolin (FSK). (J) Representative image of RT-PCR analysis of CYP3A4 in 1 donor derived culture maintained under complete differentiation medium (DM, complete) for 11 days, or after withdrawal of the indicated components, DAPT and/or Dexamethasone (Dexa).

Further analysis confirmed that the stem cell markers PROM1 and LGR5, as well as ductal (SOX9, OC2) and hepatocyte markers (HNF4a) were readily expressed (FIGS. 14A and 14G and H). Histologically, liver organoids displayed a duct-like phenotype characterized by two types of epithelia: 1) a single-layered epithelium formed by polarized cells with basal nuclei, expressing cytokeratin epithelial markers (KRT19 and KRT7), and 2) a pseudo-stratified epithelium with non-polarized E-Cadherin+, HNF4a+ and some KRT7+ cells (FIG. 14B-D). SOX9 (FIG. 14E) and EPHB2 (FIG. 14F) were detectable in almost all the cells within an organoid while LGR5 was detectable within the EPHB2+ population (FIG. 14F).

Example 9: Human Organoids in Complete Media Grow from Single Isolated Cells

Human liver cultures grown for at least 2 months in our defined medium were dissociated to single cell and sorted as described in methods. Cells were seeded at a ratio of 1 cell per well. Cells quickly proliferated and expanded. DIC images of growing single cells from human liver cultures. Magnifications: 40× (days 0-10), 4× (day 20-on).

Example 10: Upon Differentiation, Liver Cultures Upregulate HEPATOCYTE Specific Genes Human liver cultures were expanded for at least 1 month in culture and transferred to our differentiation medium as described in Methods. Expression of hepatocyte genes was determined by immunofluorescence (FIG. 10A) or qPCR (FIG. 10B) 11 days later. (FIG. 10A) Immunofluorescence staining showing albumin (ALB, red) and zona occuludens (ZO-1, green) positive cells all over the organoid, indicating that the cells start expressing the mature hepatocyte markers. (FIG. 10B) qPCR analysis indicated that both, albumin and Cytochrome p450 3A4 isoform were highly expressed upon differentiation. Graphs indicate mean±SEM of 3 independent experiments in 3 independent donor derived cultures. EM, expansion medium including FSK. DM, differentiation medium, HuLi, whole lysate from human liver.

Example 11: Liver Cultures Accumulate Glycogen, Uptake LDL and Maintain Cytochrome Activity, In Vitro To test whether the cells could have differentiated towards functional hepatocytes in vitro, we determined the ability of the cultures to accumulate glycogen, uptake LDL and have active cytochrome activity. (FIG. 11A), Glycogen accumulation was determined by PAS (Periodic-Acid Schiff) staining in organoids grown in EM or DM for 11 days. PAS positive staining (pink) was exclusively observed in the organoids after Differentiation (DM), indicating that the cells have recovered the capacity to accumulate glycogen. Magnification, 10×. (FIG. 11B) LDL uptake was analysed using Dil-ac-LDL fluorescent substrate (red) in cultures maintained in EM (left) or DM (right) for 11 days. Only cultures maintained in DM incorporated the substrate (red). Nuclei were counter-stained with DRAQ5. Scale bar, 25 µm. (C), Cyp3a4 is expressed exclusively in mature hepatocytes. It has an important role in the detoxifying function of the liver. CYP3A4 activity was measured as described in methods in cultures kept in DM for 11 days. Results are expressed as RLU per ml per million cells. HEK293T cells and HepG2 cells were used as negative and positive controls respectively. Triplicates for each condition were analysed. Results are shown as mean±SEM of 2 independent experiments in 4 independent donor-derived cultures.

Example 12: METHODS

Human Liver Organoid Culture

Liver cells were isolated by collagenase digestion as follows: tissue (0.5-1 cm$^3$) was minced, rinsed 2× with DMEM (Gibco) 1% FCS and incubated with the digestion solution (2.5 mg/ml collagenase D (Roche)+0.1 mg/ml DNase I (Sigma) in EBSS (Hyclone, Thermoscientific), for 20-40 at 37° C. The digestion was stopped by adding cold DMEM 1% FCS and the suspension was then filtered through a 70 urn Nylon cell strainer and spun 5 min at 300-400 g. The pellet was resuspended in DMEM 1% FCS and kept cold. Any material retained on the strainer was further digested for 10 min in Accutase (Innovative Cell Technologies) at 37° C. Then, the digestion was stopped and the cells were collected as before. The different fractions (collagenase and accutase) were mixed and washed with cold Advanced DMEM/F12 and spun at 300-400 g for 5 min. The cell pellet was mixed with Matrigel (BD bioscience) and 3000-10000 cells were seeded per well in a 48 well/plate. After Matrigel had solidified, culture medium was added. Culture media was based on AdDMEM/F12 (Invitrogen) supplemented with N2 and B27 without retinoic acid (both from Gibco), 1.25 mM N-Acetylcysteine (Sigma), 10 nM gastrin (Sigma) and the growth factors: 50 ng/ml EGF (Peprotech), 10% RSPO1 conditioned media (home-made), 100 ng/ml FGF10 (Peprotech), 25 ng/ml HGF, 10 mM Nicotinamide (Sigma), 5 uM TGF-beta inhibitor (A83.01 (Tocris)) and 10 uM FSK (Tocris). For the establishment of the culture, the first 3 days after isolation the medium was supplemented with 25 ng/ml Noggin (Peprotech), 30% Wnt CM (home-made prepared as described in (Barker and Huch 2010)), 10 uM Rock inhibitor (Y27632) and hES Cell cloning Recovery solution (Stemgent). Then, the medium was changed into a medium without Noggin, Wnt, Y27632, hES Cell cloning Recovery solution (Stemgent) while 25 ng/ml BMP7 (Peprotech) were supplemented on top. One week-10 days organoids were removed from the Matrigel, mechanically dissociated into small fragments, and transferred to fresh Matrigel. Passage was performed in 1:4-1:8 split ratio once per week for at least 6 months. To prepare frozen stocks, organoid cultures were dissociated and mixed with Recovery cell culture freezing medium (Gibco) and froze following standard procedures. When required, the cultures were thawed using standard thawing procedures, embedded in Matrigel and cultured as described above. For the first 3 days after thawing, the culture medium was supplemented with Y-27632 (10 µM, Sigma Aldrich).

Single Cell (Clonal) Culture

For clonogenic assays, single cell suspensions from established cultures were dissociated with TriplE express (gibco). Propidium iodide staining was used to label dead cells and FSC: Pulse-width gating to exclude cell doublets (MoFlow, Dako). Cells were embedded in Matrigel and seeded in 96 well plates at a ratio of 1 cell/well. Cells were cultured as described above with medium supplemented with Y-27632 (10 µM, Sigma Aldrich) for the first 4 days. Passage was performed in split ratios of 1:4-1:8 once per week for at least 8 months. All phase contrast pictures were acquired using a Leica DMIL microscope and a DFC420C camera.

Hepatocyte Differentiation

To enhance hepatocyte cell fate, liver organoids were seeded and kept 2-4 days under the liver expansion conditions explained above. Then, medium was changed to AdDMEM/F12 medium supplemented with 1% N2 and 1% B27 without retinoic acid (both from Gibco) and containing EGF (50 ng/ml), gastrin (10 nM, Sigma), HGF (25 ng/ml, Peprotech), FGF19 (100 ng/ml), A8301 (500 nM, Tocris Bioscience), DAPT (10 uM, Sigma), BMP7 (25 ng/ml) and Dexamethasone (30 uM). Medium was changed every other day for a period of 9-11 days.

Hepatocyte Functional Studies

To assess glycogen storage and LDL uptake, liver organoids grown in EM or DM for 11 days were stained by Periodic acid-Schiff (PAS, Sigma) and Dil-Ac-LDL (biomedical technologies), respectively, following manufacturer's instructions. To determine albumin and A1AT secretion, liver organoids were differentiated as described. Culture medium was changed every other day and culture supernatant was collected was collected 24 h after the last medium change. HepG2 and HEK293T cells (ACCC) were cultured for 24 h in the same medium without growth factors and were used as positive and negative control respectively. The amount of albumin and A1AT in culture supernatant was determined using a human specific Albumin or human specific A1AT ELISA kit (both from Assay Pro). To measure Cyp3a activity the cultures were differentiated as described and the day of the experiment the cells were removed from the matrigel and cultured with the Luciferin-PFBE substrate (50 µM) in Hepatozyme medium supplemented with 10% FBS (Gibco). As controls, HepG2 and HEK293Tcells were cultured for 24 h in DMEM 10% FBS and the day of the experiment transferred to Hepatozyme medium supplemented with 10% FBS (Gibco) and Luciferin-PFBE substrate (50 µM). Cytochrome P450 activity was measured 8 h later using the P450-Glo Assay Kit (Promega) according to manufacturer's instructions.

In Vitro Growth Curves

Expansion ratios were calculated from human liver cultures as follows: 3×103 cells were grown in our defined medium for 7 or 10 days. Then, the cultures were dissociated by incubation with TrypLE Express (Gibco) until single cells. Cell numbers were counted by trypan blue exclusion at the indicated time points. From the basic formula of the exponential curve y(t)=y0×e(growth rate×t) (y=cell numbers at final time point; y0=cell numbers at initial time point; t=time) we derived the growth rate. Then, the doubling time was calculated as doubling time=ln(2)/growth rate for each time window analyzed.

Karyotyping

Organoid cultures in exponential growing phase were incubated for 16 hours with 0.05 µg/ml colcemid (Gibco). Then, cultures were dissociated into single cells using TrypLE express (Gibco) and processed using standard karyotyping protocols. Chromosomes from 100 metaphase-arrested cells were counted.

Immunohistochemistry and Immunofluorescence

Tissues and organoids were fixed o/n with formalin or 4% PFA respectively, washed and transferred to tissue cassettes and paraffin blocks using standard methods. Tissue sections (4 µM) were prepared and stained with antibodies, H&E or PAS using standard techniques. The antibodies and dilutions used are listed in Supplementary Table I. Stained tissues were counterstained with Mayer's Hematoxylin. Pictures were taken with a Nikon E600 camera and a Leica DFDC500 microscope (Leica). For whole mount immunofluorescence staining, organoids were processed as described in Barker et al, (Barker et al, 2010). Nuclei were stained with Hoechst33342 (Molecular Probes).

Flow Cytometry Analysis

Exponentially growing organoids were cultured for at least 5 days in the presence or absence of FSK. Then, organoids were dissociated into single cells using Accutase, resuspended in DMEM+2% FBS and incubated with Lgr5 antibody (AP2745d, Abgent) for 45 min. Alexa488-conjugated donkey anti-rabbit Ig was used as secondary antibody (Molecular Probes). Cells were analyzed with a BD FACS Calibur (Becton-Dickinson); FSC: propidium iodide was used to label dead cells for exclusion and pulse-width gating to exclude cell doublets.

RT-PCR and qPCR Analysis

RNA was extracted from organoid cultures or freshly isolated tissue using the RNeasy Mini RNA Extraction Kit (Qiagen), and reverse-transcribed using reverse-transcribed using Moloney Murine Leukemia Virus reverse transcriptase (Promega). All targets were amplified (40 cycles) using gene-specific primers and MilQ syber green (Bio-Rad). Data were analyzed using BioRad CFX manager. cDNA was amplified in a thermal cycler (GeneAmp PCR System 9700; Applied Biosystems, London, UK) as previously described (Huch et al, 2009).

Image Analysis

Images of cultivated cells were acquired using either a Leica DMIL microscope and a DFC420C camera or an EVOS FL system (Life Technologies). Immunofluorescence images were acquired using a confocal microscope (Leica, SP5) or a confocal microscope (Leica, SP8). Images were analyzed and processed using Leica LAS AF Lite software (Leica SP5 confocal).

Data Analysis

All values are represented as mean±standard error of the mean (S.E.M.). Man-Whitney non-parametric test was used. $p<0.05$ was considered statistically significant. In all cases data from at least 3 independent experiments was used. All calculations were performed using SPSS package.

Table 2: List of Tested Compounds

List of all the compounds tested for their capacity to enhance human liver culture proliferation, long-term maintenance or differentiation (FIG. 12). Human liver cultures were seeded in ERFHNic medium supplemented with A8301 and the compound indicated on the list. Seeding efficiency and capacity to expand long-term the cultures was evaluated.

Example 13: FSK-Supplemented Media is Advantageous for Expansion of Pancreatic Organoids Pancreatic ductal cells from healthy human control sample (C366) were cultured in 10 different conditions from passage 0. Samples were passaged once a week. Red crosses indicated death of the culture. Arrowheads indicated culture is growing. The graph indicates that a culture medium comprising forskolin allows passaging of pancreatic organoids beyond five weeks, even in the "Wnt" medium which could not be passaged beyond five weeks in the absence of forskolin. Therefore, forskolin is also advantageous for the growth and expansion of pancreatic organoids. FRSK (Forskolin 10 uM); Nic [medium containing B27 1×, NAc (1.25 mM), Egf (50 ng/ml), Gastrin (10 nM), Fgf10 (100 ng/ml), Noggin (10% CM), Rspo (10% CM) and Nicotinamide (10 mM)]; $PGE_2$ [medium containing B27 1×, NAc (1.25 mM), Egf (50 ng/ml), Gastrin (10 nM), Fgf10 (100 ng/ml), Noggin (10% CM), Rspo (10% CM), Nicotinamide (10 mM), A8301 (500 nM) and $PGE_2$ (1 uM)]; Wnt [medium containing B27 1×, NAc (1.25 mM), Egf (50 ng/ml), Gastrin (10 nM), Fgf10 (100 ng/ml), Noggin (10% CM), Rspo (10% CM), Nicotinamide (10 mM), A8301 (500 nM) and Wnt (50% CM)]; Wnt+$PGE_2$ [medium containing B27 1×, NAc (1.25 mM), Egf (50 ng/ml), Gastrin (10 nM), Fgf10 (100 ng/ml), Noggin (10% CM), Rspo (10% CM), Nicotinamide (10 mM), A8301 (500 nM), Wnt (50% CM) and $PGE_2$ (1 uM)]; Complete [medium containing B27 1×, NAc (1.25 mM), Egf (50 ng/ml), Gastrin (10 nM), Fgf10 (100 ng/ml), Noggin (10% CM), Rspo (10% CM), Nicotinamide (10 mM), A8301 (500 nM), Wnt (50% CM), $PGE_2$ (1 uM) and p38i (10 uM)].

Example 14: Human Liver Organoid Cultures Initiate from Ductal Cells

To assess the cell-of-origin of our cultures, we FACS-purified hepatocytes and duct cells from 3 independent human hepatocyte isolations instead of liver biopsies. Hepatocyte isolations by collagenase perfusion yield high numbers of fresh, viable and functional human hepatocytes that are used for hepatocyte transplantation infusions (Gramignoli et al., 2012) (FIG. 15A). We employed EpCAM to differentially sort hepatocytes (EpCAM−) from ductal cells (EpCAM+, bile duct and canal of herring ductal/progenitor cells, FIGS. 15B and 15C) (Schmelzer et al., 2007; Yoon et al., 2011). Ductal (EpCAM+) cells developed into long-term, self-renewing organoid structures with a striking efficiency of 28.4±3.2% (FIG. 15D-E). When crude hepatocyte preparations (not differentially sorted) were directly cultured, cells grew into organoid structures with an efficiency that correlated directly with the amount of residual EpCAM+ cells in the crude preparation (FIG. 15F-G). Therefore, we concluded that in our culture system ductal cells and not hepatocytes revert to a bi-potential progenitor state (i.e. epithelial stem cells in the context of the invention).

Figure 16:
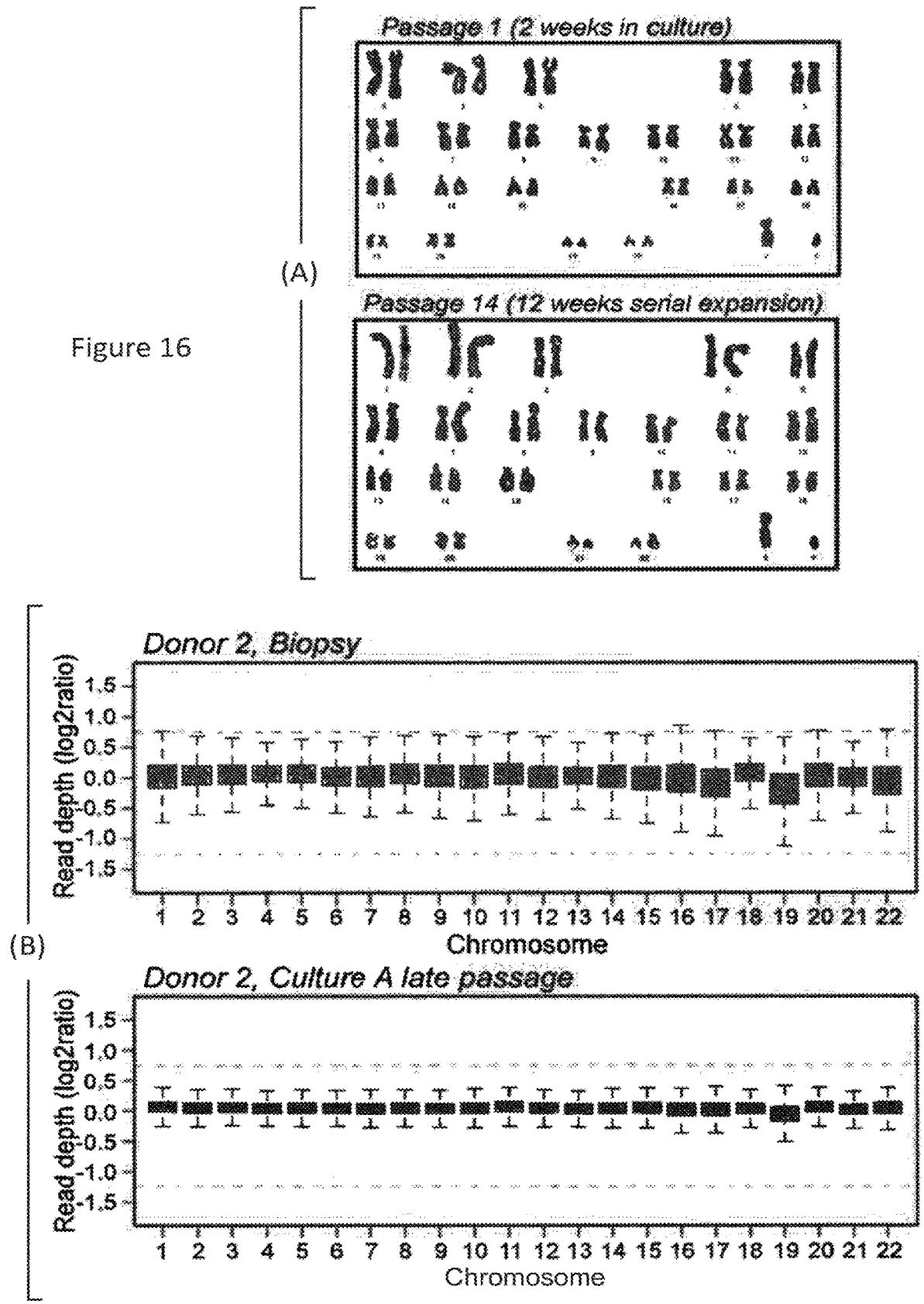
FIG. 16: Chromosomal integrity of human liver organoids. (A) Representative karyotyping image of organoids cultured for 16 days (P1) and 90 days (P14) illustrating a normal chromosomal count (n=46). No major chromosomal aberrations were observed in any of the samples analyzed (n=15). Detailed chromosomal counts for different donors are shown in supplemental FIG. S4. (B) Read-depth analysis of whole genome sequencing data over the different chromosomes for the biopsy (upper panel) and organoid culture A (lower panel) that were derived from donor 2. Read-depth was corrected for GC content and normalized for genome coverage. Dotted lines indicate log 2 values associated with a gain or deletion. (C) Copy number analysis of a region at chromosome 3 that was found to harbor a heterozygous gain in culture A of donor 2. Left panels indicate read-depth analysis of the indicated region in 5 kb bins, corrected for GC content and normalized for genome coverage, of the biopsy (upper panel) and organoid culture (lower panel). Right panels show the variant allele frequencies of informative non-reference single nucleotide polymorphisms (SNPs) in the indicated region for the biopsy (upper panel)

Example 15: Human Liver Cultures Established from Single Human Liver Cells are Genetically Stable Genetic stability is a concern for the future application of cells that have undergone derivation and expansion in culture (Lund et al., 2012). Adult stem cells may have evolved to minimize the risk of accumulating somatic mutations (Cairns, 1975). Indeed, karyotyping of clonal human liver organoids cultured for 3 months revealed that the cells maintain normal chromosome numbers over time (FIG. 16A). The ability to repeatedly generate clonal cultures from single liver stem cells allowed us to isolate sufficient DNA for whole genome sequencing (WGS) analysis and subsequent characterization of the mutational load present in the cultured cells after several months of in vitro expansion (FIG. 17A).

From two donors, we obtained biopsy samples, which we dissociated and cultured in bulk for 7 days. Subsequently, we isolated single cells by flow cytometry and established 2 independent clonal lines for each of the two livers (cultures A and B). After 3 months of expanding these cultures, a second cloning step was performed. The combined procedure allowed us to determine all the genomic variation that had accumulated in a single cell during life, derivation, and 3 months of culturing (FIG. 17B).

We observed 720-1424 base substitutions per cultures of which only a small part was introduced during the 3 months culture, which is equivalent to 13 weekly passages (63-139; FIG. 17C). The majority of the base substitutions were therefore incorporated during life or introduced during organoid derivation. Interestingly, we observe twice as many base substitutions in both cultures derived from donor 1 compared to the cultures derived from donor 2 (FIG. 17C). This is most probably the result of the high age of donor 1 (74 years) compared to donor 2 (30 years), suggesting that the majority of the somatic base substitutions we observed were acquired during life.

How do these numbers compare to published data? It has been reported that iPS cells contain 1,058-1,808 de novo base substitutions per line (determined at passage numbers between 15 and 25) when compared to their parental somatic cells (Cheng et al., 2012). Of note, these numbers do not include the variation acquired in vivo in the parental somatic cells, which we did determine here for the clonal liver organoid cultures. We therefore conclude that liver organoid cultures accumulate in the order of 10-fold fewer base substitutions during in vitro expansion compared to iPS cells. Of the total number of base substitutions only few were located in protein coding DNA (7-9 base substitutions per culture; FIG. 17D). With the exception of one synonymous mutation in culture A from donor 2, all mutations were already present in the early passage clonal cultures, indicating that they were incorporated during life or organoid derivation and not during 3 months-expansion. None of the mutated genes occurs in COSMIC databases. In iPS cells, it has been reported that an average of 6 base substitutions per line affect protein coding DNA (Cheng et al., 2012; Gore et al., 2011) which were reported to be enriched for genes mutated or being drivers in cancers (Gore et al., 2011). Next, we checked for evidence of chromosomal aberrations in the WGS data of the different liver organoid cultures. In line with our karyotyping analysis, we did not observe any chromosomal aberration (FIG. 16B). We observed 2 copy number variants (CNVs), heterozygous gains, in one of the liver organoid cultures (FIG. 16C). In the other cultures, we did not detect any CNV (FIG. 16D). Moreover, these 2 CNVs were already present in the early passage cultures and therefore did not result from long-term culturing, suggesting they were either acquired in vivo or during organoid derivation. ES cell cultures routinely show abnormal karyotypes (Baker et al., 2007) and iPS cells have been reported to harbor considerable amounts of somatic CNVs (Hussein et al., 2011; Laurent et al., 2011) (Martins-Taylor et al., 2011; Mayshar et al., 2010) (Abyzov et al., 2012), complicating their clinical use.

Example 16: Differentiation into Functional Hepatocytes In Vitro and Upon Transplantation Similar to what we had observed with the mouse liver organoid cultures under expansion conditions, the human counterparts failed to express markers of mature hepatocytes, such as Albumin or CYP3A4 (FIG. 14A and FIG. 18C, EM bars). Therefore, we defined a human differentiation medium (DM) by combining our acquired knowledge on mouse hepatocyte differentiation with known hepatocyte differentiation-promoting compounds.

Removal of the growth stimuli R-spo and FSK directly resulted in the up-regulation of Albumin and CYP3A4 gene expression (FIG. 14I). To this medium, we then added the Notch inhibitor DAPT, FGF19 and dexamethasone (FIG. 14J). When testing compounds to improve our culture conditions, we noticed that BMP7 slightly facilitated the expression of hepatocyte markers ALB and CYP3A4, without compromising the proliferation ability of the culture itself. Therefore, 5-7 days prior to the start of differentiation, we supplemented the expansion medium (EM) with 25 ng/ml BMP7, which was then maintained during the differentiation step (FIG. 18A). Using this combination of growth factors (BMP7, FGF19, HGF and EGF), small molecule inhibitors (DAPT and A8301) and Dexamethasone, the cells acquired pronounced hepatocyte morphologies, including polygonal cell shapes, as made visible by ZO-1 staining (FIG. 18B). We subsequently examined the level of maturity of the differentiated cells by using gene expression profiling, immunofluorescence and various biochemical assays.

Gene expression profiles proved that the differentiated cultures expressed high levels of hepatocyte markers (FIG. 18D). Hepatocyte specific genes such as ALB, several cytochrome enzymes, Apolipoproteins (APOB) and several complement factors (C3) were readily expressed upon differentiation in all 4 donors analyzed (FIG. 18D). We confirmed these results by qPCR and RT-PCR analysis for selected genes (ALB, several cytochromes, and TAT) (FIG. 18C and FIG. 14K) and found that the differentiated cultures express levels of cytochrome CYP3A4 expression similar to that of human liver tissue. A 100-1000× fold increase in Albumin expression was also detected on the DM-treated cultures, although the expression levels were still 1000× lower when compared to freshly isolated human liver material. Immunofluorescence visualized cells with high levels of ALB and MRP4 within the organoids (FIG. 18B). Similar results were obtained with cultures derived from EpCAM+ sorted cells (FIG. 14L-M).

We next assessed the ability of the hepatocyte cells to retain hepatocyte function in vitro. Immunohistochemistry analysis indicated that the cells could accumulate glycogen (FIG. 19A) and take up LDL (FIG. 19B). Biochemical analyses demonstrated that the differentiated cells secreted high levels of Albumin into the medium (FIG. 19C). Cytochrome family members, such as Cyp3a4, are expressed exclusively in mature hepatocytes. They play an important detoxifying function for exogenous molecules in the liver (Casciano, 2000). Upon differentiation, the cultures exhibited similar p450-3A4 activity as fresh isolated hepatocytes (FIG. 19D, compare to FIG. 15A). We also observed that the differentiated cultures hydroxylated midazolam, another indication of functional CYP3A3/4/5 activity (Wandel et al., 1994), and glucuronidated hydroxy-midazolam, thereby showing evidence of both phase I and II detoxifying reactions (FIG. 19E). We then assessed the ability of the cultured cells to synthetize bile acids, a hallmark of hepatocyte function. Upon differentiation, bile acid salts were readily secreted into the medium (FIG. 19F). Finally, the cultures also exhibited the ability to detoxify ammonia at similar levels to HepaRG cells (FIG. 19G). In all cases, the expanded human liver organoids showed stronger hepatocyte functions when compared to the standard/reference cell line HepG2 cells (FIG. 19).

To test the ability of the cultures to engraft in damaged tissue and to fully differentiate into functional hepatocytes in vivo, we treated Balb/c nude mice with CCl4-retrorsine to induce acute liver damage. As shown by others, this treatment is permissive for the engraftment of hepatocytes (Guo et al., 2002; Schmelzer et al., 2007). Using human-specific antibodies (FIG. 20A), we initially detected Krt19 positive, ductal-like cells at 2 h and d2 after transplantation, distributed throughout the liver parenchyma (FIG. 20B). At later time points, we observe Albumin+, Krt19-human cells as singlets or doublets or, more rarely, in larger hepatocyte foci in the mouse liver (FIG. 19H and FIG. 20C). This agreed with the non-chronic nature of our damage model, which provides no stimulus for expansion of the transplant after the initial engraftment. We detected human Albumin and human alpha-1-antitrypsin in the circulation of recipient mice within 7-14 days (FIG. 19I and FIG. 20D/E), at a level that remained stable for more than 60 days in 5/6 mice and for more than 120 days in 2/5 animals. While transplantation of primary human hepatocytes initially yielded higher levels of human Albumin in mouse circulation (FIG. 19I), the levels approximated those of transplanted organoids within a month. Presence of human albumin and human alpha-1-antitrypsin in mouse serum proved, together with Albumin and Krt19 stainings, that transplanted cells differentiated into human hepatocytes in vivo.

Transplantation Method:

We used a modified version of the protocol used by Guo et al. (Guo et al., 2002). In short, female BALB/c nude mice (around 7 weeks of age) were pretreated with two injections of 70 mg/kg Retrorsine (Sigma) at 30 and 14 days before transplantation. One day prior to transplantation, mice received 0.5 ml/kg CCl4 and 50 mg/animal anti-asialo GM1 (Wako pure chemical industries) via IP injection. Furthermore, animals received 7.5 ug/ml FK506 in drinking water until the end of the experiment, due to the reported positive effects on liver regeneration (He et al., 2010). On the day of transplantation, mice were anaesthetized and suspensions of 1-2×10⁶ human liver organoid cells derived from 4 independent donors (p6 to p10) were injected intrasplenically. Transplanted mice received weekly injections of 50 mg/animal anti-asialo GM1 (Wako pure chemical industries) to deplete NK cells. To monitor the transplantation state, blood samples were taken in regular intervals from the tail vein and analyzed for the presence of human albumin and human α1-antitrypsin using respective human specific ELISAs (Assaypro).

Karyotyping and Genetic stability analysis:

Organoid cultures in exponential growing phase were incubated for 16 hours with 0.05 μg/ml colcemid (Gibco). Then, cultures were dissociated into single cells using TrypLE express (Gibco) and processed using standard karyotyping protocols.

DNA libraries for WGS analysis were generated from 1 ug of genomic DNA using standard protocols (Illumina). The libraries were sequenced with paired-end (2×100 bp) runs using Illumina HiSeq 2500 sequencers to a minimal depth of 30× base coverage (average depth of ~36.9× base coverage). As reference sample, liver biopsies was sequenced to equal depth for the different donors. The data for the whole genome sequencing were deposited to the EMBL European Nucleotide Archive, accession number ERP005929.

Immunohistochemistry, Immunofluorescence and Image Analysis:

Tissues and organoids were fixed o/n with formalin or 4% PFA respectively, and stained and imaged by methods known in the art.

Microarray Methods:

For the expression analysis of human liver cultures, total RNA was isolated from liver biopsies or from organoids cultures grown in our defined medium, using Qiagen RNAase kit following manufacturer's instructions. Five hundred ng of total RNA were labeled with low RNA Input Linear Amp kit (Agilent Technologies, Palo Alto, CA). Universal human Reference RNA (Agilent) was differentially labeled and hybridized to the tissue or cultured samples. A 4×44 K Agilent Whole Human Genome dual colour Microarray (G4122F) was used. Labeling, hybridization, and washing were performed according to Agilent guidelines.

Example 17: Organoids from Human Patients Model Disease Pathogenesis In Vitro

Encouraged by the establishment of a culture medium that allows the long-term expansion of genetically stable liver cells, we explored whether our culture system would be suitable for disease modeling. A1AT deficiency is an inherited disorder that predisposes to chronic obstructive pulmonary disease and chronic liver disease (Stoller and Aboussouan, 2005). Alpha-1 antitrypsin is a protease produced in the liver, which functions to protect the lung against proteolytic damage from neutrophil elastase. The most frequent mutation causing a severe phenotype is the Z allele, which involves a substitution of glutamic acid with lysine at position 342 (Glu342Lys) in the SERPINA1 gene, which causes accumulation of misfolded α1-antitrypsin in the endoplasmic reticulum of hepatocytes. The ZZ mutant phenotype is characterized by a ~80% reduction of the protein in plasma, which subsequently causes lung emphysema (Stoller and Aboussouan, 2005).

We obtained human liver biopsies from 3 patients diagnosed with A1AT deficiency who were undergoing liver transplantation. Biopsies were divided into samples for histological characterization, RNA isolation, DNA isolation and for expansion in culture. We confirmed that all 3 patients carried the homozygous Z allele (PiZZ), by Sanger sequencing of the SERPINA1 locus (FIG. 22A). The isolated cells rapidly grew into 3-D structures generating organoids that closely resembled the organoids derived from healthy biopsies (FIG. 21A) and were grown for >4 months in culture at a 1:5 split ratio/week, similar as the cultures derived from healthy/donor biopsies.

We then confirmed the ability of the A1AT-D derived cultures (PiZZ cultures) to differentiate into functional hepatocytes in vitro. Gene expression analysis demonstrated that the cells differentiated normally. When submitted to hierarchical clustering analysis, differentiated organoids derived from A1AT-deficient patients clustered together with differentiated organoids derived from healthy donor biopsies (FIG. 22B). Of note, functional tests revealed that the differentiated cells from A1AT patients secrete high levels of Albumin and take up LDL similar to healthy donor-derived organoid cultures (FIG. 21B-D).

We then analyzed the ability of the cultured cells to mimic the pathology of the disease in vitro. Functional, healthy hepatocytes secrete A1AT protein into the bloodstream to inhibit neutrophil elastase mainly in the lungs (FIG. 21E). In A1AT-deficiency, the molecular pathogenesis of the liver disease relates to the aggregation of the protein within the endoplasmic reticulum of hepatocytes (Lawless et al., 2008). A1AT-Protein aggregates were readily observed within the cells of the differentiated organoids derived from the A1AT-D patient (FIG. 21H), similar to what was found in the original biopsy (FIG. 21G), while these aggregates were essentially absent from the organoids derived from healthy donor-material (FIG. 21F). A1AT ELISA confirmed reduced secretion of the protease inhibitor from PiZZ organoids (FIG. 21I), which mimics the reduced A1AT serum levels in patients. Likewise, supernatants from differentiated ZZ mutant organoids showed a strongly reduced ability to block elastase activity (FIG. 21J).

Advanced stages of A1AT deficiency are characterized by liver injury and cirrhosis due to combined effects of uncontrolled protease activity and apoptotic loss of functional hepatocytes (Fairbanks and Tavill, 2008). Protein misfolding and resulting ER Stress are the primary causes that drive hepatocytes from PiZZ individuals to eventual apoptosis (Lawless et al., 2008). Differentiated liver organoids from A1AT-D patients mimicked the in vivo situation and showed signs of ER stress, such as phosphorylation of eIF2α (FIG. 21K) and a slight increase in apoptosis in the differentiated state (FIGS. 22C and D).

Using a biopsy from a patient suffering from Alagille syndrome (AGS), we tested whether structural defects of the biliary tree can also be modeled. AGS is a rare genetic disorder caused by mutations in the Notch signaling pathway, which results in partial to complete biliary atresia (Kamath et al., 2013). Patient organoids could be expanded at normal rates and showed no obvious difference to donor in the undifferentiated state. However, upon differentiation to the biliary fate by withdrawal of R-spondin, Nicotinamide, TGFbi and FSK from the culture medium, AGS patient organoids failed to upregulate biliary markers such as KRT19 and KRT7, while donor (wildtype, wt) organoids readily did (FIG. 22E). Staining for KRT19 revealed that biliary cells were reduced in numbers and were unable to integrate into the epithelium. Rather, they rounded up and underwent apoptosis inside the organoid (FIG. 22F). This finding is in line with AGS mouse models, which show that Jagged-1/Notch2 is dispensable for biliary lineage specification, but required for biliary morphogenesis (Geisler et al., 2008; McCright et al., 2002). Thus, AGS liver organoids mimic the patient phenotype and constitute the first human 3D model system to study Alagille syndrome.

Methods for A1AT-D Functional Experiments:

Enzymatic Elastase inhibition assay: For measurement of the inhibitory action of α1-antitrypsin in organoid supernatants, donor and patient organoids were differentiated for 11 days. Culture medium was changed every 2-3 days and culture supernatant was collected 24 h after the last medium change. For the assay, 160 ul of supernatant are mixed with 20 ul of a 2 mg/ml N-Succinyl-Ala-Ala-Ala-p5 nitroanilide (Sigma) 100 mM Tris pH 8.0 solution in a clear-bottom 96-well plate. After addition of 6×10−4 U of Elastase (porcine pancreas, Sigma) in 100 mM Tris pH 8.0, the increase in absorbance at 410 nm is measured continuously over 30 minutes. Elastase inhibition by supernatants is measured as the decreased inclination of absorbance over time in comparison to uninhibited controls (plain medium) and compared to a dilution series of purified human α1-antitrypsin (Zemaira) in medium.

Detection of eIF2α phosphorylation: Donor and α1-antitrypsin deficient patient organoids were differentiated for 11 days. Culture medium was changed every 2-3 days and organoids were lysed in Lysis buffer (50 mM Tris pH 7.5, 50 mM NaCl, 0.5% Triton-X100, 0.5% NP40 substitute, 5 mM EGTA, 5 mM EDTA, 1× Complete protease inhibitor (Roche), 1× PhosStop (Roche)). Using standard techniques lysates were resolved by SDS-Page and blotted on PVDF membranes (Millipore).

Example 18: The Method Works Across Multiple Donors

To generalize our findings across multiple donors, we obtained 12 additional healthy human donor liver biopsies and cultured them in our improved human liver medium. Under our improved conditions (ERFHNic+Tgfbi+FSK), all 12 human liver-derived cultures grew exponentially, with a consisting doubling time of ~60 h independent of the age of the culture (2 weeks or 3 months). EdU incorporation confirmed that the cells maintained their proliferative state in vitro 3 months after the initiation of culture. Of note, cultures grown under these culture conditions could be readily frozen and thawed. Overall, these results support the fact that the combination of Wnt signaling and cAMP activation, combined with Tgf-β inhibition, successfully sustains long-term expansion of human liver progenitors in vitro.

REFERENCES

Abyzov, A., Mariani, J., Palejev, D., Zhang, Y., Haney, M. S., Tomasini, L., Ferrandino, A. F., Rosenberg Belmaker, L. A., Szekely, A., Wilson, M., et al. (2012). Somatic copy number mosaicism in human skin revealed by induced pluripotent stem cells. Nature 492, 438-442.

Baker, D. E., Harrison, N. J., Maltby, E., Smith, K., Moore, H. D., Shaw, P. J., Heath, P. R., Holden, H., and Andrews, P. W. (2007). Adaptation to culture of human embryonic stem cells and oncogenesis in vivo. Nat Biotechnol 25, 207-215.

Cairns, J. (1975). Mutation selection and the natural history of cancer. Nature 255, 197-200.

Casciano, D. A. (2000). Development and utilization of primary hepatocyte culture systems to evaluate metabolism, DNA binding, and DNA repair of xenobiotics. Drug Metab Rev 32, 1-13.

Cheng, L., Hansen, N. F., Zhao, L., Du, Y., Zou, C., Donovan, F. X., Chou, B. K., Zhou, G., Li, S., Dowey, S. N., et al. (2012). Low incidence of DNA sequence variation in human induced pluripotent stem cells generated by nonintegrating plasmid expression. Cell Stem Cell 10, 337-344.

Fairbanks, K. D., and Tavill, A. S. (2008). Liver disease in alpha 1-antitrypsin deficiency: a review. Am J Gastroenterol 103, 2136-2141; quiz 2142.

Geisler, F., Nagl, F., Mazur, P. K., Lee, M., Zimber-Strobl, U., Strobl, L. J., Radtke, F., Schmid, R. M., and Siveke, J. T. (2008). Liver-specific inactivation of Notch2, but not Notch1, compromises intrahepatic bile duct development in mice. Hepatology 48, 607-616.

Gore, A., Li, Z., Fung, H. L., Young, J. E., Agarwal, S., Antosiewicz-Bourget, J., Canto, I., Giorgetti, A., Israel, M. A., Kiskinis, E., et al. (2011). Somatic coding mutations in human induced pluripotent stem cells. Nature 471, 63-67.

Gramignoli, R., Green, M. L., Tahan, V., Dorko, K., Skvorak, K. J., Marongiu, F., Zao, W., Venkataramanan, R., Ellis, E. C., Geller, D., et al. (2012). Development and application of purified tissue dissociation enzyme mixtures for human hepatocyte isolation. Cell Transplant 21, 1245-1260.

Guo, D., Fu, T., Nelson, J. A., Superina, R. A., and Soriano, H. E. (2002). Liver repopulation after cell transplantation in mice treated with retrorsine and carbon tetrachloride. Transplantation 73, 1818-1824.

He, Z., Zhang, H., Zhang, X., Xie, D., Chen, Y., Wangensteen, K. J., Ekker, S. C., Firpo, M., Liu, C., Xiang, D., et al. (2010). Liver xeno-repopulation with human hepatocytes in Fah−/− Rag2−/− mice after pharmacological immunosuppression. Am J Pathol 177, 1311-1319.

Hussein, S. M., Batada, N. N., Vuoristo, S., Ching, R. W., Autio, R., Narva, E., Ng, S., Sourour, M., Hamalainen, R., Olsson, C., et al. (2011). Copy number variation and selection during reprogramming to pluripotency. Nature 471, 58-62.

Kamath, B. M., Spinner, N. B., and Rosenblum, N. D. (2013). Renal involvement and the role of Notch signalling in Alagille syndrome. Nat Rev Nephrol 9, 409-418.

Laurent, L. C., Ulitsky, I., Slavin, I., Tran, H., Schork, A., Morey, R., Lynch, C., Harness, J. V., Lee, S., Barrero, M. J., et al. (2011). Dynamic changes in the copy number of pluripotency and cell proliferation genes in human ESCs and iPSCs during reprogramming and time in culture. Cell Stem Cell 8, 106-118.

Lawless, M. W., Mankan, A. K., Gray, S. G., and Norris, S. (2008). Endoplasmic reticulum stress—a double edged sword for Z alpha-1 antitrypsin deficiency hepatoxicity. The international journal of biochemistry & cell biology 40, 1403-1414.

Lund, R. J., Narva, E., and Lahesmaa, R. (2012). Genetic and epigenetic stability of human pluripotent stem cells. Nat Rev Genet 13, 732-744.

Martins-Taylor, K., Nisler, B. S., Taapken, S. M., Compton, T., Crandall, L., Montgomery, K. D., Lalande, M., and Xu, R. H. (2011). Recurrent copy number variations in human induced pluripotent stem cells. Nat Biotechnol 29, 488-491.

Mayshar, Y., Ben-David, U., Lavon, N., Biancotti, J. C., Yakir, B., Clark, A. T., Plath, K., Lowry, W. E., and Benvenisty, N. (2010). Identification and classification of chromosomal aberrations in human induced pluripotent stem cells. Cell Stem Cell 7, 521-531.

McCright, B., Lozier, J., and Gridley, T. (2002). A mouse model of Alagille syndrome: Notch2 as a genetic modifier of Jag1 haploinsufficiency. Development 129, 1075-1082.

Schmelzer, E., Zhang, L., Bruce, A., Wauthier, E., Ludlow, J., Yao, H. L., Moss, N., Melhem, A., McClelland, R., Turner, W., et al. (2007). Human hepatic stem cells from fetal and postnatal donors. J Exp Med 204, 1973-1987.

Stoller, J. K., and Aboussouan, L. S. (2005). Alpha1-antitrypsin deficiency. Lancet 365, 2225-2236.

Wandel, C., Bocker, R., Bohrer, H., Browne, A., Rugheimer, E., and Martin, E. (1994). Midazolam is metabolized by at least three different cytochrome P450 enzymes. Br J Anaesth 73, 658-661.

Yoon, S. M., Gerasimidou, D., Kuwahara, R., Hytiroglou, P., Yoo, J. E., Park, Y. N., and Theise, N. D. (2011). Epithelial cell adhesion molecule (EpCAM) marks hepatocytes newly derived from stem/progenitor cells in humans. Hepatology 53, 964-973.

---

The invention claimed is:

1. A differentiation medium comprising a basal medium for animal or human cells to which is added one or more receptor tyrosine kinase ligands, a Notch inhibitor, a compound that induces the phosphorylation of SMAD1 or SMAD5, and a TGF-beta inhibitor.

2. The differentiation medium of claim 1, wherein the compound that induces the phosphorylation of SMAD1 or SMAD5 is a BMP pathway activator.

3. The differentiation medium of claim 2, wherein the BMP pathway activator is selected from one or more of BMP7, BMP4 and BMP2.

4. The differentiation medium of claim 1, wherein the one or more receptor tyrosine kinase ligands are selected from one or more of the group: FGF, HGF and EGF.

5. The differentiation medium of claim 4, wherein the FGF is an FGF able to bind to FGFR2 or FGFR4.

6. The differentiation medium of claim 5, wherein the FGF is FGF19.

7. The differentiation medium of claim 1, wherein the Notch inhibitor is a gamma-secretase inhibitor.

8. The differentiation medium of claim 1, wherein the differentiation medium further comprises a glucocorticoid.

9. The differentiation medium of claim 1, wherein the TGF-beta inhibitor is a small molecule inhibitor of ALK4, ALK5 or ALK7.

10. The differentiation medium of claim 9, wherein the TGF-beta inhibitor is selected from A83-01, SB-431542, SB-505124, SB-525334, LY 364947, SD-208, and SJN 2511.

11. The differentiation medium of claim 1, wherein the cells are epithelial stem cells are from the liver, pancreas, intestine, stomach, prostate, lung, breast, ovarian, salivary gland, hair follicle, skin, oesophagus or thyroid.

12. The differentiation medium of claim 7, wherein the gamma-secretase inhibitor is DAPT, dibenzazepine (DBZ), benzodiazepine (BZ), or LY-411575.

13. The differentiation medium of claim 8, wherein the glucocorticoid is dexamethasone or cortisone.

14. An organoid in the differentiation medium of claim 1.

15. The organoid of claim 14, wherein the organoid has a doubling time of less than 65 hours.

* * * * *

SEQUENCE LISTING

```
<160> NUMBER OF SEQ ID NOS: 6

<210> SEQ ID NO 1
<211> LENGTH: 128
<212> TYPE: PRT
<213> ORGANISM: Artificial Sequence
<220> FEATURE:
<223> OTHER INFORMATION: VL antibody
<220> FEATURE:
<221> NAME/KEY: Xaa
<222> LOCATION: 4
<223> OTHER INFORMATION: Xaa can be any amino acid

<400> SEQUENCE: 1

Met Glu Ser Xaa Thr Gln Val Phe Val Phe Leu Leu Leu Trp Leu Ser
1               5                   10                  15

Gly Ala Asp Gly Asp Ile Val Met Thr Gln Ser Pro Thr Ser Met Ser
            20                  25                  30

Ile Ser Ile Gly Asp Arg Val Thr Met Asn Cys Lys Ala Ser Gln Asn
        35                  40                  45

Val Asp Ser Asn Val Asp Trp Tyr Gln Gln Lys Thr Gly Gln Ser Pro
    50                  55                  60

Lys Leu Leu Ile Tyr Lys Ala Ser Asn Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Asn Met Gln Ala Glu Asp Leu Ala Val Tyr Tyr Cys Met Gln Ser Asn
                100                 105                 110
```

Ser Tyr Pro Leu Thr Phe Gly Ser Gly Thr Lys Leu Glu Ile Lys Arg
        115                 120                 125

<210> SEQ ID NO 2
<211> LENGTH: 118
<212> TYPE: PRT
<213> ORGANISM: Artificial Sequence
<220> FEATURE:
<223> OTHER INFORMATION: VH antibody

<400> SEQUENCE: 2

Glu Val Lys Leu Gln Glu Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Lys Gln Ser His Gly Lys Ser Leu Glu Trp Ile
        35                  40                  45

Gly Tyr Ile Asn Pro Asn Ser Gly Tyr Thr Asn Tyr Asn Glu Lys Phe
    50                  55                  60

Lys Ser Lys Ala Thr Leu Thr Val Asp Lys Ser Thr Asn Thr Ala Tyr
65                  70                  75                  80

Met Glu Leu Ser Arg Leu Thr Ser Glu Asp Ser Ala Thr Tyr Tyr Cys
                85                  90                  95

Thr Arg Phe Gly Ser Tyr Trp Tyr Phe Asp Phe Trp Gly Gln Gly Thr
            100                 105                 110

Thr Val Thr Val Ser Ser
        115

<210> SEQ ID NO 3
<211> LENGTH: 210
<212> TYPE: PRT
<213> ORGANISM: Artificial Sequence
<220> FEATURE:
<223> OTHER INFORMATION: Furin domain fragment 1

<400> SEQUENCE: 3

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln
    210

<210> SEQ ID NO 4
<211> LENGTH: 146
<212> TYPE: PRT
<213> ORGANISM: Artificial Sequence
<220> FEATURE:
<223> OTHER INFORMATION: Furin domain fragment 2

<400> SEQUENCE: 4

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg G

-continued

```
Gly Arg Cys Tyr Pro Ala Cys Pro Glu Gly Ser Ser Ala Ala Asn Gly
            100                 105                 110

Thr Met Glu Cys Ser Ser
        115

<210> SEQ ID NO 6
<211> LENGTH: 100
<212> TYPE: PRT
<213> ORGANISM: Artificial Sequence
<220> FEATURE:
<223> OTHER INFORMATION: Furin domain fragment 4

<400> SEQUENCE: 6

Ala Glu Gly Ser Gln Ala Cys Ala Lys Gly Cys Glu Leu Cys Ser Glu
1               5                   10                  15

Val Asn Gly Cys Leu Lys Cys Ser Pro Lys Leu Phe Ile Leu Leu Glu
            20                  25                  30

Arg Asn Asp Ile Arg Gln Val Gly Val Cys Leu Pro Ser Cys Pro Pro
            35                  40                  45

Gly Tyr Phe Ala Arg Asn Pro Asp Met Asn Lys Cys Ile Lys Cys Lys
    50                  55                  60

Ile Glu His Cys Glu Ala Cys Phe Ser His Asn Phe Cys Thr Lys Cys
65                  70                  75                  80

Lys Glu Gly Leu Tyr Leu His Lys Gly Arg Cys Tyr Pro Ala Cys Pro
                85                  90                  95

Glu Gly Ser Ser
            100
```